US010883116B2

(12) United States Patent
Geijsen et al.

(10) Patent No.: US 10,883,116 B2
(45) Date of Patent: Jan. 5, 2021

(54) TRANSDUCTION BUFFER

(71) Applicant: Koninklijke Nederlandse Akademie van Wetenschappen, Utrecht (NL)

(72) Inventors: Niels Geijsen, Utrecht (NL); Diego Sebastián D'Astolfo, Utrecht (NL)

(73) Assignee: Koninklijke Nederlandse Akademie van Wetenschappen, Utrecht (NL)

( * ) Notice: Subject to any disclaimer, the term of this patent is extended or adjusted under 35 U.S.C. 154(b) by 0 days.

(21) Appl. No.: 14/914,528

(22) PCT Filed: Aug. 28, 2014

(86) PCT No.: PCT/IB2014/064127
§ 371 (c)(1),
(2) Date: Feb. 25, 2016

(87) PCT Pub. No.: WO2015/028969
PCT Pub. Date: Mar. 5, 2015

(65) Prior Publication Data

US 2016/0273001 A1 Sep. 22, 2016

(30) Foreign Application Priority Data

Aug. 28, 2013 (GB) .................................. 1315321.8

(51) Int. Cl.

| | |
|---|---|
| ***A61K 38/00*** | (2006.01) |
| ***A61K 47/02*** | (2006.01) |
| ***A61K 47/20*** | (2006.01) |
| ***A61K 47/12*** | (2006.01) |
| ***A61K 47/10*** | (2017.01) |
| ***C12N 15/86*** | (2006.01) |
| ***A61K 35/545*** | (2015.01) |
| ***C12N 15/87*** | (2006.01) |
| ***A61K 35/30*** | (2015.01) |
| ***A61K 38/17*** | (2006.01) |
| ***A61K 38/45*** | (2006.01) |
| ***A61K 38/46*** | (2006.01) |
| ***A61K 47/18*** | (2017.01) |
| ***A61K 47/22*** | (2006.01) |
| ***C07K 14/32*** | (2006.01) |
| ***C07K 14/47*** | (2006.01) |
| ***C12N 7/00*** | (2006.01) |
| ***C12N 9/12*** | (2006.01) |
| ***C12N 9/16*** | (2006.01) |

(52) U.S. Cl.
CPC .............. *C12N 15/86* (2013.01); *A61K 35/30* (2013.01); *A61K 35/545* (2013.01); *A61K 38/1709* (2013.01); *A61K 38/45* (2013.01); *A61K 38/465* (2013.01); *A61K 47/10* (2013.01); *A61K 47/12* (2013.01); *A61K 47/18* (2013.01); *A61K 47/20* (2013.01); *A61K 47/22* (2013.01); *C07K 14/32* (2013.01); *C07K 14/4702* (2013.01); *C12N 7/00* (2013.01); *C12N 9/1241* (2013.01); *C12N 9/16* (2013.01); *C12N 15/87* (2013.01); *C07K 2319/21* (2013.01); *C07K 2319/50* (2013.01); *C07K 2319/55* (2013.01); *C12N 2740/15043* (2013.01); *C12Y 207/07* (2013.01); *C12Y 301/00* (2013.01)

(58) Field of Classification Search
None
See application file for complete search history.

(56) References Cited

U.S. PATENT DOCUMENTS

| | | | | |
|---|---|---|---|---|
| 5,627,159 | A | 5/1997 | Shih et al. | |
| 6,124,207 | A | 9/2000 | Robinson et al. | |
| 6,124,270 | A | 9/2000 | Haensler | |
| 6,258,792 | B1 | 7/2001 | Deshmukh et al. | |
| 7,906,109 | B2 * | 3/2011 | Menart | A61K 9/0019 424/85.1 |
| 9,526,784 | B2 * | 12/2016 | Liu | A61K 38/465 |
| 2008/0171023 | A1 * | 7/2008 | Salgaller | A61K 39/0011 424/93.7 |
| 2008/0193498 | A1 * | 8/2008 | Hausheer | A61K 31/105 424/422 |
| 2011/0016522 | A1 | 1/2011 | Sheppard | |
| 2014/0120135 | A1 * | 5/2014 | Mombarg | A61K 9/0019 424/201.1 |
| 2014/0301990 | A1 * | 10/2014 | Gregory | A61K 35/26 424/93.21 |
| 2018/0327783 | A1 | 11/2018 | Geijsen et al. | |

FOREIGN PATENT DOCUMENTS

| | | | |
|---|---|---|---|
| EP | 1046394 | A2 | 10/2000 |
| EP | 1103259 | A1 | 5/2001 |
| JP | 2000-143486 | | 5/2000 |
| JP | 2007-516281 | A | 6/2007 |
| JP | 2011-523643 | A | 8/2011 |
| WO | WO 97/06794 | | 2/1997 |
| WO | WO 99/21591 | A1 | 5/1999 |
| WO | WO 01/72280 | A2 | 10/2001 |
| WO | WO 2006/065960 | A2 | 6/2006 |
| WO | WO 2008/093982 | A1 | 8/2008 |

(Continued)

OTHER PUBLICATIONS

Wright et al., Immunization with the Recombinant PorB Outer Membrane Protein Induces a Bactericidal Immune Response against Neisseria meningitidis. Infection and Immunity, Aug. 2002, 70:8, p. 4028-4034.*

(Continued)

*Primary Examiner* — Arthur S Leonard
(74) *Attorney, Agent, or Firm* — Wolf, Greenfield & Sacks, P.C.

(57) ABSTRACT

The invention relates to transduction compounds, buffers and methods for introducing molecules into cells. The invention also relates to methods of treatment, pharmaceutical compositions and other uses of the transduction compounds and buffers. The invention also relates to modified cells obtainable by the transduction compounds, buffers and methods of the invention.

21 Claims, 36 Drawing Sheets

Specification includes a Sequence Listing.

(56) References Cited

FOREIGN PATENT DOCUMENTS

| | | | | |
|---|---|---|---|---|
| WO | WO 2008/148223 A1 | 12/2008 | | |
| WO | WO 2009/141738 A2 | 11/2009 | | |
| WO | WO 2012/050140 A1 | 4/2012 | | |
| WO | WO 2012/110010 A1 | 8/2012 | | |
| WO | WO-2013090734 A1 * | 6/2013 | | C12N 15/8205 |
| WO | WO 2017/093326 A1 | 11/2016 | | |
| WO | WO 2017/093326 A1 | 6/2017 | | |

OTHER PUBLICATIONS

Chae et al., Metabolic engineering of *Escherichia coli* for the production of 1,3-diaminopropane, a three carbon diamine. Sci. Rep. 5, 13040, 2015; pp. 1-13 (Year: 2015).*
Otto et al., Hyperosmotic stress enhances cytokine production and decreases phagocytosis in vitro. Critical Care 2008, 12:R107, pp. 1-8 (Year: 2008)*
Moore MW, Carbone FR, Bevan MJ. Introduction of soluble protein into the class I pathway of antigen processing and presentation. Cell. Sep. 9, 1988;54(6):777-85. (Year: 1988).*
Okada CY, Rechsteiner M. Introduction of macromolecules into cultured mammalian cells by osmotic lysis of pinocytic vesicles. Cell. May 1982;29(1):33-41 (Year: 1982).*
National Center for Biotechnology Information. PubChem Database. CID=3085288, https://pubchem.ncbi.nlm.nih.gov/compound/1-Propylpiperazine-Dihydrobromide (last modified on Aug. 1, 2019), pp. 1-13. (Year: 2019).*
Zhou et al., Current Methods for Loading Dendritic Cells With Tumor Antigen for the Induction of Antitumor Immunity. Journal of Immunotherapy 25(4):289-303 © 2002 (Year: 2002).*
Urnov et al., Genome editing with engineered zinc finger nucleases. Nat Rev Genet. Sep. 2010;11(9):636-46. (Year: 2010).*
Kouprina et al., Human artificial chromosome-based gene delivery vectors for biomedicine and biotechnology. Expert Opinion on Drug Delivery, 2014, 11:4, 517-535 (Year: 2014).*
International Search Report and Written Opinion for PCT/IB2014/064127 dated May 20, 2015.
International Preliminary Report on Patentability for PCT/IB2014/064127 dated Mar. 10, 2016.
[No Author Listed] Pubchem Compound [Online] Database accession No. CID 24860518. Jul. 30, 2008. Last accessed Dec. 1, 2015.
Alexander et al., Tethering, recycling and activation of the epithelial sodium-proton exchanger, NHE3. J Exp Biol. Jun. 2009;212(Pt 11):1630-7. doi: 10.1242/jeb.027375.
Al-Quobaili et al., Pancreatic duodenal homeobox factor-1 and diabetes mellitus type 2 (review). Int J Mol Med. Apr. 2008;21(4):399-404.
Beard et al., Efficient method to generate single-copy transgenic mice by site-specific integration in embryonic stem cells. Genesis. Jan. 2006;44(1):23-8.
Berridge, Cell Signalling Pathways. Cell Signalling Biology (2014).
Bitler et al., Anti-cancer therapies that utilize cell penetrating peptides. Recent Pat Anticancer Drug Discov. Jun. 2010;5(2):99-108.
Boch, TALEs of genome targeting. Nat Biotechnol. Feb. 2011;29(2):135-6. doi: 10.1038/nbt.1767.
Castellot et al., Animal cells reversibly permeable to small molecules. Proc Natl Acad Sci U S A. Jan. 1978;75(1):351-5.
Chadwick et al., MeCP2 in Rett syndrome: transcriptional repressor or chromatin architectural protein? Curr Opin Genet Dev. Apr. 2007;17(2):121-5. Epub Feb. 20, 2007.
Chiang et al., EGF upregulates Na+/H+ exchanger NHE1 by post-translational regulation that is important for cervical cancer cell invasiveness. J Cell Physiol. Mar. 2008;214(3):810-9.
Dawson et al., Organic osmolytes and embryos: substrates of the Gly and beta transport systems protect mouse zygotes against the effects of raised osmolarity. Biol Reprod. Jun. 1997;56(6):1550-8.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.
Fawell et al., Tat-mediated delivery of heterologous proteins into cells. Proc Natl Acad Sci U S A. Jan. 18. 1994;91(2):664-8.
Frankel et al. Cellular uptake of the tat protein from human immunodeficiency virus. Cell. Dec. 23, 1988;55(6):1189-93.
Garcia et al., Constitutive activation of Stat3 by the Src and JAK tyrosine kinases participates in growth regulation of human breast carcinoma cells. Oncogene. May 3, 2001;20(20):2499-513.
Goldberg et al., Non-detergent sulphobetaines: a new class of molecules that facilitate in vitro protein renaturation. Fold Des. 1996;1(1):21-7.
Gong et al., Neutron Capture Therapy of Cancer: Nanoparticles and High Molecular Weight Boron Delivery Agents. Nanotechnology for Cancer Therapy. 2006; 77-103.
Green et al., Autonomous functional domains of chemically synthesized human immunodeficiency virus tat trans-activator protein. Cell. Dec. 23, 1988;55(6):1179-88.
Grier et al., The pathophysiology of HOX genes and their role in cancer. J Pathol. Jan. 2005;205(2):154-71.
Gruber et al., RNA interference by osmotic lysis of pinosomes: liposome-independent transfection of siRNAs into mammalian cells. Biotechniques. Jul. 2004;37(1):96-102.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Hsieh et al., R11, a novel cell-permeable peptide, as an intravesical delivery vehicle. BJU Int. Nov. 2011;108(10):1666-71. doi: 10.1111/j.1464-410X.2011.10185.x. Epub Mar. 31, 2011.
Ishibashi, et al., Perforated Whole-Cell Patch Clamp Technique: A User's Guide. Springer Protocols Handbooks, 2012, pp. 71-83.
Iwakuma et al., Li-Fraumeni syndrome: a p53 family affair. Cell Cycle. Jul. 2005;4(7):865-7. Epub Jul. 4, 2005.
Jenkins et al., Intracellular pH regulation by $Na^+/H^+$ exchanger-1 (NHE1) is required for growth factor-induced mammary branching morphogenesis. Dev Biol. May 1, 2012;365(1):71-81. doi: 10.1016/j.ydbio.2012.02.010. Epub Feb. 17, 2012.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Koivusalo et al., Amiloride inhibits macropinocytosis by lowering submembranous pH and preventing Rac1 and Cdc42 signaling. J Cell Biol. Feb. 22, 2010;188(4):547-63. doi: 10.1083/jcb.200908086. Epub Feb. 15, 2010.
Kültz et al., Hyperosmolality causes growth arrest of murine kidney cells. Induction of GADD45 and GADD153 by osmosensing via stress-activated protein kinase 2. J Biol Chem. May 29, 1998;273(22):13645-51.
Lennon et al., Deletion of 7q31.1 supports involvement of FOXP2 in language impairment: clinical report and review. Am J Med Genet A. Apr. 15, 2007;143A(8):791-8.
Lundberg et al., Is VP22 nuclear homing an artifact? Nat Biotechnol. Aug. 2001;19(8):713-4.
Luo et al., Hyperosmolarity-induced apoptosis in human corneal epithelial cells is mediated by cytochrome c and MAPK pathways. Cornea. May 2007;26(4):452-60.
Maejima et al., Autophagy sequesters damaged lysosomes to control lysosomal biogenesis and kidney injury. EMBO J. Aug. 28, 2013;32(17):2336-47. doi: 10.1038/emboj.2013.171. Epub Aug. 6, 2013.
Maestro et al., Distinct roles of HNF1beta, HNF1alpha, and HNF4alpha in regulating pancreas development, beta-cell function and growth. Endocr Dev. 2007;12:33-45.
Makarova et al., Prokaryotic homologs of Argonaute proteins are predicted to function as key components of a novel system of defense against mobile genetic elements. Biol Direct. Aug. 25, 2009;4:29. doi: 10.1186/1745-6150-4-29.
Mali et al., RNA-guided human genome engineering via Cas9. Science. Feb. 15, 2013;339(6121):823-6. doi: 10.1126/science.1232033. Epub Jan. 3, 2013.

(56) References Cited

OTHER PUBLICATIONS

Mali et al., Supplementary Materials for RNA-guided human genome engineering via Cas9. Science. Feb. 15, 2013;339(6121):823-6. doi: 10.1126/science.1232033. Epub Jan. 3, 2013.
Mandal et al., Reprogramming human fibroblasts to pluripotency using modified mRNA. Nat Protoc. Mar. 2013;8(3):568-82. doi: 10.1038/nprot.2013.019. Epub Feb. 21, 2013.
Mann et al., Endocytosis and targeting of exogenous HIV-1 Tat protein. EMBO J. Jul. 1991:10(7):1733-9.
Moretti et al, MeCP2 dysfunction in Rett syndrome and related disorders. Curr Opin Genet Dev. Jun. 2006;16(3):276-81. Epub May 2, 2006.
Moscou et al., A simple cipher governs DNA recognition by TAL effectors. Science. Dec. 11, 2009;326(5959):1501. doi: 10.1126/science.1178817.
Nagahara et al., Transduction of full-length TAT fusion proteins into mammalian cells: TAT-p27Kip1 induces cell migration. Nat Med. Dec. 1998;4(12):1449-52.
Okada et al., Introduction of macromolecules into cultured mammalian cells by osmotic lysis of pinocytic vesicles. Cell. May 1982;29(1):33-41.
Paz et al., Galectin-3, a marker for vacuole lysis by invasive pathogens. Cell Microbiol. Apr. 1, 2010;12(4):530-44. doi: 10.1111/j.1462-5822.2009.01415.x. Epub Nov. 27, 2009.
Reinehr et al., Hyperosmolarity triggers CD95 membrane trafficking and sensitizes rat hepatocytes toward CD95L-induced apoptosis. Hepatology. Sep. 2002;36(3):602-14.
Rigor et al., Phosphorylation and activation of the plasma membrane Na+/H+ exchanger (NHE1) during osmotic cell shrinkage. PLoS One. 2011;6(12):e29210. doi: 10.1371/journal.pone.0029210. Epub Dec. 28, 2011.
Swarts et al., DNA-guided DNA interference by a prokaryotic Argonaute. Nature. Mar. 13, 2014;507(7491):258-61. doi: 10.1038/nature12971. Epub Feb. 16, 2014.
Symons et al., Vaccinia virus encodes a soluble type I interferon receptor of novel structure and broad species specificity. Cell. May 19, 1995;81(4):551-60.
Takai et al,. DNA transfection of mouse lymphoid cells by the combination of DEAE-dextran-mediated DNA uptake and osmotic shock procedure. Biochim Biophys Acta. Jan. 30, 1990;1048(1):105-9.
Tattersall et al., Modulation of Na+-H+ exchange isoforms NHE1 and NHE3 by insulin-like growth factor-1 in isolated bovine articular chondrocytes. J Orthop Res. Nov. 2008;26(11):1428-33. doi: 10.1002/jor.20617.
Tattersall et al., Modulation of H+ transport mechanisms by interleukin-1 in isolated bovine articular chondrocytes. Cell Physiol Biochem. 2005;16(1-3):43-50.
Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.
Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.
Van Der Vliet et al., IPEX as a result of mutations in FOXP3. Clin Dev Immunol. 2007;2007:89017. doi: 10.1155/2007/89017.
Voncken et al., Genetic modification of the mouse: general technology—pronuclear and blastocyst injection. Methods Mol Biol. 2011;693:11-36. doi: 10.1007/978-1-60761-974-1_2.
Vuillard et al., A new additive for protein crystallization. FEBS Lett. Oct. 24, 1994;353(3):294-6.
Vuillard et al., Halophilic protein stabilization by the mild solubilizing agents nondetergent sulfobetaines. Anal Biochem. Sep. 20, 1995;230(2):290-4.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Westra et al., Cascade-mediated binding and bending of negatively supercoiled DNA. RNA Biol. Sep. 2012;9(9):1134-8. doi: 10.4161/rna.21410. Epub Sep. 1, 2012.
Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.
U.S. Appl. No. 15/775,791, filed May 11, 2018, Pending.
PCT/EP2016/079294, Feb. 7, 2017, International Search Report and Written Opinion.
PCT/EP2016/079294, Jun. 14, 2018, International Preliminary Report on Patentability.
International Search Report and Written Opinion dated Feb. 7, 2017 for Application No. PCT/EP2016/079294.
International Preliminary Report on Patentability dated Jun. 14, 2018 for Application No. PCT/EP2016/079294.
D'Astolfo et al., Efficient intracellular delivery of native proteins. Cell. Apr. 23, 2015;161(3):674-90.
EP 14784521.8, Dec. 12, 2018, European Office Action.
European Office Action dated Dec. 12, 2018 for Application No. EP 14784521.8.
Dawson et al., Organic osmolytes and embryos: Substrates of the Gly and Beta transport systems protect mouse zygotes against the effects of raised osmolarity. Biol Reproduct. 1997;56:1550-8.
Dega-Szafran et al., $^1$H and $^{13}$ C NMR spectra of betaines, >$N^+$ $(CH_2)_n$ $COO^-$, and their hydrogen halides. Additivity rules for carbon-13 chemical shifts. Magn Reson Chem. 2000;38:43-50.
Mock et al., Efficient lentiviral transduction and transgene expression in primary human B cells. Human Gene Therapy Methods. Dec. 2012;23:408-15.
Sugiura et al., Novel thioredoxin-related transmembrane protein TMX4 has reductase activity. J Biol Chem. Mar. 5, 2010;285(10):7135-42.
Nam et al., Cas5d protein processes pre-crRNA and assembles into a cascade-like interference complex in subtype I-C/Dvulg CRISPR-Cas system. Structure. Sep. 5, 2012;20(9):1574-84. doi: 10.1016/j.str.2012.06.016. Epub Jul. 26, 2012.
Zou et al., Roles of Argonaute Proteins in RNA interference. J. Med Mol Biol. 2006;3(1):55-7.

* cited by examiner

Table1.

| Code # | Structure | Transduction (%) | Cell proliferation (%) |
|---|---|---|---|
| 42 |  | 255 | 77 |
| 31 |  | 242 | 81 |
| 45 |  | 230 | 111 |
| 43 |  | 189 | 108 |
| 34 |  | 185 | 97 |
| 41 |  | 163 | 29 |
| 40 |  | 160 | 37 |
| 39 |  | 144 | 71 |
| 33 |  | 142 | 67 |
| 44 |  | 140 | 101 |
| 22 |  | 135 | 69 |
| 20 |  | 133 | 95 |
| 03 |  | 127 | 82 |

| Code # | Structure | Transduction (%) | Cell proliferation (%) |
|---|---|---|---|
| 30 |  | 124 | 81 |
| 17 |  | 123 | 90 |
| 15 |  | 114 | 107 |
| 38 |  | 111 | 75 |
| 35 |  | 110 | 70 |
| 11 |  | 107 | 97 |
| 10 |  | 105 | 97 |
| 28 |  | 104 | 89 |
| 37 |  | 102 | 92 |
| 01 |  | 100 | 85 |
| 25 |  | 98 | 0 |
| 29 |  | 94 | 86 |
| 02 |  | 93 | 84 |

| Code # | Structure | Transduction (%) | Cell proliferation (%) |
|---|---|---|---|
| 21 |  | 93 | 107 |
| 36 |  | 88 | 75 |
| 26 |  | 84 | 71 |
| 16 |  | 80 | 75 |
| 06 |  | 77 | 85 |
| 04 |  | 75 | 75 |
| 19 |  | 66 | 115 |
| 23 |  | 43 | 88 |
| 24 |  | 39 | 64 |
| 12 |  | 36 | 92 |
| 14 |  | 36 | 80 |
| 13 |  | 32 | 86 |
| 05 |  | 30 | 50 |

| Code # | Structure | Transduction (%) | Cell proliferation (%) |
|---|---|---|---|
| 08 |  | 30 | 60 |
| 27 |  | 22 | 104 |
| 07 |  | 16 | 40 |
| 18 |  | 9 | 86 |
| 09 |  | 5 | 105 |
| 32 |  | 0 | 0 |
| 46 |  | | |

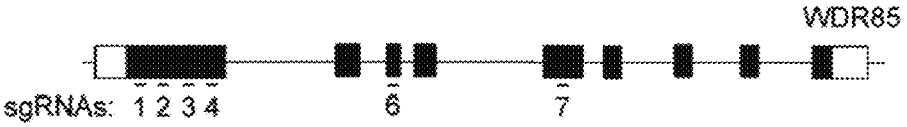

FIG. 20A

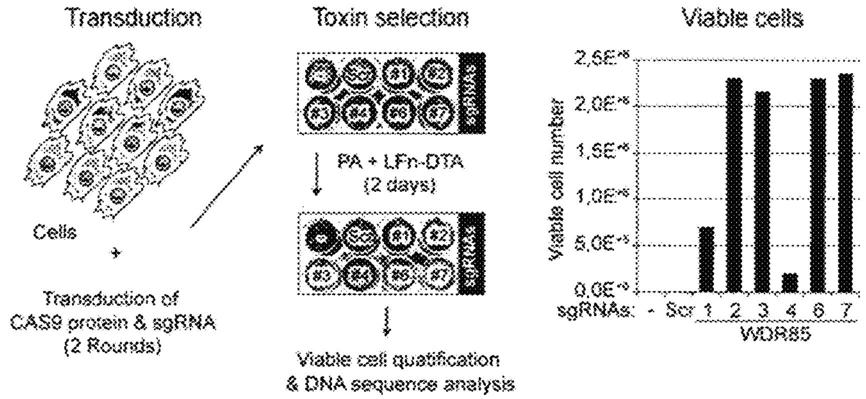

FIG. 20B sgRNA #1; 11 mutant sequences out of 11 sequences = 100% sgRNA1 target sequence

TCCCCGAGGGCTGGATGATGGGCTGTTTCGCCCTGCAAACGGTGGACACCGAGCTGACCGCGGACTCGGTGGAGTGGTGCCCCGCT WT SEQ ID NO: 20

TCCCCGAGGGCTGGATGATGGGCTGTTTCGCCCT-CAAACGGTGGACACCGAGCTGACCGCGGACTCGGTGGAGTGGTGCCCCGCT D1 SEQ ID NO: 21

TCCCCGAGGGCTGGATGATGGGCTGTTTC-----GCAAACGGTGGACACCGAGCTGACCGCGGACTCGGTGGAGTGGTGCCCCGCT D5 SEQ ID NO: 22

TCCCCGAGGGCTGGATGATGGGCTGTTTCGC--------CGGTGGACACCGAGCTGACCGCGGACTCGGTGGAGTGGTGCCCCGCT D8 SEQ ID NO: 23

TCCCCGAGGGCTGGATGATGGGCTG-------------------------------ACCGCGGACTCGGTGGAGTGGTGCCCCGCT D31 [3x] SEQ ID NO: 24

TCCCCGAGGGCTGGATGATGGGCTGTTTCGC----------------------------------TCGGTGGAGTGGTGCCCCGCT D34 SEQ ID NO: 25

TCCCCGAGGGCTGGATGATGGGCTGTTTCGCCCTGCCAAACGGTGGACACCGAGCTGACCGCGGACTCGGTGGAGTGGTGCCCCGC +1 SEQ ID NO: 26

TCCCCGAGGGCTGGATGATGGGCTGTTTCGCCCTGCAAAACGGTGGACACCGAGCTGACCGCGGACTCGGTGGAGTGGTGCCCCGC +1 SEQ ID NO: 27

TCCCCGAGGGCTGGATGATGGGCTGTTTCGCCCTGCCAAACGGTGGACACCGAGCTGACCGCGGACTCGGTGGAGTGGTGCCCCGC +1 SEQ ID NO: 28

TCCCCGAGGGCTGGATGATGGGCTGTTTCCCCCTGCAAAACGGTGGACACCGAGCTGACCGCGGACTCGGTGGAGTGGTGCCCCGC D1/+2 SEQ ID NO: 29 sgRNA #2; 11 mutant sequences out of 11 sequences = 100% sgRNA2 target sequence

ATGATGGGCTGTTTCGCCCTGCAAACGGTGGACACCGAGCTGACCGCGGACTCGGTGGAGTGGTGCCCCGCTGCAAGGCTGCAGGC WT SEQ ID NO: 30

ATGATGGGCTGTTTCGCCCTGCAAACGGTGGACACCGAGCTG-CCGCGGACTCGGTGGAGTGGTGCCCCGCTGCAAGGCTGCAGGC D1 SEQ ID NO: 31

ATGATGGGCTGTTTCGCCCTGCAAACGGTGGACACCGAGCTGAC-------TCGGTGGAGTGGTGCCCCGCTGCAAGGCTGCAGGC D7 [3x] SEQ ID NO: 32

ATGATGGGCTGTTTCGCCCTGCAAA---------------------CGGACTCGGTGGAGTGGTGCCCCGCTGCAAGGCTGCAGGC D21 SEQ ID NO: 33

ATGATGGGCTGTTTCGCCCTGCAAACGGTGGA---------------------------GTGGTGCCCCGCTGCAAGGCTGCAGGC D27 SEQ ID NO: 34

ATGATGGGCTGTTTCGCCCTGCAAACGGTGGACACCGAGCTGAACCGCGGACTCGGTGGAGTGGTGCCCCGCTGCAAGGCTGCAGGC +1 [4x] SEQ ID NO: 35

ATGATGGGCTGTTTCGCCCTGCAAACGGTGGACACCGAGCTGATCCGCGGACTCGGTGGAGTGGTGCCCCGCTGCAAGGCTGCAGGC +1 SEQ ID NO: 36

FIG. 20C sgRNA #3; 10 mutant sequences out of 10 sequences = 100%

```
                  sgRNA3 target sequence
CTGACCGCGGACTCGGTGGAGTGGTGCCCGCTGCAAGGCTGCAGGCACCTGCTGGCGTGCGGGACCTACCAGCTGCGGCGGCCGG WT          SEQ ID NO: 37
CTGACCGCGGACTCGGTGGAGTGGTGCCCGCTGCA-------AGGCACCTGCTGGCGTGCGGGACCTACCAGCTGCGGCGGCCGG D7    [3x]  SEQ ID NO: 38
CTGACCGCGGACTCGGTGGAGTGGTGCCCGCTGCA--------GGCACCTGCTGGCGTGCGGGACCTACCAGCTGCGGCGGCCGG D8          SEQ ID NO: 39
CTGACCGCGGACTCGGTGGAGTGGTGCCC-------------------CTGCTGGCGTGCGGGACCTACCAGCTGCGGCGGCCGG D19         SEQ ID NO: 40

CTGACCGCGGACTCGGTGGAGTGGTGCCCGCTGCAAGGCTTGCAGGCACCTGCTGGCGTGCGGGACCTACCAGCTGCGGCGGCCGG D1/+1       SEQ ID NO: 41
CTGACCGCGGACTCGGTGGAGTGGTGCCCGCTGCAAGGCATGCAGGCACCTGCTGGCGTGCGGGACCTACCAGCTGCGGCGGCCGG D1/+1       SEQ ID NO: 42
GGGCTCTGCGCTCGTCCGGCCG--/173/--ACCTGCTGGCGTGCGGGACCTACCAGCTGCGG---/14/--GCCTGCCGGCCCC D187/+32    SEQ ID NO: 43
CTGACCGCGG----------GCACCACTC--------------CACCTGCTGGCGTGCGGGACCTACCAGCTGCGGCGGCCGG D35/+9      SEQ ID NO: 44
CTGACCGCGGACTCGGTGGAGTGGTGC------ACGCACG---------TGCTGGCGTGCGGGACCTACCAGCTGCGGCGGCCGG D22/+7      SEQ ID NO: 45
```

sgRNA #4; 10 mutant sequences out of 10 sequences = 100%

```
                                           sgRNA4 target sequence
CTGCAGGCACCTGCTGGCGTGCGGGACCTACCAGCTGCGGCGGCCGGAGGACCGGCCTGCCGGCCCCCAGAACAAGGTGCGC WT             SEQ ID NO: 46
CTGCAGGCACCTGCTGGCGTGCGGGACCTACCAGCTGCGGCGGCCGGAG-ACCGGCCTGCCGGCCCCCAGAACAAGGTGCGC D1             SEQ ID NO: 47
CTGCAGGCACCTGCTGGCGTGCGGGACCTACCAGCTGCGGCGGC-----GACCGGCCTGCCGGCCCCCAGAACAAGGTGCGC D5             SEQ ID NO: 48
CTGCAGGCACCTGCTGGCGTGCGGGACCTACCAGCTGCGGCGGCCGGAG-------CTGCCGGCCCCCAGAACAAGGTGCGC D7     [2x]    SEQ ID NO: 49
CTGCAGGCACCTGCTGGCGTGCGGGACCTACCAGCTGCGGCG-------------CCTGCCGGCCCCCAGAACAAGGTGCGC D13            SEQ ID NO: 50
CTGCAGGCACCTGCTGGCGTGCGGGACCTACCAGCTGCGGC----------------TGCCGGCCCCCAGAACAAGGTGCGC D16            SEQ ID NO: 51
CTGCAGGCACCTGCTGGCGTGCGGGACCTACCAGCTGC----------------------TGCGGCCCCCAGAACAAGGTGCGC D22/+2 [2x]  SEQ ID NO: 52
CTGCAGGCACCTGCTGGCGTGCGGGACCTACC-------------------------TGCCGGTCCCCAGAACAAGGTGCGC D25            SEQ ID NO: 53
CTGCAGGC--------------------------------------------------------CCCCAGAACAAGGTGCGC D56            SEQ ID NO: 54
```

sgRNA #6; 10 mutant sequences out of 10 sequences = 100%

```
                                              sgRNA6 target sequence
TGGGCCCTCTCCTCAGGTGTCACATCCCGGTGGCTGGACATGCCCTCTTGGGCTTGGCAGATGCCAGTGGATCCATACAACTGCT WT        SEQ ID NO: 55
TGGGCCCTCTCCTCAGGTGTCACATCCCGGTGGCTGGACATGCCCTC-TGGGCTTGGCAGATGCCAGTGGATCCATACAACTGCT D1        SEQ ID NO: 56
TGGGCCCTCTCCTCAGGTGTCACATCCCGGTGGCTGGACATG--------GGCTTGGCAGATGCCAGTGGATCCATACAACTGCT D8        SEQ ID NO: 57
TGGGCCCTCTCCTCAGGTGTCACATCCCGGTGGCTGGACATGCCCTCT------------ATGCCAGTGGATCCATACAACTGCT D12       SEQ ID NO: 58
TGGGCCCTCTCCTCAGGTGTCACATCCCGGTGGCTGGACATGC----------------------AGTGGATCCATACAACTGCT D22       SEQ ID NO: 59
TGGGCCCTCTCCTCAGGTGTCACATCCA-------------------------TTGGCAGATGCCAGTGGATCCATACAACTGCT D26/+1    SEQ ID NO: 60
TGGGCCCTCTCCTCAGGTGTCAC----------TGCATGTCCA----------CTTGGCAGATGCCAGTGGATCCATACAACTGCT D29/+10   SEQ ID NO: 61

TGGGCCCTCTCCTCAGGTGTCACATCCCGGTGGCTGGACATGCCCTCTTTGGGCTTGGCAGATGCCAGTGGATCCATACAACTGC +1         SEQ ID NO: 62
TGGGCCCTCTCCTCAGGTGTCACATCCCGGTGGCTGGACATGCCCTCTTGTGGGCTTGGCAGATGCCAGTGGATCCATACAACTG +2         SEQ ID NO: 63
TGGGCCCTCTCCTCAGGTGTCACATCCCGGTGGCTGGACATGCCCTCTATTGGGCTTGGCAGATGCCAGTGGATCCATACAACTG +2         SEQ ID NO: 64
CATAGGAGCAGTGGGCCATACCATAT-----------//-----------GGCTTGGCAGATGCCAGTGGATCCATACAACTGCT D182      SEQ ID NO: 65
```

FIG. 20D sgRNA #7; 12 mutant sequences out of 12 sequences = 100%

```
                                               sgRNA7 target sequence
AGGGCAGCTCCACCTCCTGATGGTGAATGAGACGAGGCCCAGGCTGCAGAAAGTGGCCTCATGGCAGGCACATCAATTCGAGGCC WT        SEQ ID NO: 66
AGGGCAGCTCCACCTCCTGATGGTGAATGAGACGAGGCCCAGGCTGCAGAAAG--------TGGCAGGCACATCAATTCGAGGCC D8   [3x] SEQ ID NO: 67
AGGGCAGCTCCACCTCCTGATGGTGAATGAGACGAGGCCCAGGCTGCAGAAAGC--------------GCACATCAATTCGAGGCC D14/+1    SEQ ID NO: 68
AGGGCAGCTCCACCTCCTGATGGTGAATGAGACGAGGCCCAGGCTG------------------------CATCAATTCGAGGCC D24  [2x] SEQ ID NO: 69
AGGGCAGCTCCACCTCCTGATGGTGAATGAGACGAGGCCCAGGCT-------------------------CATCAATTCGAGGCC D25       SEQ ID NO: 70
AGGGCAGCTACACGTCCTG-----------------------------------------ATGGCAGGCACATCAATTCGAGGCC D41       SEQ ID NO: 71
AG----------------------------------------------------------------GGCACATCAATTCGAGGCC D64       SEQ ID NO: 72

AGGGCAGCTCCACCTCCTGATGGTGAATGAGACGAGGCCCAGGCTGCAGAAAGTGGCCTTCATGGCAGGCACATCAATTCGAGGC +1        SEQ ID NO: 73
AGGGCAGCTCCACCTCCTGATGGTGAATGAGACGAGGCCCAGGCTGCAGAAAGTGGCCCTCATGGCAGGCACATCAATTCGAGGC +1        SEQ ID NO: 74
TGTTTGGGAACCAGAAGA------------------------//-------------------GGCAGGCACATCAATTCGAGGCC D155      SEQ ID NO: 75
```

FIG. 20E

*WDR85 Knockout clones - sgRNA #3* sgRNA3 target sequence

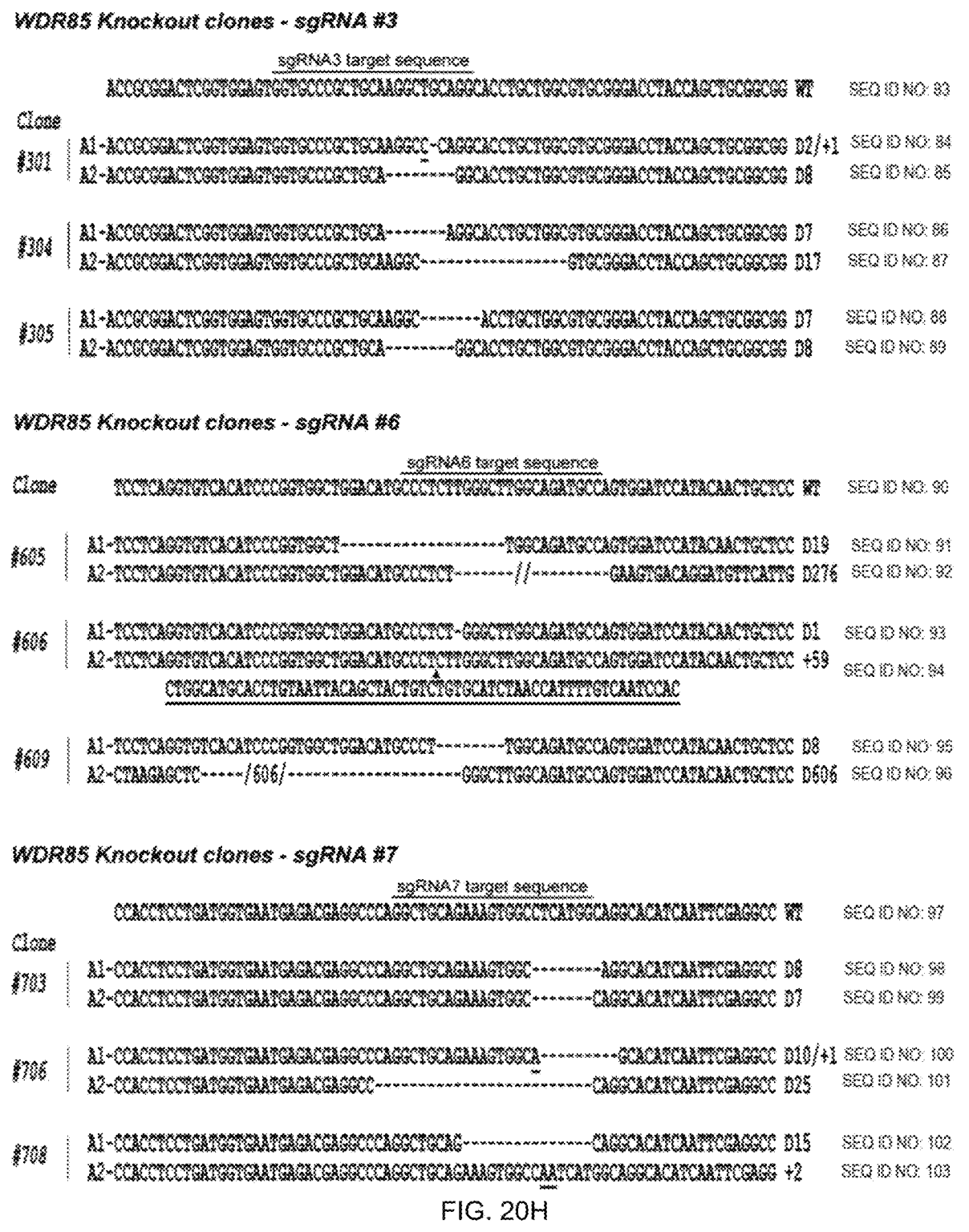

ACCGCGGACTCGGTGGAGTGGTGCCCGCTGCAAGGCTGCAGGCACCTGCTGGCGTGCGGGACCTACCAGCTGCGGCGG WT SEQ ID NO: 83

Clone

#301
A1-ACCGCGGACTCGGTGGAGTGGTGCCCGCTGCAAGGCC-CAGGCACCTGCTGGCGTGCGGGACCTACCAGCTGCGGCGG D2/+1 SEQ ID NO: 84
A2-ACCGCGGACTCGGTGGAGTGGTGCCCGCTGCA--------GGCACCTGCTGGCGTGCGGGACCTACCAGCTGCGGCGG D8 SEQ ID NO: 85

#304
A1-ACCGCGGACTCGGTGGAGTGGTGCCCGCTGCA-------AGGCACCTGCTGGCGTGCGGGACCTACCAGCTGCGGCGG D7 SEQ ID NO: 86
A2-ACCGCGGACTCGGTGGAGTGGTGCCCGCTGCAAGGC-----------------GTGCGGGACCTACCAGCTGCGGCGG D17 SEQ ID NO: 87

#305
A1-ACCGCGGACTCGGTGGAGTGGTGCCCGCTGCAAGGC-------ACCTGCTGGCGTGCGGGACCTACCAGCTGCGGCGG D7 SEQ ID NO: 88
A2-ACCGCGGACTCGGTGGAGTGGTGCCCGCTGCA--------GGCACCTGCTGGCGTGCGGGACCTACCAGCTGCGGCGG D8 SEQ ID NO: 89

*WDR85 Knockout clones - sgRNA #6* sgRNA6 target sequence

Clone TCCTCAGGTGTCACATCCCGGTGGCTGGACATGCCCTCTTGGCTTGGCAGATGCCAGTGGATCCATACAACTGCTCC WT SEQ ID NO: 90

#605
A1-TCCTCAGGTGTCACATCCCGGTGGCT-------------------TGGCAGATGCCAGTGGATCCATACAACTGCTCC D19 SEQ ID NO: 91
A2-TCCTCAGGTGTCACATCCCGGTGGCTGGACATGCCCTCT-------//---------GAAGTGACAGGATGTTCATTG D276 SEQ ID NO: 92

#606
A1-TCCTCAGGTGTCACATCCCGGTGGCTGGACATGCCCTCT-GGCTTGGCAGATGCCAGTGGATCCATACAACTGCTCC D1 SEQ ID NO: 93
A2-TCCTCAGGTGTCACATCCCGGTGGCTGGACATGCCCTCTTGGCTTGGCAGATGCCAGTGGATCCATACAACTGCTCC +59 SEQ ID NO: 94
CTGGCATGCACCTGTAATTACAGCTACTGTCTGTGCATCTAACCATTTTGTCAATCCAC

#609
A1-TCCTCAGGTGTCACATCCCGGTGGCTGGACATGCCCT--------TGGCAGATGCCAGTGGATCCATACAACTGCTCC D8 SEQ ID NO: 95
A2-CTAAGAGCTC-----/606/-------------------GGGCTTGGCAGATGCCAGTGGATCCATACAACTGCTCC D606 SEQ ID NO: 96

*WDR85 Knockout clones - sgRNA #7* sgRNA7 target sequence

CCACCTCCTGATGGTGAATGAGACGAGGCCCAGGCTGCAGAAAGTGGCCTCATGGCAGGCACATCAATTCGAGGCC WT SEQ ID NO: 97

Clone

#703
A1-CCACCTCCTGATGGTGAATGAGACGAGGCCCAGGCTGCAGAAAGTGGC--------AGGCACATCAATTCGAGGCC D8 SEQ ID NO: 98
A2-CCACCTCCTGATGGTGAATGAGACGAGGCCCAGGCTGCAGAAAGTGGC-------CAGGCACATCAATTCGAGGCC D7 SEQ ID NO: 99

#706
A1-CCACCTCCTGATGGTGAATGAGACGAGGCCCAGGCTGCAGAAAGTGGCA---------GCACATCAATTCGAGGCC D10/+1 SEQ ID NO: 100
A2-CCACCTCCTGATGGTGAATGAGACGAGGCC-------------------------CAGGCACATCAATTCGAGGCC D25 SEQ ID NO: 101

#708
A1-CCACCTCCTGATGGTGAATGAGACGAGGCCCAGGCTGCAG---------------CAGGCACATCAATTCGAGGCC D15 SEQ ID NO: 102
A2-CCACCTCCTGATGGTGAATGAGACGAGGCCCAGGCTGCAGAAAGTGGCCAATCATGGCAGGCACATCAATTCGAGG +2 SEQ ID NO: 103

FIG. 20H

SEQUENCE LISTING

<160> NUMBER OF SEQ ID NOS: 103

<210> SEQ ID NO 1
<211> LENGTH: 109
<212> TYPE: DNA
<213> ORGANISM: Artificial Sequence
<220> FEATURE:
<223> OTHER INFORMATION: Synthetic Polynucleotide

<400> SEQUENCE: 1
ggggccacta gggacaggat gttttagagc tagaaatagc aagttaaaat aaggctagtc 60
cgttatcaac ttgaaaaagt ggcaccgagt cggtgctttt ttcgctccg 109

<210> SEQ ID NO 2
<211> LENGTH: 109
<212> TYPE: DNA
<213> ORGANISM: Artificial Sequence
<220> FEATURE:
<223> OTHER INFORMATION: Synthetic Polynucleotide

<400> SEQUENCE: 2
ggggccacta ggcacacgat gttttagagc tagaaatagc aagttaaaat aaggctagtc 60
cgttatcaac ttgaaaaagt ggcaccgagt cggtgctttt ttcgctccg 109

<210> SEQ ID NO 3
<211> LENGTH: 109
<212> TYPE: DNA
<213> ORGANISM: Artificial Sequence
<220> FEATURE:
<223> OTHER INFORMATION: Synthetic Polynucleotide

<400> SEQUENCE: 3
ggggccactg gggacaggct gttttagagc tagaaatagc aagttaaaat aaggctagtc 60
cgttatcaac ttgaaaaagt ggcaccgagt cggtgctttt ttcgctccg 109

<210> SEQ ID NO 4
<211> LENGTH: 109
<212> TYPE: DNA
<213> ORGANISM: Artificial Sequence
<220> FEATURE:
<223> OTHER INFORMATION: Synthetic Polynucleotide

<400> SEQUENCE: 4
gggctgtttc gccctgcaaa gttttagagc tagaaatagc aagttaaaat aaggctagtc 60
cgttatcaac ttgaaaaagt ggcaccgagt cggtgctttt ttcgctccg 109

<210> SEQ ID NO 5
<211> LENGTH: 109
<212> TYPE: DNA
<213> ORGANISM: Artificial Sequence
<220> FEATURE:
<223> OTHER INFORMATION: Synthetic Polynucleotide

<400> SEQUENCE: 5
ggtggacacc gagctgaccg gttttagagc tagaaatagc aagttaaaat aaggctagtc 60
cgttatcaac ttgaaaaagt ggcaccgagt cggtgctttt ttcgctccg 109

<210> SEQ ID NO 6
<211> LENGTH: 109
<212> TYPE: DNA
<213> ORGANISM: Artificial Sequence
<220> FEATURE:
<223> OTHER INFORMATION: Synthetic Polynucleotide

<400> SEQUENCE: 6
ggtgcccgct gcaaggctgc gttttagagc tagaaatagc aagttaaaat aaggctagtc 60
cgttatcaac ttgaaaaagt ggcaccgagt cggtgctttt ttcgctccg 109

<210> SEQ ID NO 7
<211> LENGTH: 109
<212> TYPE: DNA
<213> ORGANISM: Artificial Sequence
<220> FEATURE:
<223> OTHER INFORMATION: Synthetic Polynucleotide

<400> SEQUENCE: 7
gggccggcag gccggtcctc gttttagagc tagaaatagc aagttaaaat aaggctagtc 60
cgttatcaac ttgaaaaagt ggcaccgagt cggtgctttt ttcgctccg 109

<210> SEQ ID NO 8
<211> LENGTH: 109
<212> TYPE: DNA
<213> ORGANISM: Artificial Sequence
<220> FEATURE:
<223> OTHER INFORMATION: Synthetic Polynucleotide

<400> SEQUENCE: 8
ggtggctgga catgccctct gttttagagc tagaaatagc aagttaaaat aaggctagtc 60
cgttatcaac ttgaaaaagt ggcaccgagt cggtgctttt ttcgctccg 109

<210> SEQ ID NO 9
<211> LENGTH: 109
<212> TYPE: DNA
<213> ORGANISM: Artificial Sequence
<220> FEATURE:
<223> OTHER INFORMATION: Synthetic Polynucleotide

<400> SEQUENCE: 9
ggcatctgcc aagcccaaga gttttagagc tagaaatagc aagttaaaat aaggctagtc 60
cgttatcaac ttgaaaaagt ggcaccgagt cggtgctttt ttcgctccg 109

<210> SEQ ID NO 10
<211> LENGTH: 109
<212> TYPE: DNA
<213> ORGANISM: Artificial Sequence
<220> FEATURE:
<223> OTHER INFORMATION: Synthetic Polynucleotide

<400> SEQUENCE: 10
ggctgcagaa agtggcctca gttttagagc tagaaatagc aagttaaaat aaggctagtc 60
cgttatcaac ttgaaaaagt ggcaccgagt cggtgctttt ttcgctccg 109

<210> SEQ ID NO 11
<211> LENGTH: 121
<212> TYPE: DNA
<213> ORGANISM: Homo sapiens

<400> SEQUENCE: 11
gtatcctgta atgctctcat tgaaacagct atatttcttt ttcagattag tgatgatgaa 60
ccaggttatg accttgattt attttgcata cctaatcatt atgctgagga tttggaaagg 120
g 121

<210> SEQ ID NO 12

-continued

<211> LENGTH: 111
<212> TYPE: DNA
<213> ORGANISM: Artificial Sequence
<220> FEATURE:
<223> OTHER INFORMATION: Synthetic Polynucleotide

<400> SEQUENCE: 12
gtatcctgta atgctctcat tgaaacagct atatttcttt ttcagattag tgatgatatg 60
accttgattt attttgcata cctaatcatt atgctgagga tttggaaagg g 111

<210> SEQ ID NO 13
<211> LENGTH: 101
<212> TYPE: DNA
<213> ORGANISM: Artificial Sequence
<220> FEATURE:
<223> OTHER INFORMATION: Synthetic Polynucleotide

<400> SEQUENCE: 13
gtatcctgta atgctctcat tgaaacagct atatttcttt ttcagattag accttgattt 60
attttgcata cctaatcatt atgctgagga tttggaaagg g 101

<210> SEQ ID NO 14
<211> LENGTH: 107
<212> TYPE: DNA
<213> ORGANISM: Artificial Sequence
<220> FEATURE:
<223> OTHER INFORMATION: Synthetic Polynucleotide

<400> SEQUENCE: 14
gtatcctgta atgctctcat tgaaacagct atatttcttt ttcagattag tgatgatgat 60
tgatttattt tgcataccta atcattatgc tgaggatttg gaaaggg 107

<210> SEQ ID NO 15
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 15
gtatcctgta atgctctcat tgaaacagct attttgcata cctaatcatt atgctgagga 60
tttggaaagg g 71

<210> SEQ ID NO 16
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 16
gtatcctgta atgctctcag gatttggaaa ggg 33

<210> SEQ ID NO 17
<211> LENGTH: 9
<212> TYPE: DNA
<213> ORGANISM: Artificial Sequence
<220> FEATURE:
<223> OTHER INFORMATION: Synthetic Polynucleotide

<400> SEQUENCE: 17 gtatcaggg 9

<210> SEQ ID NO 18
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 18
ttctctgata gactaaggta tggacaggta agtaag 36

<210> SEQ ID NO 19
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 19
taattcatta tcataccttt tactttttct tgtgtt 36

<210> SEQ ID NO 20
<211> LENGTH: 85
<212> TYPE: DNA
<213> ORGANISM: Homo sapiens

<400> SEQUENCE: 20
tccccgaggg ctggatgatg ggctgtttcg ccctgcaaac ggtggacacc gagctgaccg 60
cggactcggt ggagtggtgc ccgct 85

<210> SEQ ID NO 21
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 21
tccccgaggg ctggatgatg ggctgtttcg ccctcaaacg gtggacaccg agctgaccgc 60
ggactcggtg gagtggtgcc cgct 84

<210> SEQ ID NO 22
<211> LENGTH: 80
<212> TYPE: DNA
<213> ORGANISM: Artificial Sequence
<220> FEATURE:
<223> OTHER INFORMATION: Synthetic Polynucleotide

<400> SEQUENCE: 22
tccccgaggg ctggatgatg ggctgtttcg caaacggtgg acaccgagct gaccgcggac 60
tcggtggagt ggtgcccgct 80

<210> SEQ ID NO 23
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 23
tccccgaggg ctggatgatg ggctgtttcg ccggtggaca ccgagctgac cgcggactcg 60
gtggagtggt gcccgct 77

<210> SEQ ID NO 24

<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 24
tccccgaggg ctggatgatg ggctgaccgc ggactcggtg gagtggtgcc cgct 54

<210> SEQ ID NO 25
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 25
tccccgaggg ctggatgatg ggctgtttcg ctcggtggag tggtgcccgc t 51

<210> SEQ ID NO 26
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 26
tccccgaggg ctggatgatg ggctgtttcg ccctgccaaa cggtggacac cgagctgacc 60
gcggactcgg tggagtggtg cccgc 85

<210> SEQ ID NO 27
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 27
tccccgaggg ctggatgatg ggctgtttcg ccctgcaaaa cggtggacac cgagctgacc 60
gcggactcgg tggagtggtg cccgc 85

<210> SEQ ID NO 28
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 28
tccccgaggg ctggatgatg ggctgtttcg ccctgccaaa cggtggacac cgagctgacc 60
gcggactcgg tggagtggtg cccgc 85

<210> SEQ ID NO 29
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 29
tccccgaggg ctggatgatg ggctgtttcc ccctgcaaaa cggtggacac cgagctgacc 60
gcggactcgg tggagtggtg cccgc 85

<210> SEQ ID NO 30
<211> LENGTH: 85
<212> TYPE: DNA
<213> ORGANISM: Homo sapiens

<400> SEQUENCE: 30
atgatgggct gtttcgccct gcaaacggtg gacaccgagc tgaccgcgga ctcggtggag 60
tggtgcccgc tgcaaggctg caggc 85

<210> SEQ ID NO 31
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 31
atgatgggct gtttcgccct gcaaacggtg gacaccgagc tgccgcggac tcggtggagt 60
ggtgcccgct gcaaggctgc aggc 84

<210> SEQ ID NO 32
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 32
atgatgggct gtttcgccct gcaaacggtg gacaccgagc tgactcggtg gagtggtgcc 60
cgctgcaagg ctgcaggc 78

<210> SEQ ID NO 33
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 33
atgatgggct gtttcgccct gcaaacggac tcggtggagt ggtgcccgct gcaaggctgc 60
aggc 64

<210> SEQ ID NO 34
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 34
atgatgggct gtttcgccct gcaaacggtg gagtggtgcc cgctgcaagg ctgcaggc 58

<210> SEQ ID NO 35
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 35
atgatgggct gtttcgccct gcaaacggtg gacaccgagc tgaaccgcgg actcggtgga 60
gtggtgcccg ctgcaaggct gcaggc 86

-continued

<210> SEQ ID NO 36
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 36
atgatgggct gtttcgccct gcaaacggtg gacaccgagc tgatccgcgg actcggtgga 60
gtggtgcccg ctgcaaggct gcaggc 86

<210> SEQ ID NO 37
<211> LENGTH: 85
<212> TYPE: DNA
<213> ORGANISM: Homo sapiens

<400> SEQUENCE: 37
ctgaccgcgg actcggtgga gtggtgcccg ctgcaaggct gcaggcacct gctggcgtgc 60
gggacctacc agctgcggcg gccgg 85

<210> SEQ ID NO 38
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 38
ctgaccgcgg actcggtgga gtggtgcccg ctgcaaggca cctgctggcg tgcgggacct 60
accagctgcg gcggccgg 78

<210> SEQ ID NO 39
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 39
ctgaccgcgg actcggtgga gtggtgcccg ctgcaggcac ctgctggcgt gcgggaccta 60
ccagctgcgg cggccgg 77

<210> SEQ ID NO 40
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 40
ctgaccgcgg actcggtgga gtggtgcccc tgctggcgtg cgggacctac cagctgcggc 60
ggccgg 66

<210> SEQ ID NO 41
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 41
ctgaccgcgg actcggtgga gtggtgcccg ctgcaaggct tgcaggcacc tgctggcgtg 60
cgggacctac cagctgcggc ggccgg 86

<210> SEQ ID NO 42
<211> LENGTH: 86
<212> TYPE: DNA
<213> ORGANISM: Artificial Sequence
<220> FEATURE:
<223> OTHER INFORMATION: Synthetic Polynucleotide

<400> SEQUENCE: 42
ctgaccgcgg actcggtgga gtggtgcccg ctgcaaggca tgcaggcacc tgctggcgtg 60
cgggacctac cagctgcggc ggccgg 86

<210> SEQ ID NO 43
<211> LENGTH: 67
<212> TYPE: DNA
<213> ORGANISM: Artificial Sequence
<220> FEATURE:
<223> OTHER INFORMATION: Synthetic Polynucleotide

<400> SEQUENCE: 43
gggctctgcg ctcgtccggc cgacctgctg gcgtgcggga cctaccagct gcgggcctgc 60
cggcccc 67

<210> SEQ ID NO 44
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 44
ctgaccgcgg gcaccactcc acctgctggc gtgcgggacc taccagctgc ggcggccgg 59

<210> SEQ ID NO 45
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 45
ctgaccgcgg actcggtgga gtggtgcacg cacgtgctgg cgtgcgggac ctaccagctg 60
cggcggccgg 70

<210> SEQ ID NO 46
<211> LENGTH: 82
<212> TYPE: DNA
<213> ORGANISM: Homo sapiens

<400> SEQUENCE: 46
ctgcaggcac ctgctggcgt gcgggaccta ccagctgcgg cggccggagg accggcctgc 60
cggcccccag aacaaggtgc gc 82

<210> SEQ ID NO 47
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 47
ctgcaggcac ctgctggcgt gcgggaccta ccagctgcgg cggccggaga ccggcctgcc 60
ggcccccaga acaaggtgcg c 81

<210> SEQ ID NO 48
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 48
ctgcaggcac ctgctggcgt gcgggaccta ccagctgcgg cggcgaccgg cctgccggcc 60
cccagaacaa ggtgcgc 77

<210> SEQ ID NO 49
<211> LENGTH: 75
<212> TYPE: DNA
<213> ORGANISM: Artificial Sequence
<220> FEATURE:
<223> OTHER INFORMATION: Synthetic Polynucleotide

<400> SEQUENCE: 49
ctgcaggcac ctgctggcgt gcgggaccta ccagctgcgg cggccggagc tgccggcccc 60
cagaacaagg tgcgc 75

<210> SEQ ID NO 50
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 50
ctgcaggcac ctgctggcgt gcgggaccta ccagctgcgg cgcctgccgg cccccagaac 60
aaggtgcgc 69

<210> SEQ ID NO 51
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 51
ctgcaggcac ctgctggcgt gcgggaccta ccagctgcgg ctgccggccc ccagaacaag 60
gtgcgc 66

<210> SEQ ID NO 52
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 52
ctgcaggcac ctgctggcgt gcgggaccta ccagctgctg cggcccccag aacaaggtgc 60
gc 62

<210> SEQ ID NO 53
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 53
ctgcaggcac ctgctggcgt gcgggaccta cctgccggtc cccagaacaa ggtgcgc 57

<210> SEQ ID NO 54
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 54
ctgcaggccc ccagaacaag gtgcgc 26

<210> SEQ ID NO 55
<211> LENGTH: 85
<212> TYPE: DNA
<213> ORGANISM: Homo sapiens

<400> SEQUENCE: 55
tgggccctct cctcaggtgt cacatcccgg tggctggaca tgccctcttg ggcttggcag 60
atgccagtgg atccatacaa ctgct 85

<210> SEQ ID NO 56
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 56
tgggccctct cctcaggtgt cacatcccgg tggctggaca tgccctctgg gcttggcaga 60
tgccagtgga tccatacaac tgct 84

<210> SEQ ID NO 57
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 57
tgggccctct cctcaggtgt cacatcccgg tggctggaca tggcttggca gatgccagtg 60
gatccataca actgct 76

<210> SEQ ID NO 58
<211> LENGTH: 73
<212> TYPE: DNA
<213> ORGANISM: Artificial Sequence
<220> FEATURE:
<223> OTHER INFORMATION: Synthetic Polynucleotide

<400> SEQUENCE: 58
tgggccctct cctcaggtgt cacatcccgg tggctggaca tgccctctat gccagtggat 60
ccatacaact gct 73

<210> SEQ ID NO 59
<211> LENGTH: 63
<212> TYPE: DNA
<213> ORGANISM: Artificial Sequence
<220> FEATURE:

<223> OTHER INFORMATION: Synthetic Polynucleotide

<400> SEQUENCE: 59
tgggccctct cctcaggtgt cacatcccgg tggctggaca tgcagtggat ccatacaact 60
gct 63

<210> SEQ ID NO 60
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 60
tgggccctct cctcaggtgt cacatccatt ggcagatgcc agtggatcca tacaactgct 60

<210> SEQ ID NO 61
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 61
tgggccctct cctcaggtgt cactgcatgt ccacttggca gatgccagtg gatccataca 60
actgct 66

<210> SEQ ID NO 62
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 62
tgggccctct cctcaggtgt cacatcccgg tggctggaca tgccctcttt gggcttggca 60
gatgccagtg gatccataca actgc 85

<210> SEQ ID NO 63
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 63
tgggccctct cctcaggtgt cacatcccgg tggctggaca tgccctcttg tgggcttggc 60
agatgccagt ggatccatac aactg 85

<210> SEQ ID NO 64
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 64
tgggccctct cctcaggtgt cacatcccgg tggctggaca tgccctctat tgggcttggc 60
agatgccagt ggatccatac aactg 85

<210> SEQ ID NO 65
<211> LENGTH: 61

<212> TYPE: DNA
<213> ORGANISM: Artificial Sequence
<220> FEATURE:
<223> OTHER INFORMATION: Synthetic Polynucleotide

<400> SEQUENCE: 65
cataggagca gtgggccata ccatatggct tggcagatgc cagtggatcc atacaactgc 60
t 61

<210> SEQ ID NO 66
<211> LENGTH: 85
<212> TYPE: DNA
<213> ORGANISM: Homo sapiens

<400> SEQUENCE: 66
agggcagctc cacctcctga tggtgaatga gacgaggccc aggctgcaga aagtggcctc 60
atggcaggca catcaattcg aggcc 85

<210> SEQ ID NO 67
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 67
agggcagctc cacctcctga tggtgaatga gacgaggccc aggctgcaga aagtggcagg 60
cacatcaatt cgaggcc 77

<210> SEQ ID NO 68
<211> LENGTH: 72
<212> TYPE: DNA
<213> ORGANISM: Artificial Sequence
<220> FEATURE:
<223> OTHER INFORMATION: Synthetic Polynucleotide

<400> SEQUENCE: 68
agggcagctc cacctcctga tggtgaatga gacgaggccc aggctgcaga aagcgcacat 60
caattcgagg cc 72

<210> SEQ ID NO 69
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 69
agggcagctc cacctcctga tggtgaatga gacgaggccc aggctgcatc aattcgaggc 60
c 61

<210> SEQ ID NO 70
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 70
agggcagctc cacctcctga tggtgaatga gacgaggccc aggctcatca attcgaggcc 60

<210> SEQ ID NO 71

<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 71
agggcagcta cacgtcctga tggcaggcac atcaattcga ggcc 44

<210> SEQ ID NO 72
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 72
agggcacatc aattcgaggc c 21

<210> SEQ ID NO 73
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 73
agggcagctc cacctcctga tggtgaatga gacgaggccc aggctgcaga aagtggcctt 60
catggcaggc acatcaattc gaggc 85

<210> SEQ ID NO 74
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 74
agggcagctc cacctcctga tggtgaatga gacgaggccc aggctgcaga aagtggccct 60
catggcaggc acatcaattc gaggc 85

<210> SEQ ID NO 75
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 75
tgtttgggaa ccagaagagg caggcacatc aattcgaggc c 41

<210> SEQ ID NO 76
<211> LENGTH: 81
<212> TYPE: DNA
<213> ORGANISM: Homo sapiens

<400> SEQUENCE: 76
gctgtttcgc cctgcaaacg gtggacaccg agctgaccgc ggactcggtg gagtggtgcc 60
cgctgcaagg ctgcaggcac c 81

<210> SEQ ID NO 77
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 77
gctgtttcgc cctgcaaacg gtggacaccg agcggactcg gtggagtggt gcccgctgca 60
aggctgcagg cacc 74

<210> SEQ ID NO 78
<211> LENGTH: 72
<212> TYPE: DNA
<213> ORGANISM: Artificial Sequence
<220> FEATURE:
<223> OTHER INFORMATION: Synthetic Polynucleotide

<400> SEQUENCE: 78
gctgtttcgc cctgcaaacg gtggacaccg cggactcggt ggagtggtgc ccgctgcaag 60
gctgcaggca cc 72

<210> SEQ ID NO 79
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 79
gctgtttcgc cctgcaaacg gtggacaccg agctgaaccg cggactcggt ggagtggtgc 60
ccgctgcaag gctgcaggca c 81

<210> SEQ ID NO 80
<211> LENGTH: 156
<212> TYPE: DNA
<213> ORGANISM: Artificial Sequence
<220> FEATURE:
<223> OTHER INFORMATION: Synthetic Polynucleotide

<400> SEQUENCE: 80
gctgtttcgc cctgcaaacg gtggacaccg agctgaaact agccctgaaa atggatggcg 60
ctggagcgtc gggcccatac ccggccgtcg ccggcagtcg agagtggacg gccgcggact 120
cggtggagtg gtgcccgctg caaggctgca ggcacc 156

<210> SEQ ID NO 81
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 81
gctgtttcgc cctgcaaacg gtggacacgg actcggtgga gtggtgcccg ctgcaaggct 60
gcaggcacc 69

<210> SEQ ID NO 82
<211> LENGTH: 72
<212> TYPE: DNA
<213> ORGANISM: Artificial Sequence
<220> FEATURE:
<223> OTHER INFORMATION: Synthetic Polynucleotide

<400> SEQUENCE: 82
gctgtttcgc cctgcaaacg gtggacaccg cggactcggt ggagtggtgc ccgctgcaag 60
gctgcaggca cc 72

<210> SEQ ID NO 83
<211> LENGTH: 78
<212> TYPE: DNA
<213> ORGANISM: Homo sapiens

<400> SEQUENCE: 83
accgcggact cggtggagtg gtgcccgctg caaggctgca ggcacctgct ggcgtgcggg 60
acctaccagc tgcggcgg 78

<210> SEQ ID NO 84
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 84
accgcggact cggtggagtg gtgcccgctg caaggcccag gcacctgctg gcgtgcggga 60
cctaccagct gcggcgg 77

<210> SEQ ID NO 85
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 85
accgcggact cggtggagtg gtgcccgctg caggcacctg ctggcgtgcg ggacctacca 60
gctgcggcgg 70

<210> SEQ ID NO 86
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 86
accgcggact cggtggagtg gtgcccgctg caaggcacct gctggcgtgc gggacctacc 60
agctgcggcg g 71

<210> SEQ ID NO 87
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 87
accgcggact cggtggagtg gtgcccgctg caaggcgtgc gggacctacc agctgcggcg 60
g 61

<210> SEQ ID NO 88
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 88
accgcggact cggtggagtg gtgcccgctg caaggcacct gctggcgtgc gggacctacc 60
agctgcggcg g 71

<210> SEQ ID NO 89
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 89
accgcggact cggtggagtg gtgcccgctg caggcacctg ctggcgtgcg ggacctacca 60
gctgcggcgg 70

<210> SEQ ID NO 90
<211> LENGTH: 78
<212> TYPE: DNA
<213> ORGANISM: Homo sapiens

<400> SEQUENCE: 90
tcctcaggtg tcacatcccg gtggctggac atgccctctt gggcttggca gatgccagtg 60
gatccataca actgctcc 78

<210> SEQ ID NO 91
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 91
tcctcaggtg tcacatcccg gtggcttggc agatgccagt ggatccatac aactgctcc 59

<210> SEQ ID NO 92
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 92
tcctcaggtg tcacatcccg gtggctggac atgccctctg aagtgacagg atgttcattg 60

<210> SEQ ID NO 93
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 93
tcctcaggtg tcacatcccg gtggctggac atgccctctg ggcttggcag atgccagtgg 60
atccatacaa ctgctcc 77

<210> SEQ ID NO 94
<211> LENGTH: 137
<212> TYPE: DNA
<213> ORGANISM: Artificial Sequence
<220> FEATURE:
<223> OTHER INFORMATION: Synthetic Polynucleotide

<400> SEQUENCE: 94
tcctcaggtg tcacatcccg gtggctggac atgccctctg gcatgcacct gtaattacag 60
ctactgtctg tgcatctaac cattttgtca atccaccttg ggcttggcag atgccagtgg 120
atccatacaa ctgctcc 137

<210> SEQ ID NO 95
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 95
tcctcaggtg tcacatcccg gtggctggac atgcccttgg cagatgccag tggatccata 60
caactgctcc 70

<210> SEQ ID NO 96
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 96
ctaagagctc gggcttggca gatgccagtg gatccataca actgctcc 48

<210> SEQ ID NO 97
<211> LENGTH: 76
<212> TYPE: DNA
<213> ORGANISM: Homo sapiens

<400> SEQUENCE: 97
ccacctcctg atggtgaatg agacgaggcc caggctgcag aaagtggcct catggcaggc 60
acatcaattc gaggcc 76

<210> SEQ ID NO 98
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 98
ccacctcctg atggtgaatg agacgaggcc caggctgcag aaagtggcag gcacatcaat 60
tcgaggcc 68

<210> SEQ ID NO 99
<211> LENGTH: 69
<212> TYPE: DNA
<213> ORGANISM: Artificial Sequence
<220> FEATURE:
<223> OTHER INFORMATION: Synthetic Polynucleotide

<400> SEQUENCE: 99
ccacctcctg atggtgaatg agacgaggcc caggctgcag aaagtggcca ggcacatcaa 60
ttcgaggcc 69

<210> SEQ ID NO 100
<211> LENGTH: 67
<212> TYPE: DNA
<213> ORGANISM: Artificial Sequence
<220> FEATURE:
<223> OTHER INFORMATION: Synthetic Polynucleotide

```
<400> SEQUENCE: 100

ccacctcctg atggtgaatg agacgaggcc caggctgcag aaagtggcag cacatcaatt     60

cgaggcc                                                               67


<210> SEQ ID NO 101
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 101

ccacctcctg atggtgaatg agacgaggcc caggcacatc aattcgaggc c              51


<210> SEQ ID NO 102
<211> LENGTH: 61
<212> TYPE: DNA
<213> ORGANISM: Artificial Sequence
<220> FEATURE:
<223> OTHER INFORMATION: Synthetic Polynucleotide

<400> SEQUENCE: 102

ccacctcctg atggtgaatg agacgaggcc caggctgcag caggcacatc aattcgaggc     60

c                                                                     61


<210> SEQ ID NO 103
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 103

ccacctcctg atggtgaatg agacgaggcc caggctgcag aaagtggcca atcatggcag     60

gcacatcaat tcgagg                                                     76
```

TRANSDUCTION BUFFER

RELATED APPLICATIONS

This application is a national stage filing under 35 U.S.C. § 371 of International Application No. PCT/IB2014/064127 with an international filing date of Aug. 28, 2014, which claims the benefit of United Kingdom Patent Application No. 1315321.8, filed Aug. 28, 2013, the entire contents of each of which are incorporated by reference herein.

TECHNICAL FIELD

This invention relates to transduction buffers and methods for introducing molecules into cells.

BACKGROUND ART

The ability to introduce small- or macromolecules into cells finds important applications in research and medicine. Unfortunately, the cell membrane presents a major obstacle for the introduction of many biologically active molecules.

While the ability to introduce proteins into cells has many applications in research and medicine, a reliable, non-toxic and efficient method to do so is still lacking.

Castellot J J Jr et al., (Proc Natl Acad Sci USA. 1978 January; 75(1):351-5) contemplated a method for introducing small molecules into cells using a medium containing 4.2% (w/v) sodium chloride. They demonstrated trypan blue uptake by immortalised hamster BHK cells upon hypertonic treatment. However, the authors did not demonstrate that the trypan blue was released into the cytoplasm or other cellular compartments following uptake. Furthermore, trypan blue is a small molecule and it was not clear it the procedure would allow uptake of macromolecules as well. From data presented in this application, in particular FIG. 2G and FIG. 3E, we demonstrate that although NaCl-mediated hypertonicity induces uptake of macromolecules from the extracellular space via macropinocytosis, the addition of transduction compounds such as Non-detergent sulfobetaines or other compounds described in this application is required for release of the macropinosomes into the intracellular lumen. In addition, 4.2 grams of sodium chloride per 100 mL media translates to a media osmolality of approximately 1727 mOsm/Kg, which is not normally tolerated by primary cells. As such, the method described by Castellot and colleagues cannot be applied for the transduction of macromolecules into primary cells and/or stem cell lines.

In 1982, Okada and Rechsteiner demonstrated that hypertonic treatment induced by 0.5M Sucrose and 10% PEG1000 followed by a brief hypotonic treatment induced the intracellular uptake of macromolecules and proteins into immortalized cell lines'. Unfortunately, this technique proved limited to immortalized cell lines, and yields poor protein transduction efficiencies in primary cells. We tested the transduction of CRE recombinase protein into murine embryonic stem cells (mESCs) using the Okada method. We used a transgenic mESC line in which a CRE-recombinase inducible reporter was stably integrated in the ColA1 locus[2]. This reporter encompasses a CMV promoter followed by a LoxP-flanked Stop-casette and an eGFP reporter gene (FIG. 1A). eGFP expression is induced upon successful CRE-recombinase mediated excision of the Stop cassette (FIG. 1A). As shown by flow cytometry, transduction of mESCs with 5 μM CRE-recombinase protein yielded 6% GFP-positive mESCs, indicating that the combined hypertonic/hypotonic transduction method described by Okada and colleagues is inefficient in transducing primary (stem) cells (FIG. 1B).

A few years later, independent discoveries from Green[3] and Frankel[4,5] for the first time demonstrated that the HIV TAT protein can transduce itself across the cell membrane. The peptide sequence mediating this self-transduction was subsequently identified and shown to drive cell transduction when chemically fused to heterologous proteins[6]. Finally, Nagahara and colleagues demonstrated that TAT-peptide mediated protein transduction also worked when the TAT peptide was cloned as an in-frame fusion to the 'cargo' protein of interest[7].

A clear advantage of TAT-peptide mediated protein transduction is that the method appears to work with all cell types, including primary cells, and is generally non-toxic. However, the strong positive charge of the TAT peptide severely hampers the production of native recombinant TAT-fusion proteins in *E. coli*, with much of the recombinant protein ending up in inclusion bodies. In addition, subsequent research demonstrated that some earlier reports on self-transducing proteins were in fact the result of experimental artefact introduced during fixation of the cells[8]. In addition, this technology requires the TAT peptide to be fused to the recombinant protein and therefore limits the type and number of proteins that can be transduced. The TAT peptide itself can disrupt the function or localization of the recombinant protein leading to unexpected or unwanted results. Finally, and perhaps most importantly, the transduction efficiency of TAT-fusion proteins is quite variable and dependent on the nature and physical properties of the protein cargo.

Significant effort has capitalized on the introduction of nucleotides (DNA, RNA, siRNA) and/or therapeutic molecules into cells, and while primary cells still pose a challenge, progress has been made using cationic lipids, nanoparticles or viral vectors as transmembrane carriers.

For example, U.S. Pat. No. 6,124,207 describes the use of a cationic amphipathic transfection agent with fusogenic properties to create liposomes (detergent micelles). These liposomes are subsequently mixed with DNA to form liposome-DNA complexes prior to transfection into cells. When performed in vivo, "physiological" saline (aqueous NaCl solution at 9 g/1), also known as "normal" saline and a close approximation to osmolality of NaCl in blood, is added to the transfection formulation. This application explains that transfection efficiency of "naked" DNA is low.

Such "carrier" methods, have also been used for targeted gene modification, wherein DNA or mRNA encoding the genetic modification proteins, e.g. TALENs, CRISPR/CAS and other gene editing systems, is transfected into cells. Usually such gene modification is performed by viral transduction. These methods result in significant risk of adverse reactions, including acute immune rejection due to the high dose of injected virus and tumor formation resulting from viral integration position effects. Furthermore, the nucleic acid is expressed within the cell for several days resulting in high expression of enzymes and greater likelihood of off-target effects, e.g. genetic modification of non-target sequences within the cell. Viral transduction also remains inefficient for certain cell types. These difficulties hamper clinical application of the gene editing systems mentioned above.

The development of new technologies for the intracellular delivery of proteins has, by contrast, been at a virtual standstill. Nonetheless, the ability to introduce proteins into cells would have many applications in vaccine development, genome editing, epigenetic reprogramming, (stem) cell differentiation and the manipulation of intracellular processes. The development of better technologies for the efficient intracellular delivery of proteins and other macromolecules, particularly in primary cells, is therefore much needed.

Thus there is a need for more efficient methods for transducing proteins, and other molecules, into cells. Transduction of molecules into cells is desirable for a number of therapeutic and scientific purposes, including gene therapy.

Here we describe that a combination of salt-induced hypertonicity, a small molecule compound and osmoprotectants drives the robust and efficient introduction of small- and macromolecules into primary cells, without affecting cell viability. We provide examples of how protein, nucleotides, nanospheres and macromolecules can be introduced in a wide variety of primary cells, stem cell lines and their derivatives. In addition, we describe the simultaneous transduction of protein and nucleotides into cells.

SUMMARY OF THE INVENTION

The invention provides a method for transducing a molecule of interest into a cell, wherein the method comprises contacting said cell with the molecule of interest and a transduction buffer, wherein the transduction buffer comprises a salt, a transduction compound and preferably an osmoprotectant.

The "method for transducing a molecule of interest into a cell" is also referred to herein as the "transduction method" or "method for transduction". These terms are used interchangeably to refer to the same methods.

The invention also provides a transduction buffer comprising a salt and a transduction compound. The invention also provides a transduction buffer comprising a salt, a transduction compound and optionally an osmoprotectant and/or a cell culture medium.

The invention also provides the use of the transduction buffer of the invention, for transducing a molecule of interest into a cell.

The invention also provides the use of a transduction buffer of the invention for genetic modification, for example genetic modification of specific target sequences (also referred to herein as "gene editing"). Examples of gene editing systems that can be introduced into cells using transduction compounds, buffers and methods of the invention generally involve a protein with nuclease activity, for example endonuclease or exonuclease activity. The nuclease activity may be present in the wild type version of the protein or it may be added, e.g. by recombinant methods, to generate a fusion protein. Examples of gene editing systems that can be introduced into cells using transduction compounds, buffers and methods of the invention include proteins that "inherently" target a particular sequence, such as zinc finger nucleases (ZFNs) and TALENS, and also proteins that are "guided" to target sequences using nucleic acids (e.g. small guide RNAs [sgRNAs] or guide DNA [gDNA]), for example as part of the CRISPR-Cas9 system, the Cascade system, TtAgo and other Argonaute systems, and other FOKI-nuclease associated proteins.

By "inherently" it is meant that the protein does not require an additional guide molecule to reach its target sequence.

The invention also provides a transduction buffer according to the invention, for use in therapy.

The invention also provides a pharmaceutical composition comprising the transduction buffer of the invention.

The invention also provides the use of an osmoprotectant for transducing a molecule of interest into a cell. For example, the invention provides the use of glycine and/or glycerol as an osmoprotectant for transducing a molecule of interest into a cell.

The invention also provides the use of a transduction compound as described herein, such as a non-detergent betaine or any compound described in FIGS. 7A-7D, for transducing a molecule of interest into a cell.

The invention also provides the use of a transduction compound selected from FIGS. 7A-7D for transducing a molecule of interest into a cell.

The invention also provides the following compounds: #10, #11, #16, #42, #34, #41, #40, #39, #33, #15, #11, #29, #36 and #46 (as numbered in FIGS. 7A-7D).

The invention also provides a method for modifying a nucleic acid, such as a genetic sequence, in a cell, wherein the method comprises contacting said cell with a protein capable of modifying a nucleic acid and a transduction buffer, wherein the transduction buffer comprises (i) a transduction compound, (ii) a salt or an activator/enhancer of a sodium-hydrogen transporter, and preferably (iii) an osmoprotectant.

DETAILED DESCRIPTION OF THE INVENTION

Transduction is the internalisation of molecules into a cell, from the external environment. A small number of proteins and peptides have the inherent property of being able to penetrate the cell membrane. Other proteins can have this transducing property conferred upon them by altering the environmental conditions of the cell or by modifying the protein of interest for transduction.

The invention provides improved methods and buffers for transduction of molecules into cells. In particular the invention provides a novel buffer composition that allows efficient transduction of molecules into cells, without the need to modify the molecule and with minimal loss of cell viability.

Specifically, the inventors have found that a transduction buffer comprising a salt, a transduction compound and, preferably, an osmoprotectant, allows surprisingly efficient uptake of proteins, and other molecules, into cells. The inventors were trying to improve the efficiency of the transport of OCT4 tagged with a cell penetrating peptide (CPP) into stem cells, with the aim of generating iPS cells. They unexpectedly discovered that they could achieve surprisingly good efficiency with a transduction buffer containing a salt in combination with a protein stabilizer, so much so that the CPP tag could be removed and efficient transduction still occurred. The inventors have found that the level of transduction can also be improved by the addition of an osmoprotectant, which increases the efficiency of transduction and also increases the viability and continued proliferation of the transduced cells. They have shown that the method works for other molecules, such as small molecules, nucleic acids and proteins with a range of sizes, charges and functions. They have also demonstrated that the method works for transduction into all the tested cell types, including a variety of primary cells, stem cell lines and their derivatives. Furthermore, they contemplate that the transduction buffer can be used in vivo, in particular when a viscosity enhancer is added to the transduction buffer. Thus the buffer has many uses for transducing a range of molecules into a range of cells, both in vitro and in vivo.

Without wishing to be bound by theory, the inventors hypothesise that a transduction buffer comprising the combination of a salt and a transduction compound (as defined below) activates the macropinocytosis pathway. This hypothesis is supported by a number of experiments by the inventors, involving inhibition of alternative transport pathways (see the Examples). For instance, it is supported by Example 14, which describes the use of a Galectin3-GFP reporter system and demonstrates macropinosome vesicle leakage during protein transduction. Example 14 therefore indicates that the transduction buffer described herein promotes uptake of proteins, and other molecules, by macropinocytosis and induction of macropinosome vesicle leakage to release the transduced molecule of interest into the cytosol. Macropinocytosis is a type of fluid-phase endocytosis characterized by its independence of clathrin and formation of relatively large-sized vesicles, with diameters ranging from 0.2 to 1 μm Despite being generally poorly characterized with few specific markers, macropinocytosis has been shown to be important for immune surveillance in dendritic cells. In other types of cells, macropinocytosis occurs at a low spontaneous rate but is rapidly induced in response to growth factors. The function of macropinocytosis in the cells outside of the immune system remains elusive. The inventors hypothesise that their transduction buffer activates the macropinocytosis pathway and enhances uptake of molecules by this pathway into the cell. It also enhances release of molecules from endosomes into the cell cytosol. The salt is hypothesized to perform two roles: firstly it generates hyperosmolality and secondly it binds and activates key membrane transport proteins involved in macropinocytosis. The transduction compound is thought to enhance uptake of the protein or other molecule of interest into vesicles. It is also thought to maintain the native structure and stability of the molecule of interest and perhaps aid in the intracellular release from the macropinocytotic vesicles. The combination of the salt with the transduction compound appears to be important for efficient transduction. To the best of our knowledge, this combination has not previously been used to stimulate transduction of proteins or other molecules into cells.

Methods for Transduction

The invention provides a method for transducing a molecule of interest into a cell, wherein the method comprises the steps of contacting said cell with the molecule of interest and contacting said cell with a transduction buffer comprising a salt and a transduction compound.

The molecule of interest and the transduction buffer are contacted with the cell in combination, either simultaneously, sequentially, or separately in any order. In a preferred embodiment, they are administered simultaneously (e.g. from a container containing the combination). Thus, in some embodiments, the transduction buffer comprises the molecule of interest. In some embodiments, the method involves the step of mixing the transduction buffer and the molecule of interest.

In some embodiments, the method comprises the step of obtaining and/or maintaining the cells in culture medium prior to transduction. In some embodiments, the cell is plated in a culture medium, suitable for the particular cell, prior to transduction. In some embodiments, the method further comprises contacting the cell with a culture medium during transduction. In some embodiments, the method includes the step of mixing the transduction buffer with a culture medium.

In some embodiments, the method comprises the steps of obtaining the cells and maintaining the cells in culture medium prior to transduction and contacting the cell with culture medium during transduction. In some embodiments, the method includes the step of mixing the transduction buffer with a culture medium prior to contacting the cell with the transduction buffer. In some embodiments, after transduction, the transduction buffer is aspirated and/or the cells are washed, e.g. once or twice. Typically, a regular culture medium, suitable for the particular cell type, will be added to the cells at this stage. In some embodiments, the method comprises the step of obtaining the cells and/or maintaining the cells in culture medium after transduction.

In some embodiments, the osmolality of the final transduction buffer is adjusted to the desired osmolality by addition of salt. In a preferred embodiment, the final transduction buffer, comprising the molecule of interest and/or the culture medium, is hypertonic with respect to the cell cytosol.

The method for transduction may be performed in vivo or in vitro.

In some embodiments, the transduction method does not involve a transmembrane carrier, for example selected from a viral plasmid, a nanoparticle, a liposome or other lipid vesicle (including micelles). In some embodiments, the transduction method is non-viral, meaning that it does not rely on a viral transfection system and/or does not involve a viral plasmid, for example as a transmembrane carrier. In some embodiments the transduction method does not involve cationic lipids, for example as transmembrane carriers. In some embodiments, the transduction method does not involve liposomes, for example as transmembrane carriers. In some embodiments, the transduction method does not involve nanoparticles, for example as transmembrane carriers. In some embodiments, the transduction method does not involve outer membrane vesicles (OMVs), for example as transmembrane carriers. In some embodiments the methods does not involve cell penetrating peptides.

In some embodiments, the method involves activating or enhancing macropinocytosis and/or enhancing endosomal lysis, thus enhancing uptake of molecules, particularly the molecule of interest, into the cell. In the context of this application, it is to be understood that "endosomes", which are internal invaginations of the cell membrane involved in macropinocytosis, and comprising a complex mixture of lipids, differ from "liposomes" or "micelles", which are synthetic lipid vesicles typically formed from a fewer types of lipid molecule, and from "OMVs", which are bacterial vesicles which may be modified to make them suitable as transmembrane carriers.

In one embodiment (the "first protocol" or "Protocol 12/500"), transduction is performed for about 12 hours at an osmolality of about 500 mOsm/Kg. For example, the day before (about 12 to 24 hours before) transduction, cells are plated in the appropriate culture media without antibiotics. The following day (the day of transduction), 1× "transduction buffer 500" (transduction buffer with an osmolality of 500 mOsm/Kg) is prepared with the molecule of interest. 5× transduction buffer and the molecule of interest are mixed with cell culture media to obtain 1× transduction buffer at an osmolality of 500 mOsm/Kg. This mixture of media/transduction buffer/molecule of interest is added to the cell. The cell is incubated with the molecule of interest in the transduction buffer for about 12 hrs, after which time, the transduction media is removed and exchanged for regular culture media.

In another embodiment (the "second protocol" or "Protocol 3/700"), transduction is performed for about 3 hours at an osmolality of about 700 mOsm/Kg. For example, the day before (about 12 to 24 hours before) transduction, cells are plated in the appropriate culture media without antibiotics.

The following day, 1×"transduction buffer 500" is prepared with the molecule of interest. NaCl or RbCl or another salt (see below) is added to adjust the final osmolality to 700 mOsm/Kg. For example, 411 of 5M NaCl is added to 94 μl of 1× "transduction buffer 500" to obtain a final osmolality of 700 mOsm/Kg. The cell is incubated with the molecule of interest in the transduction buffer for about 3 hrs, after which time, the transduction media is removed and exchanged for regular culture media.

In another embodiment (the "third protocol" or "Protocol 2/1000), transduction is performed for about 2 hours at an osmolality of about 1000 mOsm/Kg. For example, the day before (about 12 to 24 hours before) transduction, cells are plated in the appropriate culture media without antibiotics. The following day, 4 volumes of 1× "transduction buffer 1000" are mixed with 1 volume 5× "transduction buffer 500" containing the molecule of interest. The cell is incubated with the molecule of interest in the transduction buffer for about 2 hours, after which time the transduction media is removed and exchanged for regular culture media.

In another embodiment (the "fourth protocol" or "Cas9-adapted transduction protocol"), transduction is performed for about 60 to 90 minutes at an osmolality of about 1250 mOsm/Kg. The transduction compound is preferably used at a concentration of about 250 mM. This protocol is particularly useful for transducing molecules with low solubility, including, for example, the Cas9 nuclease protein which is part of the CAS/CRISPR gene editing system. For example, the day before (about 12 to 24 hours before) transduction, cells are plated in the appropriate culture media, preferably without antibiotics. The following day, the molecule of interest is added to the transduction buffer. The cells are incubated with the molecule of interest in the transduction buffer for about 60 to 90 minutes, after which time the transduction media is removed and exchanged for regular culture media.

In another embodiment, transduction is performed at combined osmolarities. For example, for about 2 hours at an osmolarity of about 1000 mOsm/Kg followed by about 10 hours at an osmolarity of about 500 mOsm/Kg. For example, the day before (about 12 to 24 hours before) transduction, cells are plated in the appropriate culture media without antibiotics. The following day, 4 volumes of 1× "transduction buffer 1000" are mixed with 1 volume 5× "transduction buffer 500" containing the molecule of interest. The cell is incubated with the molecule of interest in the transduction buffer for about 2 hours, after which time the transduction media is removed and exchanged for 1× "transduction buffer 500" (transduction buffer with an osmolality of 500 mOsm/Kg), with or without the molecule of interest. The cell is incubated with the molecule of interest in the 1× "transduction buffer 500" for about 10-12 hrs, after which time, the transduction media is removed and exchanged for regular culture media.

For the avoidance of any doubt, it is to be understood that these methods and protocols are compatible and combinable with the transduction compounds, salts, osmoprotectants, and other additional components of the transduction buffer described in detail below. These protocols and methods can be used to transduce various molecules of interest, including combinations of molecules of interest into cells, as described in detail below.

Transduction Compound for Transduction

Inclusion of a transduction compound in the transduction buffer is required for efficient transduction. Thus the invention provides buffers comprising at least one transduction compound as described herein.

The inventors have found that various compounds, when used in the context of the transduction buffer of the invention, allow efficient transduction of a molecule of interest into a cell. Thus a "transduction compound" as used herein, refers to any compound that enhances transduction of a molecule of interest into a cell, when used in the context of a transduction buffer of the invention. The beta-lactamase assay, as described in the examples, can be used to determine whether or not a compound is a transduction compound. If a further assay is required to test the efficacy of a transduction compound, particularly to demonstrate the involvement of the macropinocytosis mechanism, the Gal3-GFP assay described in Example 14 can be used.

There is accordingly provided, in one aspect, a method for identifying a transduction compound, wherein the method comprises

- contacting a cell which has been modified to express a galectin-3-GFP (GAL3-GFP) fusion protein with a candidate transduction compound, using a transduction buffer or protocol described herein (e.g. the first protocol, second protocol, third protocol or fourth protocol described above); and
- observing localisation of GAL3-GFP by green fluorescent emission;
- wherein localisation of GAL3-GFP to intracellular vesicles is indicative of an effective transduction compound.

In some embodiments, the method for identifying a transduction compound further comprises isolating the effective transduction compound and, optionally, incorporating the transduction compound into a transduction buffer described herein or using the transduction compound in a transduction method described herein. In some embodiments, the candidate transduction compound replaces the known transduction compound in the transduction buffer or protocol described herein. In other embodiments, the candidate transduction compound is additional to a known transduction compound in the transduction buffer or protocol described herein. In a preferred embodiment, the green fluorescent emission is compared to a control cell which has been treated in the same way except that it does not contain the candidate transduction compound. In some embodiments, the transduction compound is any transduction compound identifiable by this method.

The first transduction compound that the inventors discovered was a non-detergent sulfobetaine (NDSB; e.g. NDSB-201). The inventors tested derivatives of this compound (such as non-detergent carbobetaines [NDCBs] and found a number of other related compounds that are also transduction compounds. Although there are a variety of compound structures that work, there are a number of common features that can be drawn from the various different compounds, as described in more detail below.

The inventors have found that transduction compounds generally comprise at least one hydrophilic functional group. In some embodiments the transduction compound has only one hydrophilic functional group; examples of such compounds include pentanoic acid (example compound #23 in FIGS. 7A-7D) and n-butylamine (example compound #24 in FIGS. 7A-7D). In some embodiments, the transduction compound has more than one hydrophilic functional group, e.g. 2, 3, 4, 5 or more.

While the transduction compound allows substantial freedom at its termini, it appears that a hydrophilic group is preferred at either end of the carbon chain Therefore, in preferred embodiments, the transduction compound is a compound having at least two hydrophilic groups, each separated by a short hydrophobic group, such as C1-5 alkylene. An alkylene with 6 or more carbons in the chain is likely to be toxic to the cells. The hydrophilic groups may be the same or different.

In some embodiments, the transduction compound is a betaine. As used herein, the term "betaine" refers to any neutral chemical compound with a cationic functional group, which bears no hydrogen atom, and with an anionic functional group. Non-limiting examples of cationic functional groups include quaternary ammonium cations. Non-limiting examples of anionic functional groups include carboxylate, sulfonate and phosphate anions.

In some embodiments, the transduction compound is not a detergent. In some embodiments, the transduction compound is a non-detergent betaine. The term "non-detergent betaine" (NDB) refers to a betaine which does not form micelles in solution. Thus transduction compounds that are not detergents do not form liposomes or micelles in solution.

For example, in some embodiments, the transduction compound is a non-detergent sulfobetaine (NDSB). NDSBs are betaines having a sulfonate group separated from a quaternary nitrogen group, by a short hydrophobic group, such as C1-5 alkylene.

In some embodiments, the transduction compound is a small molecule compound. In some embodiments, the transduction compound has fewer than 50 carbon atoms, fewer than 30 carbon atoms, fewer than 25 carbon atoms or fewer than 20 carbon atoms. In some embodiments, the transduction compound has a mass of less than 1000 g/mol, less than 500 g/mol, less than 400 g/mol, less than 360 g/mol, less than 300 g/mol, less than 200 g/mol.

Without wishing to be bound by theory, the inventors hypothesise that these compounds can fold towards each other creating a hydrophobic and a hydrophilic side of the molecule allowing the compound to function particularly well as a transduction compound, for example as shown below.

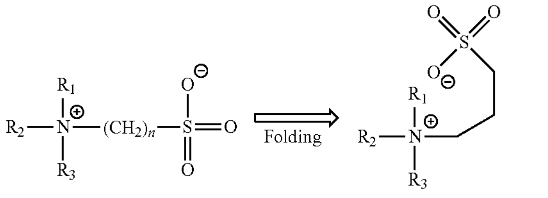

In some embodiments, the quaternary nitrogen atom is part of an aliphatic or aromatic ring structure. In some embodiments, the transduction compound is an NDSB selected from dimethylethyl-(3-sulphopropyl)-ammonium salt (NDSB-195, Vuillard et al (1994) FEBS Letters, 353, 294-296; Goldberg et al (1995/1996) Folding & Design, 1, 21-27), 3-(1-pyridino)-1-propanesulfonate (NDSB-201), dimethylbenzylammonium propanesulfonate (NDSB-256), dimethyl-t-butyl-(3-sulphopropyl) ammonium salt (NDSB-222t), 3-(1-methylpiperidine)-1-propanesulfonate (NDSB221), dimethyl-(2-hydroxyethyl)-(sulphopropyl)-ammonium salt (NDSB-211; Vuillard et al (1995) Anal Biochem, 230, 290-294). In a preferred embodiment, the transduction compound is NDSB-201.

It has also been found that non-detergent carboxybetaines (NDCBs) function as transduction compounds. Thus in some embodiments, the transduction compound is an NDCB. NDCBs are betaines having a carboxylate group separated from a quaternary nitrogen group, by a short hydrophobic group, such as C1-5 alkylene. NDCBs may be able to fold up in solution as described above for NDSBs, enhancing their transduction promoting capability. The inventors found that substitution of the sulfonate group of an NDSB for a carboxylate group to form an NDCB does not negatively affect the transduction efficiency. As shown in the examples below, many NDCBs work with a greater efficiency and with reduced impact on cell viability and/or cell proliferation than NDSBs.

Non-betaine compounds which are zwitterionic in solution across a broad range of pHs also function as transduction compounds. For example, some amino acids, such as GABA (gamma-aminobutyric acid), which are zwitterionic in solution, also function as transduction compounds. Zwitterionic compounds often comprise at least one acidic and at least one basic functional group, which may become ionised in solution. Acidic groups include carboxylic acid, sulfonic acid and phosphonic acid functional groups. Basic groups include amino groups. Thus, in some embodiments, the transduction compound is a zwitterion, for example, a non-detergent zwitterion, preferably comprising at least one acidic functional group and at least one basic functional group. In certain preferred embodiments the acidic functional group is separated from the at least one basic group, by a short hydrophobic group, such as C1-5 alkylene.

It has also been surprisingly found that non-zwitterionic compounds operate as transduction compounds. Instead of having a negatively charged functional group (such as carboxylate or sulfonate as described above), compounds comprising bioisosteric groups such as an amide or tetrazole also function as transduction compounds. Thus, in some embodiments the transduction compound comprises an amide or tetrazole functional group. In certain preferred embodiments the transducing promoting agent (the transduction compound) comprises an amide or tetrazole functional group separated from another hydrophilic group, preferably amino or ammonium, by a short hydrophobic group, such as C1-5 alkylene.

Thus in some embodiments, the transduction compound is a zwitterion or a non-zwitterionic compound with a group that is bioisosteric to a negatively charged functional group. It is thought that owing to the bioisosteric group, in combination with a positively charged functional group, these non-zwitterionic compounds have some "zwitterionic properties", e.g. to allow the folding mechanism described above. Groups that can be bioisosteric to a negatively charged functional group include, but are not limited to, amide and tetrazole functional groups (for example, see compounds #43, #15, #29, #34, #30, #31 and #45). FIGS. 6A-6G shows the results of studies looking at the structural-functional relationships of transduction compounds.

In accordance with the above, the transduction compound may be a compound of formula I

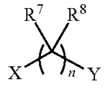

I wherein:

X is selected from $NR^1R^2$, $NR^1R^2R^3+$, OH and $COOR^4$;

Y is selected from $SO_3H$, $SO_3$, $COO^-$, $CONH_2$, $COOR^{12}$, $CONR^5R^6$, tetrazole, OH, $NR^{10}R^{11}$, and H;

n is 1, 2, 3, 4, 5 or 6;

$R^1$, $R^2$ and $R^3$, are each independently selected from H, C1-6 alkyl, C5-10 aryl, C6-15 aralkyl, $COR^9$; C1-6 alkyl, C5-10 aryl and C6-15 aralkyl may optionally be substituted with $R^Y$, OH or COOH;

or $R^1$ and $R^2$ may come together with the nitrogen to which they are attached to form heterocyclyl;

or when X is $NR^1R^2R^3$+, $R^3$ may be absent and $R^1$ and $R^2$ may come together with the nitrogen to which they are attached to form heteroaryl;

$R^4$, $R^5$, $R^6$, $R^9$, $R^{10}$, $R^{11}$, $R^{12}$ are independently selected from H and C1-6 alkyl;

$R^7$ and $R^8$ are independently selected from H, C1-6 alkyl and OH; or $R^7$ may come together with $R^1$ to form heterocyclyl;

heterocyclyl is a monocyclic ring which is saturated or partially unsaturated, containing where possible 1 or 2 ring members independently selected from N, $NR^{13}$, $NR^{13}R^{14}$+ and O, and 2 to 5 carbon atoms; heterocyclyl may optionally be substituted with C1-C6 alkyl, C1-C6 carboxylic acid or C1-C6 alkyl substituted with $R^Y$;

heteroaryl is a 5 or 6 membered aromatic ring containing, where possible, 1, 2 or 3 ring members independently selected from N, $NR^{13}$, $NR^{13}R^{14}$+ and O; heteroaryl may optionally be substituted with C1-C6 alkyl, C1-C6 carboxylic acid or C1-C6 alkyl substituted with $R^Y$;

$R^{13}$ and $R^{14}$ are independently selected from H, C1-6 alkyl, C1-C6 carboxylic acid and C1-C6 alkyl substituted with $R^Y$;

alkyl is a linear or branched saturated hydrocarbon;

$R^Y$ is selected from $SO_3H$, $SO_3^-$, $COO^-$, $CONH_2$, $COOR^{12}$, $CONR^5R^6$, tetrazole, OH and $NR^{10}R^{11}$;

C1-6 carboxylic acid means —COOH or a C1-5 alkyl chain substituted with COOH and tautomers, solvates, zwitterions and salts thereof.

Transduction compounds may in some embodiments comprise a quaternary or basic nitrogen group. Thus in some embodiments the transduction compound is a compound of formula I wherein X is $NR^1R^2R^3$+ or $NR^1R^2$.

In some embodiments $R^1$, $R^2$ and $R^3$, are each independently selected from H and C1-6 alkyl which may optionally be substituted with $R^Y$, OH or COOH; or $R^1$ and $R^2$ may come together with the nitrogen to which they are attached to form heterocyclyl, preferably piperidine, piperazine or morpholine, which may be optionally substituted; or $R^3$ may be absent and $R^1$ and $R^2$ may come together with the nitrogen to which they are attached to form heteroaryl, preferably pyridyl, which may be optionally substituted.

In some embodiments the transduction compound is a compound of formula I wherein Y is selected from $SO_3H$, $SO_3^-$, $COO^-$, $COOR^{12}$, $CONR^5R^6$ and tetrazole, preferably selected from $SO_3H$, $SO_3^-$, $COO^-$, $COOR^{12}$ and $CONR^5R^6$, and more preferably selected from $COO^-$, COOH and $CONR^5R^6$.

In some embodiments $R^Y$ is selected from $SO_3H$, $SO_3^-$, $COO^-$, $COOR^{12}$, $CONR^5R^6$ and tetrazole, preferably $R^Y$ is selected from $SO_3H$, $SO_3^-$, $COO^-$, $COOR^{12}$ and $CONR^5R^6$, and more preferably $R^Y$ is selected from $COO^-$, COOH and $CONR^5R^6$.

It has been found that when the carbon chain separating X and Y is three carbon atoms long transduction is promoted more efficiently. Thus in some embodiments, the transduction compound is a compound of formula I wherein n is 3. In other embodiments, n is 1, 2, 3, 4, 5 or more. In some embodiments, n is 5 or less, 4 or less, 3 or less or 2 or less.

In some preferred embodiments, the transduction compound is a compound belonging to a subset of formula I, according to formula II

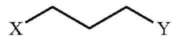

(II)

wherein

X is selected from $NR^1R^2$ and $NR^1R^2R^3$+;

Y is selected from $SO_3H$, $SO_3^-$, $COO^-$, $CONH_2$, $COOR^{12}$ and $CONR^5R^6$;

$R^1$, $R^2$ and $R^3$, are each independently selected from H and C1-6 alkyl which may optionally be substituted with OH or COOH; or $R^1$ and $R^2$ may come together with the nitrogen to which they are attached to form heterocyclyl, preferably piperidine, piperazine or morpholine, which may be optionally substituted; or when X is $NR^1R^2R^3$+, $R^3$ may be absent and $R^1$ and $R^2$ may come together with the nitrogen to which they are attached to form heteroaryl, preferably pyridyl, which may be optionally substituted;

and all other groups are as defined in formula I above.

In some embodiments, the transduction compound contains a quaternary nitrogen group. Thus, in some embodiments the transduction compound is a compound of formula I or II wherein X is $NR^1R^2R^3$+. In some embodiments the transduction compound is a compound of formula I or II wherein X is $NH_3$+.

In some embodiments, the quaternary nitrogen may be part of an aliphatic or aromatic ring structure. Thus, in some embodiments the transduction compound is a compound of formula I or II wherein X is

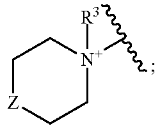

(a)

Z is selected from $C(R^{15})_2$, $NR^{13}$, $NR^{13}R^{14}$+ and O;

each $R^{15}$ is independently selected from H, C1-6 alkyl, C1-C6 carboxylic acid and C1-C6 alkyl substituted with $R^Y$;

$R^3$ is selected from H, C1-6 alkyl, C5-10 aryl, C6-15 aralkyl, $COR^9$; C1-6 alkyl, C5-10 aryl and C6-15 aralkyl may optionally be substituted with $R^Y$, OH or COOH. Preferably $R_3$ is —$CH_3$;

$R^{13}$ and $R^{14}$ are independently selected from H, C1-6 alkyl, C1-C6 carboxylic acid and C1-C6 alkyl substituted with $R^Y$.

In some embodiments the transduction compound is a compound of formula I or II wherein X is (a), Z is $NR^{13}$ or $NR^{13}R^{14}$+ and $R^{13}$ is —$CH_2CH_2CH_2R^Y$. Alternatively, in other embodiments the transduction compound is a compound of formula I or II wherein X is (a), Z is $CH_2$ and $R^3$ is —$CH_3$.

In other embodiments the transduction compound is a compound of formula I or II wherein X is

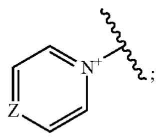

(b)

Z is selected from $CR^{15}$ and $NR^{13}$+;

$R^{15}$ is selected from H, C1-6 alkyl and C1-C6 carboxylic acid and C1-C6 alkyl substituted with $R^Y$;

$R^{13}$ is selected from H, C1-6 alkyl, C1-C6 carboxylic acid and C1-C6 alkyl substituted with $R^Y$.

In some embodiments the transduction compound is a compound of formula I or II wherein X is (b), Z is $NR^{13}$ and $R^{13}$ is $—CH_2CH_2CH_2R^Y$. Alternatively, in other embodiments the transduction compound is a compound of formula I or II wherein X is (b) and Z is CH.

In some embodiments the transduction compound is a compound selected from the compounds in FIGS. 7A-7D "Compound #" as used herein, refers to the compounds in FIGS. 7A-7D using the compounds numbers (#) in the left-hand column.

In some embodiments the transduction compound is selected from compound #10, #11, #16, #42, #34, #41, #40, #39, #33, #15, #11, #29, #46 and #36.

In some embodiments the transduction compound is not compound #32. In some embodiments, the transduction compound is not any of the compounds selected from compounds #27, #07, #18, #09 and #32. These compounds all display less than 30% transduction compared to control compound #1. Where statements refer to "the compounds in FIGS. 7A-7D" it is understood that in some embodiments, this refers to all compounds in FIGS. 7A-7D except for compound #32, or all compounds in Table except for compounds #27, #07, #18, #09 and #32.

In some embodiments, the transduction buffer comprises one transduction compound. In some embodiments, the transduction buffer comprises two or more (e.g. 2, 3, 4, 5, 6 or more) transduction compounds, for example two or more of the recited transduction compounds, in any possible combination. Examples of combinations of transduction compounds are provided in FIG. 6F. In some embodiments, the transduction buffer comprises compound #1 and compound #18. In some embodiments, the transduction buffer comprises compound #1 and compound #34. In some embodiments, the transduction buffer comprises compound #1 and compound #20.

In some embodiments, the concentration of the transduction compound is between about 0.1 mM and about 500 mM, between about 1 mM and about 400 mM, between about 1 mM and about 300 mM, between about 1 mM and about 200 mM, between about 1 mM and about 100 mM, between about 2 mM and about 200 mM, between about 2 mM and 100 mM, between about 2 mM and about 80 mM, between about 3 mM and about 75 mM, between about 4 mM and about 70 mM, between about 5 mM and about 60 mM, between about 10 mM and about 50 mM, between about 25 mM and 40 mM, or about 30 mM. In some embodiments, the concentration of the transduction compound is about 25 mM, for example the concentration of the transduction compound is, in some embodiments, between about 10 and about 25 mM, or about 25 mM. In some embodiments, the concentration of the transduction compound is at least 1 mM, at least 2 mM, at least 3 mM, at least 4 mM, at least 5 mM, at least 10 mM, at least 20 mM, at least 30 mM, at least 40 mM, at least 50 mM, at least 60 mM, at least 70 mM or at least 80 mM, at least 90 mM, at least 100 mM, at least 150 mM, at least 200 mM, at least 300 mM, at least 400 mM or 500 mM.

In some embodiments, the concentration of the transduction compound is about 100 mM to about 500 mM, about 200 mM to about 400 mM, 200 mM to about 300 mM, or about 250 mM. These higher concentration ranges are particularly useful, for example, when transducing proteins of low solubility, such as Cas9. It is to be understood that the optimum concentration of transduction compound will also depend on the compound and its efficiency, but can be determined readily by the person skilled in the art, for example using the experiments and assays described in the examples.

The invention provides compound #10. The invention also provides compound #11. The invention also provides compound #16. The invention also provides compound #42. The invention also provides compound #34. The invention also provides compound #41. The invention also provides compound #40. The invention also provides compound #39. The invention also provides compound #33. The invention also provides compound #15. The invention also provides compound #11. The invention also provides compound #29. The invention also provides compound #36. The invention also provides compound #46. These compounds appear to be new. The invention also provides a transduction compound, as described anywhere herein, for use in a method for treatment of the human or animal body by therapy. In particular, there is provided compound #10, compound #11 or compound #16 for use in a method for treatment of the human or animal body by therapy.

In some embodiments, the transduction compound is compound #15 (BU-2026-05). This compound is advantageous because it results in high efficiency of transduction, whilst maintaining good cellular viability, even when used at high concentrations (see FIGS. 7A-7D).

In some embodiments, the transduction compound is compound #10. In some embodiments, the transduction compound is compound #11. In some embodiments, the transduction compound is compound #16. In some embodiments, the transduction compound is compound #42. In some embodiments, the transduction compound is compound #34. In some embodiments, the transduction compound is compound #41. In some embodiments, the transduction compound is compound #11. In some embodiments, the transduction compound is compound #40. In some embodiments, the transduction compound is compound #39. In some embodiments, the transduction compound is compound #33. In some embodiments, the transduction compound is compound #29. In some embodiments, the transduction compound is compound #15. In some embodiments, the transduction compound is compound #36. In some embodiments, the transduction compound is compound #46. In some embodiments, the transduction compound is compound #20. Compound #20 has been shown to result in particularly good cell survival rates compared to other transduction compounds (for instance, see FIG. 19B).

In some embodiments, the transduction compound is any compound that has 20% or more, 30% or more, 40% or more, 50% or more, 60% or more, 70% or more, 80% or more, 90% or more, 100% or more, 110% or more, 120% or more, 150% or more, 200% or more, 300% or more, 400% or more, 500% or more, 600% or more, 700% or more, 800% or more, 1000% or more transduction efficiency compared to reference compound #1 in FIGS. 7A-7D (NDSB-201), as determined by the methods described in Example 1.

Similarly, in some embodiments, the transduction method (as a whole) has 20% or more, 30% or more, 40% or more, 50% or more, 60% or more, 70% or more, 80% or more, 90% or more, 100% or more, 110% or more, 120% or more, 150% or more, 200% or more, 300% or more, 400% or more, 500% or more, 600% or more, 700% or more, 800% or more, 1000% or more transduction efficiency, using the method comprising compound #1 as shown in Table as a control (i.e. as 100% transduction efficiency).

Non-limiting examples of transduction compounds with more than 100% transduction efficiency compared to reference compound #1 in FIGS. 7A-7D include reference compounds #30, #17, #15, #38, #35, #11, #10, #28 and #37. These compounds are particularly effective transduction compounds. Thus in some embodiments that transduction compound is selected from compounds #30, #17, #15, #38, #35, #11, #10, #28 and #37.

Other preferred transduction compounds include #42, #1, #45, #43, #44, #15, #10, #11, #28, #37 and #46. Thus in some embodiments the transduction compound is selected from compounds #42, #1, #45, #43, #44, #15, #10, #11, #28, #37 and #46. These are compounds that have or are expected to have transduction efficiency of 50% or more relative to control compound #1 and/or 75% or more viability relative to control compound #1.

In some situations it may be advantageous to use a transduction compound in the buffer that causes a reduction in cell proliferation or viability. For example, in the case of vaccine development, some toxicity may be an advantage. Antigens transduced into cells are displayed to the immune system. If the displaying cells are ill or dying, the immune response can be enhanced. Transduction compounds suitable for such purposes include compounds #40, #41, #25, #35 and #38. Thus in some embodiments, the transduction compound is selected from compounds #40, #41, #25, #35 and #38.

In other embodiments, the transduction compound is selected from the compounds #10, #11, #16, #42, #34, #41, #40, #39, #33, #15, #11, #29, #36 and #46. These are the transduction compounds believed to be new compounds.

The transduction compounds described herein can exist as monomers, dimers or multimers. For example, compound #42 is active as a dimer. Thus in some embodiments, the transduction compound is used in its monomeric, dimeric or multimeric form. In some embodiments, the transduction compound is the dimeric form of compound #42.

The invention also provides the use of a transduction compound as described above for transducing one or more molecule into a cell.

GABA Agonists

As mentioned above, one of the compounds found to be a transduction compound was a gamma-aminobutyric acid (GABA, compound #20) which an important neurotransmitter in the brain. GABA acts by stimulating the activation of GABA-receptors, of which three classes have been identified: GABA-A, GABA-B and GABA-C. GABA receptors are stimulated by a remarkably wide range of chemical structures ranging from simple structures like ethanol and GABA itself, to seemingly unrelated benzodiazepines, muscimol, baclofen. As the chemical structure of effective protein transduction compounds also displays a degree of freedom, the inventors hypothesise that GABA signalling might play an active role in the transduction effect. Indeed, the inventors found that addition of GABA agonists to the transduction buffer comprising a salt and a transduction compound (such as NDSB-201), resulted in increased transduction of β-lactamase into mouse embryonic fibroblast (MEFs). Thus GABA agonists can be included in the transduction buffer to further enhance transduction efficiency.

Methods for identifying GABA agonists are known in the art. For example, GABA agonists suitable for use in the transduction buffer can be identified by an assay which measures activation of GABA receptors by a given compound by measuring changes in membrane potential using patch clamp technology on brain slices (Patch Clamp Techniques, Springer Protocols Handbooks, 2012, pp 71-83). There are also commercial assays available for identifying GABA-B agonists (e.g. "Ready-to-assay" by Millipore). Suitable GABA agonists for use in the transduction buffers described herein can be identified using such assays.

Thus, in some embodiments, the transduction buffer further comprises a GABA agonist. A GABA agonist includes any compound that activates the GABA signalling pathway, for example any compound that binds to and/or activates a GABA receptor (e.g. GABA-A, GABA-B and/or GABA-C receptors), for example, as identified using the patch clamp assay or the Millipore assay referenced above. Examples of GABA agonists include, but are not limited to, SKF-97541, acamprosate, barbiturates, benzodiazepines, ethanol, methaqualone, muscimol, nonbenzodiazepines (zaleplon, zolpidem, zopiclone), picamilon, progabide, tiagabine, baclofen, 1,4-Butanediol, GBL (γ-Butyrolactone), GHB (γ-Hydroxybutyric acid), GHV (γ-Hydroxyvaleric acid), GVL (γ-Valerolactone), lesogaberan, phenibut, (Z)-4-Amino-2-butenoic acid, (+)-cis-2-aminomethylcyclopropane carboxylic acid, N4-Chloroacetylcytosine arabinoside, GABOB (γ-Amino-beta-hydroxybutyric acid), and progabide.

In some embodiments, the transduction buffer comprises a salt and a transduction compound and additionally comprises muscimol and/or SKF-97541.

In some embodiments, the GABA agonist is included in the transduction buffer at concentrations in micro- or nanomolar ranges. For example, in some embodiments, the GABA agonist has a concentration of about 0.1 μM and about 100 μM, between about 1 μM and about 90 μM, between about, 2 μM and about 80 μM, between about 3 μM and about 75 μM, between about 4 μM and about 70 μM, between about 5 μM and about 60 μM, between about 10 μM and about 50 μM, between about 25 μM and 40 μM, or about 30 μM. In some embodiments, the GABA agonist has a concentration of about 10 μM, of about 25 μM or of about 50 μM. In other embodiments, the GABA agonist has a concentration of between about 0.1 nM and about 100 nM, between about 1 nM and about 90 nM, between about 2 nM and about 80 nM, between about 3 nM and about 75 nM, between about 4 nM and about 70 nM, between about 5 nM and about 60 nM, between about 10 nM and about 50 nM, between about 25 nM and 40 nM, or about 30 nM. In some embodiments, the GABA agonist has a concentration of about 10 nM, of about 25 nM or of about 50 nM.

Other neurotransmitters may similarly enhance transduction. Therefore, in some embodiments, the transduction buffer comprises a salt, a transduction compound and additionally comprises a neurotransmitter.

Salt for Use in the Transduction Buffer

The salt for use in the transduction buffer of the invention is any salt that works in the context of the method of the invention, i.e. any salt that allows transduction of molecules into cells when combined with a transduction compound.

As shown in FIG. 5A, all Na-related salts tested (according to the periodic table) including LiCl, KCl, CsCl, RbCl had protein transducing activity, with Na and Rb demonstrating the highest activity. In addition, it was tested whether other Na-salts could induce protein uptake. As shown in FIG. 5A, sodium gluconate effectively mediated β-Lactamase transduction with efficiency similar to NaCl and RbCl. Finally, it was tested whether increasing tonicity using unrelated compounds would also trigger protein transduction. As shown in FIG. 5A, sucrose, lactulose, sorbitol and mannitol all failed to induce protein transduction at 700 mOsm/Kg, suggesting that protein transduction is specifically dependent on hypertonicity induced by sodium or sodium-related salts. Assays for identifying hypertonicity-inducing salts suitable for use in the transduction buffer of the invention are provided in the examples (see Example 6).

Thus preferably, the salt can increase tonicity across a cell membrane, i.e. the salt is a "hypertonic" salt. Tonicity is explained in more detail below.

Thus in some embodiments, the salt is a sodium, lithium, potassium, caesium, or a rubidium salt, preferably a sodium or rubidium salt. In some embodiments, the salt is a chloride, gluconate, carbonate, sulphonate, sulphate, sulphide, bromide, iodide or fluoride, preferably the chloride or gluconate. Non-limiting examples include sodium chloride, sodium gluconate, lithium chloride, lithium gluconate, potassium chloride, potassium gluconate, caesium chloride, caesium gluconate, rubidium chloride and rubidium gluconate. In some embodiments, one salt is included in the transduction buffer. In some embodiments, more than one salt is included in the transduction buffer, for example, two, three, four or five salts.

Interestingly, protein transduction was strongly inhibited by specific inhibitors of Na+/H+ exchange such as EIPA or DMA, specific inhibitors of a family of sodium-hydrogen antiporter (Nhe) proteins (FIG. 5B). These data suggest that the transduction process involves active cellular uptake of exogenously applied compounds through macropinocytosis. This was further confirmed by comparing the transduction of mouse embryonic fibroblasts (MEFs) from Nhe1 knockout embryos with Nhe1 heterozygous and wild-type MEFs. As shown in FIG. 5C, protein transduction was almost completely abrogated in Nhe1 null fibroblasts. Fibroblasts from Nhe1+/− heterozygous embryos displayed reduced protein transduction activity compared to wild-type littermates (FIG. 5C). These results demonstrate that Nhe1 is an important mediator of protein transduction, but a residual protein transduction activity remains in the absence of Nhe1 expression. Without wishing to be bound by theory, the inventors hypothesise that activation of such Nhe transporters leads to activation of the macropinocytosis pathway, which is the first step in the transduction process.

Thus, in a preferred embodiment, the salt is any salt able to bind to and/or activate a sodium/hydrogen (Na+/H+) transporter, such as an Nhe transporter, for example an Nhe1 transporter. Nhe1 is a ubiquitous membrane-bound enzyme involved in volume- and pH-regulation of vertebrate cells.

In some embodiments, the transduction buffer comprises an activator and/or enhancer of a sodium/hydrogen transporter, such as the Nhe1 transporter, as a replacement for, or in addition to the salt. For example, several growth factors have been shown to induce macropinocytosis by activating Nhe1 and enhancing Na+/H+ exchange. Accordingly, in some embodiments, the activator or enhancer of an sodium/hydrogen transporter is a cytokine or growth factor. In some embodiments, the activator or enhancer of a sodium/hydrogen transporter is epidermal growth factor (EGF), Fibroblast growth factor (FGF), Platelet-derived growth factor (PDGF), Insulin, Insulin-like growth factor (IGF). Small molecule agonists of cytokine or growth factor signalling can also induce Nhe1 activity. Other examples of activators of NHE1 include, but are not limited to, small molecule agonists of cytokine or growth factor signalling, angiotensin II, glucocorticoids and hormones (Alexander R T, J Exp Biol 212, 1630-1637, 2009). In some embodiments, the transduction buffer comprises more than one activator and/or enhancer of a sodium/hydrogentransporter, for example one, two, three, four or five. Any combination of the above activators and/or enhancers is contemplated, with or without a salt, as described above.

In one embodiment, the invention provides a transduction buffer comprising an activator and/or enhancer of a sodium/hydrogen transporter, such as an Nhe transporter and a transduction compound.

Other activators and/or enhancers of macropinocytosis or endosomal lysis can also be useful in the context of the invention. For example, a short dTAT-HA2 fusion peptide, previously shown to enhance macropinosome escape of proteins, was demonstrated by the present inventors to enhance protein transduction, and was particularly effective in mouse embryonic stem cells (mESCs). Therefore, in some embodiments, the transduction buffer additionally comprises an activator and/or enhancer of macropinocytosis or a facilitator of macropinosomal escape. In some embodiments, the transduction buffer additionally comprises dTAT-HA2 fusion peptide. In some embodiments, the transduction buffer additionally comprises a lysogenic peptide. For example, in some embodiments, the transduction buffer additionally comprises an activator and/or enhancer of endosomal lysis.

There is also provided the use of a lysogenic peptide for enhancing transduction of a molecule of interest into a cell, preferably as part of a transduction buffer described herein.

Inhibition of Transduction

The inventors have shown that transduction by the methods described herein occurs via macropinocytosis and requires actin remodelling. Thus, specific inhibitors of these processes can prevent transduction.

In some embodiments, the transduction methods can be inhibited by Cytochalasin D or Latrunculin A, or other specific inhibitors of actin polymerization and vesicle transport. Similarly, the transduction methods can be inhibited by specific inhibitors of Na+/H+ exchange by Nhe transporters, such as EIPA or DMA.

Osmolality Ranges

The salt, as defined above, is added to the transduction buffer in appropriate quantities to achieve the desired osmolality. The osmolality of the transduction buffer can be determined by methods known in the art using an osmometer or can be calculated, e.g. if the osmolar pressure of the media which makes up the remaining volume of the buffer is known. Thus, the salt can be added to adjust the osmolality of the buffer to the desired level (see for instance, Example 6).

Osmolality is the concentration of a solution in terms of osmoles of solutes per kilogram of solvent. It differs from osmolarity which is the concentration of osmoles of solutes per volume of solvent. Osmolarity is temperature dependent because water changes its volume with temperature. Therefore, osmolality is the preferred measure because it is not temperature dependent. If the concentration of solutes is very low, osmolarity and osmolality are considered equivalent.

Tonicity, by contrast, is defined by the concentration of all solutes that do not cross a cell membrane, i.e. the concentration of solutes that result in osmotic pressure across a cell membrane. In the context of the transduction buffer, hyperosmolality is achieved using hypertonic salts, such as the salts described above. For the transduction method to work, it is important that there is osmotic pressure across the cell membrane. Thus, whilst the transduction buffer can be defined by osmolality (in isolation of the cell), the method of transduction requires the transduction buffer to be hypertonic with respect to the cell cytosol. A cell placed in a hypertonic solution, such as a transduction buffer described herein, will lose water by osmosis. This causes the cell to shrink and tends to increase the space in between cells in a population. To compensate for the loss in cell volume, the cells activate macropinocytosis, i.e. the influx of macromolecules from the extracellular environment. It is to be understood that the optimum osmolality of the transduction buffer is cell-type specific and is defined, in part, by the osmolality of the culture media used to maintain the cell prior to transduction and/or the osmolality of the cell cytosol.

Thus in some embodiments, the method for transducing a molecule of interest into a cell involves the step of increasing the osmotic pressure outside of the cell. In some embodiments, there is osmotic pressure across the cell membrane. In some embodiments, the transduction buffer is hypertonic with respect to the culture media in which the cell was maintained prior to transduction and/or with respect to the cell cytosol. In other words, in some embodiments, the osmolality of the transduction buffer is greater than the osmolality of the culture media in which the cell was maintained prior to transduction and/or greater than the cell cytosol.

Normal osmolality of human serum is about 275-295 mOsm/kg. While temporary elevation of serum osmolality has been used to reduce brain edema in stroke patients, prolonged elevated global osmolality in a human can lead to complications and in serious cases can be fatal. For this reason, pharmaceutical compositions are typically isotonic (have approximately the same osmolality as serum). Individual cells, however, can survive at much higher osmolalities (e.g. up to about 1000 mOsm/kg). Thus, live organisms are able to tolerate moderate elevation of osmolality for several days and temporary high osmolalities locally.

Hyperosmolality refers to an abnormal increase in the osmolality of a solution, especially a body fluid or culture medium. The osmolality at which human cells are maintained is typically about 275-295 mOsm/Kg but, for example, preimplantation embryos are grown at an osmolality of about 250-260 mOsm/Kg. Therefore, in the context of a typical human cell, hyperosmolality refers to an osmolality of more than about 250 mOsm/kg. Thus a transduction buffer with an osmolality of more than about 295 mOsm/kg is likely to be hypertonic with respect to a typical human cell, whereas a transduction buffer with an osmolality of more than about 260 mOsm/kg is likely to be hypertonic with respect to early embryos. Hypo-osmolality refers to an abnormal decrease in the osmolality of a solution, especially a body fluid. Therefore, in the context of typical human cells hypo-osmolality refers to an osmolality of less than about 295 mOsm/kg. Thus a transduction buffer with a tonic salt-mediated osmolality of less than about 295 mOsm/kg is likely to be hypotonic with respect to a typical human cell. In the context of a typical embryo, hypo-osmolality refers to an osmolality of less than about 260 mOsm/kg. Thus a transduction buffer with a tonic salt-mediated osmolality of less than about 260 mOsm/kg is likely to be hypotonic with respect to a typical early embryo.

Osmotic shock is a sudden change in the solute concentration around a cell, causing a rapid change in the movement of water across its cell membrane. In a preferred embodiment, the method for transduction does not require or involve hypo-osmotic shock of the cells or a hypo-osmotic environment at any stage. In some embodiments, the method for transducing a cell involves hyperosmotic shock. However, any osmotic shock or stress is preferably kept to a minimum (see section below on osmoprotectants).

In some embodiments, the transduction buffer is not isotonic and/or not iso-osmolar with respect to the culture media in which the cell was maintained prior to transduction and/or with respect to the cell cytosol. In some embodiments, the transduction buffer is not hypotonic with respect to the culture media in which the cell was maintained prior to transduction and/or with respect to the cell cytosol. In a preferred embodiment, the transduction buffer is hypertonic and/or hyperosmolar with respect to the culture media in which the cell was maintained prior to transduction and/or with respect to the cell cytosol.

In some embodiments, the transduction buffer has an osmolality of more than 250 mOsm/kg, for example more than 300 mOsm/kg. For example, the transduction buffer may have an osmolality of more than 350 mOsm/kg, more than 400 mOsm/kg, more than 450 mOsm/kg, more than 500 mOsm/kg, more than 550 mOsm/kg, more than 600 mOsm/kg, more than 650 mOsm/kg, more than 700 mOsm/kg, more than 750 mOsm/kg, more than 800 mOsm/kg, more than 850 mOsm/kg, more than 900 mOsm/kg, more than 950 mOsm/kg, more than 1000 mOsm/kg, more than 1100 mOsm/kg, more than 1200 mOsm/kg, more than 1300 mOsm/kg, more than 1400 mOsm/kg or more than 1500 mOsm/kg, more than 1600 mOsm/kg, more than 1700 mOsm/kg, more than 1800 mOsm/kg, or more than 1900 mOsm/kg, more than 2000 mOsm/kg, more than 2100 mOsm/kg, more than 2200 mOsm/kg, more than 2300 mOsm/kg, more than 2400 mOsm/kg, more than 2500 mOsm/kg, more than 2500 mOsm/kg, more than 2600 mOsm/kg, more than 2700 mOsm/kg, more than 2800 mOsm/kg, more than 2900 mOsm/kg, or about 3000 mOsm/kg.

In some embodiments, the transduction buffer has an osmolality of less than 3000 mOsm/kg, for example less than 2500 mOsm/kg. For example, the transduction buffer may have an osmolality of less than 2000 mOsm/kg, less than 1900 mOsm/kg, less than 1800 mOsm/kg, less than 1700 mOsm/kg, less than 1600 mOsm/kg, less than 1500 mOsm/kg, less than 1400 mOsm/kg, less than 1300 mOsm/kg, less than 1200 mOsm/kg, less than 1000 mOsm/kg, less than 900 mOsm/kg, less than 800 mOsm/kg or less than 700 mOsm/kg, less than 600 mOsm/kg, less than 500 mOsm/kg, less than 400 mOsm/kg, or about 400 mOsm/kg.

In some embodiments, the transduction buffer has an osmolality of at least 250 mOsm/kg, at least 300 mOsm/kg. For example, the transduction buffer may have an osmolality of at least 350 mOsm/kg, at least 400 mOsm/kg, at least 450 mOsm/kg, at least 500 mOsm/kg, at least 550 mOsm/kg, at least 600 mOsm/kg, at least 650 mOsm/kg, at least 700 mOsm/kg, at least 750 mOsm/kg, at least 800 mOsm/kg, at least 850 mOsm/kg, at least 900 mOsm/kg, at least 950 mOsm/kg, at least 1000 mOsm/kg, at least 1100 mOsm/kg, at least 1200 mOsm/kg, at least 1300 mOsm/kg, at least 1400 mOsm/kg at least 1500 mOsm/kg, at least 1600 mOsm/kg, at least 1700 mOsm/kg, at least 1800 mOsm/kg, at least 1900 mOsm/kg, at least 2000 mOsm/kg, at least 2100 mOsm/kg, at least 2200 mOsm/kg, at least 2300 mOsm/kg, at least 2400 mOsm/kg, at least 2500 mOsm/kg, at least 2600 mOsm/kg, at least 2700 mOsm/kg, at least 2800 mOsm/kg, at least 2900 mOsm/kg, at least 3000 mOsm/kg, or about 3000 mOsm/kg. In some embodiments, the transduction buffer has an osmolality of at least 1250 mOsm/kg.

In some embodiments the osmolality is in the range of about 250 mOsm/kg to about 1500 mOsm/kg, about 300 mOsm/kg to about 1500 mOsm/kg, about 400 mOsm/kg to about 1500 mOsm/kg, about 500 mOsm/kg to about 1500 mOsm/kg, about 600 mOsm/kg to about 1500 mOsm/kg, about 700 mOsm/kg to about 1500 mOsm/kg, about 800 mOsm/kg to about 1500 mOsm/kg, about 900 mOsm/kg to about 1500 mOsm/kg, about 1000 mOsm/kg to about 1500 mOsm/kg, about 1100 mOsm/kg to about 1500 mOsm/kg, about 1200 mOsm/kg to about 1500 mOsm/kg, about 1300 mOsm/kg to about 1500 mOsm/kg or about 1400 mOsm/kg to about 1500 mOsm/kg, about 300 mOsm/kg to about 1000 mOsm/kg, about 300 mOsm/kg to about 800 mOsm/kg, about 300 mOsm/kg to about 600 mOsm/kg, about 400 mOsm/kg to about 600 mOsm/kg, about 450 mOsm/kg to about 550 mOsm/kg, about 400 mOsm/kg to about 800 mOsm/kg, about 500 mOsm/kg to about 800 mOsm/kg, about 600 mOsm/kg to about 800 mOsm/kg, or about 700 mOsm/kg to about 800 mOsm/kg, about 750 mOsm/kg to about 850 mOsm/kg. In some embodiments, the osmolality is in the range of about 800 mOsm/kg to about 900 mOsm/kg, about 850 mOsm/kg to about 950 mOsm/kg, about 900 mOsm/kg to about 1000 mOsm/kg, about 950 mOsm/kg to about 1050 mOsm/kg, about 1000 mOsm/kg to about 1100 mOsm/kg, about 1050 mOsm/kg to about 1150 mOsm/kg, about 1100 mOsm/kg to about 1200 mOsm/kg, about 1150 mOsm/kg to about 1250 mOsm/kg, about 1200 mOsm/kg to about 1300 mOsm/kg, about 1250 mOsm/kg to about 1350 mOsm/kg, about 1300 mOsm/kg to about 1400 mOsm/kg, about 1350 mOsm/kg to about 1450 mOsm/kg, about 1400 mOsm/kg to about 1500 mOsm/kg, about 1600 mOsm/kg to about 1800 mOsm/kg, or about 1700 mOsm/kg to about 1800 mOsm/kg, about 1750 mOsm/kg to about 1850 mOsm/kg, about 1800 mOsm/kg to about 1900 mOsm/kg, about 1850 mOsm/kg to about 1950 mOsm/kg, about 1900 mOsm/kg to about 2000 mOsm/kg, about 1950 mOsm/kg to about 2050 mOsm/kg, about 2000 mOsm/kg to about 2100 mOsm/kg, about 2050 mOsm/kg to about 2150 mOsm/kg, about 2100 mOsm/kg to about 2200 mOsm/kg, about 2150 mOsm/kg to about 2250 mOsm/kg, about 2200 mOsm/kg to about 2300 mOsm/kg, about 2250 mOsm/kg to about 2350 mOsm/kg, about 2300 mOsm/kg to about 2400 mOsm/kg, about 2350 mOsm/kg to about 2450 mOsm/kg, about 2400 mOsm/kg to about 2500 mOsm/kg, about 2600 mOsm/kg to about 2800 mOsm/kg, or about 2700 mOsm/kg to about 2800 mOsm/kg, about 2750 mOsm/kg to about 2850 mOsm/kg, about 2800 mOsm/kg to about 2900 mOsm/kg, about 2850 mOsm/kg to about 2950 mOsm/kg, about 2900 mOsm/kg to about 3000 mOsm/kg.

In some embodiments the osmolality is in the range of about 250 mOsm/kg to about 3000 mOsm/kg, about 300 mOsm/kg to about 3000 mOsm/kg, about 350 mOsm/kg to about 3000 mOsm/kg, about 400 mOsm/kg to about 3000 mOsm/kg, about 450 mOsm/kg to about 3000 mOsm/kg, about 500 mOsm/kg to about 3000 mOsm/kg.

In one embodiment, the osmolality of the transduction buffer is about 800 mOsm/kg. It has been demonstrated that this osmolality is appropriate for mouse embryonic fibroblasts (MEFs). In another embodiment, the osmolality of the transduction buffer is about 500 mOsm/kg. It has been demonstrated that this osmolality is appropriate for mouse embryonic stem cells (mESC), human induced pluripotent stem cells (hIPSC) and murine and human neural stem cells. However, as explained above, the skilled person will appreciate that, depending on the target cell type, nature of the transduced molecule and the osmolality of cell environment prior to transduction, the preferred osmolality of the transduction buffer will change.

Higher osmolalities may also be preferable when the molecule of interest is a poorly soluble protein. For example, an osmolality of about 1000 mOsm/kg is preferred for poorly soluble proteins. In some embodiments an osmolality of about 1250 mOsmol/Kg is preferred, for example, for poorly soluble proteins, e.g. for transduction of the Cas9 nuclease protein, e.g. in the context of CRISPR-Cas9 gene editing.

In general, the greater the osmolality of the transduction buffer, the more efficient the buffer is, i.e. the less time required for transduction. However, there is also a trade-off because high osmololalities can cause osmotic stress and reduce cell proliferation and/or viability (see below).

The inventors have developed assays to optimise the time for transduction (the "incubation time" or "transduction time"—see below) and the osmolality of the buffer (see FIG. 11 and the Example 6).

Therefore, the skilled person could use these assays to optimise the time for transduction and/or the osmolality of the buffer.

Osmoprotectant for Transduction

The salt in the transduction buffer increases the osmolality of the transduction buffer such that during transduction methods the transduction buffer is hypertonic with respect to the cell. This can cause osmotic stress to cells and in certain circumstances this can reduce cell proliferation or viability (for example, as measured by BrdU incorporation; see the Examples section). The inventors found that addition of osmoprotectants can protect against these effects.

Osmoprotectants are small molecules that act as osmolytes and help protect cells and organisms from osmotic stress. Chemically, osmoprotectants can be divided into three types: betaines and allied compounds, polyols and sugars (e.g. glycerol, mannitol and trehalose), and amino acids. Betaines are methyl derivatives of glycine in which the nitrogen atom is fully methylated, i.e. they are quaternary ammonium compounds. Other methyl derivatives of glycine useful in the context of this invention include, but are not limited to, sarcosine and dimethylglycine. It will be clear to the skilled person that some of the transduction compounds described herein can thus function as osmoprotectants. A non-limiting example of a transduction compound that also functions as an osmoprotectant is GABA. However, not all osmoprotectants enhance transduction. Similarly, not all transduction compounds function as osmoprotectants. Therefore, in some embodiments an osmoprotectant is added to the transduction buffer in addition to the transduction compound (which may or may not function as an osmoprotectant in this context).

The inventors found that a number of different types of osmoprotectants and a number of different combinations of osmoprotectants could increase cell viability (see for example, FIGS. 4A-4E), when used in a method of transduction.

In some embodiments, the osmoprotectant is a betaine or allied compound, polyol or sugar, and/or an amino acid, for example, selected from glycine, histidine, alanine, isoleucine, arginine, asparagine, leucine, aspartic acid, lysine, glutamic acid, cysteine, methionine, phenylalanine, glutamine, threonine, tryptophan, proline, valine, ornithine, selenocysteine, serine, tyrosine and proline. In some embodiments the osmoprotectant is glycine or a derivative thereof. In some embodiments the osmoprotectant is a methyl derivative of glycine such as sarcosine, dimethylglycine or betaine.

In other embodiments, the osmoprotectant is selected from glycine, glycerol, taurine, glycinebetaine, myo-inositol, glutamine, glutamate, arginine, mannitol and trehalose. In a preferred embodiment, the osmoprotectant is glycine or glycerol.

In some embodiments, the transduction buffer comprises more than one type of osmoprotectant, for example, glycine and glycerol. Glycine and glycerol is a preferred combination because it provided the best protection in murine embryonic fibroblast cells (as shown in FIG. 4B), embryonic stem cells and human iPS cells. However, any combination of osmoprotectants may be suitable for use in the transduction buffer of the invention. For example, any combination of osmoprotectants described herein, for example any combination of 2, 3, 4, 5, 6, 7 or all of glycine, glycerol, taurine, glycinebetaine, myo-inositol, glutamine, glutamate, arginine, mannitol and trehalose.

The type (or combination of types) of osmoprotectant selected for use with the invention may depend upon the type of cell to be transduced. The suitability of an osmoprotectant can be easily determined by the skilled person by assay (IV) described in Example 6.

The concentration of osmoprotectant selected for use with the invention may depend upon the type of cell to be transduced but can be easily determined by the skilled person by methods well known in the art. In some embodiments, the osmoprotectant is at a concentration of between about 5 and about 500 mM, between about 1 and about 500 mM, between about 1 and about 400 mM, between about 1 and about 300 mM, between about 1 and about 200 mM, between about 1 and about 100 mM, between about 10 and about 50 mM, between about 15 and about 50 mM, between about 20 and about 40 mM. For example, in some embodiments, the osmoprotectant is used at a concentration of about 15 mM or about 20 mM or about 30 mM. In some embodiments, the osmoprotectant is used at a concentration of at least 15 mM, at least 20 mM, at least 30 mM, at least 40 mM, at least 50 mM at least 60 mM, at least 70 mM, at least 80 mM, at least 90 mM, at least 100 mM, at least 200 mM, at least 300 mM, at least 400 mM or about 500 mM. In some embodiments, the osmoprotectant is used at a concentration of 500 mM or less, 400 mM or less, 300 mM or less, 200 mM or less, 100 mM or less, 50 mM or less, 40 mM or less, 30 mM or less or 20 mM or less. For example, in a preferred embodiment, glycine and/or taurine are used at a concentration of about 15 mM and/or glycerol is used at a concentration of about 30 mM.

The invention also provides the use of one or more (e.g. 1, 2, 3, 4, 5, 6, 7, 8 or more) osmoprotectants, such as any osmoprotectant or combination of osmoprotectants described herein, for transducing a molecule into a cell. For example, the invention provides the use of glycine and/or glycerol as osmoprotectants for transducing molecules into a cell.

Other Components of the Transduction Buffer

It is to be understood that the any of the additional components of the transduction buffer described herein may be part of the transduction buffer. Alternatively, they may be added simultaneously or sequentially to the cells in any combination as a step in the method of transduction.

The transduction buffer may additionally comprise components that make it particularly suitable for use with live cells or live cell culture or application in vivo. For example, in some embodiments the transduction buffer comprises one or more of (e.g. 2, 3, 4, 5, 6 or 7) of a biological pH buffer, a viscosity enhancer, and/or one or more growth factor(s), salts, amino acids, vitamins and nutrients.

A transduction buffer of the invention will normally be formulated in deionized, distilled water, although suitable alternatives may be used including, but not limited to cell culture media or therapeutic solutions. It will typically be sterilized prior to use to prevent contamination, e.g. by ultraviolet light, heating, irradiation or filtration. It may be frozen (e.g. at between −20° C. or −80° C., for examples at −20° C. or at −80° C.) for storage or transport. The transduction buffer may contain one or more antibiotics, such as doxycycline or tetracycline, to prevent contamination. However, some antibiotics, particularly non cell-permeable antibiotics (such as penicillin and/or streptomycin), can be toxic to the cells when transduced into the cells. Therefore, in some embodiments, the transduction buffer does not comprise an antibiotic, for example the transduction buffer does not comprise a non cell-permeable antibiotic. In some embodiments, the transduction buffer does not comprise penicillin.

The transduction buffer may be buffered by a biological pH buffer at a pH of between about 6 and about 8, for example a pH of between about 7.2 and about 7.6 or a pH of about 7.4. A pH outside of this range (i.e. higher than 8 or lower than 6) might be appropriate for administration to particular tissues, as would easily be determined by the person skilled in the art. For example, stomach pH can drop to as low as 1 or 2. Therefore, a transduction buffer for administration to the stomach may have a pH of less than 7, less than 6, less than 5, less than 4, less than 3, less than 2, for example a pH of 7, 6, 5, 4, 3, 2 or 1. A biological pH buffer is a pH buffer that is suitable for use with live cells, i.e. which has minimal negative impact on cell viability. The biological pH buffer may be a carbonate based buffer or any other suitable buffer. A number of biological pH buffers are known in the art (see for example the biological buffers provided in Plant Microtechnique and Microscopy, Oxford University Press, Steven E. Ruzin, ISBN: 0-19-508956-1; and www.sigmaaldrich com/life-science/core-bioreagents/biological-buffers/biological-buffer-products.html).

Examples of biological pH buffers include, but are not limited to PBS, TES, TRIS, PIPES, MOPS, MES, Good's buffers, Trizma or HEPES. Thus in some embodiments the transduction buffer additionally comprises PBS, TES, TRIS, PIPES, MOPS, MES, Good's buffers, Trizma or HEPES.

Some of the transduction compounds are also excellent buffering compounds, so can act as buffers instead of, or in addition to, the biological buffer.

The transduction buffer may be supplemented with purified, natural, recombinant, semi-synthetic and/or synthetic growth factors (see for instance, Example 4). Any suitable growth factor or combination of growth factors may be used. Non-limiting examples of suitable growth factors include EGF, FGF, HGF, PDGF, BDNF, VEGF or IGF. Any combination of suitable growth factors may be used. Non-limiting examples of growth factor combinations include any one or more (e.g. 1, 2, 3, 4, 5 or 6) of the growth factors in the list consisting of: EGF, FGF, HGF, PDGF, BDNF, VEGF or IGF. The growth factors added may, in some circumstances depend on the cell to be transduced, and it is known in the art how to select appropriate growth factors for a particular cell.

The growth factor or growth factors is preferably added at a concentration of between about 1 and about 500 ng/ml or of at least 5 and not higher than 500 ng/ml. A preferred concentration is at least 1, 2, 5, 10, 20, 25, 30, 40, 45, 50, 60, 70, 80, 90, 100, 200, 300, 400 ng/ml and not higher than 600, 500, 450, 400, 350, 300, 250, 200, 150, or 100 ng/ml. A more preferred concentration is at least 10 ng/ml and not higher than 500 ng/ml. An even more preferred concentration is about 50 ng/ml or is 50 ng/ml. The skilled person will be aware that the optimal concentration of a growth factor is both dependent upon the growth factor and the cell to be transduced. The optimal concentration can be determined by methods known in the art and by the methods described in the examples herein.

In some embodiments, the transduction buffer is supplemented with a cytokine. Similarly, to growth factors, different cytokines are suitable for the culture of different cell types and suitable cytokines are known in the art. Other cell type specific factors known in the art can also be added to the transduction buffer, such as, but not limited to LIF (for maintaining the stem cell state of embryonic stem cells) and GM-CSF for dendritic cells.

The invention also provides the use of growth factors, cytokines and/or neurotransmitters and/or small molecule agonists of those signalling pathways for enhancing transduction of a molecule of interest into cell, preferably when used in or with a transduction buffer as described herein.

In some embodiments the transduction buffer additionally comprises a viscosity enhancer. This is particularly preferred when the transduction buffer is for use in vivo because it prevents unwanted dispersion of the transduction buffer. This, therefore, helps to keep the buffer in contact with the cells being transduced. In some embodiments, the viscosity enhancer is polyvinylpyrrolidone (PVP), polyvinyl alcohol, methylcellulose, hydroxypropylmethylcellulose, hydroxyethylcellulose, sodium carboxymethyl cellulose (NaCMC), propylene glycol alginate (PGA) or sodium alginate (SA). A preferred viscosity enhancer is non-toxic and suitable for use with live cells and/or in vivo.

In some embodiments, the transduction buffer additionally comprises an antioxidant, such as ethylenediaminetetraacetic acid (EDTA), sodium bisulfate, sodium metabisulfite, ascorbic acid or thiourea.

In some embodiments, the transduction buffer additionally comprises a basal culture medium. Suitable culture media are available commercially, and include, but are not limited to, Dulbecco's Modified Eagle Media (DMEM), Minimal Essential Medium (MEM), Knockout-DMEM (KO-DMEM), Glasgow Minimal Essential Medium (G-MEM), Basal Medium Eagle (BME), DMEM/Ham's F12, Advanced DMEM/Ham's F12, Iscove's Modified Dulbecco's Media and Minimal Essential Media (MEM), Ham's F-10, Ham's F-12, Medium 199, and RPMI 1640 Media.

In some embodiments, the transduction buffer additionally comprises serum. However, in a preferred embodiment, the transduction buffer does not comprise an undefined component such as fetal bovine serum or fetal calf serum. Various different serum replacement formulations are commercially available and are known to the skilled person. Where a serum replacement is used, it may for example be used at between about 0.1% and about 50% by volume of the medium, according to conventional techniques.

Transduction is typically performed in culture medium that is appropriate for the regular maintenance of the particular cell type. As with any of the factors described herein, this culture medium may be part of the transduction buffer or it may be added to the cells separately in the transduction method. In a preferred embodiment, there is no serum or a reduced concentration of serum in the culture medium used during transduction.

The concentration ranges provided for all components of the buffer are final concentrations when the buffer is in use for transduction (e.g. concentrations when the buffer is formulated in deionized, distilled water, cell culture medium or a therapeutic composition).

Proteins for transduction are typically provided in a 5× or 10× concentrate, which when added to the cell culture media gives the concentrations described herein.

Molecule of Interest for Transduction

In a preferred embodiment, more than one molecule of interest (i.e. multiple copies of the molecule of interest) is transduced into a cell. For example, at least 2, at least 10, at least 20, at least 50, at least 100, at least 500, at least 1000, at least 2000, at least 5000, at least 10,000 molecules of interest, at least $10^4$, at least $10^5$, at least $10^6$, at least $10^7$, or more than $10^7$ molecules of interest are transduced into the cell.

The transduction buffer and methods of the invention can be used to transduce many different types of biological and synthetic molecules into cells. For example, the molecule of interest may be a protein (including peptides and polypeptides), nucleic acid, polysaccharide (such as dextran), vesicle (such as an exosome), nanoparticle, small molecule, virus or other organism.

In some embodiments one or more (e.g. 1, 2, 3, 4, 5, 6, 7, 8, 9, 10 or more) different types of molecules of interest are transduced into a cell. In some embodiments, multiple molecules of interest are transduced into the cell, for example in the form of complex mixtures. Non-limiting examples of complex mixtures include cell and/or tissue extracts. For example, extracts from murine embryonic stem cells have been shown to initiate partial reprogramming of the transformed 293T cell line, which was permeabilised using Streptolysin, which creates large pores in the cell membrane. While this method is obviously not well tolerated by cells, it does allow the diffusion of molecules into the cells. The inventors hypothesise that the efficient transduction of cell- or nuclear extracts of murine embryonic stem cells or human pluripotent stem cells into somatic cells such as for example skin fibroblasts, will allow efficient and complete reprogramming of these cells into pluripotent stem cells. Similarly, extracts of other cell types or tissues may confer the identity or functional properties of those cells or tissues onto the transduced cell type. Accordingly, the invention provides a method for reprogramming a cell, such as a somatic cell, to a pluripotent cell (i.e. an iPS cell). This is also an important tool for identifying new pathways or transcription factors that mediate cell fate or function. Thus in some embodiments, there is provided a method for identifying new pathways or transcription factors that mediate cell fate or function, wherein the method comprises transducing cell and/or tissue extracts into a cell using the transduction methods described herein.

In some embodiments, the molecule of interest is a macromolecule.

In some embodiments, the molecule of interest is a protein. Non-limiting examples of proteins include monoclonal antibodies, cytokines, tissue growth factors and therapeutic proteins. In some embodiments, the molecule of interest is a biological drug (also known as a biologic). In some embodiments the protein is an enzyme. For example, the enzyme may be an enzyme that targets and modifies nucleic acids, such as a restriction enzyme, an endonuclease, Cre-recombinase or flippase. In some embodiments the endonuclease is a modified endonuclease, such as a TAL effector nuclease (TALEN) (Boch, J "TALEs of genome targeting". *Nature Biotechnology* 29 (2): 135-6, 2011). Such endonucleases can be used to modify nucleic acids in the cell. For example, they can be designed to target specific DNA sequences to introduce mutations or deletions for gene silencing or activation (e.g. by exon skipping). The inventors have shown that TALENs can be transduced into cells and that they can introduce genetic mutations, including insertions and deletions. In addition, TALE-DNA binding domains can be coupled to other effector domains, such as a DNA methyltransferase domain (which will methylate cytosine residues in DNA at specific sites), histone modifying domains, such as for example methyltransferase- or acyltransferase domains, which modify histones around the TALE target site, or other protein effector domains. Beta-lactamase is another example of an enzyme which can be transduced by the buffers and methods described herein. Thus in some embodiments, the molecule of interest is beta-lactamase. In some embodiments, the protein is a transcription factor. Transduction of transcription factors into cells can be used to drive gene expression and to rewire cell fate, phenotype or identity. For example, OCT2, OCT3, OCT4, SOX2, KLF4, C-MYC, N-MYC, NANOG, ESRRB and LIN28 have all been used for the generation of induced pluripotent stem (iPS) cells. Typically, they are introduced into cells by viral vectors. However, the transduction method of the invention could replace this method. Thus, in some embodiments the molecule of interest for transduction is a transcription factor involved in the regulation, definition or change in the cell cycle and/or cell identity. In other embodiments, the transcription factor is a transcription factor involved in the maintenance or differentiation of stem cells. For example, in some embodiments, the transcription factor is selected from OCT2, OCT3, OCT4, SOX2, KLF4, C-MYC, N-MYC, NANOG, ESRRB and LIN28.

A number of transcription factors are also associated with certain diseases and disorders (see table A).

tion factor is selected from MECP2, HNFs, IPF1/Pdx1, FOXP2, FOXP3, p53, STAT and HOX. In some embodiments, two or more (e.g. 2, 3, 4, 5, 6, 7 or more) transcription factors are included in the transduction buffer or methods of the invention, for example 2, 3, 4, 5, 6, 7 or all of the transcription factors in the list consisting of MECP2, HNFs, IPF1/Pdx1, FOXP2, FOXP3, p53, STAT and HOX.

In some embodiments, when the molecule of interest is a protein, it is protein that can modify nucleic acids, e.g. part of a gene editing system. Proteins that can modify nucleic acids typically have nuclease enzyme activity, for example endonuclease or exonuclease activity. Thus in some embodiments, the molecule of interest has nuclease enzyme activity or is a nuclease. The nuclease activity may be present in the wild type version of the protein or it may be added, e.g. by recombinant methods, to generate a fusion protein. Thus in some embodiments, the molecule of interest is a fusion protein, for example a fusion protein with nuclease activity, for example a transcription factor fused to a domain with nuclease activity. In some embodiments, the molecule of interest is a gene editing system or is part of a gene editing system. In some embodiments, gene editing systems comprise a protein that can modify a nucleic acid as discussed above and optionally comprise further molecules, such as guide molecules. In some embodiments the gene editing system comprises or consists of proteins that target a specific sequence, such as zinc finger nucleases (ZFNs) or TALENS.

TABLE A

| Condition | Description | References |
|---|---|---|
| Rett syndrome | Mutations in the MECP2 transcription factor are associated with Rett syndrome, a neurodevelopmental disorder. | Moretti P, Zoghbi H Y (June 2006). *Curr. Opin. Genet. Dev.* 16 (3): 276-81. Chadwick L H, Wade P A (April 2007). *Curr. Opin. Genet. Dev.* 17 (2): 121-5. |
| Diabetes | A rare form of diabetes called MODY (Maturity onset diabetes of the young) can be caused by mutations in hepatocyte nuclear factors (HNFs) or insulin promoter factor-1 (IPF1/Pdx1). | Maestro M A, Cardalda C, Boj S F, Luco R F, Servitja J M, Ferrer J (2007). *Endocr Dev* 12: 33-45. Al-Quobaili F, Montenarh M (April 2008). *Int. J. Mol. Med.* 21 (4): 399-404. |
| Developmental verbal dyspraxia | Mutations in the FOXP2 transcription factor are associated with developmental verbal dyspraxia, a disease in which individuals are unable to produce the finely coordinated movements required for speech. | Lennon P A, Cooper M L, Peiffer D A, Gunderson K L, Patel A, Peters S, Cheung S W, Bacino C A (April 2007). *Am. J. Med. Genet. A* 143A (8): 791-8. |
| Autoimmune diseases | Mutations in the FOXP3 transcription factor cause a rare form of autoimmune disease called IPEX. | van der Vliet H J, Nieuwenhuis E E (2007). *Clin. Dev. Immunol.* 2007: 89017. |
| Li-Fraumeni syndrome | Caused by mutations in the tumor suppressor p53. | Iwakuma T, Lozano G, Flores E R (July 2005). *Cell Cycle* 4 (7): 865-7. |
| Breast cancer | The STAT family is relevant to breast cancer. | Garcia, Roy, et al. "Constitutive activation of Stat3 by the Src and JAK tyrosine kinases participates in growth regulation of human breast carcinoma cells." *Oncogene* 20.20 (2001): 2499-2513. |
| Multiple cancers | The HOX family are involved in a variety of cancers. | Grier, D. G., et al. "The pathophysiology of HOX genes and their role in cancer." *The Journal of pathology* 205.2 (2005): 154-171. |

Replacement of errant transcription factors by transduction could be useful for therapy or research purposes. Therefore, in some embodiments, the transcription factor is a transcription factor associated with a disease or disorder. In some embodiments the disease or disorder is selected from a cancer, a metabolic disease, a cardiovascular disease, a neurodegenerative disease, an autoimmune disease. In some embodiments, the disease or disorder is an inherited disease. For example, in some embodiments, the transcrip- In some embodiments, the gene editing system comprises a protein that is guided to its target sequences by a (separate) guide molecule. Examples of such proteins that are guided to their target sequence include but are not limited to Cas9 nuclease, proteins from the Cascade system, TtAgo and other Argonaute proteins, and other FOKI-nuclease associated proteins.

In some embodiments, the guide molecule is a guide nucleic acid, such as an sgRNAs or gDNA. Guide nucleic acids, such as sgRNA or gDNA can be designed by methods known in the art to target a specific sequence in the target nucleic acid (see for example, Mali, P., et al., RNA-guided human genome engineering via Cas9. Science, 2013. 339 (6121): p. 823-6 for sgRNA; and Swarts, D. et al, DNA-guided DNA interference by a prokaryotic Argonaute. Nature, 2014. 507, 258-261 for gDNA). Thus, in some embodiments, the molecule of interest is a guide nucleic acid, for example an sgRNA or a gDNA (see further comments below in connection with nucleic acids). Examples of small guide RNAs suitable for use with the invention include sgRNA #1, sgRNA #2, sgRNA #3, sgRNA #4, sgRNA #5, sgRNA #6 or sgRNA #7 as shown in FIGS. 20A-20H. The following small guide RNAs were shown to result in particularly efficient gene editing: sgRNA #2, sgRNA #3, sgRNA #5, sgRNA #6 and sgRNA #7 (see FIG. 20B).

In some embodiments, the protein is a signalling molecule. In some embodiments, the protein activates or inhibits a specific signalling pathway or a network of signalling pathways. For example, in some embodiments the protein activates or inhibits a growth factor-induced signalling pathway, a cytokine signalling pathway or a hormone-induced signalling pathway. In some embodiments the protein activates or inhibits a signalling pathway selected from Wnt, Hedgehog, BMP, SMAD, Hippo, Notch, JAK/STAT, NF-kB, cAMP, PLC or other signalling pathway known in the art (e.g. see Cell Signalling Biology, Michael J. Berridge, Module 2, Cell Signalling Pathways, Portland Press Limited 2012).

In some embodiments, the molecule of interest is an antibody. Typically, antibodies are extracellular molecules. Therefore, when found associated with targets within cells they are targeted for destruction, together with any target molecule that they are bound to. Thus, the inventors hypothesise that by targeting antibodies to intracellular targets and transducing them into the cell using the transduction buffers and methods of the present invention, said intracellular targets could be specifically targeted for destruction. Antibodies targeting intracellular targets are sometimes called "intrabodies". Internalization of cancer-fighting antibodies may support cancer therapy by blocking of tumour-specific protein—protein interactions (Bitler, B. G. and Schroeder, J. A. Recent Patents on Anti-Cancer Drug Discovery, 5:99-108, 2010).

In some embodiments, the protein of interest is less than 10, less than 20, less than 40, less than 70, less than 100, less than 150, less than 200, less than 300, less than 750, less than 1000, less than 1500, less than 2000, less than 5000, less than 10,000 amino acids in length. In other embodiments, the protein of interest is 5 or more, 10 or more, 20 or more, 40 or more, 70 or more, 100 or more, 150 or more, 200 or more, 300 or more, 750 or more, 1000 or more, 2000 or more, 5000 or more amino acids in length. In some embodiments, the protein of interest may be any range in length selected from any of the above values. In some embodiments, the protein is 10-5000, 12-1800, 30-1200, 35-800, 40-500, 5-200, 5-50, 5-30, 5-20, 5-12, 2-50, 2-30, 2-20, or 2-12 amino acids in length.

In a preferred embodiment of the invention, the transduction compound, buffer or method is suitable for transduction of a protein into a cell. In a further preferred embodiment, the transduction compound, buffer or method is suitable for transduction of a protein and nucleic acid into a cell, either simultaneously, sequentially or separately.

In embodiments in which the molecule of interest is a nucleic acid, the nucleic acid is DNA, cDNA, RNA, miRNA, siRNA or any modified version thereof. In some embodiment, the nucleic acid is an oligonucleotide or a polynucleotide. In some embodiments the nucleic acid is an antisense oligonucleotide. In some embodiments, the nucleic acid is a two-dimensional or three-dimensional nucleic acid structure, such as a DNA cage (e.g. for drug delivery). The DNA may be synthetic, recombinant, foreign or native to the cell that it is transduced into. In some embodiments the DNA is plasmid DNA. Plasmid DNA is usually taken up by endocytosis. However, the inventors have surprising shown that, using the transduction buffer, they can shift the mechanism of nucleic acid uptake from being primarily by endocytosis to primarily by macropinocytosis. This means that nucleic acids and enzymes targeting nucleic acids for recombination and modification can be transduced into cells simultaneously for genetic modification and gene therapy. In some embodiments, the nucleic acid has a region of homology to a sequence of interest with the cell, for example to allow homologous recombination. In some embodiments, the nucleic acid is small guide RNA (sgRNA), for example, for use with the CRISPR/Cas9 gene editing system or other gene editing systems, or a small guide DNA (gDNA), for example, for use with the TtAgo gene editing system or other gene editing systems. In some embodiments, the molecule of interest is not a nucleic acid.

In some embodiments, the nucleic acid of interest is less than 10, less than 20, less than 40, less than 70, less than 100, less than 150, less than 200, less than 300, less than 750, less than 1000, less than 1500, less than 2000, less than 5000, less than 10,000 nucleotides, less than 15,000 nucleotides, less than 20,000 nucleotides, less than 50,000 nucleotides, less than 100,000 nucleotides, less than 200,000 nucleotides, less than 250,000 nucleotides (or equivalent bases) in length. In other embodiments, the nucleic acid of interest is 1 or more, 5 or more, 10 or more, 20 or more, 40 or more, 70 or more, 100 or more, 150 or more, 200 or more, 300 or more, 750 or more, 1000 or more, 2000 or more, 5000 or more, 10,000 or more, 20,000 or more, 50,000 or more, 100,000 or more, 200,000 or more, 250,000 or more nucleotides (or equivalent bases) in length. In some embodiments, the nucleic acid of interest may be any range in length selected from any of the above values. In some embodiments, the nucleic acid is 10-10,000, 10-5000, 12-1800, 30-1200, 35-800, 40-500, 2-50, 5-30, 5-20, or 5-12 nucleotides (or equivalent bases) in length. In some embodiments, the molecule of interest is a whole or a part of a chromosome.

In some embodiments, the molecule of interest is between about 30 kDa to about 500 kDa, for example between about 30 kDa and about 200 kDa. For example, in some embodiments, the molecule of interest is about 30, about 40, about 50, about 60, about 70, about 80, about 90, about 100, about 110, about 120, about 130, about 140, about 150, about 160, about 170, about 180, about 190, or about 200 kDa. The inventors have demonstrated that molecules ranging from about 30 kDa (e.g. Oct-4) to about 140 kDa (e.g. a TALEN protein) can be transduced into cells using the buffer and methods of the invention. In some embodiments, the molecule of interest is more than 30, more than 40, more than 50, more than 60, more than 70, more than 80, more than 90, more than 100, more than 110, more than 120, more than 130, more than 140, more than 150, more than 160, more than 170, more than 180, more than 190, or more than 200 kDa. These sizes are particularly applicable where the molecule of interest is a protein or peptide. Where the molecule of interest is a nucleic acid molecule, such as an oligonucleotide or a polynucleotide, the size is typically defined by the number of nucleotides. In some embodiments, the molecule of interest is a small molecule. A small molecule is typically a low molecular weight (<800 Daltons) organic compound that may serve as an enzyme substrate or regulator of biological processes.

Transduction of small molecules is useful for drug delivery.

In some embodiments, the molecule of interest is a macromolecule.

In some embodiments, the molecule of interest has a net positive charge. In another embodiment, the molecule of interest has a net negative charge. In some embodiments, the molecule of interest is zwitterionic. In some embodiments, the molecule of interest is polar. In another embodiment, the molecule of interest is non-polar. In some embodiments, the molecule of interest is predominantly hydrophobic. In another embodiment, the molecule is hydrophilic. In another embodiment, the molecule is neutral. In some embodiments, the molecule of interest is soluble at about pH 7. The solubility may be improved by the transduction buffer.

In some embodiments, the transduction buffer comprises the molecule of interest for transduction. In other embodiments the transduction buffer comprises more than one molecule of interest for transduction, for example two, three, four, five or more molecules of interest.

Any combination of molecules of interest described herein may be included in the transduction buffer or used in the methods for transduction disclosed herein. For example, in one embodiment, the transduction buffer comprises a nucleic acid and a protein, such as an endonuclease or Cre-recombinase (e.g. for genetic modification of said nucleic acid) as molecules of interest for transduction. In some embodiments, the transduction buffer comprises a protein and a polysaccharide as molecules of interest for transduction.

In some embodiments, the transduction buffer comprises a nucleic acid and a lipid as molecules of interest for transduction. In some embodiments, the transduction buffer comprises a nucleic acid, a protein and a lipid as molecules of interest for transduction.

In some embodiments, the methods for transduction involve the following non-limiting examples of combinations of molecules of interest: two or more different proteins (such as TALEN pairs), two or more nucleic acid molecules, nucleic acid and protein (such as DNA and protein), polysaccharides (such as dextran) and protein, nucleic acid and lipid, protein and lipid, nucleic acid, and protein and lipid. Specific examples of nucleic acid and protein pairs include guide nucleic acids and proteins with nuclease activity, for example sgDNA and Cas9, or gDNA and TtAgo, In some embodiments, the nucleic acid and protein are present as nucleic acid-protein complexes.

The same principle applies for the methods of the invention, i.e. the cell may be contacted with two, three, four, five or more molecules of interest. For example, a TALEN protein and a nucleic acid and optionally a lipid may be transduced into a cell simultaneously.

The concentration of the molecule of interest for transduction depends upon the molecule of interest, the cell, and the purpose of transduction. The skilled person can determine the appropriate concentration. In some embodiments, the molecule of interest for transduction is added at millimolar, micromolar or nanomolar concentrations. In some embodiments, the molecule of interest is added to the transduction buffer at a concentration of between about 1 nM and about 1 mM, between about 10 nM and about 500 μM, between about 10 nM and about 100 μM, between about 10 nM and about 50 μM, between about 10 nM and about 10 μM, between about 10 nM and about 1 μM, between about 10 nM and about 500 nM, between about 10 nM and about 100 nM, between about 50 nM and 100 nM, between about 100 nM and about 500 nM, between about 100 nM and about 1 μM, between about 100 nM and about 5 μM, between about 100 nM and about 10 μM, between about 100 nM and about 50 μM, or between about 100 nM and about 100 μM. Where the molecule of interest is a protein, the concentration may be between about 10 nM and about 1 mM, for example between 10 nM and 100 μM, or between about 100 nM and about 1 μM. In some embodiments, the concentration of the molecule of interest is between about 1 μM and about 5 μM, for example about 1 μM or about 5 μM.

In some embodiments, the molecule of interest is not modified. For example, in some embodiments, the molecule of interest is not associated with a carrier molecule and/or does not comprise a tag, wherein the tag facilitates transduction into the cell. For example, in one embodiment, the protein of interest is not tagged with a cell penetrating peptide or TAT protein. In a further example, in one embodiment nucleic acid is naked nucleic acid. It is surprising that using methods of the invention, any molecule of interest can be transduced into a cell without modification. In some embodiments, the molecule of interest is not in a complex with the transduction compound. In some embodiments, the molecule of interest is not in or associated with a micelle or a liposome. In some embodiments, the molecule of interest is not in a complex with the transduction compound. In some embodiments, the molecule of interest is not in or associated with a viral vector.

The inventors have shown that the methods and buffers described herein can be used to transduce viruses into cells (for example, see Example 9). Therefore, in some embodiments, the invention provides a method for transducing a virus into a cell or population of cells, wherein the method comprises contacting a cell or population of cells with a transduction buffer and contacting the cell or population of cells with a virus. In one embodiment, the invention provides a method for transducing a virus into a cell or population of cells, wherein the method comprises contacting a cell or population of cells with a transduction buffer according to the present invention and contacting the cells with a virus. The transduction buffer may be mixed with the virus before administration to the cells or may be administered simultaneously, sequentially or separately from the virus.

In addition, the inventors have also observed that in the presence of transduction buffer a population of cells shrinks creating space between the cells and making the cells more accessible. This could further enhance the transduction of viruses into cells. Thus, in some embodiments, the method of transducing a molecule of interest into cells involves reduction in the size of the cells and/or increase in space between cells. Without wishing to be bound by theory, the inventors hypothesise that the shrinking is a result of the hyperosmolality induced by the salt in the transduction buffer. Nevertheless, the macropinocytosis mechanism already described above is still likely to play an important role in enhancing transduction of viruses into cells.

Cell for Transduction

The transduction method can be used to transduce a molecule of interest into any cell, including a primary cell or a stem cell (including their derivatives, such as progenitor cells), a normal healthy cell or a diseased cell.

In a preferred embodiment, the cell involved in the transduction method is a mammalian cell. This is because the transduction buffer and method are thought to be particularly well suited to the mammalian macropinocytosis system (see below for more details). However, it is also envisaged that in some embodiments, the methods might be useful for transducing molecules into other animal cells, plant cells, yeast cells, insect cells, or bacterial cells. Thus, in some embodiments, the cell is an animal cell, a plant cell, a yeast cell, an insect cell or a bacterial cell. In some embodiments, the cell is not a bacterial cell.

In preferred embodiments, the mammalian cell is a human, primate, rodent (e.g. mouse or rat), rabbit, dog, cat, horse, cow or pig cell. These mammals are useful for research purposes and/or may benefit from treatment or diagnosis comprising transduction buffers and methods of the invention. In some embodiments, the cell is a non-human cell.

In some embodiments the cell is in vivo, optionally in situ. For example, when treating or diagnosing a medical condition, the molecule of interest could be administered directly and locally in combination with the transduction buffer to an organism or tissue in need thereof.

In an alternative embodiment, the cell is in vitro. For example, the cell may be in a culture medium, wherein the culture medium optionally supports the maintenance, differentiation and/or expansion of the cell.

In some embodiments, the cell is derived from an established cell line, such as an established human cell line. In some embodiments, the established cell line is an immortalised cell line. In other embodiments the cell line is a primary cell line. Several prior art methods for transduction do not work in primary cells (see background section). Therefore, it is surprising that the transduction buffers and methods of the present invention can be used to transduce molecules into primary cells.

Examples of established human cell lines suitable for use in the context of the invention include but are not limited to HeLa, ESTDAB database, DU145 (prostate cancer), Lncap (prostate cancer), MCF-7 (breast cancer), MDA-MB-438 (breast cancer), PC3 (prostate cancer), T47D (breast cancer), THP-1 (acute myeloid leukemia), COS7 (immortalised CV-1 cells from kidney tissue), U87 (glioblastoma), SHSY5Y human neuroblastoma cells, cloned from a myeloma, Saos-2 cells (bone cancer). The ESTDAB database (www.ebi.ac.uk/ipd/estdab/directory.html) and National Cancer Institute (NCI-60) provide further examples of cancer cell lines which are suitable for use with the present invention. In some embodiments, the established cell line is a primate cell line, such as Vero (African green monkey Chlorocebus kidney epithelial cell line initiated in 1962). In some embodiments, the established cell line is a rodent cell line, such as GH3 (pituitary tumor), PC12 (pheochromocytoma) or MC3T3 (embryonic calvarium). Other mammalian cell lines suitable for use with the transduction buffer and methods disclosed herein include the Madin-Darby canine kidney (MDCK) epithelial cell line, Chinese hamster ovary (CHO) cell line and Caco-2 cells. In some embodiments the cell is a KBM7 cell.

In some embodiments, the cell is a primary cell. A primary cell or cell line is derived from a cell taken directly from a living organism, and has not been immortalized. In other words, a primary cell or cell line is genetically and phenotypically stable.

In some embodiments, the cell is a stem cell or a cell derived by differentiation of a stem cell. In some embodiments the stem cell is a pluripotent stem cell, such as an embryonic stem cell, optionally a human embryonic stem cell. In some embodiments, the cell is not a human embryonic stem cell. In some embodiments, the stem cell is not obtained by methods that involve the use of human embryos for commercial or industrial purposes. In some embodiments, the stem cell is not obtained by methods that necessarily involve the destruction of a human embryo. In some embodiments the stem cell is a murine embryonic stem cell. In other embodiments, the stem cell is an adult stem cell, such as a neural, adipose or hematopoietic stem cell. In some embodiments the cell is a murine or human neural stem cell, neuron cell or glia cell. In some embodiments the stem cell is an induced pluripotent stem cell. In some embodiments the cell is a somatic cell or a germ cell.

In some embodiments, the cell is a cell belonging to the immune system, such as a T cell, B cell or leukocyte, including but not limited to a phagocyte (macrophage, neutrophil, or dendritic cell), mast cell, eosinophil, basophil, and natural killer cell. In some embodiments, the cell is a dendritic cell.

In some embodiments the cells for transduction are cultured in an atmosphere comprising between about 4% and about 10% $CO_2$, about 5% and about 9% $CO_2$, about 6% and about 8% $CO_2$, preferably about 5% $CO_2$.

In all embodiments, where the disclosure refers to a "cell", it refers to a single cell and also applies to a "cell population", for example of 2 or more, 10 or more, 100 or more, 1000 or more, $10^4$ or more, $10^5$ or more, $10^6$ or more, $10^7$ or more, $10^8$ or more cells.

Thus, the invention also provides a transduced cell or population of cells obtained or obtainable using the transduction buffer and/or the methods described herein. The invention provides a cell or population of cells comprising a molecule of interest wherein the molecule of interest has been transduced into the cell using the transduction buffer and/or methods described herein.

Cell Viability

In a preferred embodiment, the transduction buffer and methods of the invention have minimal impact on the viability of the cells. Cell viability is important for many applications of the transduced cells, including but not limited to transplantation of transduced cells; the use of transduced cells to generate genetically modified embryos for research models; and the use of transduced cells in research etc (see section on "Uses of the invention"). One measure of cell viability is cellular proliferation (e.g the BrdU incorporation assay, as described in Example 5). Continuing cellular proliferation demonstrates that the normal cell cycle is still functioning.

Assays to measure proliferation, viability and cytotoxicity are known in the art and available commercially (e.g. from Sigma Aldrich). Such assays can be used to monitor the response and health of cells in culture after treatment with various stimuli. The proper choice of an assay method depends on the number and type of cells used as well as the expected outcome. Assays for cell proliferation may monitor the number of cells over time, the number of cellular divisions, metabolic activity or DNA synthesis. Cell counting using viability dyes such as trypan blue or calcein-AM can provide both the rate of proliferation as well as the percentage of viable cells. 5(6)-Carboxyfluorescein diacetate N-succinimidyl ester (CFSE) is a popular choice for measuring the number of cellular divisions a population has undergone. Upon entering the cell, CFSE is cleaved by intracellular esterases to form the fluorescent compound and the succinimidyl ester group covalently reacts with primary amines on intracellular proteins. Upon division, the fluorescence intensity of each daughter cell is halved which allows for the simple detection of the number of cell divisions by flow cytometry. Assays that measure metabolic activity are suitable for analyzing proliferation, viability, and cytotoxicity. The reduction of tetrazolium salts such as MTT and XTT to coloured formazan compounds or the bioreduction of resazurin only occurs in metabolically active cells. Actively proliferating cells increase their metabolic activity while cells exposed to toxins will have decreased activity.

An example of an assay that measures proliferation is the BrdU incorporation assay, which measures BrdU incorporation into cellular DNA during cell proliferation.

In a preferred embodiment, when the cells being subjected to the transduction methods of the invention are subjected to the BrdU incorporation assay, more than 50%, more than 55%, more than 60%, more than 65%, more than 70%, more than 75%, more than 80%, more than 85%, more than 90%, more than 95%, more than 99% or all cells demonstrate incorporation of BrdU into cellular DNA of the cells.

Viability of cells can also be assessed by staining for markers of apoptosis (e.g. annexin V, caspases activators etc) or by assessing propidium iodide uptake as a sign of cell death. Cells that do not stain positive for such markers of apoptosis (e.g. AnnexinV, caspase activation) or that do not take up propidium iodide are viable cells.

In a preferred embodiment, more than 50%, more than 55%, more than 60%, more than 65%, more than 70%, more than 75%, more than 80%, more than 85%, more than 90%, more than 95%, more than 99% or all cells are viable after one, two, three, four or five rounds of transduction, as assessed using annexin V staining.

Transduction of certain molecules can trigger cell death pathways in cells. For example, foreign DNA/RNA introduced into cells can trigger the interferon response pathway which can result in cell death. In some embodiments, the methods and/or transduction buffer of the invention uses/comprises one or more inhibitors of cell death Inhibitors of cell death, such as inhibitors of the interferon response pathway, can help to prevent the apoptotic response and thus improve cell survival. Such inhibitors can act at several levels of the interferon response pathway, for example, they may be inhibitors of extracellular binding of interferon to its receptor, inhibitors of intracellular interferon signalling, inhibitors of downstream effectors of the Interferon response (e.g. RNaseL, PKR, Jak/STAT signalling, Mx inhibitors). Other types of inhibitors that may be used include proteins or small molecule compounds that can ameliorate detection of foreign RNA/DNA in the cell, such as the Influenza A NS1 protein. A combination of inhibitors can also be used. Examples of such inhibitors are known in the art. The inventors, for example, used interferon inhibitor protein B18R (Nat Protoc. 2013 March; 8(3):568-82. doi: 10.1038/nprot.2013.019. Epub 2013 Feb. 21. Reprogramming human fibroblasts to pluripotency using modified mRNA. Mandal PK1, Rossi D J; and Cell. 1995 May 19; 81(4):551-60. Vaccinia virus encodes a soluble type I interferon receptor of novel structure and broad species specificity. Symons JA1, Alcami A, Smith G L.). Therefore, in some embodiments, the transduction buffer further comprises one or more inhibitor of cell death, preferably an inhibitor of the interferon response pathway. In some embodiments the inhibitor is added before, during and/or after transduction. In some embodiments the inhibitor is used at a concentration of about 10 ng/ml to about 1000 ng/ml, about 100 ng/m to about 500 ng/ml, about 200 ng/ml to about 400 ng/ml, about 200 ng/ml to about 300 ng/ml, or about 250 ng/ml. In some embodiments, the inhibitor is B18R, which is preferably used at about 250 ng/ml, before (e.g. 3 hours before) transduction, during transduction and after (e.g. 48 hours after) transduction. Such inhibitors are particularly useful when transducing nucleic acid molecules into cells (for example when transducing small inhibitory RNAs (siRNAs) or small guide nucleic acid molecules, such as sgRNAs or gDNAs, into cells with a nuclease, such as Cas9, in the context of a gene editing system) but may be useful for all types of molecules of interest, particularly those that might activate cell death pathways, particularly via the interferon response pathway. They are compatible with all transduction buffers and protocols described herein.

Efficiency/Time for Transduction

In order to transduce a molecule of interest into a cell, the molecule of interest and cell are in contact for a sufficient length of time for the molecule to transduce into the cell.

Generally, the amount of uptake into the cell correlates with the amount of time the cell is in contact with the transduction buffer and molecule of interest. This is known herein as the "incubation time" or the "transduction time".

In a preferred embodiment, the incubation time is between about 1 and about 24 hours, for example between about 2 and about 12 hours or between about 2 and about 5 hours. In some embodiments the incubation time is at least 30 minutes, at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours or more than 13 hours. In some embodiments the incubation time is less than 48 hours, less than 24 hours, less than 20 hours, less than 15 hours, less than 13 hours, less than 12 hours, less than 11 hours, less than 10 hours, less than 9 hours, less than 8 hours, less than 7 hours, less than 6 hours, less than 5 hours, less than 4 hours, less than 3 hours, less than 2 hours, or less than 1 hour. In some embodiments the transduction time is 3 hours. In some embodiments the transduction time is 12 hours. In some embodiments, the incubation time is between about 30 minutes and about 1 hour. In some embodiments, the incubation time is between about 1 minute and about 30 minutes, between about 30 minutes and about 60 minutes, between about 30 minutes and about 90 minutes, between about 60 minutes and about 90 minutes, or less than about 90 minutes, or less than about 60 minutes.

The rate of transduction will depend upon the cell type (and the efficiency of transduction mechanisms) and the molecule of interest to be transduced (its size, charge, hydrophobicity etc). The inventors have also shown that the higher the osmolality of the transduction buffer, the greater the rate of transduction. Thus, at higher osmolality, the rate of transduction is typically higher and shorter incubation times are required. Conversely, at lower osmolality, the rate of transduction is lower and longer incubation times are required to achieve equivalent levels of transduction.

However, as mentioned elsewhere in this disclosure, hyperosmolality can negatively affect cell viability and therefore, the incubation time must be balanced with osmolality and cell viability. By adding osmoprotectants, the cell viability is protected and thus higher osmolalities and shorter incubation times can be used. The optimum osmolality, incubation time and concentration of osmoprotectants can be determined by the skilled person using trial and error and optimisation tests (for example, see FIGS. 3A-3E). For example, in some embodiments in MEF cells, using an osmolality of between 650 and 800 mOsm/kg and including glycerol and glycine in the transduction buffer, the incubation time for transduction of beta-lactamase may be 3 hours. In an alternative embodiment in MEF cells, using an osmolality of only 450 to 650 mOsm/kg (i.e. a lower osmolality) and including glycerol and glycine, the incubation time required for optimal transduction may be longer, e.g. closer to 12 hours. Similarly, in some embodiments in mES cells, using an osmolality of between 450 and 600 mOsm/kg and including glycerol and glycine in the transduction buffer, the incubation time for optimal transduction of beta-lactamase may be about 12 hours.

Transduction can be detected qualitatively or quantitatively using reporter constructs known in the art and available commercially, e.g. a luciferase or a GFP reporter construct, wherein levels of fluorescence correspond to levels of expression (see the Examples section for more details).

In some embodiments, the method comprises one round of transduction. However, in other embodiments, multiple rounds of transduction may be desirable. For example, in some embodiments 2, 3, 4, 5, 6, 7, 8, 9, 10 or more rounds of transduction are carried out on the same cells. Each round of transduction may involve transduction of the same molecule or of different molecules of interest.

In between each round of transduction, there may be a "recovery period" of at least 1, at least 2, at least 3, at least 4, at least 5, at least 6, at least 7, at least 8, at least 9, at least 10, at least 11 or at least 12 hours. In some embodiments, the recovery period is at least 10, at least 20, at least 30, at least 40 or at least 50 minutes.

In some embodiments there is no recovery period, or there is a recovery period of less than 24 hours, less than 12 hours, less than 6 hours, less than 3 hours, less than 1 hour, less than 30 minutes or less than 10 minutes.

During the recovery periods, the transduction buffer is removed from the cells and the cells are typically cultured in cell culture medium suitable for the particular cell type.

Exemplary Transduction Buffers and Methods

Non-limiting examples of transduction buffers and methods are provided below. It is to be understood that any combination of compatible embodiments described herein can be used for a transduction buffer or method for transduction comprising a transduction buffer. Some examples of combinable embodiments are provided below.

In some embodiments, there is provided a method for transducing a molecule of interest into a cell, wherein the method comprises contacting the cell with a molecule of interest and contacting the cell with a transduction buffer comprising a salt which binds to and/or activates a sodium/hydrogen transporter protein, a transduction compound and optionally glycine and/or glycerol as osmoprotectants, wherein the transduction compound is a small molecule compound. In some embodiments, the transduction compound is a small molecule compound and is not a detergent. In some embodiments, the transduction compound is a small molecule compound and is not a detergent and is a zwitterion or a non-zwitterionic compound with a group that is bioisoteric to a negatively charged functional group. In some embodiments, the transduction compound is a small molecule compound and is not a detergent and is a zwitterion. In some embodiments the transduction compound is a small molecule compound and is a zwitterion or a non-zwitterionic compound with a group that is bioisoteric to a negatively charged functional group.

In some embodiments, there is provided a method for transducing a molecule of interest into a cell, wherein the method comprises contacting the cell with a molecule of interest and contacting the cell with a transduction buffer comprising a salt which binds to and/or activates a sodium/hydrogen transporter protein, a transduction compound selected from FIGS. 7A-7D and optionally glycine and/or glycerol as osmoprotectants.

In some embodiments, there is provided a method for transducing a molecule of interest into a cell, wherein the method comprises contacting the cell with a molecule of interest and contacting the cell with a transduction buffer comprising a salt, wherein the salt is sodium, lithium, potassium, caesium or rubidium chloride or gluconate, a transduction compound selected from FIGS. 7A-7D, and optionally glycine and/or glycerol as osmoprotectants.

In some embodiments, there is provided a method for transducing a molecule of interest into a cell, wherein the method comprises contacting the cell with a molecule of interest and contacting the cell with a transduction buffer comprising sodium chloride, a transduction compound selected from FIGS. 7A-7D, and optionally glycine and/or glycerol as osmoprotectants.

In some embodiments, there is provided a method for transducing a molecule of interest into a cell, wherein the method comprises contacting the cell with a molecule of interest and contacting the cell with a transduction buffer comprising rubidium chloride, a transduction compound selected from FIGS. 7A-7D, and optionally glycine and/or glycerol as osmoprotectants.

In some embodiments, there is provided a method for transducing a molecule of interest into a cell, wherein the method comprises contacting the cell with a molecule of interest and contacting the cell with a transduction buffer comprising a salt which binds to and/or activates a sodium/hydrogen transporter protein, a transduction compound according to Formula I or Formula II, and optionally glycine and/or glycerol as osmoprotectants.

In some embodiments, there is provided a method for transducing a molecule of interest into a cell, wherein the method comprises contacting the cell with a molecule of interest and contacting the cell with a transduction buffer comprising a salt, wherein the salt is sodium, lithium potassium, caesium or rubidium chloride or gluconate, a transduction compound according to Formula I or Formula II, and optionally glycine and/or glycerol as osmoprotectants.

In some embodiments, there is provided a method for transducing a molecule of interest into a cell, wherein the method comprises contacting the cell with a molecule of interest and contacting the cell with a transduction buffer comprising sodium chloride, a transduction compound according to Formula I or Formula II, and optionally glycine and/or glycerol as osmoprotectants.

In some embodiments, there is provided a method for transducing a molecule of interest into a cell, wherein the method comprises contacting the cell with a molecule of interest and contacting the cell with a transduction buffer comprising a salt which binds to and/or activates a sodium/hydrogen transporter protein, GABA as a transduction compound and optionally glycine and/or glycerol as osmoprotectants.

In some embodiments, there is provided a method for transducing a molecule of interest into a cell, wherein the method comprises contacting the cell with a molecule of interest and contacting the cell with a transduction buffer comprising a salt, wherein the salt is sodium, lithium, potassium, caesium or rubidium chloride or gluconate, GABA as a transduction compound and optionally glycine and/or glycerol as osmoprotectants.

In some embodiments, there is provided a method for transducing a molecule of interest into a cell, wherein the method comprises contacting the cell with a molecule of interest and contacting the cell with a transduction buffer comprising sodium chloride, GABA as a transduction compound and optionally glycine and/or glycerol as osmoprotectants.

In some embodiments, the transduction buffer has an osmolality of at least 250 mOsm/kg, at least 300 mOsm/kg, or at least 700 mOsm/kg. In some embodiments, the transduction buffer has an osmolality of at least 400 mOsm/kg. In some embodiments, the transduction buffer has an osmolality of at least 1000 mOsm/kg. In some embodiments, the transduction method involves the step of inducing osmotic pressure across the cell membrane. In some embodiments, the transduction buffer is hypertonic with respect to the culture media in which the cell was maintained prior to transduction and/or with respect to the cell cytosol.

In some embodiments, the transduction method involves activation of macropinocytosis and/or activation of endosomal lysis. In some embodiments, the transduction method (as a whole) has 20% or more, 30% or more, 40% or more, 50% or more, 60% or more, 70% or more, 80% or more, 90% or more, 100% or more, 110% or more, 120% or more, 150% or more, 200% or more, 300% or more, 400% or more, 500% or more, 600% or more, 700% or more or 800% or more transduction efficiency, e.g. wherein the method involving compound #1 as shown in FIGS. 7A-7D is a control (i.e represents 100% transduction efficiency).

In a preferred embodiment, more than 75% of the cells are viable after transduction, as assessed using annexin V staining.

In some embodiments, the transduction buffer further comprises one or more of a GABA agonist, a growth factor, a Tat-HA2 fusion peptide and a sodium/hydrogen transporter enhancer.

In some embodiments, the method comprises the step of obtaining and/or maintaining the cells in culture medium prior to transduction. In some embodiments, the method further comprises contacting the cell with a culture medium during transduction, preferably in the absence of antibiotics.

In some embodiments, the transduction buffer comprises a cell-permeable antibiotic, such as for example doxycycline or tetracycline.

In some embodiments, the transduction buffer additionally comprises one or more (e.g. 1, 2, 3, 4 or 5) of a viscosity enhancer, growth factor, cytokine, neurotransmitter, or agonists thereof, such as a GABA agonist.

In some embodiments, the method comprises contacting the cell with the transduction buffer for a period of at least 30 minutes, preferably for about 12 hours. In some embodiments the method involves at least two rounds of transduction i.e. the cell is contacted by the transduction buffer and the molecule of interest for at least two continuous periods of at least 30 minutes with a recovery period in between.

In some embodiments, the cell is a primary cell.

In one embodiment the transduction buffer comprises sodium chloride, a transduction compound selected from FIGS. 7A-7D, and glycine and/or glycerol. The compound selected from FIGS. 7A-7D is at a concentration of about 5 to about 50 mM. The glycine is at a concentration of about 15 mM. The glycerol is at a concentration of about 30 mM. The sodium chloride may be added to adjust the osmolality to approximately 700 mOsm/Kg. The final volume may be made up using water or culture medium, such as DMEM medium. The molecule of interest for transduction is added at an appropriate concentration depending on the molecule type. In one non-limiting example, the concentration of the molecule of interest may be between about 10 nM and about 100 μM. In some embodiments, the transduction buffer further comprises a Tat-HA2 fusion peptide, which may be at a concentration of about 5 μM. In some embodiments, the buffer further comprises a GABA agonist. In some embodiments, the transduction buffer further comprises one or more growth factors and/or cytokines and/or neurotransmitters and/or small molecule agonists of these signalling pathways.

In another embodiment, the transduction buffer comprises sodium chloride, a transduction compound selected from FIGS. 7A-7D, and glycine and/or glycerol. The compound selected from FIGS. 7A-7D is at a concentration of about 50 to about 500 mM. The glycine is at a concentration of about 300 mM. The glycerol is at a concentration of about 150 mM. The sodium chloride may be added to adjust the osmolality to approximately 1000 mOsm/Kg. The final volume may be made up using water or culture medium, such as DMEM medium. The molecule of interest for transduction is added at an appropriate concentration depending on the molecule type. In one non-limiting example, the concentration of the molecule of interest may be between about 10 nM and about 100 μM. In some embodiments, the transduction buffer further comprises a Tat-HA2 fusion peptide, which may be at a concentration of about 5 μM. In some embodiments, the buffer further comprises a GABA agonist. In some embodiments, the transduction buffer further comprises one or more growth factors and/or cytokines and/or neurotransmitters and/or small molecule agonists of these signalling pathways.

In some embodiments the transduction compound is an NDCB or an NDSB, such as NDSB-201 or a compound selected from compounds #42, #1, #45, #43, #44, #15, #10, #11, #28, #37 and #46 shown in FIGS. 7A-7D.

In some embodiments, the transduction method comprises contacting mESCs, iPSCs, human iPSC-derived glial cells or neurons with the molecule of interest. In some embodiments the molecule of interest is a protein at a concentration of between about 1 nM and about 100 μM, for example about 1 μM or about 5 μM. In some embodiments the protein of interest is CRE. The transduction buffer may comprise a salt and a transduction compound, and optionally additionally comprises 5 μM Tat-HA2 fusion peptide and optionally an osmoprotectant. In a further embodiment, the method involves two sequential rounds of transduction, wherein the cells are contacted with the protein of interest, such as CRE, for 12 hours in each round of transduction, with a 12-hour recovery period between each round of transduction.

Mouse embryonic stem (mES) cells can be transduced using the following protocol (the "transduction protocol" in the examples): 75,000 mES cells per well are seeded onto gelatin-coated plates using mES media; on the following day, the molecule of interest (e.g. a protein, such as Cre protein) in 5× transduction buffer is diluted with mES media (e.g. by 1:5); the complete mixture is then added to the cell; after about 12 hrs, the transduction media is replaced by mES media.

Mouse Neural Stem cells can be transduced using the following protocol (the "transduction protocol" in the examples): neurospheres are plated with neuronal stem cells media; next, the molecule of interest (e.g. 20 μl of protein, such as. CRE) in 5× transduction buffer is added to the cells and mixed carefully; about 12 hrs later, transduction media is replaced by fresh neural stem cell media.

Human iPS cells can be transduced using the following protocol (the "transduction protocol 12/500" in the examples). Cells are passaged by mechanical dissociation into small clumps e.g. following mTeSR1 or TeSR-E8 manufacturer's instructions and seeded on a matrigel coated plate to reach about a 50% confluency. The following day, the molecule of interest (e.g. a protein, such as CRE protein)

in 5× transduction buffer is diluted (e.g. 1:5) with mTeSR1 or TeSR-E8. The complete mixture is then added to cells. After 12 hrs of transduction, media is replaced by fresh mTeSR1 or TeSR-E8 media and cells can be incubated for 24-48 hrs.

In some embodiments, the transduction buffer is used to transduce DNA and lipids into a cell (for example, see Example 7 and FIG. 12). In some embodiments, the transduction buffer comprises plasmid DNA and a lipid. For example, the transduction buffer comprises 100 ng plasmid DNA, 0.8 μl Lipofectamine LTX lipid reagent, 0.1 μl plus reagent (Life Technologies) and 20 μl of 5× transduction buffer. The final transduction buffer comprises 100 μl mESC media and Leukemia Inhibitory Factor (LIF). LIF is used in the context of ES cells to maintain the stem cell state.

In some embodiments, the transduction buffer is used to transduce DNA and protein into a cell (for example, see Example 8 and FIG. 13). For example, in some embodiments, the transduction buffer comprises 100 ng plasmid DNA, 0.8 μl Lipofectamine LTX lipid, 0.1 μl plus reagent (Life Technologies) and 20 μl CRE protein in 5× transduction buffer. The final transduction buffer comprises 1000 mESC media and LIF.

In some embodiments, the transduction buffer enhances viral incorporation into cells, such as human iPS cells (for example, see Example 9 and FIG. 14). For example, in some embodiments, the transduction buffer additionally comprises concentrated viral stock, polybrene, and human iPSC culture media.

In some embodiments, the methods of transduction are suitable for transducing proteins with low solubility (see Example 10). In some embodiments, a transduction buffer suitable for transducing proteins with low solubility has an osmolality of about 1000 mOsm/kg, comprises a transduction compound at a concentration of about 250 mM, and comprises an osmoprotectant at a concentration of about 150-300 mM.

In some embodiments, the transduction buffer comprises 500 mM NaCl, 250 mM NDSB-201, 300 mM glycine, 150 mM Glycerol in D-MEM N2/B27 and LIF. This is the "2/1000" transduction buffer. It is suitable for transducing proteins with low solubility.

In one embodiment is provided a method for transducing mES cells. The method for transducing mES cells comprises adding 80 μl of 2/1000 transduction buffer to 20 μl CRE protein (or other molecule of interest) in 5× transduction buffer 12/500. The cells are incubated for 2 hrs. Following incubation, the transduction buffer is replaced with mESC media.

In some embodiments, human iPS cells can be transduced with TALEN proteins (for example, see Example 11). In some embodiments, human iPS cells are incubated with about 2 μM TALEN protein for about 12 hs. For example, about 20 μl TALEN protein in 5× transduction buffer is mixed with about 80 μl of human iPS cell media.

In some embodiments, the transduction buffer can be used for simultaneous transduction of proteins and large molecules into a cell (for example, see Example 12). For example, in one embodiment is provided a method for transducing Dextran and BSA into MEFs. The method comprises incubating the cells with 5 μg/ml of Dextran and 1 μg of BSA in 1× transduction media (protocol 3/700) for 30 min. Subsequently, cells are washed twice in 1× transduction buffer.

In some embodiments, the transduction buffer and methods can be used for transduction of a protein that is capable of modifying a nucleic acid or of a gene editing system into cells. In some embodiments, there is provided a method for transducing a protein that is capable of modifying a nucleic acid or a gene editing system, such as a Cas9 nuclease and an sgRNA, into a cell, wherein the method comprises incubating the cell with about 250 mM of a transduction compound (e.g. compound #20) at an osmolality of about 1250 mOsmol/kg, for about 60 minutes. In some embodiments, two subsequent rounds of transduction may be used. In a preferred embodiment, cells are incubated with about 250 ng/ml of B18R protein before (e.g. about 3 hours before) transduction, and/or during transduction and/or after (e.g. about 48 hours after) transduction. In some embodiment, glycine (e.g. 15 mM) and/or glycerol (e.g. 30 mM) are included as osmoprotectants. The skilled person will understand that other suitable protocols may alternatively be used which fall within the scope of the invention.

The invention also provides a method for modifying a nucleic acid, such as a genetic sequence, in a cell, wherein the method comprises contacting said cell with a protein capable of modifying a nucleic acid and a transduction buffer, wherein the transduction buffer comprises (i) a transduction compound, (ii) a salt or an activator/enhancer of a sodium-hydrogen transporter, and preferably (iii) an osmoprotectant. In some embodiments, the protein capable of modifying a nucleic acid is targeted to a specific target sequence, for example wherein the protein is a zinc finger nucleaseor a TALEN, Cas9, a Cas9 analog, a DNA-targeted FokI-nuclease-associated protein, a Cascade complex, a TtAgo protein or other Argonaute protein or their derivatives. In some embodiments, the cell is further contacted with a guide molecule to direct the protein to a target genetic sequence. In some embodiments, the osmolality is adjusted to between about 1000 mOsm/kg and about 1500 mOsm/kg, preferably about 1250 mOsm/kg. In some embodiments, the transduction compound is used at a concentration of about 200 nM to about 400 nM, preferably about 250 mM. In some embodiments, transduction is carried out for about 1 hour to about 24 hours or from about 1 hour to about 12 hours. In some embodiments, the transduction buffer further comprises an inhibitor of the interferon response pathway, for example, B18R. In some embodiments, the cell is a stem cell, such as an iPS cell or a stem cell line, including for example human stem cell lines. In some embodiments, the osmoprotectant is selected from selected from glycine, glycerol, taurine, glycinebetaine, myo-inositol, glutamine, glutamate, arginine, mannitol and trehalose.

In some embodiments, in the method for modifying a nucleic acid, such as a genetic sequence, in a cell, the protein capable of modifying a nucleic acid is present in the cell for less than 10 days, less than 5 days, less than 4 days, less than 3 days, less than 2 days, less than 1 day, less than 12 hours, less than 6 hours, or less than 1 hour. If the protein capable of modifying a nucleic acid is present in the cell for too long, it can start to have damaging off-target effects (i.e. modify non-target sequences). This is often a problem with traditional forms of transfection which involve expression of the protein from an expression plasmid over a number of days.

In some embodiments, the method for modifying a nucleic acid, such as a genetic sequence, in a cell, further comprises isolating or using the modified cell. The invention also provides a modified cell obtainable or obtained by these methods. In some embodiments the modified cell comprises a transduced gene editing system. In some embodiments, the modified cell does not comprise a viral vector. In some embodiments, the modified cell does not comprise a nanoparticle carrier. In some embodiments, the cell does not comprise a cell penetrating peptide.

Pharmaceutical Composition

In some embodiments, the invention provides a pharmaceutical composition comprising the transduction buffer of the invention and a molecule of interest for transduction. In some embodiments, the invention provides a pharmaceutical composition comprising the transduction buffer. In some embodiments, the molecule of interest and transduction buffer components are administered simultaneously or sequentially.

The pharmaceutical composition can include further components in addition to the transduction buffer and a molecule of interest. For example, a pharmaceutical composition will usually include a pharmaceutically acceptable carrier, which can be any substance that does not itself induce the production of antibodies harmful to the patient receiving the composition, and which can be administered without undue toxicity. Suitable pharmaceutically acceptable carriers are well known in the art. Pharmaceutically acceptable carriers can, for example, include liquids such as water, saline, glycerol and ethanol. Auxiliary substances, such as wetting or emulsifying agents, pH buffering substances, and the like, can also be present in pharmaceutical compositions (see Gennaro (2000) Remington: The Science and Practice of Pharmacy. 20th edition, ISBN: 0683306472).

In some embodiments, there is provided a pharmaceutical composition comprising a transduction compound or transduction compound and a protein capable of modifying a nucleic acid, such as a gene editing system.

The pharmaceutical composition may be sterile and/or pyrogen-free.

The invention also provides a container (e.g. vial) or delivery device (e.g. syringe) pre-filled with a pharmaceutical composition of the invention. The invention also provides a process for providing such a container or device, comprising introducing into the container or device a composition of the invention.

The appropriate dose may vary depending upon the health and physical condition of the individual to be treated, age, the taxonomic group of individual to be treated (e.g. human, non-human primate, primate, etc.), the degree of transduction desired, the formulation of the pharmaceutical composition, the treating doctor's assessment of the medical situation, and other relevant factors. The dose may fall in a relatively broad range that can be determined through routine trials.

Compositions of the invention may be prepared in various liquid forms. For example, the compositions may be prepared as injectables, either as solutions or suspensions. Injectables for local sub-cutaneous or intramuscular administration are typical. Injection may be via a needle (e.g. a hypodermic needle), but needle-free injection may alternatively be used.

Compositions may include an antimicrobial. Antimicrobials such as thiomersal and 2-phenoxyethanol are commonly found in pharmaceutical compositions, but it is preferred to use either a mercury-free preservative or no preservative at all.

Compositions may comprise detergent e.g. a Tween (polysorbate), such as Tween 80. Detergents are generally present at low levels e.g. <0.01%. In some embodiments, the buffer does not comprise a detergent. In some embodiments, the method for transduction does not involve the use of a detergent during transduction.

Effective dosage volumes can be routinely established, depending on the purpose of the composition. Typical human dose of the composition might be, for example about 0.5 ml e.g. for intramuscular injection (e.g. local injection into the muscle or tissue of interest). Similar doses may be used for other delivery routes.

The invention also provides a kit comprising a transduction buffer of the invention or a pharmaceutical composition of the invention. The kit may additionally comprise cells and/or molecules of interest for transduction. The kit may also comprise instructions for use. The kit may include the various components of the transduction buffer in one or more separate containers, e.g. 1, 2, 3, 4, 5, 6 or more separate containers. For example, the kit may comprise a container comprising a salt solution, a container comprising the transduction compound, a container comprising the molecule of interest, a container comprising the osmoprotectant and/or a container comprising a diluent or media. In addition the kit may comprise any one or more of the additional other components as described herein, wherein they are suitable for simultaneous, sequential or separate administration with the transduction buffer.

Uses of the Invention

The invention provides the use of the transduction buffer, for transducing a molecule of interest into a cell.

Transduction of molecules into a cell can be useful for both research and therapeutic reasons.

In some embodiments, the transduction buffers and methods of the invention can be used for genetic modification. For example, in some embodiments, transduction of certain enzymes into cells can result in modification of the cell's genome or modification of foreign nucleic acid sequences. For example, the transduced molecule (such as an enzyme) may result in insertion, deletion, substitution, translocation, inversion or modification of one or more (for example a sequence of 2, 3, 4, 5, 6, 7, 8, 9, 10, 20, 30, 40, 50, 60, 70, 80, 90, 100, 200, 300, 400, 500, 600, 700, 800, 900, 1000, 2000, $10^4$, $10^5$, $10^6$, $10^7$ or more) nucleic acids. For example, Cre-Lox recombination is a site-specific recombinase technology widely used to carry out deletions, insertions, translocations and inversions in the DNA of cells (Turan, S.; Galla, M.; Ernst, E.; Qiao, J.; Voelkel, C.; Schiedlmeier, B.; Zehe, C.; Bode, J. (2011). "Recombinase-mediated cassette exchange (RMCE): traditional concepts and current challenges". J. Mol. Biol. 407 (2): 193-221). It allows the DNA modification to be targeted to a specific cell type or be triggered by a specific external stimulus. It is implemented both in eukaryotic and prokaryotic systems. The system consists of a single enzyme, Cre recombinase, which recombines a pair of short target sequences called the Lox sequences. This system can be implemented without inserting any extra supporting proteins or sequences. The Cre enzyme and the original Lox site called the LoxP sequence are derived from a bacteriophage P1. Placing Lox sequences appropriately will allow genes to be activated, repressed, or exchanged for other genes. At a DNA level many types of manipulations can be carried out. The activity of the Cre enzyme can be controlled so that it is expressed in a particular cell type or triggered by an external stimulus, such as a chemical signal or a heat shock. These targeted DNA changes are useful in cell lineage tracing and when mutants are lethal if expressed globally. The Cre-Lox system is very similar in action and in usage to the FLP-FRT recombination system, which involves the recombination of sequences between short flippase recognition target (FRT) sites by the recombinase (Flp) derived from the 2 μm plasmid of *Saccharomyces cerevisiae*. Thus, in some embodiments, the invention provides the use of the transduction buffer in a Cre-Lox or a FLP-FRT recombination system for transducing Cre recombinase or flippase into a cell. The invention also provides a method for transducing a molecule of interest into a cell, wherein the molecule of interest is Cre recombinase or flippase.

In some embodiments, the transduction compound, buffer or method can be used for genetic modification of specific gene sequences, also referred to herein as "gene editing". In some embodiments, the invention also provides a method for modifying a genetic sequence in a cell, wherein the method comprises a transduction method of the invention, and wherein the molecule of interest is a protein capable of modifying a nucleic acid, preferably a specific gene sequence, and optionally is part of a gene editing system. In recent years, two essentially different gene editing systems have been developed that differ in the way they find their specific genomic target sequence. One type, represented by zinc-finger nucleases (ZFNs) and TALENs, uses customizable domains within the nuclease protein itself to recognize specific target DNA sequence in the genome. The other type is represented by the Cas9/CRISPR, Cascade and TtAgo and other Argonaute protein systems, sometimes coupled as fusion protein to a nuclease domain, such as the FokI nuclease domain, which use a common protein (complex) that is the same regardless of the genomic target site, which is targeted to a specific target by an associated nucleotide sequence (such as an sgRNA or gDNA). Traditionally, these gene editing systems have been transfected into cells as nucleic acids encoding the protein/RNA machinery; the transfected nucleic acids are then expressed within the cells. Traditional methods for nucleic acid transfection involve viral vectors, electroporation or carrier nanoparticles or liposomes. These methods hamper clinical applications and are inefficient for certain cell types as explained elsewhere. The inventors have shown by contrast that transduction compounds, buffers and methods described herein are capable of directly delivering proteins and/or nucleic acids into cells (e.g. as part of gene editing systems) allowing rapid, non-viral and highly efficient gene editing. Specifically, they have shown that both "types" of gene editing machinery mentioned above can be transduced using the transduction compounds, buffers and methods of the invention. Thus in some embodiments, the transduction methods of the invention are used for genetic modification, wherein the transduction does not require or does not comprise the use of viral vectors (in particular, does not comprise the use of viral vectors for expressing proteins inside cells), does not require or does not comprise the use of electroporation, does not require or does not comprise the use of carrier nanoparticles and/or does not require or does not comprise the use of liposomes.

In some embodiments, the invention provides a cell obtainable or obtained by the transduction methods of the present invention, for example, wherein the cell does not comprise a viral vector (for example, does not comprise the viral vectors encoding proteins that can modify genes), or for example, wherein the cell does not comprise carrier nanoparticles, micelles or liposomes.

In some embodiments, the molecule to be transduced into a cell is an endonuclease. Endonucleases are enzymes that cut DNA strands at a specific sequence. Transcription activator-like effectors (TALEs) are engineered transcriptional regulators that have been designed to bind a particular desired DNA sequence (Moscou, J & Bogdanove, A J *Science* 326 (5959): 1501, 2009). By combining such an engineered TALE with an endonuclease domain (which cuts DNA strands), one can engineer endonucleases that are specific for any desired DNA sequence. When these restriction enzymes are introduced into cells, they can be used for genome editing in situ, a technique known as genome editing with engineered nucleases.

Transcription activator-like endonucleases (TALENs) can be used to edit genomes by inducing double-strand breaks (DSB), which cells respond to with repair mechanisms (Zhang, F et. al. *Nature Biotechnology* 29 (2): 149-53, 2011). Thus, in some embodiments, the invention provides the use of the transduction buffer in restriction enzyme-based or endonuclease-based (such as TALEN-based) genetic engineering. Accordingly, in some embodiments the molecule of interest to be transduced into a cell is a TALEN. Foreign nucleic acid sequences may also be introduced into the cell by methods of the present invention or by alternative transduction methods. DNA may optionally be introduced into a genome through non-homologous exon joining in the presence of exogenous double-stranded DNA fragments.

Homology directed repair can also introduce foreign DNA at the double-stranded break as the transfected double-stranded sequences are used as templates for the repair enzymes. Thus, TALENs have been used to generate stably modified human embryonic stem cell and induced pluripotent stem cell (iPS cell) clones, to generate knockout *C. elegans*, knockout rats, and knockout zebrafish. Therefore, in some embodiments, genetic modification by TALENs or other transduced molecules, could be used to replace injection techniques currently used for the modification of pre-implantation embryos or blastocysts for the generation of genetically-modified animals (e.g. for the generation of model organisms displaying particular traits or with particular genetic diseases or disorders) (Voncken J W. Methods Mol Biol. 2011; 693:11-36). By coupling other domains onto the TALE backbone, one can also modify or regulate DNA in other ways. For example, the addition of a transactivation domain instead of the endonuclease domain, turns a TALE into a transcriptional activator. The addition of a repressor domain results in a TALE that shuts gene transcription off. Addition of a methylation domain allows DNA methylation at specific sites. Similarly, addition of a histone modification domain (for example histone acetylase) allows histone modification at specific sites etc. These are all envisaged as molecules for use with the invention.

In some embodiments, a protein nuclease and a guide nucleic acid (such as an sgRNA or gDNA) are transduced into the cell simultaneously or sequentially, using transduction compounds, buffers and/or methods of the invention. For example, in some embodiments, a Cas9 nuclease and an sgRNA are transduced into the cell simultaneously or sequentially. Small guide RNAs and guide DNAs can be designed to target a specific DNA sequence and thus this combination can be used for specific gene editing. As mentioned above, this combination is known as the CRISPR/Cas9 system. Other similar systems and alternatives to Cas9 nuclease, include proteins from the Cascade system, TtAgo and other Argonaute proteins, and other FOKI-nuclease associated proteins.

Thus in some embodiments, the invention provides a method, for transducing a gene editing system, such as a TALEN system, a CRISPR/Cas9 system (preferably including systems involving Cas analogs from different species), a FokI nuclease system, a Cascade system, a TtAgo system or other Argonaute protein systems, into a cell. The transduction compounds and buffers described herein can be used for such methods and can allow gene editing in cells, without the need for viral transfection (see comments above).

In some embodiments the nucleic acid targeted by the gene editing system is endogenous nucleic acid, e.g. genomic DNA. In other embodiments, nucleic acid targeted by the gene editing system is exogenous nucleic acid, which may, for example, be transduced into the cell with the gene editing system as part of the transduction method.

In some embodiments, such gene editing systems can be used to generate targeted gene mutations including but not limited to monoallelic or biallelic gene knockouts. For example, see Example 14 where the inventors demonstrated bialleic WDR85 gene disruption. When transduced into the cells using the methods of the invention, (for example, instead of using prior art viral transfection methods), the gene editing systems result in highly efficient monoallelic or biallelic gene knockouts. Thus, in some embodiments, the methods of the invention result in at least 1%, at least 2%, at least 5%, at least 10%, at least 20%, at least 30%, at least 40%, at least 50%, at least 60%, or at least 70% monoallelic or biallelic gene modification (or knockout).

Gene editing can also be used to study gene functions in animals and for gene therapy in animals, including humans. It is also useful in the field of synthetic biology for engineering cells and organisms to perform novel functions. In addition, gene functions can be studied modified cell lines, such as stem cell lines. Therefore, in some embodiments, the transduction compounds, methods or buffers of the invention, particularly when used in combination with the gene editing embodiments, can be used to study gene function, for gene therapy or for synthetic biology.

In some embodiments, in such methods, enzymes such as those described above are transduced into the embryonic or blastocyst cell to genetically modify the cell, prior to implantation into the animal. Thus in some embodiments, the transduction buffer and methods of the invention could be used to generate model organisms, such as knockout organisms. In other embodiments, it is contemplated that the transduction buffer and methods of the invention could be used for treating genetically inherited disorders in humans, e.g. at the human embryo or blastocyst stage (e.g. pre-implantation genetics). The invention thus provides a method for transducing a molecule of interest into a cell wherein the molecules of interest are nucleic acids and/or enzymes which modify nucleic acids, and optionally wherein the cell is an embryonic or blastocyst cell.

In some embodiments, the genetic modification involves the integration of foreign DNA into the host genome, wherein the foreign DNA is the molecule of interest that is transduced into a cell using the methods of the present invention. However, to avoid aberrant integration and genome disruption, in some embodiments the genetic modification involves a non-integrative approach, i.e. the modified nucleic acid is not integrated into the genome.

The transduction buffer and methods of the invention could also be used to generate iPS cells, either by genetically modifying cells to express certain transcription factors involved in pluripotent stem cell maintenance, or by transducing the transcription factors directly into the cells. Examples of transcription factors involved in the induction of pluripotency include but are not limited to OCT2/3/4, SOX2, KLF4, C-MYC, N-MYC, NANOG, ESRRB and LIN28.

In some embodiments, the invention provides a transduction buffer or pharmaceutical composition, for use in therapy, prophylaxis or diagnosis.

The invention also provides methods for therapy or diagnosis comprising transducing a molecule of interest into a cell. The cell may be an in vivo cell, in which case the treatment is a direct treatment. Alternatively, the cell may be transduced in vitro, e.g. for in vitro diagnosis. Alternatively, the cell may be transduced in vitro prior to transplantation of the cell into a patient. The transplantation may be autologous or allogenic, i.e. the transduced cell may be transplanted back into the same patient that it was taken from (autologous) or into a different person (allogenic). In a preferred embodiment the transplantation is autologous.

Biological drugs (also known as biologics) including monoclonal antibodies, cytokines, tissue growth factors and therapeutic proteins are becoming increasingly important alternatives to chemical small molecules for use in therapy. However, there are a number of difficulties associated with biological drugs, in particular relating to their delivery to the target of interest. The transduction buffers and methods of the present invention could be used to improve delivery of biologics to cells. For example, in some embodiments the molecule of interest in the methods of the invention is a biologic, for example selected from a monoclonal antibody, cytokine, tissue growth factor and therapeutic protein. The cell of interest may be transduced in vitro and transplanted back into the patient, or the cell may be transduced in vivo.

In some embodiments there is provided a protein that modifies a nucleic acid, for example a gene editing system (such as ZNF, TALEN, CRISPR/Cas9, the Cascade system, TtAgo and other Argonaute systems, and other FOKI-nuclease associated proteins), for use in therapy. In some embodiments, said therapy comprises a method of transducing a molecule into a cell according to the invention. A number of diseases and conditions can be treated by transduction of proteins that modify a nucleic acid, for example gene editing systems, and it would be clear to the skilled person which diseases or conditions can be treated. Conditions and diseases treatable by transduction of a protein that modifies a nucleic acid, for example a gene editing system, include but are not limited to genetic diseases such as, sickle cell disease, Leber's congenital amaurosis, X-linked SCID, ADA-SCID, adrenoleukodystrophy, chronic lymphocytic leukemia (CLL), acute lymphocytic leukemia (ALL), multiple myeloma, haemophilia and Parkinson's disease. The therapy may be somatic or germline gene therapy, i.e. in some embodiments the cell in the transduction method is a somatic cell or a germ cell.

The transduction buffer and methods of the invention can also be used to load antigens into antigen-presenting cells for presentation to the immune system. This advantageously produces a novel vaccine manufacturing process. For example, antigens have been loaded into dendritic cells in vitro and then transplanted back into the body. However, the methods used up until now have damaged the dendritic cells, e.g. because they have forced the proteins into the cells using mechanisms such as endocytosis. Dendritic cells already have very active macropinocytosis pathways. Therefore, by using methods of the invention, the dendritic cells could be loaded with antigen via the macropinocytosis pathway, with negligible damage to the cell. This method could either be carried out in vitro prior to transplantation of the cells into the patient or the antigens could be transduced into dendritic cells (or other antigen presenting cells) in vivo, e.g. by sub-cutaneous injection.

Accordingly, there is provided the use of the transduction buffer for transducing antigens into antigen presenting cells. There is also provided a method for transducing antigens into antigen presenting cells. The invention also provides the use of the transduction buffer and/or methods of the invention for manufacturing a vaccine, for example, whereby the vaccine comprises antigen-presenting cells that have been transduced by the methods of the present invention, i.e. wherein the antigen of interest has been transduced into the cell. Similarly, the invention provides a method of vaccinating, treating or preventing a subject comprising administering a cell to the subject, wherein the cell has been transduced by a method of the present invention. Likewise the invention provides a cell for use in a method of vaccinating, treating or preventing a subject, wherein the method comprises comprising administering a cell to the subject, wherein the cell has been transduced by a method of the present invention.

In some embodiments, the invention provides the use of a transduction buffer described herein in a method for cationic lipid-mediated DNA transfection. The invention provides a method for transducing lipid and DNA into cell, wherein the method is as described herein.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%. It also refers specifically to the exact value, e.g in the above example, to exactly 10%. Where necessary, the word "about" may be omitted from the definition of the invention.

The term "a" or "an", unless specifically stated otherwise, means "one or more". For example, it can mean "only one" or it can mean "more than one", for example "two, three, four, five or more".

Unless specifically stated, a process comprising a step of mixing two or more components does not require any specific order of mixing. Thus components can be mixed in any order. Where there are three components then two components can be combined with each other, and then the combination may be combined with the third component, etc.

It will be understood that the invention will be described by way of example only and modifications may be made whilst remaining within the scope and spirit of the invention.

Figure 1B:
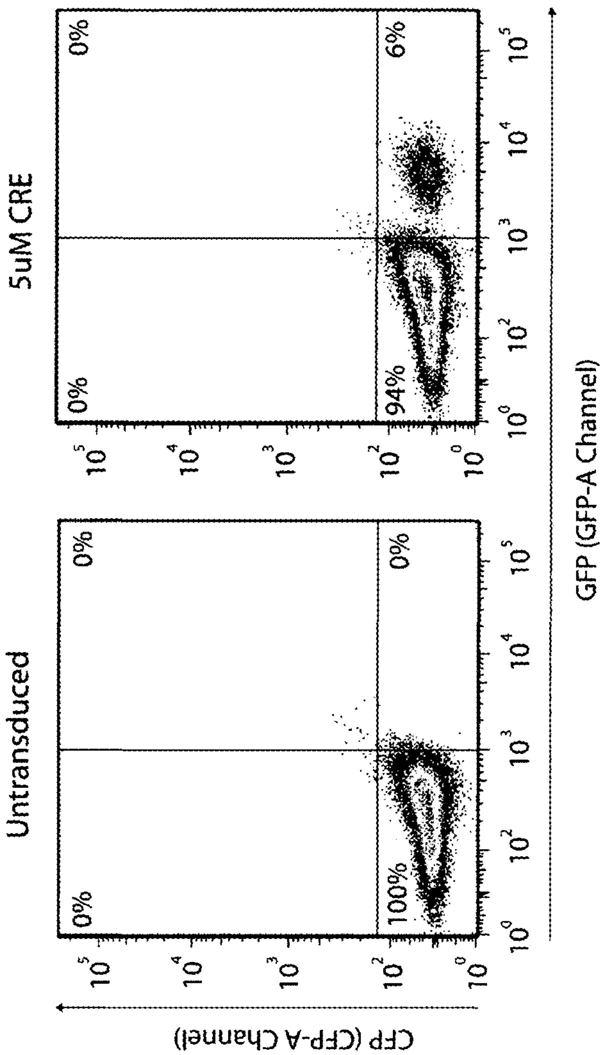
FIGS. 1A-1B: Cre recombinase protein transduction using the method described by Okada, et al.

(A) Schematic representation of Cre recombinase reporter. A CMV-Lox-Stop-Lox-eGFP reporter was targeted to the ColA1 locus of murine ESCs[2]. Intracellular CRE-recombinase excises the Stop cassette thereby inducing eGFP expression.

(B) FACS plots of mESCs transduced with 5 μM of recombinant CRE protein (right panel) compare to untransduced cells (left panel) using the Okada's method. The percentage successfully transduced GFP-positive cells is indicated.

FIGS. 2A-2H: Protein transduction independent of transduction peptide domain.

(A) Schematic representation of recombinant proteins. Domains in the recombinant proteins are indicated: H6: 6×Histidine purification tag; LFn: N-terminal transduction domain of Anthrax LF protein; SUMO-1: Sumo cleavage domain; Oct4: murine Oct4 (Pou5f1) protein; VP16: VP16 transactivation domain.

(B) Schematic representation of the luciferase reporter constructs used in this study. Top: Oct4-reporter containing 6 tandem repeats of the Oct4 DNA recognition sequence. Middle: Control construct lacking Oct4 binding sequence; Bottom: Control construct to monitor transfection efficiency, expressing Renilla-Luciferase.

(C) Schematic depiction of the timeline of the protein transduction assay.

(D) COS7 cells were transfected with 6×OCT4-TK-Luc reporter followed by protein transduction. Specificity controls were cells transfected with TK-Luc reporter (black bars) or 6×Oct4-TK-Luc (grey bars) in combination with empty or OCT4 expressing lentivirus. Firefly luciferase activity was normalized with a co-transfected Renilla luciferase construct. PA; Protective Antigen, the co-factor required for LFn-mediated transduction.

(E) Schematic representation of the OCT4 recombinant proteins used in this study.

(F) COS7 cells were transfected with 6×OCT4-TK-Luc reporter and 12 hs later transduced with indicated OCT4 proteins at increasing concentration as indicated in the figure. Firefly luciferase activity was normalized by co-transfecting Renilla luciferase construct as in (D). As a control, cells were transduced with empty and OCT4 expressing lentivirus ("EV" and "OCT-4", respectively).

(G) COS7 cells were transfected with OCT4-TK-Luc reporter and transduced with OCT4-VP16 protein (black bar "+") or without protein (white bar "+"). Bars A-G represent cells transduced with OCT4-VP16 protein under transduction media minus one component. Firefly luciferase activity was normalized with co-transfected Renilla luciferase construct.

(H) Structure of the non-detergent sulfobetaine 201 (NDSB-201) compound.

FIGS. 3A-3E: Protein transduction is dependent on time, protein concentration, salt-induced hypertonicity and NDSB-201.

(A) Schematic outline of the β-lactamase reporter assay. The non-fluorescent CCF2/AM crosses the cell membrane through diffusion and becomes trapped in the cytoplasm through intracellular esterification, which also activate the fluorescent properties of now called CCF2. When CCF2 is exited at 409 nm it emits a fluorescent signal at 520 nm (green signal). Cleavage of CCF2 by intracellular β-lactamase results in a shift in the emission wavelength of the remaining cleavage product to 447 nm (blue signal). The ratio between the green and blue signal is a measure for the amount of (transduced) intracellular β-lactamase.

(B) β-Lactamase reporter assay. Murine embryonic fibroblasts (MEFs) were transduced with 1 μM β-lactamase protein, 25 mM NDSB-201 at an osmolality of 700 mOsm/Kg induced by NaCl for the indicated time (solid bars). Controls cells were treated as above, but in isotonic media (300 mOsm/Kg, open circles).

(C) β-Lactamase reporter assay on MEFs transduced with increasing concentrations of β-Lactamase protein (as indicated), 25 mM NDSB-201 at 700 mOsm/Kg osmolality induced by NaCl during 3 hs (solid bars). Controls cells were treated as above, but in isotonic media (300 mOsm/Kg, open circles).

(D) β-lactamase reporter assay on MEFs transduced with 1 μM of β-lactamase protein, 25 mM NDSB-201 at different osmolalities (as indicated) induced by NaCl during 3 hs. (red bars). Controls cells were treated as above, but in isotonic media (300 mOsm/Kg, open circles).

(E) β-lactamase reporter assay on MEFs transduced with 1 μM of β-lactamase protein with different concentrations of NDSB-201 (as indicated) at 700 mOsm/Kg osmolality induced by NaCl (solid bars). Controls cells were treated as above, but in isotonic media (300 mOsm/Kg, open circles).

FIGS. 4A-4E: Addition of osmoprotectants to the transduction media ameliorates hypertonicity-induced cell-cycle Inhibition.

(A)β-lactamase assay (solid bars) and cell proliferation (BrdU incorporation) assay (white squares). MEFs were transduced with or without 1 μM β-lactamase with 25 mM NDSB-201 at different osmolalities and time points (as indicated). Relative β-lactamase activity of cells treated without β-lactamase proteins at 300 mOsm/Kg was set at 1. For the BrdU incorporation assay, relative Brdu incorporation values of untreated cells and mitomycin C treated cells were set at 100% and 0%, respectively.

(B) Analysis of the effect of osmoprotectants on cell proliferation. MEFs were transduced with 1 μM β-lactamase using transduction media containing 25 mM NDSB-201 at 700 mOsm/Kg adjusted with NaCl (Control, 3rd bar from left) or transduced under same condition with addition of indicated osmoprotectants. Untreated cells (bar #1) and mitomycin C (bar #2) treated cells were considered as relative Brdu incorporation values of 100% and 0%, respectively.

(C) Combined addition of Glycerol and Glycine ameliorates transduction buffer-induced cell cycle inhibition in MEFs. MEFs were transduced with or without β-lactamase as indicated with addiction of 30 mM of Glycerol and 15 mM of Glycine (+2G). Relative β-lactamase activity of cells treated without β-lactamase proteins at 300 mOsm/Kg was set at 1. For the BrdU incorporation assay, relative Brdu incorporation values of untreated cells and mitomycin C treated cells were set at 100% and 0%, respectively.

Figure 4B:
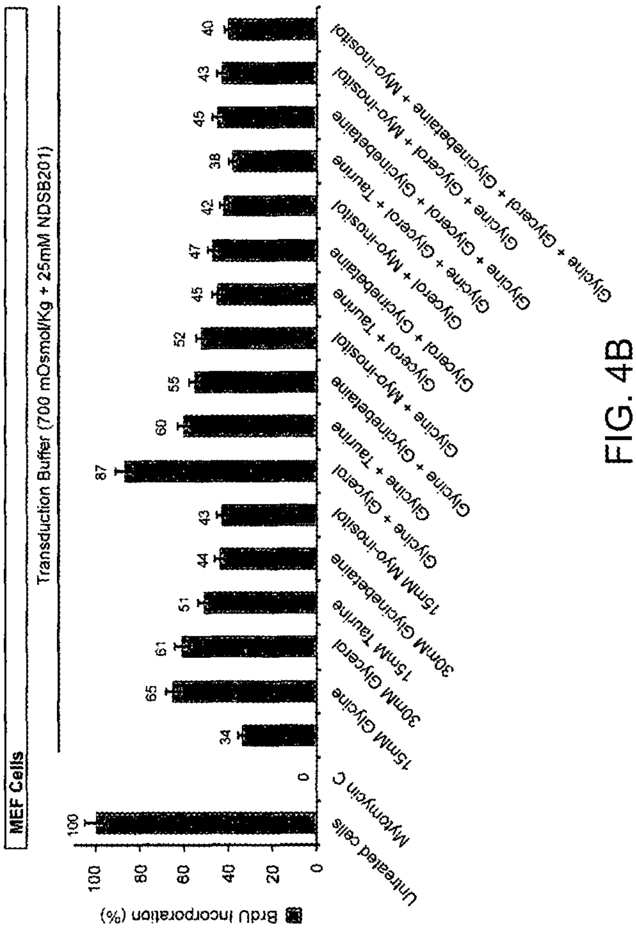
Figure 4A:
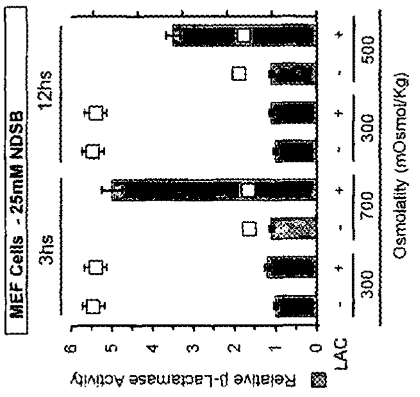
Figure 4E:
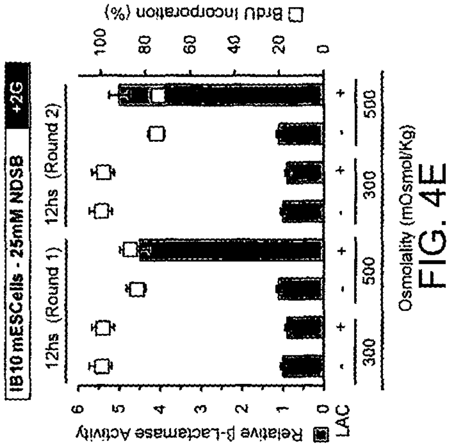
Figure 4D:
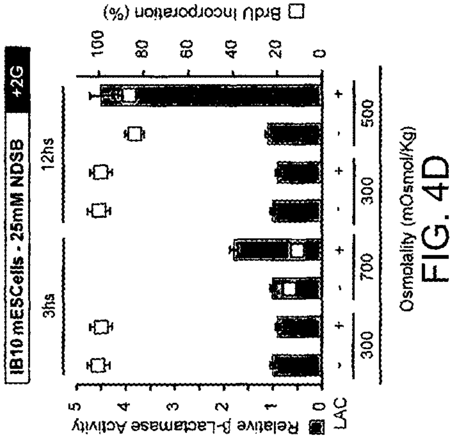
Figure 4C:
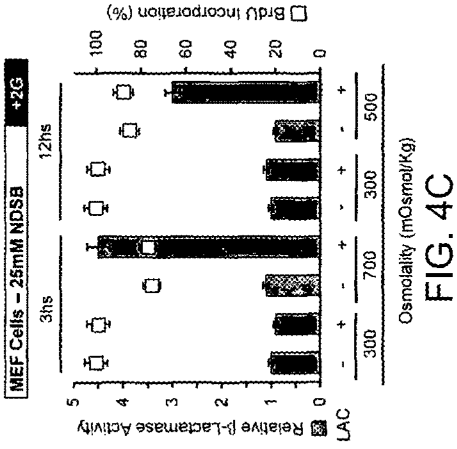

(D) Murine ESCs were transduced as described in (FIG. 4C).

(E) Repeated transduction of murine ESCs. mESC were transduced with 1 μM β-lactamase with 25 mM NDSB-201 at 500 mOsm/Kg with addition of 30 mM of Glycerol and 15 mM of Glycine for 12 hs (Round1) followed by a 12-hour recovery period and a second 12 hr transduction. β-lactamase transduction and BrdU incorporation were measured after each round of transduction as indicated. Relative β-lactamase activity of cells treated without β-lactamase proteins at 300 mOsm/Kg was set at 1. For the BrdU incorporation assay, relative BrdU incorporation values of untreated cells and mitomycin C treated cells were set at 100% and 0%, respectively.

FIGS. 5A-5E: Protein transduction is mediated by macropinocytosis and enhanced by macropinocytosis inducers and enhancers of macropinosomal escape.

(A) Analysis of the transduction activity of different hypertonic compounds. MEFs were transduced for 3 hours with 1 μM β-lactamase protein at an osmolality of 700 mOsm/Kg induced by different compounds as indicated (solid bars, transduction with NDSB, open circles, control transduction in the absence of NDSB-201) and with addition of 30 mM of Glycerol and 15 mM of Glycine. Relative β-lactamase protein uptake in isotonic media (left bar) was set at 1.

(B) Analysis of the effect of inhibitors of different endocytic pathways. MEFs were transduced for 3 hours with 1 μM β-lactamase protein at a NaCl adjusted osmolality of 700 mOsm/Kg in transduction buffer containing 25 mM NDSB201, 30 mM of Glycerol and 15 mM of Glycine in the presence of small molecule inhibitors of Clathrin-mediated endocytosis (Pitstop2 and chlorpromazine), Caveolin-mediated endocytosis (Dynasore and Nystatin), macropinocytosis (5-(N-ethyl N-isopropyl)-amiloride (EIPA), or 5-(N,N-dimethyl) amiloride hydrochloride (DMA)) or actin polymerization (CytochalasinD and Latrunculin A) as indicated. Relative β-lactamase protein uptake in isotonic media (left bar) was set at 1.

(C) Role of Nhe1 in protein transduction. MEFs were isolated from Wild-type, Nhe1 heterozygous (+/−) and Nhe1 knock-out (−/−) embryos and transduced for 3 hours with 1 μM β-lactamase protein at a NaCl adjusted osmolality of 700 mOsm/Kg in transduction buffer containing 25 mM NDSB201, 30 mM of Glycerol and 15 mM of Glycine. Relative transduction of wild-type cells was set at 100% and β-lactamase incorporation by wild-type cells in isotonic media (left bar) was set at 0%.

(D) Effect of growth factors and peptide enhancers of macropinosomeal escape on protein transduction of MEFs. MEFs were transduced for 3 hours with 1 μM β-lactamase protein at a NaCl adjusted osmolality of 700 mOsm/Kg in transduction buffer containing 25 mM NDSB201, 30 mM of Glycerol and 15 mM of Glycine in the presence of the indicated growth factor (bars 3-10 from left) or different concentrations of the dTAT-HA2 fusogenic peptide (bars 11-13 from left). Relative β-lactamase protein uptake in isotonic media (left bar) was set at 1. Open circles indicate relative BrdU incorporation by the transduced cells. BrdU incorporation of untransduced cells was set at 100% and BrdU incorporation of mitomycin C-treated cells was set at 0%.

(E) Effect of growth factors and peptide enhancers of macropinosomeal escape on protein transduction of murine ESCs. MEFs were transduced for 12 hours with 1 μM β-lactamase protein at a NaCl adjusted osmolality of 500 mOsm/Kg in transduction buffer containing 25 mM NDSB201, 30 mM of Glycerol and 15 mM of Glycine in the presence of the indicated growth factor (bars 3-8 from left) or different concentrations of the dTAT-HA2 fusogenic peptide (bars 9-11 from left). Relative β-lactamase protein uptake in isotonic media (left bar) was set at 1. Open circles indicate relative BrdU incorporation by the transduced cells. BrdU incorporation of untransduced cells was set at 100% and BrdU incorporation of mitomycin C-treated cells was set at 0%.

FIGS. 6A-6G: Structure-Activity relationship of protein transduction compounds.

(A) Top panel. Chemical structures of tested transduction compounds. Bottom panel. β-lactamase and BrdU incorporation assays using the different transduction compounds. MEFs were transduced for 3 hours with 1 μM β-lactamase protein at a NaCl adjusted osmolality of 700 mOsm/Kg in transduction buffer containing 30 mM of Glycerol and 15 mM of Glycine and 25 mM of the indicated transduction compounds. β-lactamase incorporation of the reference compound (NDSB201, #01) was set at 100%. Open circles indicate relative BrdU incorporation by the transduced cells. BrdU incorporation of untransduced cells was set at 100% and BrdU incorporation of mitomycin C-treated cells was set at 0%.

(B) Top panel. First row: examples of compounds with sulfonic group. Second row: examples of compounds with carboxy group. Third row: examples of compounds with amide group. Forth row: examples of compounds with secondary amide group. Fifth row: examples of compounds with tertiary amide group. Bottom row additional variants containing a bioisostere variant and a dimer variant Bottom panel. β-lactamase and BrdU incorporation assays using the different transduction compounds. MEFs were transduced for 3 hours with 1 μM β-lactamase protein at a NaCl adjusted osmolality of 700 mOsm/Kg in transduction buffer containing 30 mM of Glycerol and 15 mM of Glycine and 25 mM of the indicated transduction compounds. β-lactamase incorporation of the reference compound (NDSB201, #01) was set at 100%. Open circles indicate relative BrdU incorporation by the transduced cells. BrdU incorporation of untransduced cells was set at 100% and BrdU incorporation of mitomycin C-treated cells was set at 0%.

(C) Top panel. Compounds in left columns contain amine and sulfonate or carboxy group. Central column show same compounds as in left without amine group. Right columns shows same compounds as in left without sulfonate or carboxy group. Bottom panel. β-lactamase and BrdU incorporation assays using the different transduction compounds. MEFs were transduced for 3 hours with 1 μM β-lactamase protein at a NaCl adjusted osmolality of 700 mOsm/Kg in transduction buffer containing 30 mM of Glycerol and 15 mM of Glycine and 25 mM of the indicated transduction compounds. β-lactamase incorporation of the reference compound (NDSB201, #01) was set at 100%. Open circles indicate relative BrdU incorporation by the transduced cells. BrdU incorporation of untransduced cells was set at 100% and BrdU incorporation of mitomycin C-treated cells was set at 0%.

(D) Top panel. Analysis of the role of the carbon-chain length. Indicated are examples of two transduction compounds (#11 and #20, grey shaded area) and carbon-chain length variations of these. Bottom panel. β-lactamase and BrdU incorporation assays using the transduction compounds indicated in the top panel. MEFs were transduced for 3 hours with 1 μM β-lactamase protein at a NaCl adjusted osmolality of 700 mOsm/Kg in transduction buffer containing 30 mM of Glycerol and 15 mM of Glycine and 25 mM of the indicated transduction compounds. β-lactamase incorporation of the reference compound (NDSB201, #01) was set at 100%. Open circles indicate relative BrdU incorporation by the transduced cells. BrdU incorporation of untransduced cells was set at 100% and BrdU incorporation of mitomycin C-treated cells was set at 0%.

(E) Transduction activity and BrdU incorporation of 45 different transduction compounds upon β-lactamase protein transduction in MEFs. MEFs were transduced for 3 hours with 1 μM β-lactamase protein at a NaCl adjusted osmolality of 700 mOsm/Kg in transduction buffer containing 30 mM of Glycerol and 15 mM of Glycine and 25 mM of the indicated transduction compounds. β-lactamase incorporation of the reference compound (NDSB201, #01) was set at 100%. Open circles indicate relative BrdU incorporation by the transduced cells. BrdU incorporation of untransduced cells was set at 100% and BrdU incorporation of mitomycin C-treated cells was set at 0%.

(F) Effect of combining different transduction compounds on total protein transduction activity. MEFs were transduced for 3 hours with 1 μM β-lactamase protein at a NaCl adjusted osmolality of 700 mOsm/Kg in transduction buffer containing 30 mM of Glycerol and 15 mM of Glycine and equimolar quantities of the indicated transduction compounds such that the final concentration of transduction compound in the buffer was 25 mM. β-lactamase incorporation of the reference compound (NDSB201, #01) was set at 100%. Open circles indicate relative BrdU incorporation by the transduced cells. BrdU incorporation of untransduced cells was set at 100% and BrdU incorporation of mitomycin C-treated cells was set at 0%.

(G) Evaluation of GABA receptor agonists on protein transduction. MEFs were transduced for 3 hours with 1 μM β-lactamase protein at a NaCl adjusted osmolality of 700 mOsm/Kg in transduction buffer containing 30 mM of Glycerol and 15 mM of Glycine and 25 mM NDSB201 plus the indicated GABA agonists. β-lactamase incorporation of the reference compound (NDSB201, #01) was set at 100%. Open circles indicate relative BrdU incorporation by the transduced cells. BrdU incorporation of untransduced cells was set at 100% and BrdU incorporation of mitomycin C-treated cells was set at 0%.

FIGS. 7A-7D: Table 1

List of transduction compounds their protein transduction activity and effect on cell proliferation in transduction buffer. First column: transduction compound number; Second column: chemical structure of the transduction compound. Third column: Relative β-lactamase protein transduction activity; Fourth column: Relative BrdU incorporation 24 hrs after β-lactamase transduction. MEFs were transduced for 3 hours with 1 μM β-lactamase protein at a NaCl adjusted osmolality of 700 mOsm/Kg in transduction buffer containing 30 mM of Glycerol and 15 mM of Glycine and 25 mM of the indicated transduction compounds. β-lactamase incorporation of the reference compound (NDSB201, #01) was set at 100%. Open circles indicate relative BrdU incorporation by the transduced cells. BrdU incorporation of untransduced cells was set at 100% and BrdU incorporation of mitomycin C-treated cells was set at 0%.

FIGS. 8A-8F: Cre protein transduction in mES cells.

(A) Schematic representation of Cre recombinase reporter. A CMV-Lox-Stop-Lox-eGFP reporter was targeted to the ColA1 locus of murine ESCs[2]. Intracellular CRE-recombinase excises the Stop cassette thereby inducing eGFP expression.

(B) FACS density plots showing on top mES cells transduced with CRE at different concentrations and with multiple rounds of transductions. Lower panel, shows mES cells transduced with 5 μM of CRE protein with different concentrations of fusogenic peptides. Signal from the CFP channel was used as a control for autofluorescence.

Figure 8B:
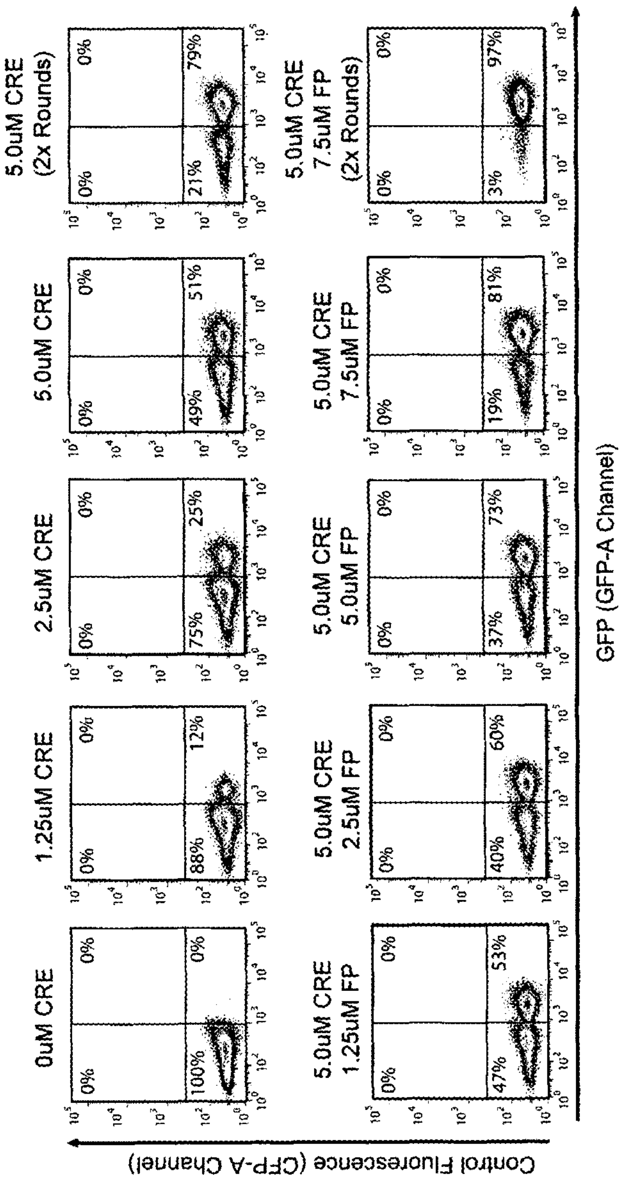
Figure 8A:
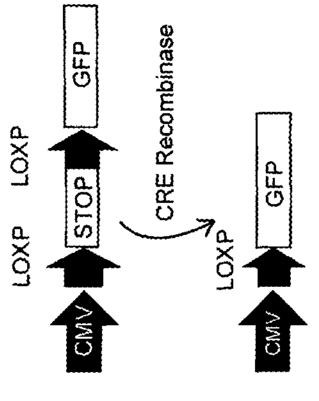

(C) Microscopy images of samples of with two rounds of CRE transductions as described in FIG. 8B. Dashed line indicates the border of each colony.

Figure 8C:
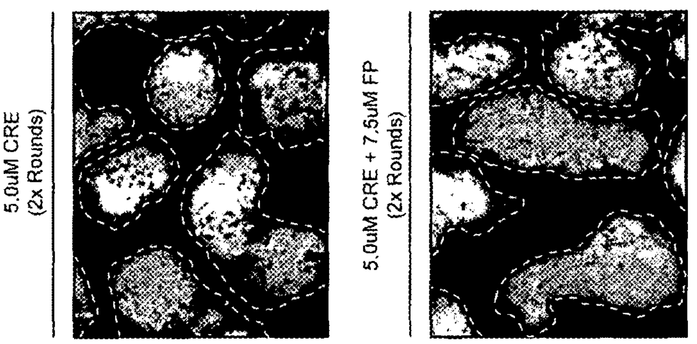

(D) Cell proliferation curves of samples shown in FIG. 8C. Top & bottom graph. After 2 days, transduced (white circle) or untransduced (grey bars) cells were counted every day to make cell proliferation curves.

(E) qRT-PCR analysis of pluripotent genes expression of untransduced and transduced mES cells of samples shown in FIG 8C. GAPDH was used as loading control.

Figure 8D:
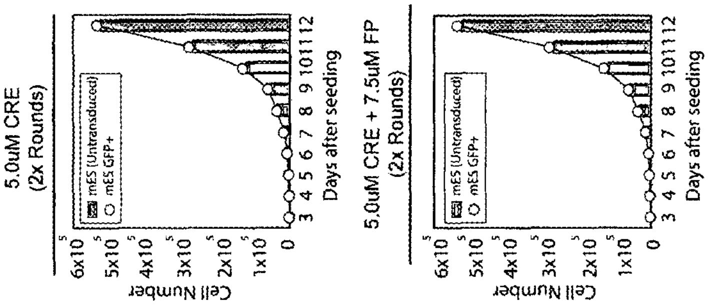
Figure 8E:
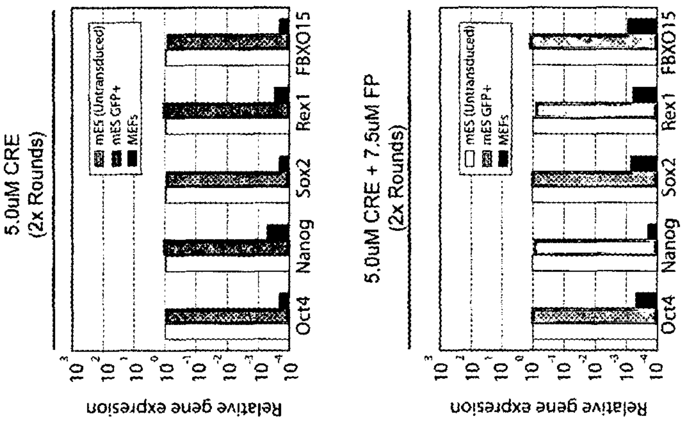
Figure 8F:

(F) To test the pluripotency of the transduced mESCs, double-transduced GFP+ ESCs from the experiment in FIG. 8B were injected into host blastocyst embryos and transplanted into pseudopregnant foster mice. As shown in FIG. 8F, double-transduced mESCs efficiently contributed to chimera formation, both in the transduction without (FIG. 8F, upper panel) and with Tat-HA2 fusion peptide (FIG. 8F, lower panel).

Figures 9A, 9B:
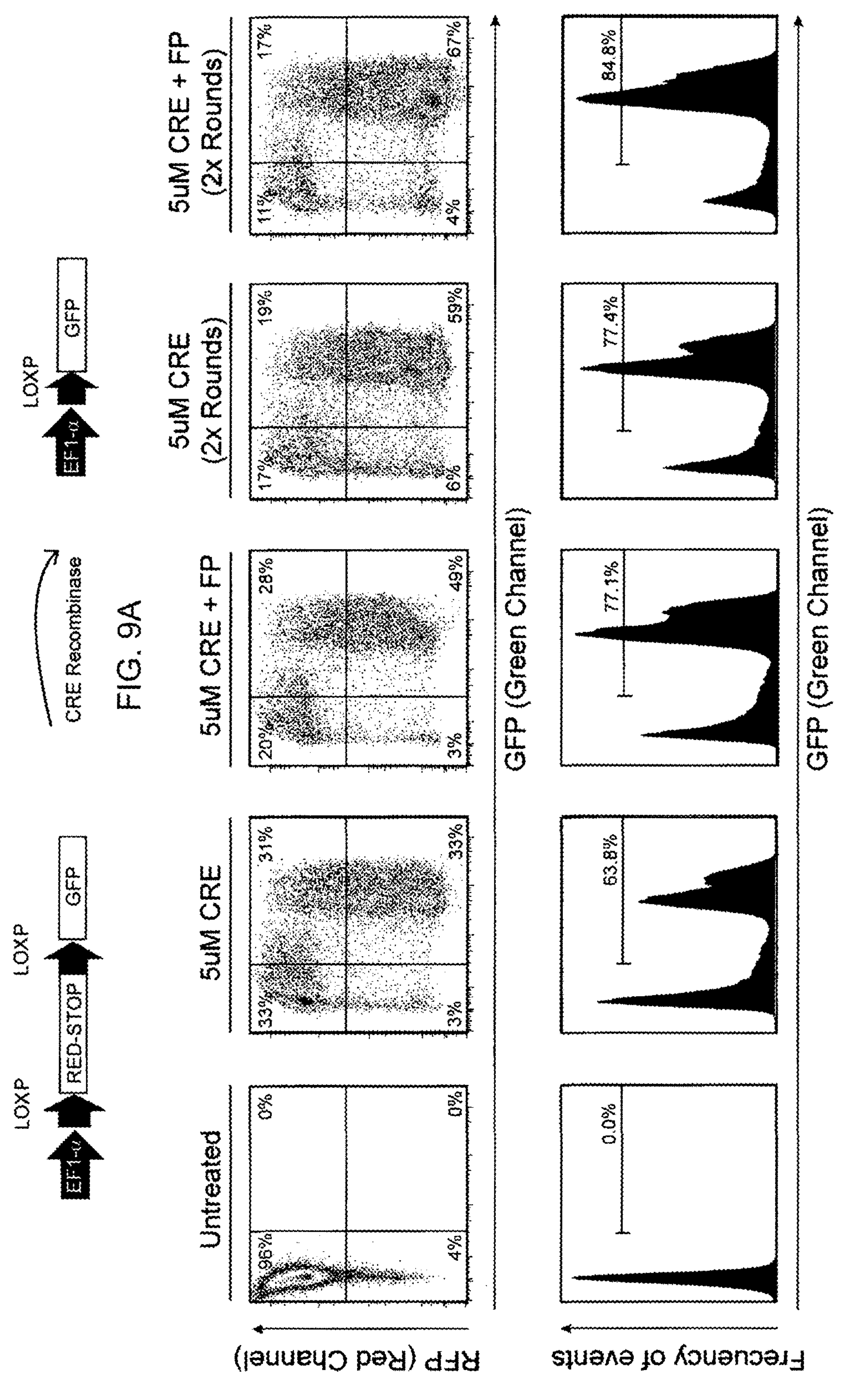
Figure 9C:
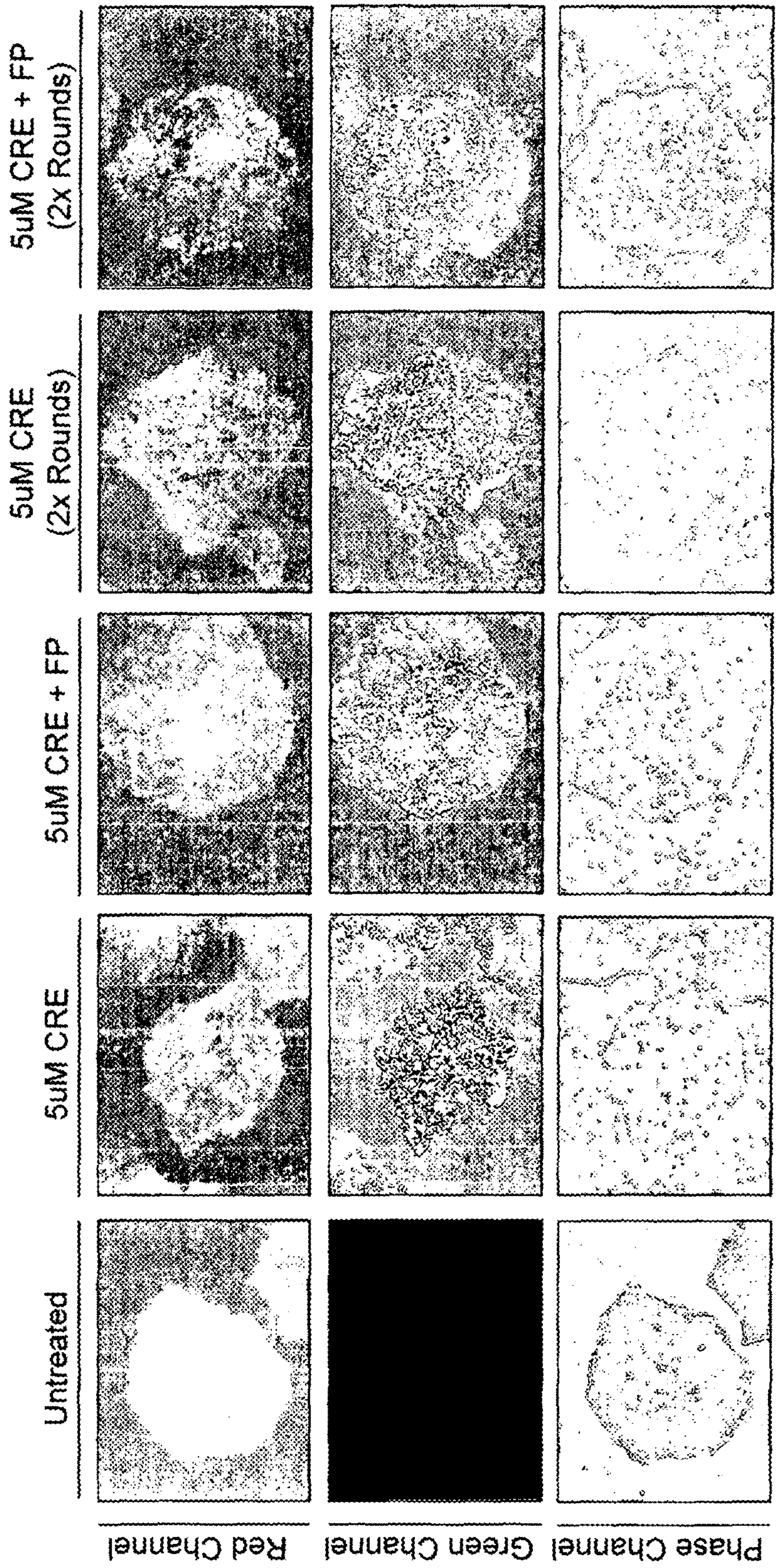

FIGS. 9A-9C: CRE protein transduction in Human induced pluripotent stem cells (iPSCs).

(A) Schematic depiction of the CRE recombinase reporter. EF1a-Lox-dsRED-Stop-Lox-EGFP/ires-PuroR construct was introduced in human iPSCs via lentiviral infection and subsequent puromycin selection. Obtained cells contain multiple copies of the lentiviral reporter construct Untransduced cells express Red fluorescent protein. CRE-mediated excision of the LoxP-flanked dsRED-STOP cassette abrogates dsRed expression and induces the expression of EGFP reporter protein.

(B) Top panel. FACS density plots of Cre transduced human iPSCs. The x-axis shows the GFP signal and y-axis shows dsRED signal. Human iPSCs were transduced with CRE protein or with CRE protein plus Fusogenic peptides as indicated. Right panels show multiple rounds of transduction. The control was cells incubated with transduction media in the absence of CRE protein. Bottom panel. Shows histograms of top density plot panels. Also, it is shown quantification of GFP positive cells over total cell population.

(C) Representative fluorescence and phase contrast images of human iPSCs transduced as in FIG. 9B. Top row and medium row indicate RED and GREEN fluorescence channel, respectively. Lower row show phase contrast channel.

Figure 10A:
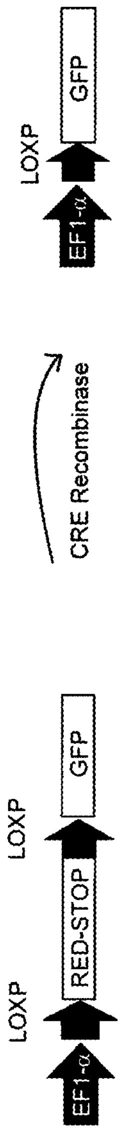
Figure 10B:
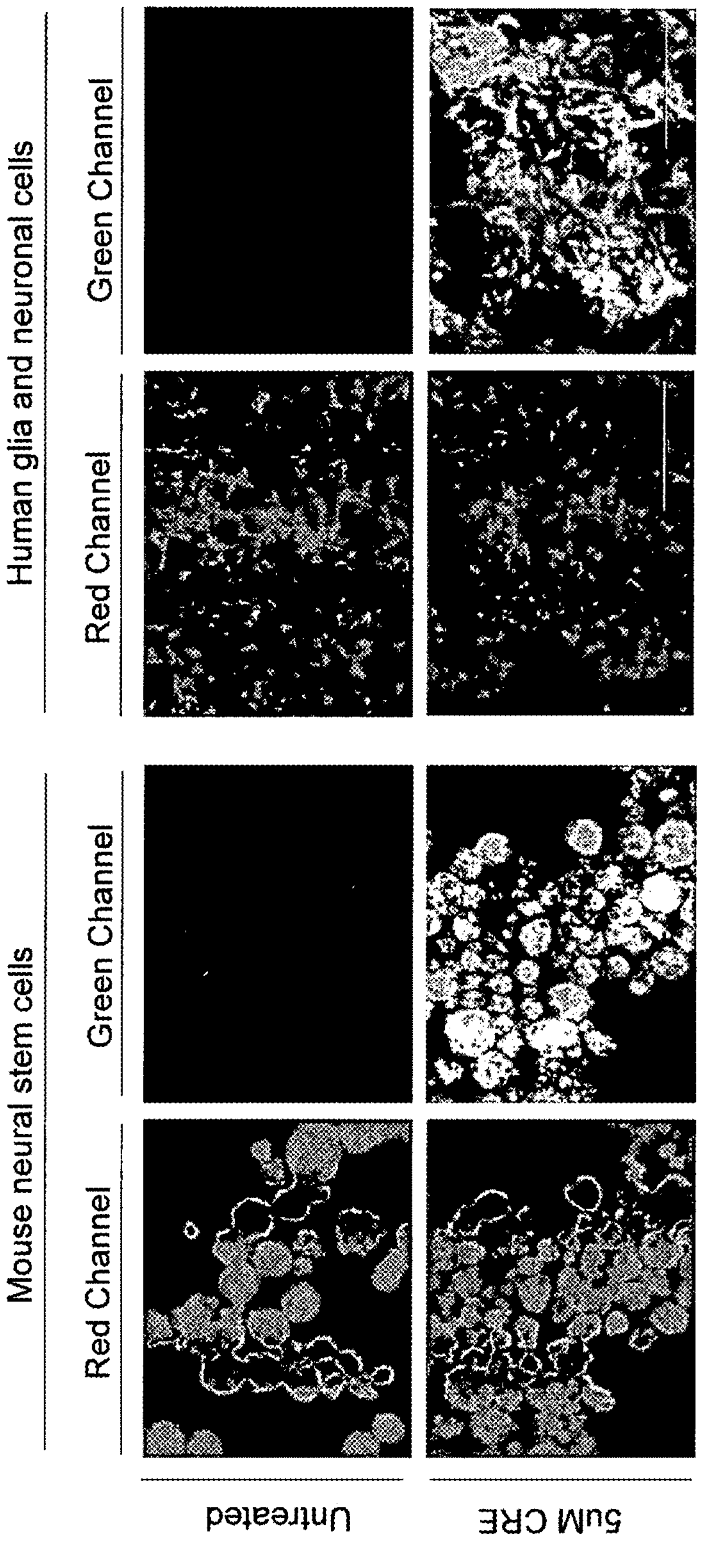

FIGS. 10A-10B: Cre protein transduction in different neural cell types (A) Schematic depiction of the CRE recombinase reporter. EF1a-Lox-dsRED-Stop-Lox-EGFP/ires-PuroR construct was introduced into neural progenitor cells and human iPSCs and their derived neural derivatives as indicated via lentiviral infection and subsequent puromycin selection. Obtained cells contain multiple copies of the lentiviral reporter construct Untransduced cells express Red fluorescent protein. CRE-mediated excision of the LoxP-flanked dsRED-STOP cassette abrogates dsRed expression and induces the expression of EGFP reporter protein.

(B) Representative fluorescent images of different cell types transduced with CRE protein or left untransduced.

Figure 11:
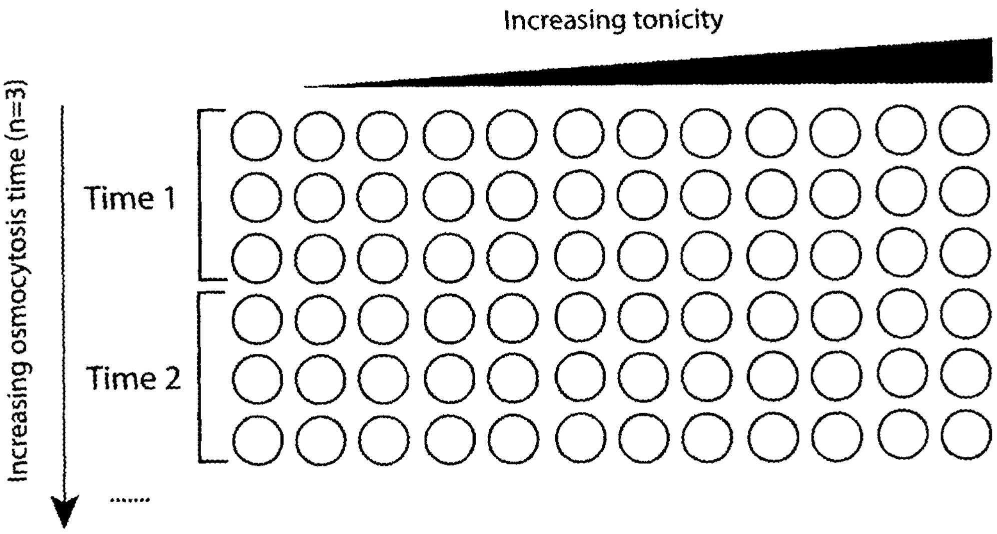

FIG. 11: Schematic representation of multi-well setup to optimize transduction time and media tonicity FIG. 12: Transduction buffer enhances DNA-Lipid transfection in mES cells.

Flow cytometry analysis of the incorporation of a plasmid DNA expression vector into murine embryonic stem cells. Red fluorescent protein (RFP) is expressed from the expression vector after successful incorporation. Certain murine embryonic stem cell lines are resilient to standard plasmid transfection with cationic lipids. Left panel: mESCs transfected with the RFP expression plasmid using Lipofectamine LTX (Life technologies) according to the manufacturer's protocol. Cells were analyzed for RFP expression using flow cytometry. Right panel: Addition of transduction buffer to the plasmid DNA/Lipofectamine LTX transfection mix results in efficient transfection of reporter DNA into the murine ESCs. Y axis displays red channel fluorescence and x axis displays green channel fluorescence.

Figure 13:
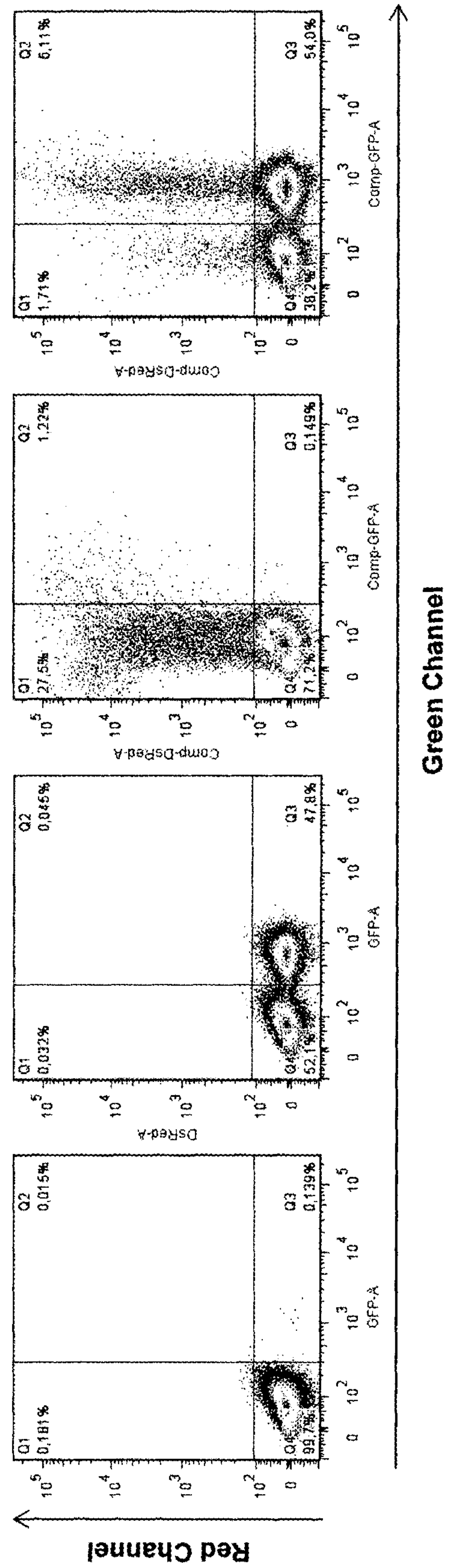

FIG. 13: Dual incorporation of DNA and Protein using transduction buffer.

Flow cytometry analysis of the incorporation of a plasmid DNA expression vector into murine embryonic stem cells. Red fluorescent protein (RFP) is expressed from the expression vector after successful incorporation. In addition, transduction of Cre recombinase protein into the Lox-Stop-Lox-GFP reporter murine ES cells results in activation of the GFP reporter gene. From left to right (as indicated above the FACS panels): Control mES Lox-Stop-Lox-GFP cells under transduction buffer incubated for 12 hrs without Cre recombinase protein or RFP reporter plasmid DNA; 5 μM Cre recombinase protein; plasmid DNA containing a Red Fluorescent Protein (RFP) reporter gene; and 5 μM CRE protein together with RFP-DNA/Lipid complexes. Y axis displays red channel fluorescence and x axis displays green channel fluorescence.

Figure 14:
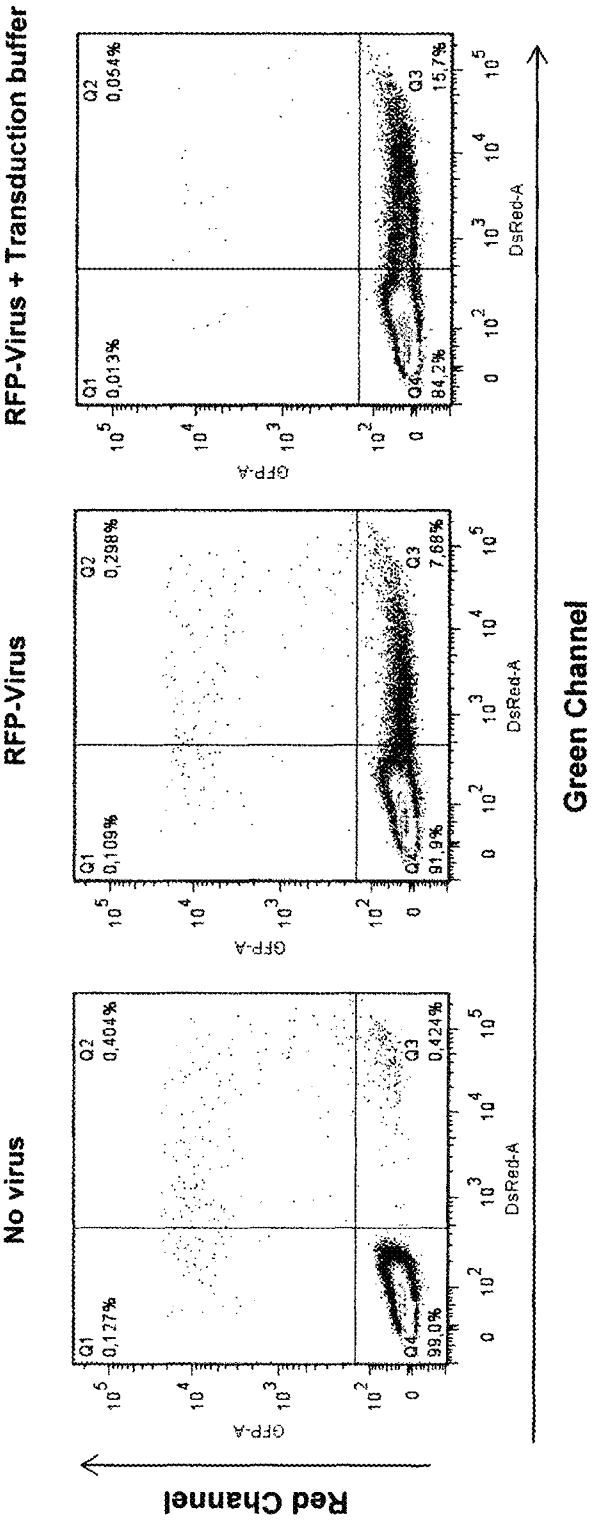

FIG. 14: Transduction buffer enhances viral incorporation in human iPS cells.

Human iPS cells were transduced with lentiviral particles expressing expressing red fluorescent protein (RFP). FACS panels demonstrate untreated (control) human iPS cells (left panel); cells transduced for 12 hrs with lentiviral particles expressing red fluorescent protein (RFP) (middle panel); and cells transduced for 12 hrs with lentiviral particles expressing RFP in the presence of 1× transduction buffer (Buffer 12/500, right panel). Y axis displays red channel fluorescence and x axis displays green channel fluoresce.

Figure 15:
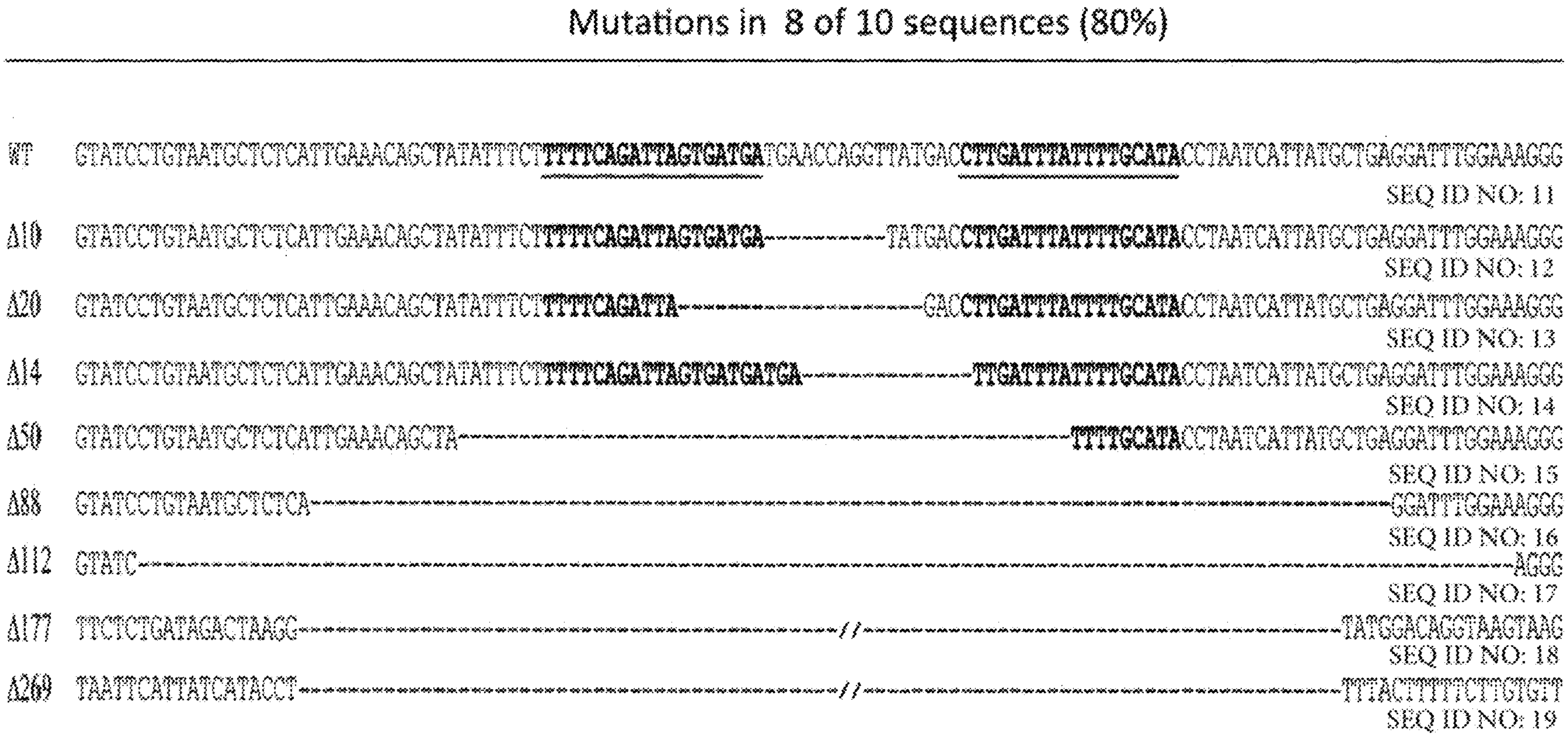

FIG. 15: HPRT gene disruption mediated by TALEN proteins in human iPS cells.

Male human iPS cells were transduced with a TALEN protein pair targeting the HPRT gene on the X chromosome. The wild-type (WT) sequence is displayed at the top with the target TALEN half-sites underlined. Upon TALEN transduction, 6TG-resistant iPSC clones were isolated and analysed for deletions at the TALEN target site. Deletions are indicated by blue dashes. The size of deletions (D) are indicated to the left of each mutated site. Mutation frequencies are calculated as the number of mutants identified, divided by the total number of sequence analyzed.

Figure 16A:
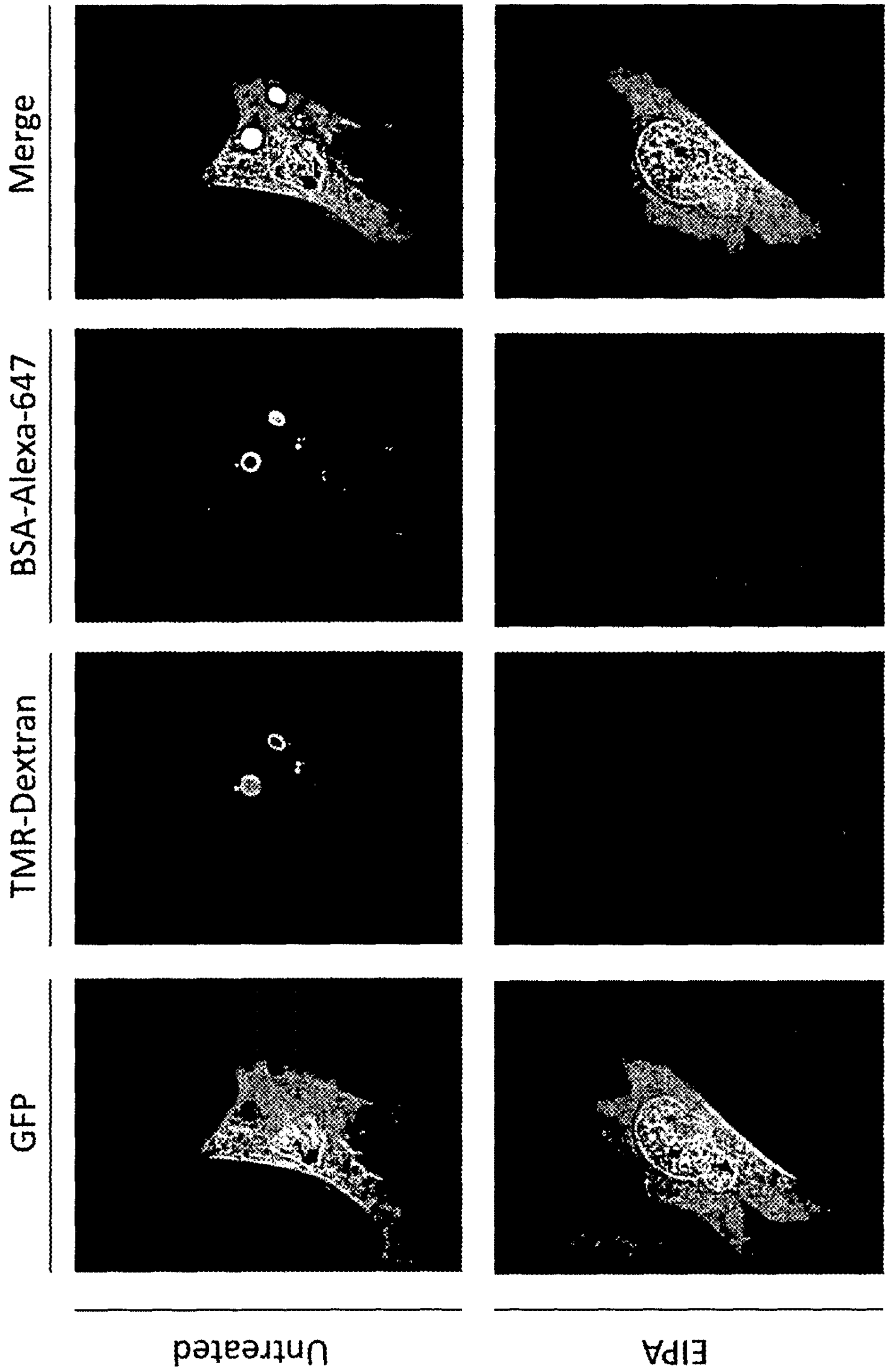
Figure 16B:
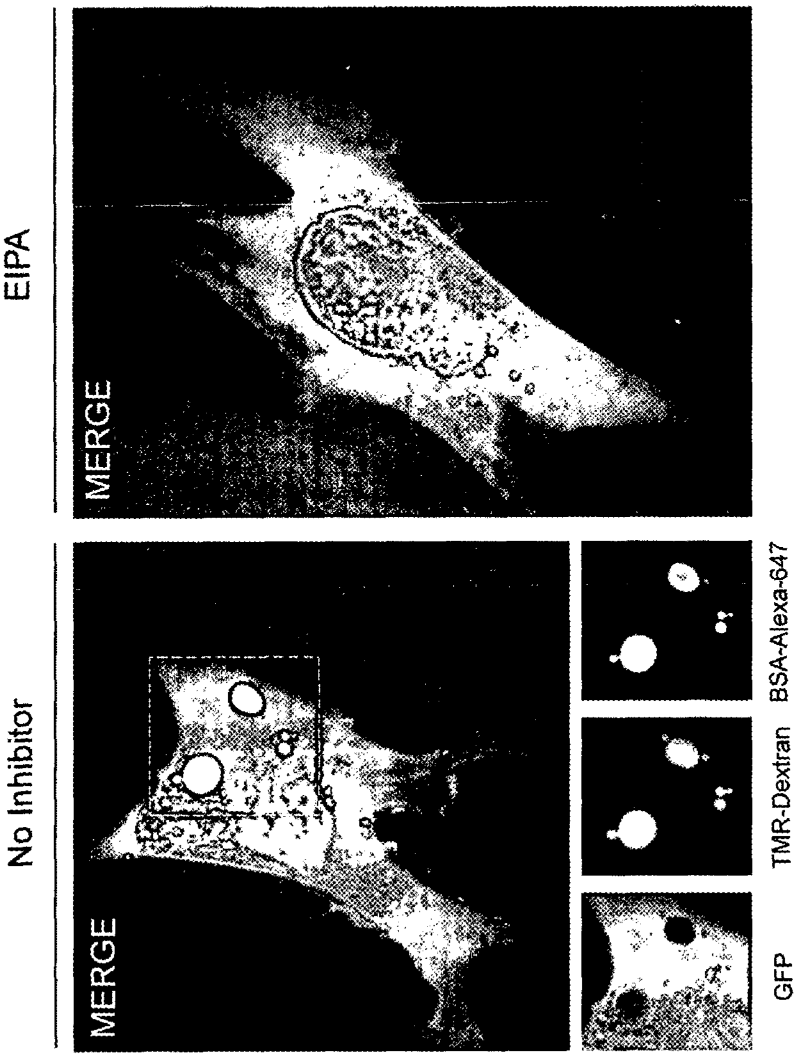

FIGS. 16A-16B: Co-transduction of polysaccharide Dextran and protein.

(A) To assess if the transduction buffer would permit the simultaneous transduction of proteins and large molecules, we analyzed macropinocytosis mediated uptake of TMR-dextran (red) and fluorescently labeled BSA protein (cyan) by GFP-expressing murine embryonic fibroblasts (MEFs).

(B) The macropinocytosis inhibitor, EIPA (Ethylisopropylamiloride), inhibits uptake of TMR-dextran or BSA protein. Nuclei were stained with Hoescht 33342 (blue).

Figure 17A:
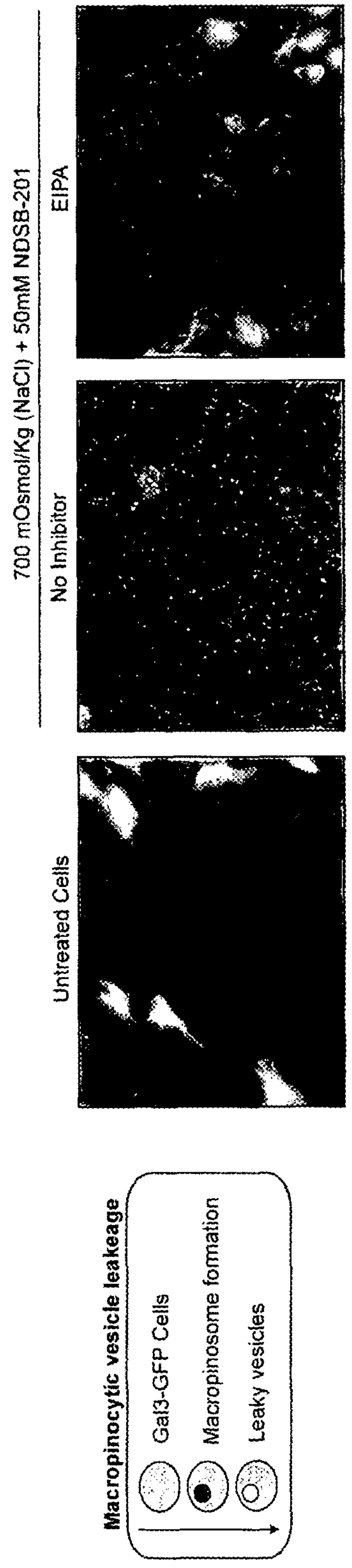
Figure 17B:
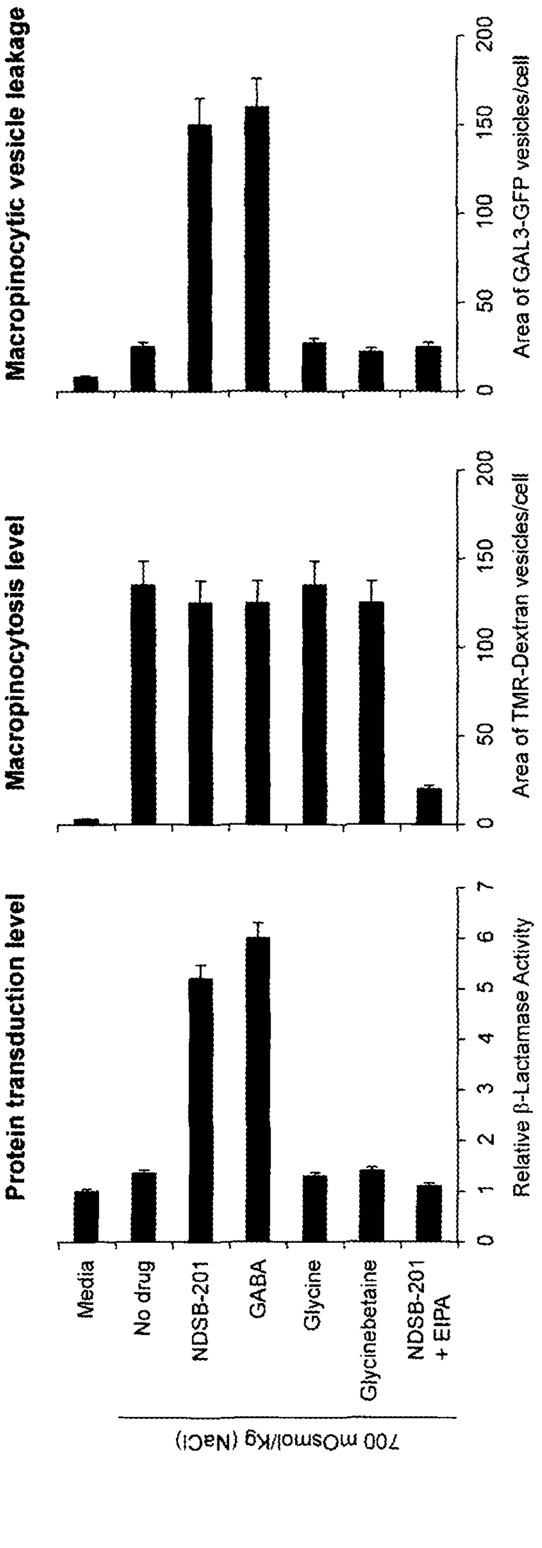

FIGS. 17A-17B: NDSB-201 and GABA molecules induces macropinocome vesicle leakage.

(A) Left Panel. Schematic representation of the GAL3-GFP reporter assay. Upon initiation of transduction, extracellularly applied protein is taken up into macropinosomes (grey vesicles). Intracellular disruption of the macropinosome membrane releases the macropinosome content into the cytoplasm. At the same time, the compromised macropinosome membrane now allows entry of cytosolic GAL3-GFP protein, which binds to—and accumulates at the intra-macropinosome carbohydrates resulting in a bright fluorescent signal (white vesicles). Right Panel. GAL3-GFP cells were incubated with transduction media at 700 mOsmol/Kg with or without the macropinocytosis inhibitor EIPA. Untreated cells were included as negative control. Note that under transducing conditions (middle panel), GAL3-GFP accumulates in the compromised macropinosomes.

(B) Measurement of protein transduction activity, macropinocytosis and macropinosome vesicle release of NDSB-201 and examples of derivative compounds. Cells were incubated with transduction buffer at 700 mOsmol/Kg with different transduction compounds or left untreated, as indicated. Left panel. Relative β-Lactamase protein incorporation in MEF cells. Signal form untreated cells were set at 1. Medium panel. Macropinocytosis level was measure by TMRdextran incorporation in cells treated as before. Macropinocytosis level were determined by measuring total area of dextran positive vesicles per cell. Right panel. Gal3-GFP MEF cells were treated as before. Vesicle Leakage levels were determined by measuring total area of Gal3-GFP positive vesicles per cell.

Figure 18:
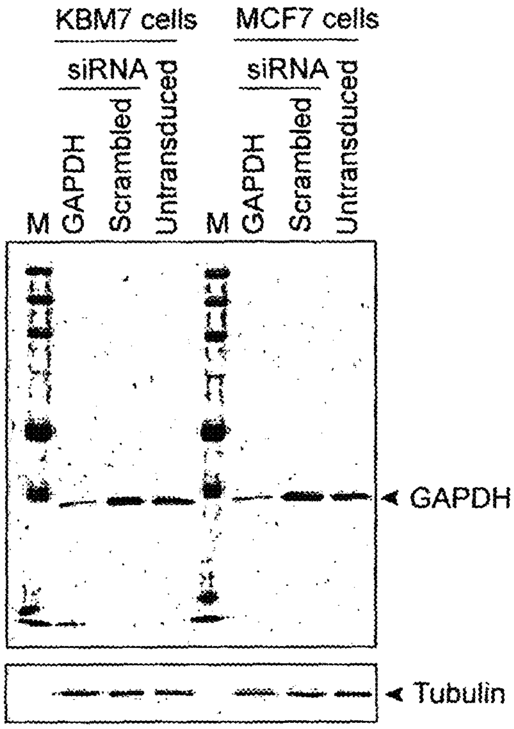

FIG. 18: Endogenous gene knockdown induced by siRNA transduction in human cells.

KBM7 and MCF7 cells were transduced with 25 μM of GAPDH and Scrambled siRNAs or left untreated. After 3 days of transduction GAPDH protein levels were determined by Western blot. Tubulin protein level is shown as loading control.

FIGS. 19A-19F: Gene editing using simultaneous transduction of recombinant Cas9 protein and short guide RNA (sgRNA).

(A) Solubility test of recombinant Cas9 protein at different concentration of NaCl and NDSB-201 (Compound #01) or GABA (compound #20). Protein aggregation was determined by semi-quantitative turbidimetric assay. Cristal clear solutions (no cas9 protein aggregation) are represented with white squares. Turbid solutions caused by Cas9 aggregates are depicted with grey squares.

(B) BrdU incorporation rate was determined in KBM7 cells incubated with osmocytosis buffer with NDSB-201 or GABA at different time points. Untreated cells were considering as 100% of BrdU incorporation.

(C) Top panel. Schematic depiction of the CRE recombinase reporter. EF1a-Lox-dsRED-Stop-Lox-EGFP/ires-PuroR construct was introduced in KBM7 cells via lentiviral infection and subsequent puromycin selection. Obtained cells contain multiple copies of the lentiviral reporter construct. Untransduced cells express Red fluorescent protein. CRE-mediated excision of the LoxP-flanked dsRED-STOP cassette abrogates dsRed expression and induces the expression of EGFP reporter protein. Bottom panel. KBM7 cells transduced with CRE protein with osmocytosis media at 1250 mOsmol/Kg with 250 mM GABA (compound #20) during 60 minutes. Upper panels represent fluorescent pictures in green and red channel. Bottom panels represent FACS plots showing in x axes green fluorescence and in y axes red fluorescence or frequency of events. Percentages of events are depicted in the corresponding area.

(D) Top panel. Schematic representation of the in-vitro transcribed small guide RNAs containing 20 nts of guide sequence and 80 nts of scaffold sequence. Bottom panel. Protein gel of recombinant purified CAS9 protein.

(E) Schematic representation of the CRISPR-CAS9 reporter system. KBM7 cells were transduced with a lentiviral vector containing the CRISPR-CAS target sequence followed by an out-of-frame sequence of dTomato gene. CRISPR-CAS9 induced DNA double strand break in the target sequence followed by non-homologous-end-joining (NHEJ) repair, induces DNA deletions and/or insertions, which restore the dTomato reading frame and induce cellular fluorescence.

(F) CRISPR-CAS9 reporter KBM7 cells were transduced with CAS9 protein and on-target sgRNA or left untreated. Specificity controls were performed by transducing cells with CAS9 protein and Off-target sgRNAs. The percentage of dTomato-positive cells was determined by flow-cytometry analysis. Bottom panels show phase contrast and fluorescent images for indicated conditions.

FIGS. 20A-20H: Endogenous gene disruption induced by CRISPR-CAS9 transduction.

(A) Scheme of WDR85 gene and binding sites of 5 different sgRNAs.

(B) Schematic depiction of of CAS9-sgRNA transduction and diphtheria toxin selection. KBM7 cells were transduced twice with CAS9-sgRNAs. After 7 days of last round of transduction cells were incubated with diphtheria toxin protein components (PA; protective antigen and LFn-DTA; Lethal factor n-terminal domain fused to diphtheria toxin). Bar graph shows viable cell number after 2 days of diphtheria toxin selection.

(C) DNA sequences of CRISPR-CAS9-induced mutations at endogenous WDR85 gene in KBM7 cells. The wild-type (WT) sequence is shown at the top. Start codon is indicated with underlined ATG. Deletions are indicated by dashes and insertions with underlines text. The sizes of the insertions (+) or deletions (D) are indicated to the right of each mutated site. The number of the times that each mutant was isolated is shown in parenthesis. Note that for several of the target sequences, we also identified larger deletions and/or insertions that extend beyond the sequences of CRISPR/CAS9 target site.

(D) DNA sequences of CRISPR-CAS9-induced mutations at endogenous WDR85 gene in KBM7 cells. The wild-type (WT) sequence is shown at the top. Start codon is indicated with underlined ATG. Deletions are indicated by dashes and insertions with underlines text. The sizes of the insertions (+) or deletions (D) are indicated to the right of each mutated site. The number of the times that each mutant was isolated is shown in parenthesis. Note that for several of the target sequences, we also identified larger deletions andZor insertions that extend beyond the sequences of CRISPR/CAS9 target site.

(E) DNA sequences of CRISPR-CAS9-induced mutations at endogenous WDR85 gene in KBM7 cells. The wild-type (WT) sequence is shown at the top. Start codon is indicated with underlined ATG. Deletions are indicated by dashes and insertions with underlines text. The sizes of the insertions (+) or deletions (D) are indicated to the right of each mutated site. The number of the times that each mutant was isolated is shown in parenthesis. Note that for several of the target sequences, we also identified larger deletions andZor insertions that extend beyond the sequences of CRISPR/CAS9 target site.

(F) Schematic representation to quantify biallelic gene knockout by CAS9-sgRNA transduction. KBM7 cells were transduced twice with CAS9-sgRNAs. After 3 days cells were isolated by single-cell deposition into 384-well plates using a flow cytometer. 7 days later growing clones were counted and treated with diphtheria toxin. After 2 days diphtheria toxin surviving clones were counted. WDR85 Knockout efficiency was calculated as the percentage of diphtheria toxin surviving clones respective to total single cell clones obtained originally.

(G) DNA sequences of diphtheria toxin surviving clones. A1=allele 1 and A2=Allele2. The sizes of the insertions (+) or deletions (D) are indicated to the right of each mutated site. The number of the times that each mutant was isolated is shown in parenthesis. Note that for several of the target sequences, we also identified larger deletions and/or insertions that extend beyond the sequences of CRISPR/CAS9 target site.

(H) DNA sequences of diphtheria toxin surviving clones. A1=allele 1 and A2=Allele2. The sizes of the insertions (+) or deletions (D) are indicated to the right of each mutated site. The number of the times that each mutant was isolated is shown in parenthesis. Note that for several of the target sequencesI we also identified larger deletions andZor insertions that extend beyond the sequences of CRISPR/CAS9 target site.

EXAMPLE 1

The ability to introduce small- or macromolecules into cells finds important applications in research and medicine. Unfortunately, the cell membrane presents a major obstacle for the introduction of many biologically active molecules. Significant effort has capitalized on the introduction of nucleotides (DNA, RNA, siRNA) and/or therapeutic molecules into cells, and while primary cells still pose a challenge, progress has been made using cationic lipids, nanoparticles or viral vectors as transmembrane carriers. In comparison, the development of new technologies for the intracellular delivery of proteins has been at a virtual standstill. Nonetheless, the ability to introduce proteins into cells would have many applications in vaccine development, genome editing, epigenetic reprogramming, (stem) cell differentiation and the manipulation of intracellular processes. The development of better technologies for the efficient intracellular delivery of proteins and other macromolecules, particularly in primary cells, is therefore much needed. Here we describe that a combination of salt-induced hypertonicity, a small molecule compound and osmoprotectants drives the robust and efficient introduction of small- and macromolecules into primary cells, without affecting cell viability. We provide examples of how protein, nucleotides, nanospheres and macromolecules can be introduced in a wide variety of primary cells, stem cell lines and their derivatives.

Figure 1A:
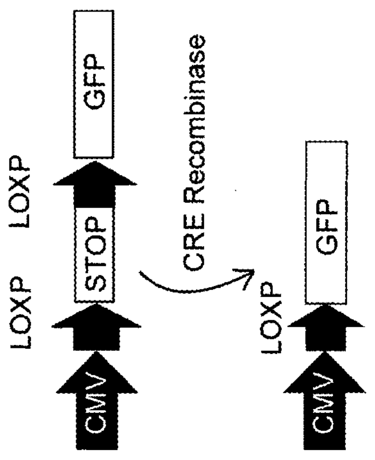

While the ability to introduce proteins into cells has many applications in research and medicine, a reliable, non-toxic and efficient method to do so is still lacking. In 1982, Okada and Rechsteiner demonstrated that hypertonic treatment induced by 0.5M Sucrose and 10% PEG1000 followed by a brief hypotonic treatment induced the intracellular uptake of macromolecules and proteins into immortalized cell lines'. Unfortunately, this technique proved limited to immortalized cell lines, and yields poor protein transduction efficiencies in primary cells. We tested the transduction of CRE recombinase protein into murine embryonic stem cells (mESCs) using the Okada method. We used a transgenic mESC line in which a CRE-recombinase inducible reporter was stably integrated in the ColA1 locus[2]. This reporter encompasses a CMV promoter followed by a LoxP-flanked Stop-casette and an eGFP reporter gene (FIG. 1A). eGFP expression is induced upon successful CRE-recombinase mediated excision of the Stop cassette (FIG. 1A). As shown by flow cytometry, transduction of mESCs with 5 μM CRE-recombinase protein yielded 6% GFP-positive mESCs, indicating that the combined hypertonic/hypotonic transduction method described by Okada and colleagues is inefficient in transducing primary (stem) cells (FIG. 1B).

A few years later, independent discoveries from Green[3] and Frankel[4,5] for the first time demonstrated that the HIV TAT protein can transduce itself across the cell membrane. The peptide sequence mediating this self-transduction was subsequently identified and shown to drive cell transduction when chemically fused to heterologous proteins[6]. Finally, Nagahara and colleagues demonstrated that TAT-peptide mediated protein transduction also worked when the TAT peptide was cloned as an in-frame fusion to the 'cargo' protein of interest[7].

A clear advantage of TAT-peptide mediated protein transduction is that the method appears to work with all cell types, including primary cells, and is generally non-toxic. However, the strong positive charge of the TAT peptide severely hampers the production of native recombinant TAT-fusion proteins in *E. Coli*, with much of the recombinant protein ending up in inclusion bodies. In addition, subsequent research demonstrated that some earlier reports on self-transducing proteins were in fact the result of experimental artifact introduced during fixation of the cells[8]. In addition, this technology requires the TAT peptide to be fused to the recombinant protein and therefore limits the type and number of proteins that can be transduced. The TAT peptide itself can disrupt the function or localization of the recombinant protein leading to unexpected or unwanted results. Finally, and perhaps most importantly, the transduction efficiency of TAT-fusion proteins is quite variable and dependent on the nature and physical properties of the protein cargo.

A Protein Transduction Reagent

Figure 2A:
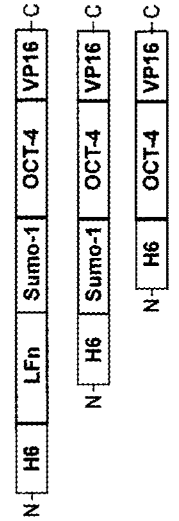
Figure 2B:
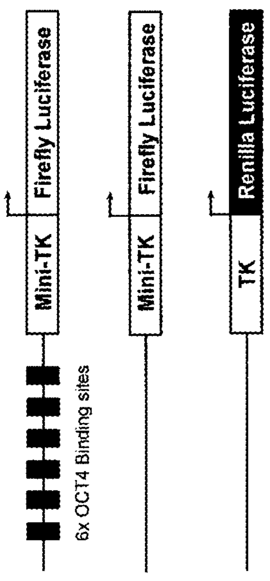
Figure 2C:
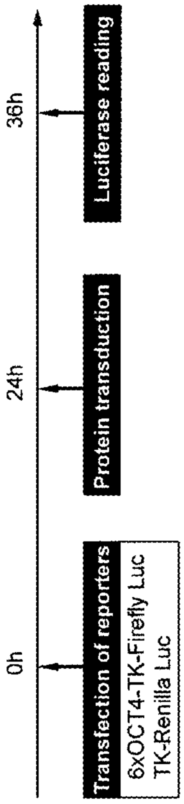
Figure 2D:
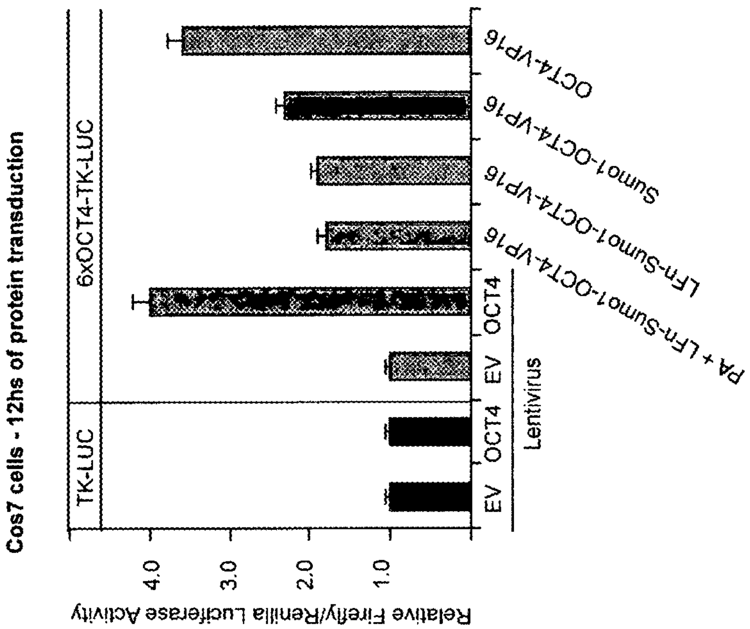

We sought to develop a more reliable and efficient method for protein transduction. Since bacterial toxins are often proteins that are transduced at very high efficiency, we hypothesized that (parts of) such toxin systems could act as a transportation system for the delivery of recombinant proteins. To test this idea, we analyzed whether the transcriptional regulator OCT4 (POU5F1) could be transduced into cells when fused to the N-terminal domain of the Anthrax Lethal Factor (LFn). To this end we generated a recombinant fusion protein consisting of a His-purification tag, LFn-transduction domain, a SUMO cleavage site, human OCT4 and a VP16 transactivation domain (FIG. 2A). The latter was added to further boost the transcriptional activity of the recombinant factor. In addition, we generated control constructs lacking the LFn transduction domain or the LFn transduction domain and the SUMO-cleavage domain (FIG. 2A). COS7 reporter cells were generated by transfecting COS7 cells with a reporter construct containing 6 repeats of the oct4 target sequence followed by a minimal TK promoter and the Firefly luciferase gene (FIG. 2B). As a control, we transduced COS7 cells with a Luciferase reporter vector without the Oct4 binding sites (FIG. 2B). To control for variations in transfection efficiency, we co-transfected the COS7 cells with a ubiquitously expressed Renilla-Luciferase vector (FIG. 2B). A timeline of the transduction is shown in FIG. 2C. Transduction of COS7 cells with recombinant LFn-OCT4-SUM01-VP16 protein resulted in activation of the luciferase reporter activity (FIG. 2D). Unexpectedly however, the control transduction of the control protein lacking the LFn transduction domain demonstrated similar, if not slightly better transduction efficiency (FIG. 2D). In addition, the control protein lacking the LFn transduction domain and the SUMO cleavage domain demonstrated efficient transduction into the COS7 cells, comparable to the control infection of the cells with a lentiviral vector expressing Oct4 (FIG. 2D).

Figure 2E:
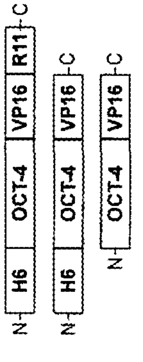
Figure 2F:
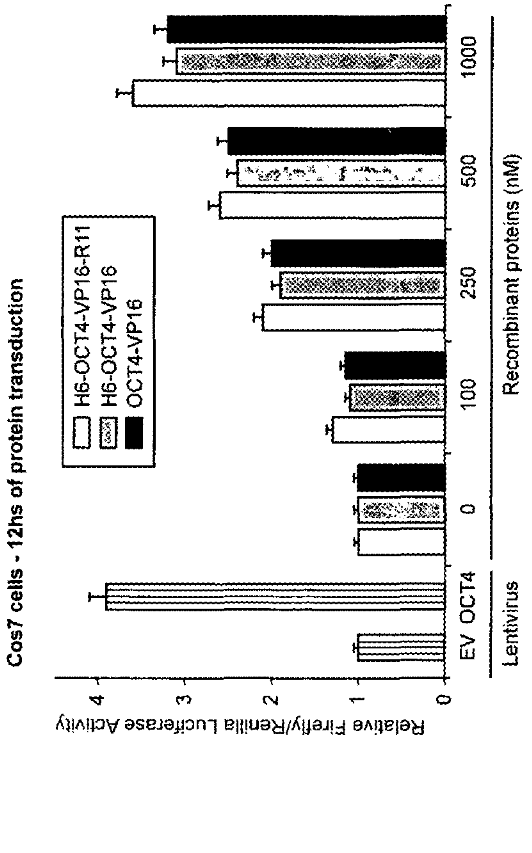
Figure 2G:
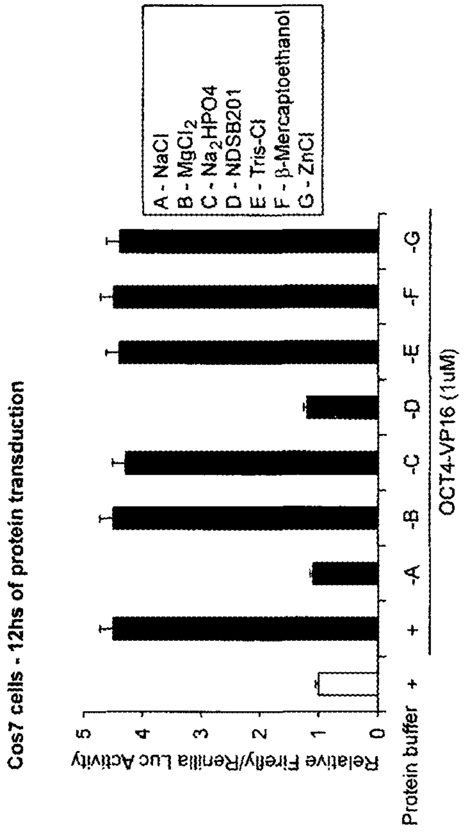
Figure 2H:
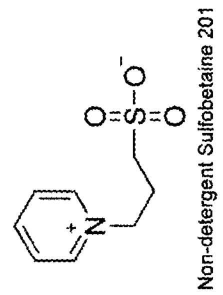

As mentioned above, short peptide sequences are able to mediate the transduction of recombinant proteins across the cell membrane. Since we added a 6× Histidine (6×His) tag to the recombinant Oct4 protein to facilitate protein purification, we assessed whether Oct4 protein transduction was mediated by this peptide tag. To this end, we made several recombinant proteins indicated in FIG. 2E, either containing a His-purification tag (H6) and an R11 transduction peptide[9], or His-tag only, or no peptide tag (FIG. 2E). We tested the ability of these recombinant proteins to activate the Oct4-reporter. As shown in FIG. 2F, H6-Oct4-VP16-R11, H6-Oct4-VP16 and Oct4-VP16 displayed similar reporter activation, demonstrating that the 6×His purification tag was neither required for, nor enhanced or inhibited protein transduction (FIG. 2F, blue and red bars). As a negative control we infected the reporter cells with a control lentiviral expression vector (FIG. 2F, white bar). As a positive control, we infected the reporter cells with a lentiviral Oct4 expression vector (FIG. 2F, black bar).

Above results suggested that the recombinant Oct4 proteins transduced in the absence of transduction peptide sequences and prompted us to test if one or more components added to the culture system were responsible for the observed protein transduction. By omitting individual components of the buffer containing the recombinant protein (Indicated in the legend of FIG. 2G), we identified NaCl hyperosmolarity and Non-detergent sulfobetaine 201

(NDSB 201) as important factors in the protein transduction process (FIGS. 2G and 2H) Omission of either factor abrogated Oct4-reporter activation by recombinant Oct4-VP16 protein.

The Effect of Time, Osmolality, Transduction Compound Concentration, Protein Concentration.

Figures 3A, 3B, 3C, 3D, 3E:
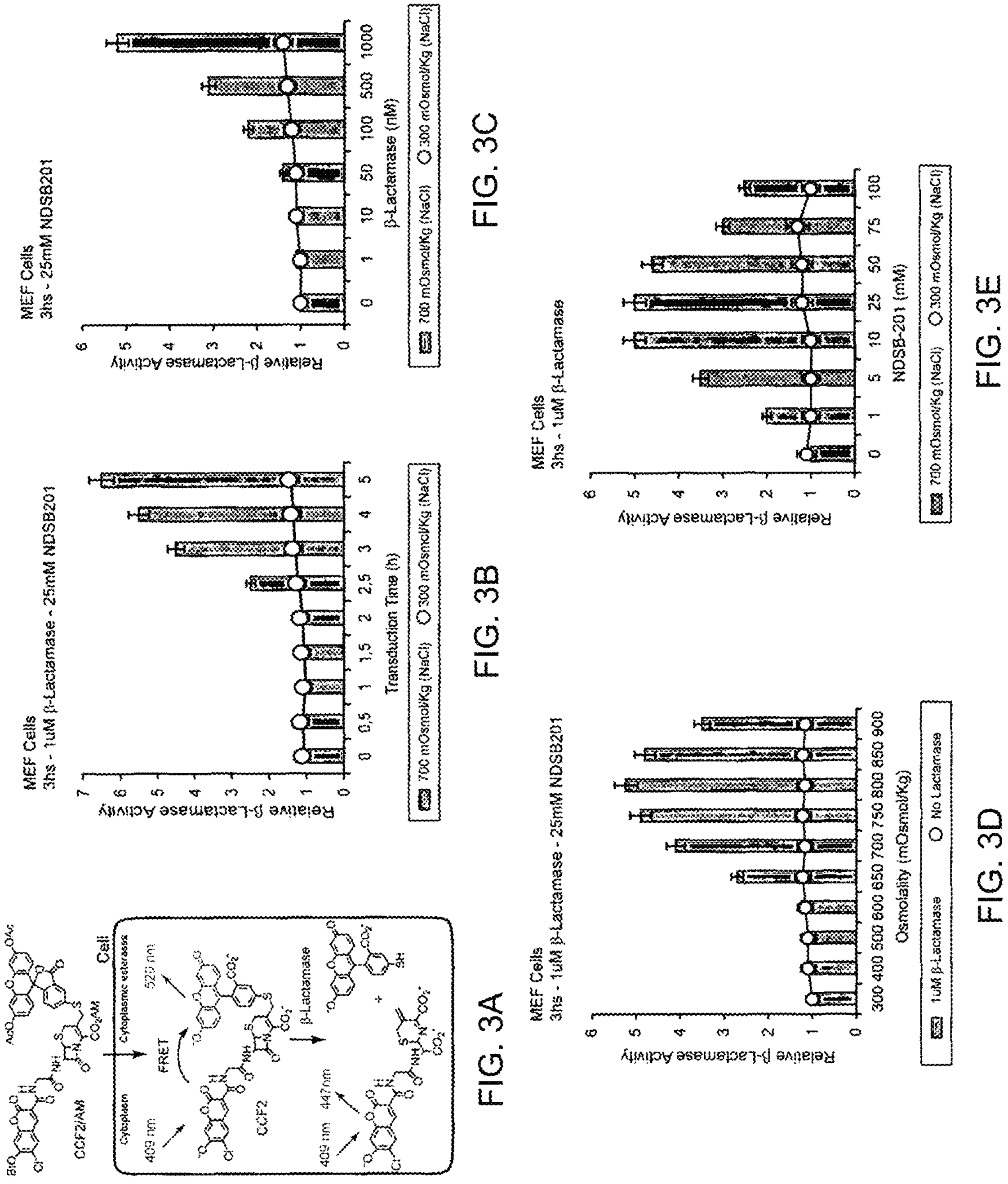

To further characterize the protein transduction process we analyzed the effect of time, osmolality, transduction compound concentration and protein concentration on the transduction process. To this end, we set up a β-Lactamase protein transduction assay and measured intracellular β-Lactamase activity using CCF2-AM, an intracellular fluorescent β-Lactamase substrate that changes emission wavelength when cleaved by the enzyme (FIG. 3A). Hence, the change in emission fluorescence is a quantitative measure for intracellular β-Lactamase activity. While we used the immortalized COS7 cell line in our initial studies, we wanted to know if the compound-mediated protein transduction would also allow the transduction of protein into primary cells. We therefore transduced murine embryonic fibroblasts (MEFs) with β-Lactamase (1 μM final concentration), using NaCl-adjusted hypertonic media (700 mOsm/Kg) and 25 mM NDSB201. β-Lactamase activity was set at 1 at the start of the experiment and relative intracellular β-Lactamase activity was measured as a function of time (FIG. 3B, bars). As a control, β-Lactamase transduction was measured in isotonic media in the presence of 25 mM NSDB201 (FIG. 3B, open circles). As shown in FIG. 3B, under these conditions intracellular β-Lactamase activity could be observed 2.5 hours after the initiation of protein transduction. Longer transduction times resulted in an increase in intracellular β-Lactamase activity (FIG. 3B).

To assure that the observed β-Lactamase activity was a result of the transduced protein, we performed a dose-response test and measured β-Lactamase activity as a function of β-Lactamase concentration either in transduction media (25 mM NDSB201 and 700 mOsm/Kg) or isotonic media with addition of 25 mM NDSB201. MEFs were transduced with β-Lactamase protein for 3 hours and intracellular β-Lactamase activity was measured as described. As shown in FIG. 3C, in transduction media, β-Lactamase protein was efficiently transduced in a concentration-dependent manner. In contrast, no intracellular β-Lactamase activity was observed when β-Lactamase protein was added in isotonic media.

These results demonstrate the accuracy of the β-Lactamase assay and demonstrate that β-Lactamase protein is transduced into cells in a protein concentration-dependent manner.

Next we measured the effect of media tonicity on the transduction process. As above, MEFs were transduced for 3 hours with 1 μM β-Lactamase in MEF media containing 25 mM NDSB201 and increasing media tonicity, adjusted with NaCl (FIG. 3D). As a control, we measured substrate cleavage as a function of media osmolality in the absence of transduced β-Lactamase protein (FIG. 3D, open circles) to verify that the media tonicity did not in itself affect the β-Lactamase activity assay. As shown, increased NaCl concentration resulted in increased β-Lactamase transduction with maximal transduction at approximately 700-800 mOsm/Kg. At osmolalities beyond 850 mOsm/Kg we observed cell loss, presumably due to toxicity of the high media tonicity.

Finally we explored the effect of the concentration of the transduction compound, NDSB201, on the β-Lactamase transduction. Again, MEFs were transduced with β-Lactamase (1 μM final concentration) for 3 hours in hypertonic MEF media adjusted to 700 mOsm/kg with NaCl and at varying NDSB201 concentrations (FIG. 3E). As a control, β-Lactamase transduction was measured as a function of varying NDSB201 concentration in in isotonic media (FIG. 3E, open circles) Increased NSDB201 concentration resulted in a transient increase in β-Lactamase transduction peaking at 10-25 mM NSDB201 (FIG. 3E). Under hyperosmotic conditions, higher NSDB201 concentrations resulted in cell loss.

Above results demonstrate that protein transduction is dependent on protein concentration, transduction time, NDSB201 concentration and NaCl adjusted media tonicity.

Addition of Osmoprotectants Ameliorates Hypertonic Stress

We noticed that while the combination of NaCl-induced hyperosmolarity and NDSB201 allowed efficient transduction of protein, it also appeared to affect cell proliferation and cell survival, and high media tonicity and/or high NSDB201 concentration appeared to have a detrimental effect on the cells. Hyperosmotic stress has been shown to induce cell cycle arrest and apoptosis in mammalian cells[10-13]. To explore whether the hyperosmotic conditions during the transduction affected cell proliferation, we measured BrdU incorporation in MEFs upon protein transduction either for 3 hours at 700 mOsm/Kg or for 12 hours at 500 mOsm/Kg (FIG. 4A). BrdU incorporation was measured 24 hours after the start of protein transduction. BrdU incorporation of MEFs maintained in isotonic conditions was set at 100% and dropped below 40% upon addition of the protein transduction buffer alone, or protein transduction buffer+β-Lactamase (FIG. 4A). These results demonstrate that, as suspected, the transduction conditions negatively impacted cell proliferation, independent of the transduced protein.

Osmoprotectants are compounds that help cells cope with osmotic stress by accumulating in the cytosol, thereby balancing the osmotic difference between the intra- and extracellular environment. We tested whether the addition of osmoprotectants (indicated in FIG. 4B) to the media would prevent the cell cycle arrest during protein transduction. As before, we measured BrdU incorporation 24 hours after the start of the transduction. β-Lactamase protein was transduced for 3 hours in MEF media adjusted with NaCl to 700 mOsm/Kg and with 25 mM NDSB201 with addition of osmoprotectants, alone or in combination as indicated in FIG. 4B. As shown, the addition of osmoprotectants during protein transduction ameliorated the cell cycle arrest induced by the transduction media. The combination of Glycerol and Glycine appeared most effective at ameliorating the cell proliferation block in MEFs and was affective both during a 3 hour transduction at 700 mOsm/Kg as well as during a 12 hour transduction at 500 mOsm/Kg (FIG. 4C). Next we tested whether osmoprotectants could also prevent cell cycle block during the transduction of other cell types. To this effect, we transduced murine ESCs either for 3 hours at 700 mOsm/Kg or for 12 hours at 500 mOsm/Kg. While the osmoprotectant combination of Glycerol and Glycine was ineffective at preventing the reduction in cell proliferation in mESC at 700 mOsm/Kg, it enabled continued cell proliferation during the 12 hour transduction at 500 mOsm/Kg (FIG. 4D). Finally we tested whether the addition of osmoprotectants would allow multiple sequential rounds of protein transduction whilst preventing cell cycle arrest We performed multiple rounds of transduction of mESCs for 12 hours at 500 mOsm/Kg with an intermediate 12 hours recovery period. As shown in FIG. 4E, in the presence of osmoprotectants, multiple rounds of transduction were well tolerated by the mESCs, without significant negative impact on cell proliferation.

Protein Transduction Requires Active Cellular Uptake Via Macropinocytosis

Figures 5A, 5B, 5C:
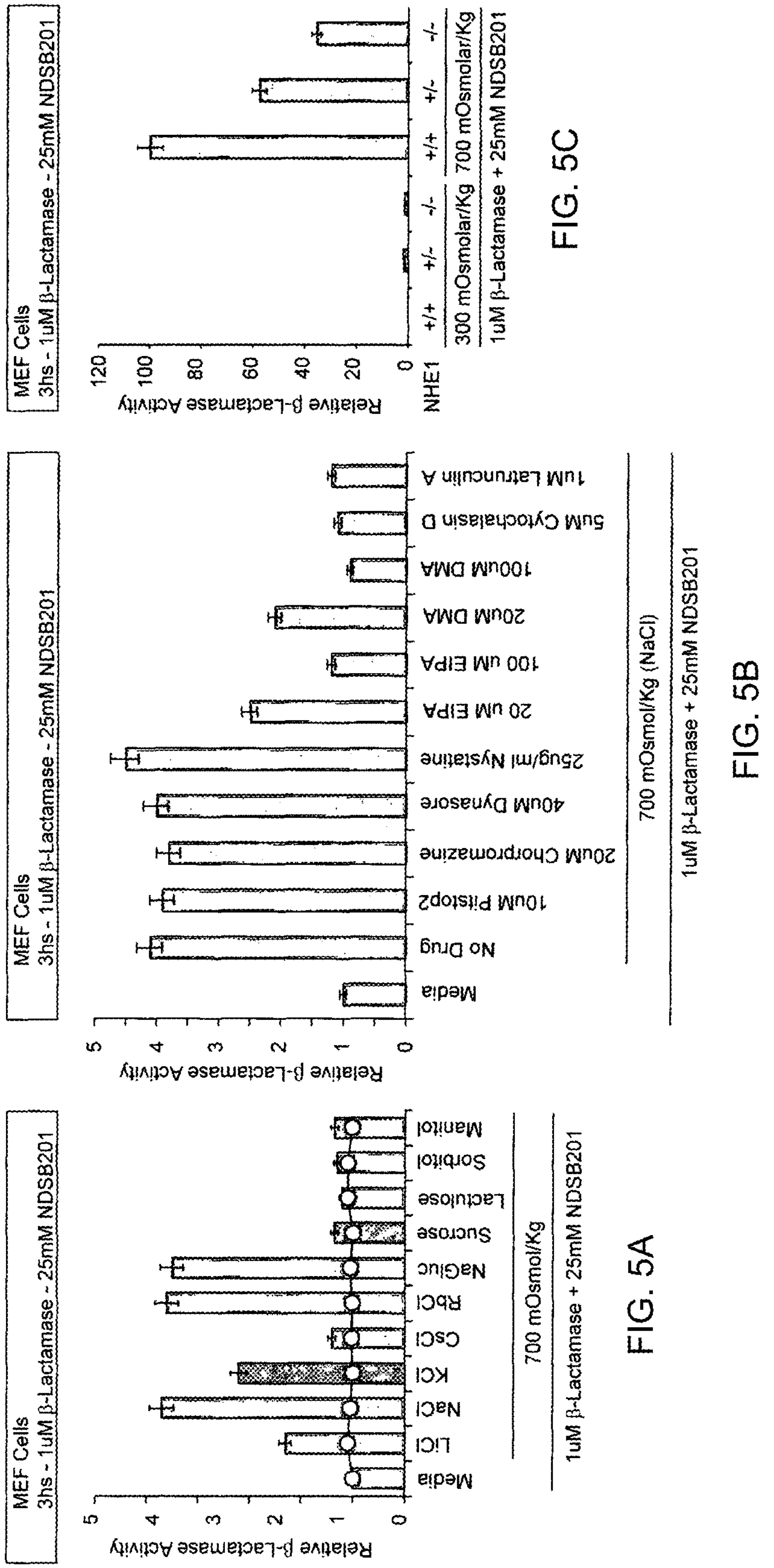

To further dissect the mechanism by which media hypertonicity induces protein transduction, we explored whether the effect was specific to the NaCl used to increase media osmolarity. MEFs were transduced with β-Lactamase for 3 hours in the presence of NDSB201 (25 mM) and osmoprotectants and media tonicity was adjusted to 700 mOsm/Kg using NaCl, or related salts according to the periodic table of elements, including LiCl, KCl, CsCl and RbCl. As shown in FIG. 5A, all Na-related salts had protein transducing activity, with Na and Rb demonstrating the highest activity. In addition, we tested whether other Na-salts could induce protein uptake. As shown in FIG. 5A, Sodium Gluconate effectively mediated β-Lactamase transduction with efficiency similar to NaCl and RbCl. Finally, we tested whether increasing media tonicity using unrelated compounds would also trigger protein transduction. As shown in FIG. 5A, Sucrose, Lactulose, Sorbitol and Manitol all failed to induce protein transduction at 700 mOsm/Kg, suggesting that protein transduction is specifically dependent on hypertonicity induced by sodium or sodium-related salts.

Since the conditions that trigger protein transduction require that hypertonicity is specifically induced by Na+ and related ions, it seemed unlikely that the transduction occurred simply through enhanced permeabilization of the plasma membrane. We hypothesized that protein transduction involved an active mode of endocytic transport and used specific inhibitors of different types of endocytosis to explore the mechanism of entry that was exploited by our protein transduction buffer. As anticipated, treatment of cells with Cytochalasin D or Latrunculin A, specific inhibitors of actin polymerization and vesicle transport, completely blocked protein transduction (FIG. 5B), confirming that protein transduction requires Actin remodeling. However, specific inhibitors of endocytosis, including Pitstop2 and Chlorpromazine (inhibitors of Clathrin-mediated endocytosis), and Dynasore and Nystatin (inhibitors of Caveolin-mediated endocytosis) were all ineffective in inhibiting protein transduction (FIG. 5B). These data suggest that protein transduction does not occur through classical clathrin-mediated or caveolin-mediated endocytic pathways. In contrast to other types of endocytosis, macropinocytosis is uniquely susceptible to inhibitors of Na+/H+ exchange. Interestingly protein transduction was strongly inhibited by specific inhibitors of Na+/H+ exchange such as EIPA or DMA, specific inhibitors of a family of Sodium-hydrogen Antiporter (Nhe) proteins (FIG. 5B). These data suggest that the protein transduction process involves active cellular uptake of exogenously applied through macropinocytosis.

The Sodium-hydrogen Antiporter-1 (Nhe1) is a ubiquitously expressed Na+/H+ exchange factor that functions to regulate cell volume and intracellular pH in vertebrate cells. It is activated in response to osmotic stress, leading to extrusion of intracellular H+ ions in exchange for extracellular Na+. Although this exchange in itself is osmotically neutral, extruded H+ is replaced from intracellular buffers resulting in a net increase in intracellular osmolarity and increase in cell volume by osmosis. In addition, Nhe1 activation induces macropinocytosis-mediated active fluid uptake from the extracellular space. While the exact molecular link between Nhe1 activation and macropinocytosis is still unclear, experimental evidence suggests that local modulation of intracellular pH by Nhe1 in the vicinity of the plasma membrane is required for actin polymerization and macropinosome formation[14]. The role of Nhe1 in coping with osmotic stress and regulation of macropinocytosis, it's specific role in the transport of Na+ and related ions, and the fact that protein transduction is inhibited by inhibitors of Na+/H+ exchange, made this transporter an interesting candidate as a mediator of NaCl-induced protein transduction. To further confirm that the effect of EIPA and DMA was due to the inhibition of Nhe1, we compared the transduction of MEFs from Nhe1 knockout embryos with Nhe1 heterozygous and wild-type MEFs. As shown in FIG. 5C, protein transduction was almost completely abrogated in Nhe1 null fibroblasts. Fibroblasts from Nhe1+/− heterozygous embryos displayed reduced protein transduction activity compared to wild-type littermates (FIG. 5C). These results demonstrate that Nhe1 is an important mediator of protein transduction, but a residual protein transduction activity remains in the absence of Nhe1 expression. Nhe1 is a member of Solute Carrier Family of antiporters, and it is likely that a residual antiporter is responsible for the residual protein transduction activity. This is further supported by our finding that EIPA, a specific inhibitor of NHE antiporters completely inhibits protein transduction.

Activators of Nhe1 Enhance Protein Transduction

Figure 5D:
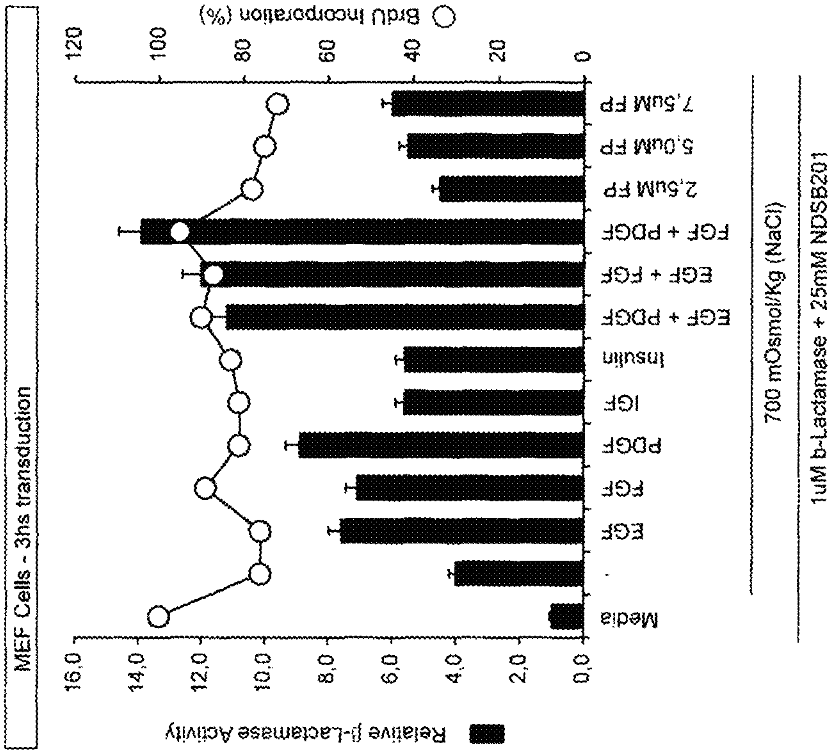
Figure 5E:
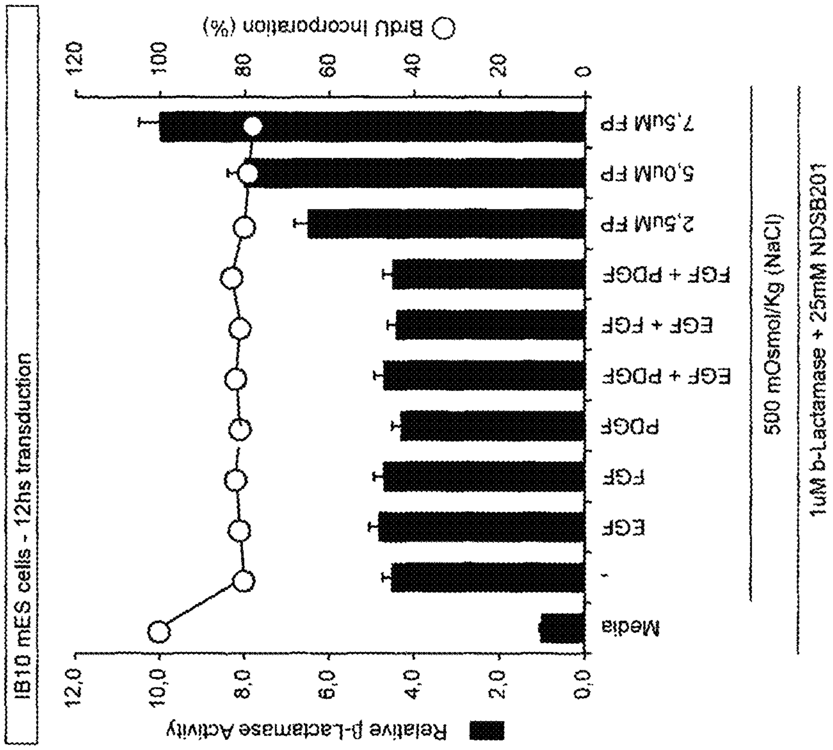

Our finding that Nhe1 is an important mediator of protein transduction prompted us to explore whether activators of Nhe1 can enhance the protein transduction process. Several growth factors gave been shown to induce macropinocytosis by activating Nhe1 and enhance Na+/H+ exchange[15-19]. We explored the effect of epidermal growth factor (EGF), Fibroblast growth factor (FGF), Platelet-derived growth factor (PDGF), Insulin, Insulin-like growth factor (IGF) and combinations of these factors on protein transduction. As shown in FIG. 5D, Insulin and IGF had a small, but significant stimulatory effect on protein transduction of MEFs. In addition, EGF, FGF and PDGF resulted in a doubling of β-lactamase uptake. Finally, Combinations of these factors demonstrated an additive effect on β-lactamase transduction (FIG. 5D). Inhibition of Nhe activity with EIPA completely blocked protein transduction, even in the presence of FGF and PDGF, demonstrating that the enhanced protein transduction induced by these growth factors was not mediated by alternative endocytic mechanisms. A short dTAT-HA2 peptide has been shown to enhance macropinosome escape of proteins[20]. We tested if addition of the dTAT-HA2 peptide could further enhance protein transduction of β-lactamase protein into MEFs. To this end, we titrated different concentrations of dTAT-HA2 peptide into the transduction buffer. As shown in FIG. 5D, addition of the dTAT-HA2 peptide had a small enhancing effect on protein transduction. Finally, we tested if growth factor stimulation or addition of dTAT-HA2 peptide could enhance protein transduction of other cells as well. We transduced murine ESCs with 1 μM β-lactamase protein at 500 mOsm/Kg for 12 hours in the presence of indicated growth factors or dTAT-HA2 fusion peptide. As shown in FIG. 5E, addition of growth factors had a minor effect on mESC protein transduction, but addition of dTAT-HA2 fusion peptide resulted in a profound increase in β-lactamase incorporation into mESCs.

Chemical Properties of the Protein Transduction Compound

Figure 6B:
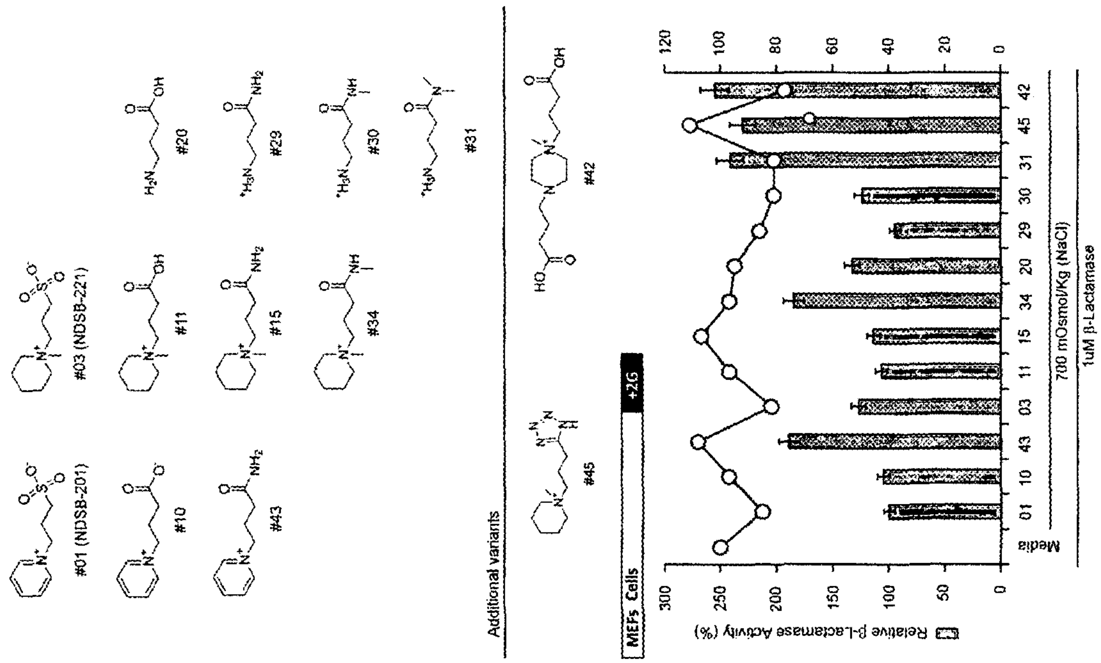
Figure 6A:
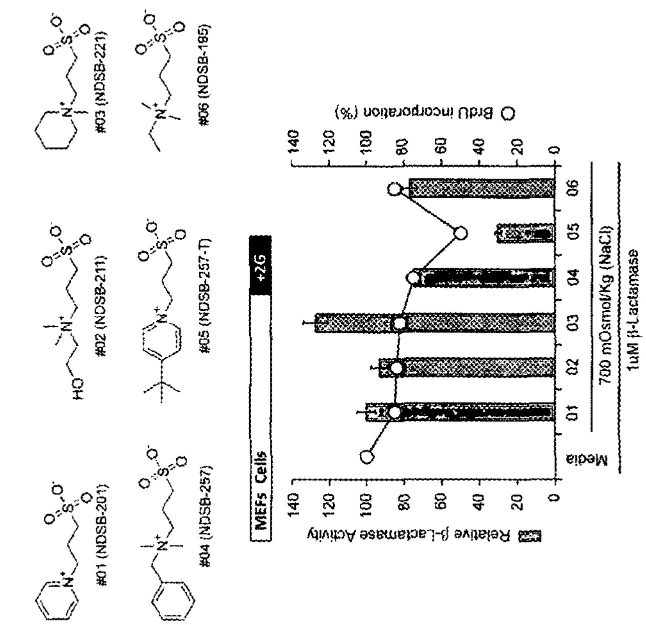

Our finding that salt-induced hypertonicity in combination with NDSB201 triggered efficient protein transduction prompted us to explore whether other Non-detergent sulfobetaines could trigger protein transduction as well. We tested the protein transducing activity of six commercially available NDSBs (Chemical structures indicated in FIG. 6A). FIG. 6A shows the transduction of β-Lactamase by NDSB201 (#01) as well as 5 additional NDSB compounds (#02-06) all at 25 mM final concentration into MEFs (3 hours at 700 mOSm/Kg). Open circles indicate BrdU incorporation measured 24 hrs after start of the protein transduction. These results demonstrated that while all NDSB compounds facilitated protein transduction, they vary in their transduction efficiency and effect on cell proliferation. NDSB201 (#01) and NDSB221 (#03) appeared the most efficient in β-Lactamase transduction and hence we explored further variations on these two compounds. NDSBs consist of a rather heterogeneous group of compounds that consist of a 2-6 carbon backbone that separates a sulfonic acid terminus on one side and a tetravalent nitrogen atom on the other. We first explored whether the sulfonic acid group could be replaced with other end-groups by substituting sulfonic acid in #01 and #03 for caboxylic acid (yielding compounds #10 and #11, FIG. 6B) or an amide (yielding compounds #43 and #15, FIG. 6B). As shown in the bar graph of FIG. 6B, substitution of sulfonic acid did not have a negative impact on transduction efficiency. However, the substitutions further reduced the negative effect of the transduction buffer on cell cycle as shown by an enhanced BrdU uptake (FIG. 6B, open circles). In addition, the pyridine or piperidine rings structure in the transduction compound (compounds #01 and #03 respectively) could also be substituted a trivalent of tetravalent amine (compounds #20 and #29, FIG. 6B) without significant change in transduction activity. Next we examined whether the ability of the amide to donate protons (Compounds #29 and #15) was required for transduction activity, by substituting one or two protons with CH3 (yielding compounds #30, #31 and #34). As shown, this methyl substitution enhanced the transduction activity of the compounds (FIG. 6B). Finally, we examined whether bioisosteres of the sulfonic acid (Compound #45) or dimerization of the transduction compound (Compound #42) affected transduction activity. As shown in FIG. 6B, compounds #45 and #42 demonstrated high transduction efficiency compared to the original NDSB201 (#01) with equal or better cell proliferation (FIG. 6B).

Figure 6C:
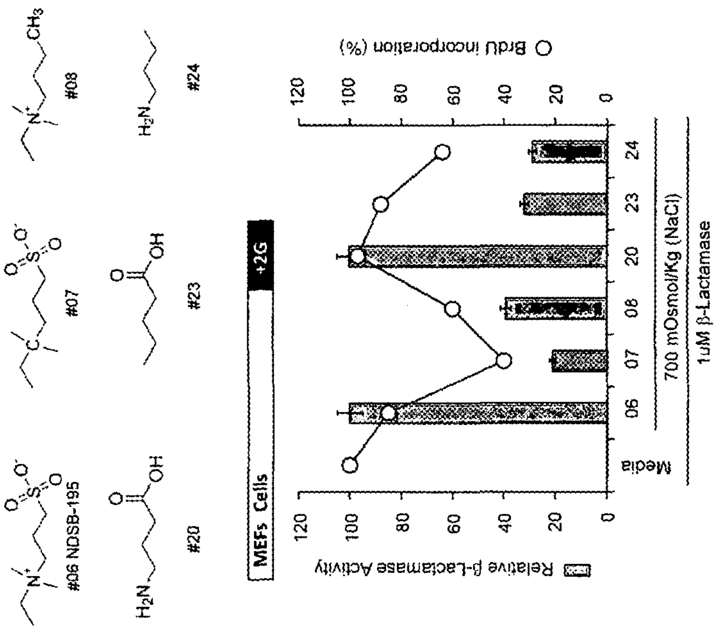

Thus, variations on the original transduction compound NDSB201 (#01) demonstrate that there is substantial chemical freedom regarding substitutions of the pyridine ring and the sulfonic acid, which can be substituted by the structures described above. Neither the tetravalency of the nitrogen and/or its incorporation in a ring structure, nor the proton-donor properties of the sulfonic acid appeared important for the transduction activity. However, all tested active substitutions had hydrophilic ends separated by a hydrophobic carbon chain. We therefore next examined if substitution of these hydrophilic end groups by a hydrophobic CH3 group would affect transduction activity. We compared the activity of NDSB195 (#06) and two derivatives in which either the nitrogen (#07) or the sulphonic acid (#08) were replaced by C or CH3 respectively (FIG. 6C). In addition, we explored the effect of these substitutions on a transduction compound with a trivalent nitrogen and carboxylic acid terminus (FIG. 6C, #20 and derived #23 and #24). As shown in the graph in FIG. 6C, carbon substitution of either group greatly diminished transduction activity of the compound. Moreover, substituted compounds (#07, #08, #23 and #24) displayed severe cell cycle inhibition (FIG. 6C, open circles). Thus, while the transduction compound allows substantial freedom at its termini, it appears that a hydrophilic group is preferred at either end of the carbon chain.

Figure 6D:
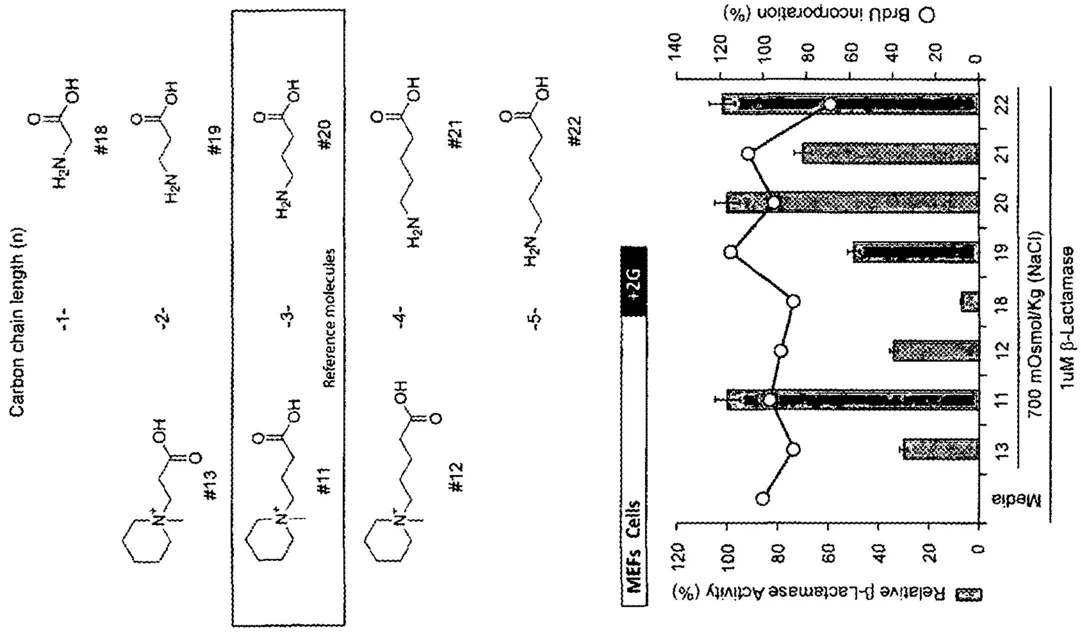

The hydrophilic termini are separated by a 3-carbon chain. We next tested whether the length of the carbon chain was critical for transduction activity. We tested compounds with 1 (#18), 2 (#13 and #19), 3 (reference compounds #11 and #20), 4 (#12 and #21) and 5 (#22) carbons in the chain. As shown in FIG. 6D, transduction activity was highest in the reference compounds β-carbon chain). The compound with the 5-carbon chain (FIG. 6D, #22) demonstrated similar transduction activity but displayed reduced cell cycle progression. From our results it appears that while compounds with a carbon chain length of 2-5 display transduction activity, a 3-carbon chain is preferred.

Figure 6E:
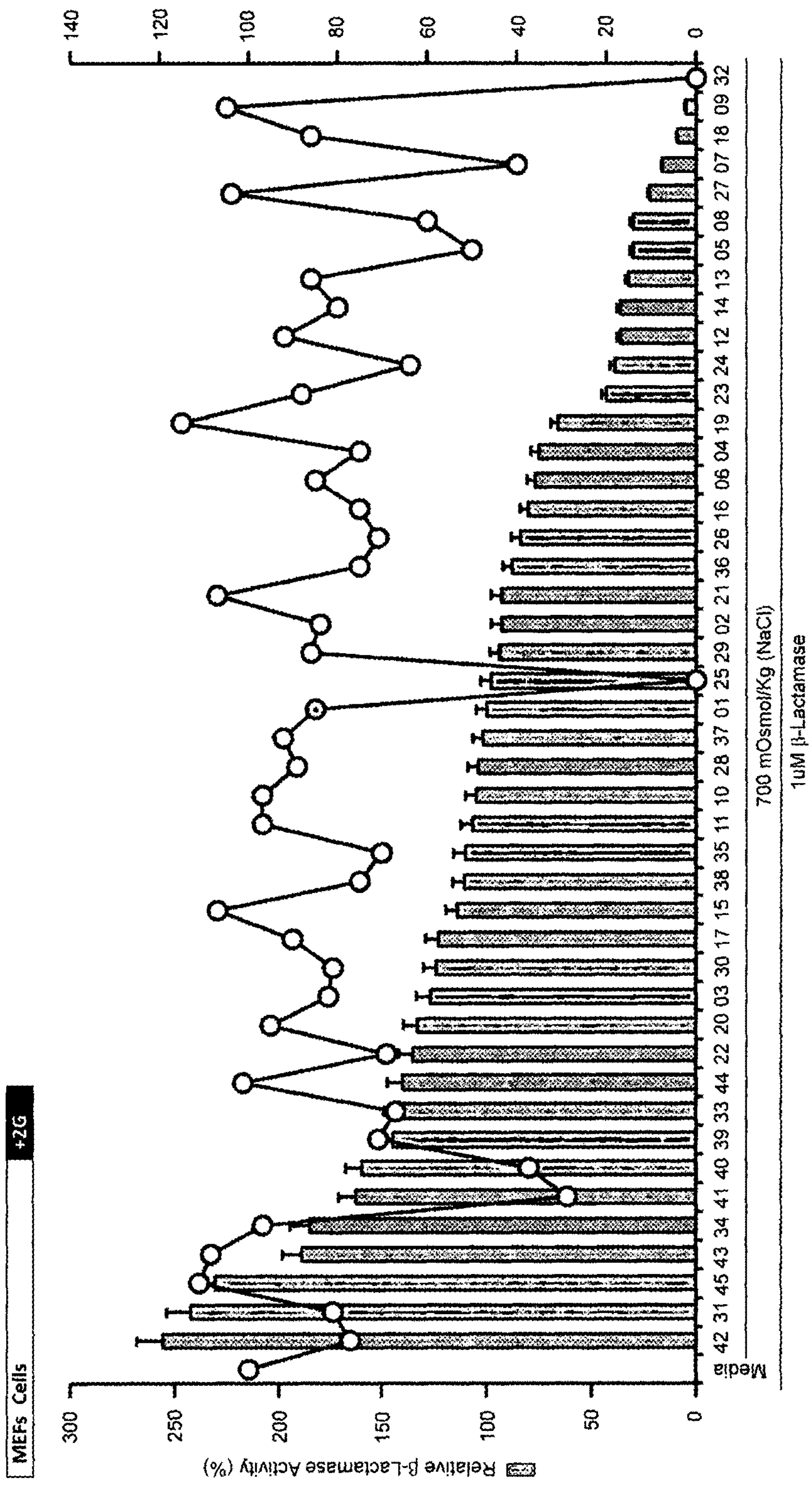
Figure 6G:
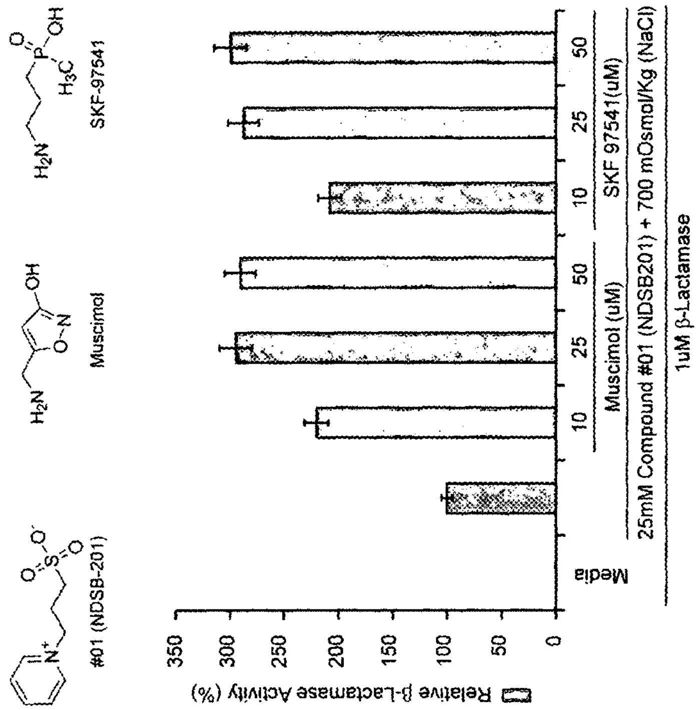
Figure 6F:
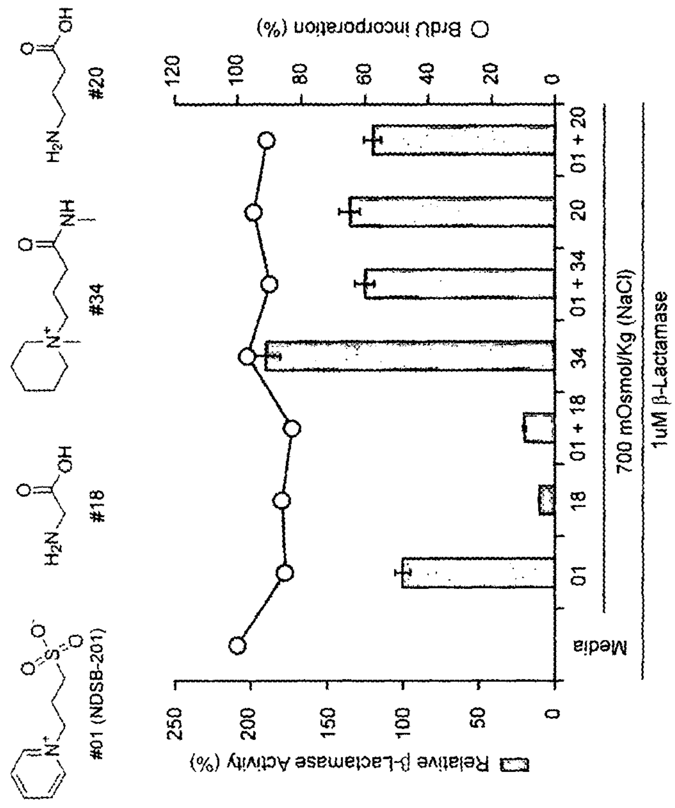
Figure 7A:
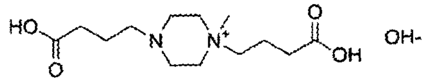
Figure 7A:
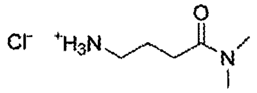
Figure 7A:
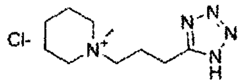
Figure 7A:
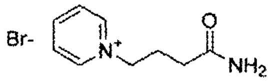
Figure 7A:
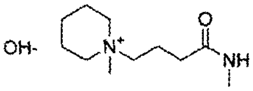
Figure 7A:
Figure 7A:
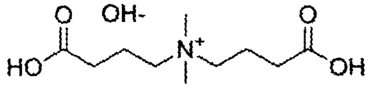
Figure 7A:
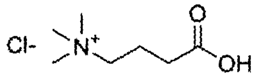
Figure 7A:
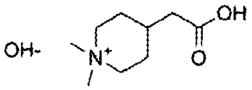
Figure 7A:
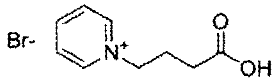
Figure 7A:
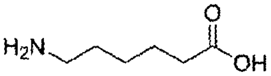
Figure 7A:
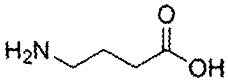
Figure 7A:
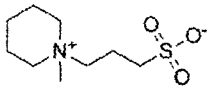
Figure 7B:
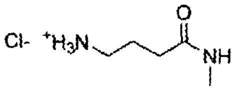
Figure 7B:
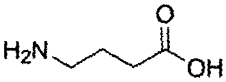
Figure 7B:
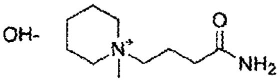
Figure 7B:
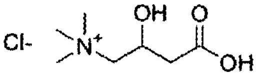
Figure 7B:
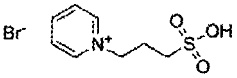
Figure 7B:
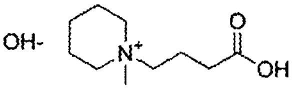
Figure 7B:
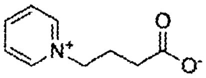
Figure 7B:
Figure 7B:
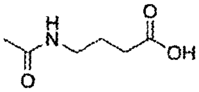
Figure 7B:
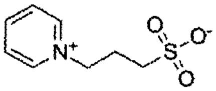
Figure 7B:
Figure 7B:
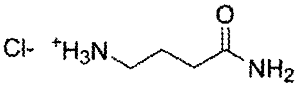
Figure 7B:
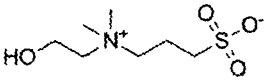
Figure 7C:
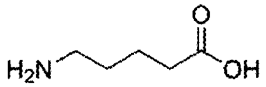
Figure 7C:
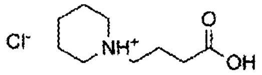
Figure 7C:
Figure 7C:
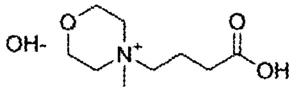
Figure 7C:
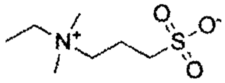
Figure 7C:
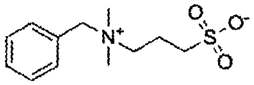
Figure 7C:
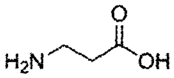
Figure 7C:
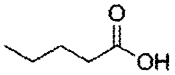
Figure 7C:
Figure 7C:
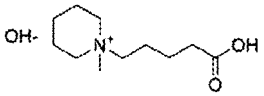
Figure 7C:
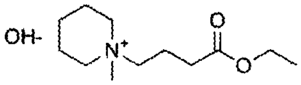
Figure 7C:
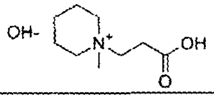
Figure 7C:
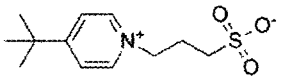
Figure 7D:
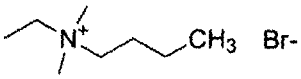
Figure 7D:
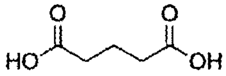
Figure 7D:
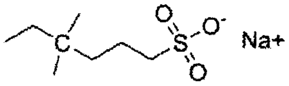
Figure 7D:
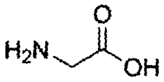
Figure 7D:
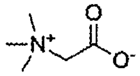
Figure 7D:
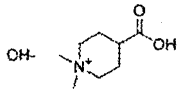
Figure 7D:
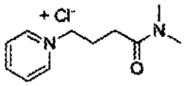

As demonstrated above, an unexpectedly wide range of compounds display transduction activity. To further dissect the chemical properties of effective protein transduction compounds, we explored the protein transducing activity of a wide variety of Non-detergent sulfobetaine-related compounds. A full list of tested compounds as well as a graph displaying the protein transduction activity as well as their effect on cell proliferation is shown in FIG. 6E with accompanying legend in FIGS. 7A-7D. The reference compound NDSB201 (#01) is indicated in blue. As shown, transduction compounds display a wide range in transduction activity and cell proliferation. This prompted us to test whether combinations of transduction compounds would have an additive or even synergistic effect on transduction activity and/or cell proliferation. FIG. 6F displays the results of various combinations of transduction compounds. The transduction efficiency of the reference compound NDSB201 (#01) was set at 100% (FIG. 6F, blue bar). Glycine (#18), which has a single carbon chain, displays poor transduction activity (9% of reference compound, FIG. 6F). When combined with the reference transduction compound at equimolar concentration (12.5 mM each), transduction activity was approximately 15%, suggesting that combined compounds do not have an additive effect, but rather the compound with the lowest transduction activity dominates the total activity. This is further exemplified when our reference compound was combined with compound #34, which on its own displayed a transduction efficiency of 180%. However, combined with the reference compound, transduction activity dropped to 120%. When compounds with comparable transduction activity are combined (reference compound #01 and compound #20) transduction activity remains largely unchanged (FIG. 6F).

One of the NDSB201 derivatives we tested was gamma-aminobutyric acid (GABA, compound #20) an important neurotransmitter in the brain. GABA acts by stimulating the activation of GABA-receptors, of which three classes have been identified; GABA-A, GABA-B and GABA-C. Interestingly, GABA receptors are stimulated by a remarkably wide range of chemical structures ranging from simple structures like ethanol and GABA itself, to seemingly unrelated benzodiazepines, muscimol, baclofen and a long list of other compounds. Since the chemical structure of effective protein transduction compounds also displays a large degree of freedom, we explored whether GABA signaling plays an active role in the protein transduction effect We tested the effect of specific GABA agonists on β-lactamase transduction. MEFs were transduced with 1 μM β-lactamase for 3 hours at 700 mOsm/Kg and with 25 mM NDSB201 in the presence or absence of GABA agonists Muscimol and SKF-97541. As shown in FIG. 6G, addition of GABA agonists enhanced protein transduction approximately 300% (FIG. 6G).

Protein Transduction of Murine Embryonic Stem Cells

To explore protein transduction of murine embryonic stem cells in more detail, we used a transgenic mESC line in which a CRE-recombinase inducible reporter was stably integrated in the ColA1 locus[2]. This reporter encompasses a CMV promoter followed by a LoxP-flanked Stop-casette and a eGFP reporter gene (FIG. 8A). eGFP expression is induced upon successful CRE-recombinase mediated excision of the Stop cassette. Indeed, transduction of increasing concentration of recombinant CRE protein into murine ESCs results in a dose-dependent increase in GFP+ ESCs (FIG. 8B, upper panels, 12 hour transduction at 500 mOsm/Kg with glycerol and glycine). Two sequential rounds of transduction (12 hrs each as above, with a 12 hour recovery period in-between) with 5 μM CRE resulted in 79% GFP+ ESCs (FIG. 8B, upper panels). Furthermore, addition of 5 μM Tat-HA2 fusion peptide, known to enhance endosomal lysis of macropinocytotic vesicles[20], further increased the percentage of GFP+ cells to 81% after single transduction and 97% transduced cells after two rounds of protein transduction (FIG. 8B, lower panels). A fluorescence microscopy image of the cells in FIG. 8/B is shown in FIG. 8C. Next we tested whether protein transduction affected ESC proliferation. After two rounds of CRE-protein transduction, the doubly transduced cells in FIG. 8B were trypsinized, seeded onto MEFs feeders, and cell proliferation was monitored by cell counting. Untransduced cells were used as a control. As shown in FIG. 8D, two rounds of CRE protein transduction did not affect ESC proliferation, neither in the absence (FIG. 8D, top panel) or presence (FIG. 8D, bottom panel) of Tat-HA2 fusion peptide. Next we explored the expression of key pluripotency factors in the double transduced mESCs by qRTPCR. FIG. 8E demonstrated that the expression of Oct4, Nanog, Sox2, Rex1 and FBox15 was unchanged in double-transduced mESCs compared to untransduced control ESCs, either in the absence (FIG. 8E, top panel) or presence (FIG. 8E, bottom panel) of Tat-HA2 fusion peptide. Murine ESCs are pluripotent, meaning they have the capacity to differentiate into derivative of the three germ layers. A stringent test of mESC pluripotency is their ability to form chimeras. To test the pluripotency of the transduced mESCs, double-transduced GFP+ ESCs from the experiment in FIG. 8B were injected into host blastocyst embryos and transplanted into pseudopregnant foster mice. As shown in FIG. 8F, double-transduced mESCs efficiently contributed to chimera formation, both in the transduction without (FIG. 8F, upper panel) and with Tat-HA2 fusion peptide (FIG. 8F, lower panel).

Protein Transduction of Human Induced Pluripotent Stem Cells (iPSCs).

To explore whether our transduction buffer would allow the transduction of human induced pluripotent stem cells (iPSCs) as well, we employed a similar strategy as used for the murine ESCs (FIGS. 8A-8F) with a slight adaptation. We transduced human iPSC with a lentiviral reporter which, upon protein transduction of CRE-recombinase, results in the removal of an expressed dsRed fluorescent reporter gene and subsequent activation of an eGFP reporter gene (FIG. 9A). Hence, the fluorescence signal of successfully transduced hiPSCs would shift from red to green. As with the murine ESCs, transduction of human iPSCs with 5 μM CRE protein resulted in efficient removal of the dsRed reporter and shift to eGFP expression in 64% of the cells as analyzed by flow cytometry (FIG. 9B, left two panels, 12 hours transduction at 500 mOsm/Kg). Note that some cells remain double positive for GFP and dsRed. This is due to the fact that multiple copies of the lentiviral reporter construct are present in the iPSCs, and not all copies are loxed-out. Addition of the Tat-HA2 fusion peptide further increased transduction efficiency to 77% (FIG. 9B, middle panel). Double CRE protein transduction yielded 78% eGFP cells without added tat-HA2 fusion peptide and 84% GFP+ hiPSCs when 5 μM Tat-HA2 fusion peptide was added. FIG. 9C shows the fluorescence microscopy images of the cells in (FIG. 9B).

Protein Transduction of Murine and Human Neural Stem Cells, Neurons and Glia.

A similar strategy of CRE-recombinase mediated red-to-green reporter shift as described above, was utilized to assess the transduction of murine and human neurons, glia and neural stem cells. FIG. 10A depicts a schematic representation of the assay. CRE protein transduction of murine neurospheres resulted in efficient activation of the eGFP reporter (FIG. 10B, left panels). Similarly, human iPSC-derived glial cells and neurons were transduced with 5 μM CRE, resulting in efficient activation of the eGFP reporter. Since the fluorescent reporter construct was introduced into the iPSC-derived glial cells and neurons using lentiviral infection, cells likely incorporated multiple copies of this reporter. Thus, while CRE protein transduction resulted in efficient activation of the eGFP reporter, cells continued to express dsRed from additional copies of the reporter.

REFERENCES

1. Okada, C. Y. & Rechsteiner, M. Introduction of macromolecules into cultured mammalian cells by osmotic lysis of pinocytic vesicles. *Cell* 29, 33-41 (1982).
2. Beard, C., Hochedlinger, K., Plath, K., Wutz, A. & Jaenisch, R. Efficient method to generate single-copy transgenic mice by site-specific integration in embryonic stem cells. *Genesis New York N.Y.* 2000 44, 23-28 (2006).
3. Green, M. & Loewenstein, P. M. Autonomous functional domains of chemically synthesized human immunodeficiency virus tat trans-activator protein. *Cell* 55, 1179-1188 (1988).
4. Frankel, A. D. & Pabo, C. O. Cellular uptake of the tat protein from human immunodeficiency virus. *Cell* 55, 1189-1193 (1988).
5. Mann, D. A. & Frankel, A. D. Endocytosis and targeting of exogenous HIV-1 Tat protein. *the The European Molecular Biology Organization Journal* 10, 1733-1739 (1991).
6. Fawell, S. et al. Tat-mediated delivery of heterologous proteins into cells. *Proceedings of the National Academy of Sciences of the United States of America* 91, 664-8 (1994).
7. Nagahara, H. et al. Transduction of full-length TAT fusion proteins into mammalian cells: TAT-p27Kip1 induces cell migration. *Nature medicine* 4, 1449-52 (1998).
8. Lundberg M. & Johansson, M. Is VP22 nuclear homing an artifact? *Nature biotechnology* 19, 713-4 (2001).
9. Hsieh, J.-T., Zhou, J., Gore, C. & Zimmern, P. R11, a novel cell-permeable peptide, as an intravesical delivery vehicle. *BJU international* 108, 1666-71 (2011).
10. Katz, D., Madhany, S. & Burg M. B. Hyperosmolality causes growth arrest of murine kidney cells. Induction of GADD45 and GADD153 by osmosensing via stress-activated protein kinase 2. *The Journal of biological chemistry* 273, 13645-51 (1998).
11. Luo, L., Li, D.-Q. & Pflugfelder, S. C. Hyperosmolarity-induced apoptosis in human corneal epithelial cells is mediated by cytochrome c and MAPK pathways. *Cornea* 26, 452-60 (2007).
12. Reinehr, R., Graf, D., Fischer, R., Schliess, F. & Häussinger, D. Hyperosmolarity triggers CD95 membrane trafficking and sensitizes rat hepatocytes toward CD95L-induced apoptosis. *Hepatology* (Baltimore, Md.) 36, 602-14 (2002).
13. Dawson, K. M. & Baltz, J. M. Organic osmolytes and embryos: substrates of the Gly and beta transport systems protect mouse zygotes against the effects of raised osmolarity. *Biology of reproduction* 56, 1550-8 (1997).
14. Koivusalo, M. et al. Amiloride inhibits macropinocytosis by lowering submembranous pH and preventing Rac1 and Cdc42 signaling. *The Journal of cell biology* 188, 547-63 (2010).
15. Jenkins, E. C. et al. Intracellular pH regulation by Na+/H+ exchanger-1 (NHE1) is required for growth factor-induced mammary branching morphogenesis. *Developmental biology* 365, 71-81 (2012).
16. Chiang Y., Chou, C.-Y., Hsu, K.-F., Huang, Y.-F. & Shen, M.-R. EGF upregulates Na+/H+ exchanger NHE1 by post-translational regulation that is important for cervical cancer cell invasiveness. *Journal of cellular physiology* 214, 810-9 (2008).
17. Rigor, R. R., Damoc, C., Phinney, B. S. & Cala, P. M. Phosphorylation and activation of the plasma membrane Na+/H+ exchanger (NHE1) during osmotic cell shrinkage. *PloS one* 6, e29210 (2011).
18. Tattersall, A. L. & Wilkins, R. J. Modulation of Na+-H+ exchange isoforms NHE1 and NHE3 by insulin-like growth factor-1 in isolated bovine articular chondrocytes. *Journal of orthopaedic research: official publication of the Orthopaedic Research Society* 26, 1428-33 (2008).
19. Tattersall, A. L., Browning, J. A. & Wilkins, R. J. Modulation of H+ transport mechanisms by interleukin-1 in isolated bovine articular chondrocytes. *Cellular physiology and biochemistry international journal of experimental cellular physiology, biochemistry, and pharmacology* 16, 43-50 (2005).
20. Wadia, J. S., Stan, R V & Dowdy, S. F. Transducible TAT-HA fusogenic peptide enhances escape of TAT-fusion proteins after lipid raft macropinocytosis. *Nature Medicine* 10, 310-315 (2004).

Materials and Methods

DMEM containing 4.5 g/l glucose (Life technologies, cat. 31966-021).
DMEM PHENOL-RED FREE containing 4.5 g/l glucose (Life technologies, cat. 21063-029).
DPBS without calcium and magnesium (Life technologies, cat. 14190-094).
L-Glutamine, 100× (Life technologies, cat. 25030-123).
NEAA; Nonessential amino acid solution, 100× (NEAA; Life technologies, cat. 11140-035).
2-mercaptoethanol solution, 14.3M (Sigma, cat. M3148-25 ml).
Penicillin/Streptomycin solution, 100× (Life technologies, cat. 15140-130).
0.05% Trypsin-EDTA (Life technologies, cat 25300-054).
Gelatin (Sigma, cat. no. G1890) (see REAGENT SETUP).
Puromycin (Life technologies, Cat A11138-03).
mTeSR1™ (StemCell technologies, cat 5850).
TeSR™-E8™ (StemCell technologies, cat. 05840).
Matrigel-growth factor reduced (BD, Cat. 354230).
Dispase (StemCell technologies, cat 7923).
Murine embryonic fibroblasts (MEFs) serum (Sigma, Cat F7524).
Murine embryonic stem cell (mES) Serum (Greiner Bio-One, Cat 758073).
5× Transduction buffer (See REAGENT SETUP).
MEFs Media (See REAGENT SETUP).
mES Media (See REAGENT SETUP).
mES Transduction media (See REAGENT SETUP).
Neural stem cell media (See REAGENT SETUP).
N2 Supplement, 100× (Life technologies, cat. 17502-048).
B27 Supplement, 50× (Life technologies, cat 12587-010).
Lysozyme (Sigma, Cat L6876-1G).
Benzonase Endonuclease (Sigma, Cat. E1014-25KU).
Imidazole (Sigma, Cat I5513-5G).
NDSB-201 (Sigma, Cat 82804-50G).
NDCB-165 (SYNCOM B.V., The Netherlands).
Glycerol (Sigma, Cat G2025).
Glycine (Sigma, Cat. 50046).
NaCl—Sodium chloride (Sigma, Cat S5886).
$NaH_2PO4$—Sodium phosphate monobasic (Sigma Cat, S5011).
$MgCl_2$— Magnesium chloride (Sigma, Cat M4880).
Cell Proliferation ELISA, BrdU (Roche, Cat. 11669915001).
Caspase-Glo 3/7 Assay (Promega, Cat, G8090).
EGF (Life Technologies, Cat PHG0311).
FGF2 (Life Technologies, Cat. 13256-029).
PDGF (Life Technologies, Cat. PMG0044).
Insulin (Sigma, Cat. I9278-5ML).
IGF (R&D Systems, Cat. 791-MG-050).
TAT-HA2 Fusion Peptide (Eurogentec Nederland b.v., Cat AS-64876).
INF7-TAT Fusion Peptide (Eurogentec Nederland b.v., Cat AS-64908).
Chaperone plasmid sets (TAKARA, cat. 3340).
Ampicillin (Sigma, Cat A9518).
Chloranphenicol (Sigma, Cat C0378).
hLIF (Human Leukemia Inhibitory Factor, Stock 1000×; R&D systems, Cat. 7734-LF-025).
Coomassie Stain (Biorad, Cat 161-0786).
CCF2-AM Loading Kit (Life Technologies, Cat. K1032).
Poly-D-lysine hydrobromide (Sigma, Cat P6407).

Equipment

Ni-NTA Superflow Columns (Qiagen, Cat. 30622).
Amicon Ultra-15 Centrifugal Filter Unit (Millipore, Cat UFC903008).
Zeba Spin Desalting Columns (Thermo Scientific, Cat. 87772).
96 Well Flat Clear Bottom Black Polystyrene TC (Corning, Cat 3603).
100-mm Tissue culture dish (Greiner Bio-one, Cat 664160).
6-Well tissue culture plate (Greiner Bio-one, cat. 657160).
24-Well tissue culture plate (Greiner Bio-one, cat. 662160).
96-Well tissue culture plate (Greiner Bio-one, cat. 655180).
2-ml Plastic disposable pipette (Greiner Bio-one, cat 710180).
5-ml Plastic disposable pipette (Greiner Bio-one, cat 606188).
10-ml Plastic disposable pipette (Greiner Bio-one, cat no. 607188).
50-ml Plastic disposable pipette (Greiner Bio-one, cat. 768180).
0.22-mm Pore size filter (Millex GP; Millipore, cat SLGP033RS).
0.45-mm Pore size cellulose acetate filter (FP30/0.45 CA-S, Schleicher & Schuell).
10-ml Disposable syringe (Terumo, cat SS-10ESZ).
Dissecting forceps! CAUTION Sterilize by autoclave.
Dissecting scissors! CAUTION Sterilize by autoclave.
Luminometer (Berthold Technologies, Centro $XS^3$ LB 960).
Fluorometer (Molecular Devices, SpectraMax M5e).
Fluorescence microscope (Nikon, Eclipse TS100).
Flow Cytometer (BD Biosciences, FACS-ARIAII).

Terms Used

Transduction: Intracellular delivery of target molecules (small molecules, polymers, peptide, protein, RNA, DNA, siRNA or nanostructures)

Transduction target: The molecule introduced by transduction (small molecules, polymers, peptide, protein, RNA, DNA, siRNA or nanostructures)

Transduction hypertonicity: Media hypertonicity that induces transduction

Reagent Setup

5× Transduction Buffer.

25 mM $NaH_2PO_4$, 500 mM NaCl, 75 mM Glycine, 150 mM Glycerol, 250 mM NDB, 1.25 mM $MgCL_2$, 1 mM 2-mercaptoethanol. To prepare 500 ml of 5× transduction buffer, mix 1.5 g of $NaH_2PO_4$ and 14.6 g of NACL then add miliQ $H_2O$ until 400 ml. adjust pH using 10M NaOH to reach a final pH of 8.0. Then, add while mixing 2.8 g of Glycine, 25 g of NDSB-201, 60 mg of $MgCl_2$, 5.5 ml of glycerol, 7 μl of 2-mercaptoethanol. Finally fill to 500 ml with miliQ $H_2O$. Filter sterilize by using a 0.22 um filter. Store at room temperature.

1× Transduction Buffer 500

To make 1× Transduction buffer 500, combine 1 volume of 5× Transduction buffer with the protein of interest with 4 volumes of isotonic cell culture media to reach a final tonicity of 500 mOsm/Kg.

1× Transduction Buffer 700

To make 1× Transduction buffer 700, combine 1 volume of 5× Transduction buffer with the protein of interest with 4 volumes of isotonic cell culture media. Finally, add the appropriate amount of NaCl or RbCl salts to reach a final tonicity of 700 mOsm/Kg.

MEF Media

DMEM containing 10% FBS with 50 U/ml penicillin and 50 mg/ml streptomycin. To prepare 500 ml of MEF medium, mix 50 ml of MEF serum and 2.5 ml of penicillin/streptomycin, and then fill to 500 ml with DMEM. Store at 4° C.

Neural Stem Cell Media

DMEM/F12 containing 1×B27 and 10 ng/ml of EGF with 50 U penicillin and 50 mg/ml streptomycin. To prepare 500 ml of neural stem cell media, 10 ml of B27 and 2.5 ml of penicillin streptomycin, and then fill to 500 ml with DMEM/F12. Store at 4° C.

mES Media

DMEM containing 15% FBS (vol/vol), 2 mM L-Glutamine, 10 mM NEAA, $1\times10^{-4}$ M 2-mercaptoethanol, 20 ng/ml hLIF, 50 U penicillin and 50 mg/ml streptomycin. To prepare 500 ml of the medium, mix 75 ml of mES serum, 5 ml of L-Glutamine, 5 ml of nonessential amino acids, 3.5 μl of 2-mercaptoethanol, 2.5 ml of penicillin/streptomycin and 500 μl of hLIF and then fill to 500 ml with DMEM. Store at 4° C.

mES Transduction Media (Used for mES Cells)

DMEM PHENOL-RED FREE containing 1×N2 and 1×B27 (vol/vol), 2 mM L-Glutamine, 10 mM NEAA, $1\times10^{-4}$ M 2-mercaptoethanol and 20 ng/ml of hLIF. To prepare 500 ml of the medium, mix 5 ml of N2, 10 ml of B27, 5 ml of L-Glutamine, 5 ml NEAA, 500 μl of hLIF and 3.5 μl of 2-mercaptoethanol and then fill to 500 ml with DMEM PHENOL-RED FREE. Store at 4° C.

Gelatin Coating of Culture Vessels

Dissolve 1 g of gelatin powder in 100 ml of distilled water, autoclave, and store at 4° C. as the 10× gelatin stock solution. To prepare 0.1% (1×) gelatin solution, thaw the 10× gelatin stocks in a microwave and/or autoclave, and then add 50 ml of the 10× solution to 450 ml of distilled water. Filter the solution with a 0.22-μm filter unit and store at 4° C. To coat culture dishes, add appropriate volume of 0.1% (1×) gelatin solution to cover the entire area of the dish bottom. For example, 1, 3, or 5 ml of gelatin solution is used for a 35-, 60-, or 100-mm dish, respectively. Incubate the dishes for at least 30 min at 37° C. in a sterile environment. Before using, aspirate off the excess gelatin solution.

Gelatin stock is prepared as 10× concentrate (1% w/v) stocks.

Methods:

Cell Culture

Mouse Embryonic Fibroblasts (MEFs) were obtained by isolation of embryos of 13.5-day-pregnant mice. First, the embryos were washed with phosphate-buffered saline (PBS) and the head and visceral tissues were removed. Remaining tissue was washed in cold PBS, minced using a pair of scissors and incubated 20 min at 37° C. in a 0.1 mM trypsin/1 mM EDTA solution (3 ml per embryo). After this incubation, an additional 3 ml per embryo of 0.1 mM trypsin/1 mM EDTA solution was added, and the mixture was incubated again at 37° C. for 20 min. After trypsinization, 6 ml per embryo of MEF media was added and pipetted up and down a few times to help with tissue dissociation. After incubation of the tissue/medium mixture for 5 min at room temperature, the supernatant was transferred into a new tube. Cells were collected by centrifugation (200×g for 5 min at 4° C.) and resuspended in MEF media. $1\times10^6$ cells (passage N° 1) were cultured on 100 mm dishes at 37° C. with 5% CO2 in MEF media.

Lox-RFP/STOP-Lox-eGFP MEFS cells were made by transducing them with lentiviral particles containing the EF1-α vector which drives the expression of Lox-RFP/STOP-Lox-eGFP cassette coupled to IRES-puromycin resistant gene. After 48 hrs of transduction, cells were cultured in MEF media with 1 μg/ml of puromycin during a 1 week. After 7 days of selection, almost all cells expressed the RFP marker. Cells were maintained in MEF media with 1 ug/ml of puromycin. Cells were frozen at passage N° 3 for future experiments.

IB10 mES cells were obtained from the lab of Dr. Hans Clevers (Hubrecht Institute, The Netherlands). V6.5 ES cells were a gift from the lab of Dr. Rudolf Jaenisch. Lox-Stop-Lox-GFP mES cells were a gift of Dr. Konrad Hochedlinger. All mES cells were maintained on a layer of irradiated MEF cells in mES media.

Mouse Embryonic Neural Stem cells were obtained from embryos head of 14-day pregnant mice as described before (REF1). Cells were maintained in neural stem cell media containing 10 ng/ml of EGF. After 2 weeks, is possible to observe the formation of neurospheres. Lox-RFP/STOP-Lox-eGFP transgenic neural stem cells were generated by transducing cells with lentiviral particles expressing a Lox-RFP/STOP-Lox-eGFP cassette coupled to IRES-puromycin resistant gene. 2 days after lentiviral transduction of neural stem cells, puromycin was added to media at concentration of 0.75 μg/ml. After 10 days of selection more than 95% of cells express RFP. Cells were maintained in neural stem cell media with 0.75 μg/ml of puromycin.

Human embryonic stem cells were cultured on matrigel in mTeSR1 or mTeSR-E8 media at 37° C. Culture media was replaced every day. Lox-RFP/STOP-Lox-eGFP transgenic H1 cells were generated by transducing cells with lentiviral particles expressing a Lox-RFP/STOP-Lox-eGFP cassette coupled to IRES-puromycin resistant gene. 2 days after lentiviral transduction of human ES cells, puromycin was added to mTeSR1 media at concentration of 0.75 μg/ml. After 10 days of selection more than 95% of cells express RFP. Cells were maintained in mTeSR1 or TeSR-E8 media with 0.75 ug/ml of puromycin.

Protein Expression, Purification and Buffer Exchange in Transduction Buffer

Proteins were overexpressed and purified from the *E. coli* strain BL21 (DE3) with chaperones together the expressing plasmid pET15 with the gene of interest. Several sets of Chaperones are available from Takara, and for each protein the optimal chaperone set can be determined according to the manufacturers protocol provided with the chaperone plasmid-sets. Overnight cultures were added 1:100 to x mL of LB media containing 50 ug/mL ampicillin and 20 ug/ml Chloramphenicol and placed in a shaking 37° C. incubator. Cultures were grown until an OD600 of 0.75 was reached at which point the culture was incubated with shaking at 16° C. After 1 h, IPTG was added at 1 mM, and cultures were incubated with shaking at 16° C. during 16 hrs. Cells were harvested by centrifugation and lysed by treatment with lysozyme (1 mg/mL) and benzonase (1 U/ml) at 4° C. for 1 h. Lysates were cleared by centrifugation and the supernatant was loaded onto a Ni-NTA column. The proteins were eluted by an imidazole gradient in 5× transduction buffer. After SDS-gel electrophoresis and Coomassie staining of every elution fraction, the high purity protein fractions were pooled and concentrated by using amicon filters. To remove the imidazole, Zeba Spin Desalting Columns were used according to the manufacturer's instructions, and the protein was eluted in 5× transduction buffer. At this point, protein can be further purified or aliquoted and snap-frozen in liquid nitrogen. A small fraction of protein solution was used to perform protein quantification by Bradford assay and SDS-gel electrophoresis coupled with Coomassie staining to determine protein concentration and purity, respectively. In our hands it was possible to freeze and thaw multiple times several proteins in 5× transduction buffer with minimal loss of activity.

Transduction

To establish the optimal transduction conditions, several parameters need to be optimized for each specific cell type. Specifically, these are; Tonicity and type of tonicity inducing-salt, transduction time, type and concentration of osmoprotectant, type and concentration of transduction compound. Specific procedures for optimization of each of these parameters are listed below. We use mainly two different transduction protocols for all primary cells and cell lines tested so far. We use culture media without antibiotics for the transduction. Although transduction works in the presence of serum, we have found that it is most efficient in serum-free conditions.

As a starting point for optimization, we determine which of two transduction protocols works best for the specific target cell type and osmocytosed target From there, the transduction buffer that yields the best results in terms of transduction efficiency, cell survival, cell proliferation and cell function can be further optimized as outlined below. In the first protocol transduction is performed for 12 hours at a tonicity of 500 mOsm/Kg (Protocol 12/500). In brief, a day before protein transduction, cells were plated in the appropriate culture media without antibiotics. Next day, prepare 1× transduction buffer 500 with the osmocytosed target. In brief, 5× transduction buffer and the osmocytosed target are mixed with cell culture media to obtain 1× transduction buffer at a tonicity of 500 mOsm/KG. This mixture of media/transduction buffer/osmocytosed target is added to the cells. Cells are incubated with proteins in transduction buffer for 12 hrs., after which transduction media is removed and exchanged for regular culture media.

In the second protocol protein transduction is performed for 3 hours at a tonicity 700 mOsm/Kg (protocol 3/700). In brief, 1 day before transduction, cells were plated in the appropriate culture media without antibiotics. Next day, prepare 1× transduction buffer 500 with the osmocytosed target as described above. Finally, NaCl or RbCl or another transduction hypertonicity-inducing salt (see below) is added to adjust the final tonicity to 700 mOsm/Kg. For example, 2 μl of 5M NaCl is added to 98 μl of 1× transduction buffer 500 to obtain a final tonicity of 700 mOsm/Kg.

In the examples below, we test the efficiency of the 12/500 and 3/700 protocols by transducing beta-lactamase or Cre protein as outlined below. However, efficiency and target cell response to the transduction buffer can be measured using other reporter molecules, including, but not limited to for example reporter DNA, RNA, siRNA, circRNA, small molecules and/or fluorescent probes.

The mixture of media/transduction buffer/and target osmocytosed molecule was added to cells. Cells were incubated with proteins in transduction buffer for 3 hrs. After that, the transduction media was removed and exchanged for regular culture media.

Subsequent rounds of transduction can be performed with recovery time intervals of typically 12 to 24 hours.

β-Lactamase Transduction Measurement.

β-lactamase transduction was performed using the 3/700 protocol above in murine embryonic fibroblasts (MEFs). A black, clear-bottom 96 well-plate was coated with 0.15 mg/ml of Poly-D-Lysine for 1 h at room temperature. 12,000 MEFs cells were seeded per well in MEF media without antibiotics. Next day, cells were transduced using the transduction protocol 3/700 as describe above. The β-lactamase protein in 5× transduction buffer was diluted 1/5 in DMEM phenol-red free media without antibiotics. Na- or Rb-salt was added to adjust the final tonicity to 700 mOsm/Kg. The complete mixture was then added to cells. After 3 hrs., the transduction media was replaced by fresh MEF media for 30 min. Subsequently, cells were washed once with phenol-red-free DMEM. β-lactamase activity was measured using the CCF2-AM kit following the manufacturer's instructions. In brief, 120 μl of CCF2-AM loading media was added per well and cells were incubated for 1 h at room temperature. Cells were washed two times with DMEM phenol-red free and incubated for an additional 30-60 min. Fluorescence emission was measured at 409 nm and 510 nm following manufacturer's instructions. All tests were done in triplicate.

β-lactamase transduction in mES cells was performed in a similar manner using the 12/500 rotocol (above). mES cells were plated at 75,000 cells per well in in gelatin-coated 96-well plates in mES culture media. Next day, cells were transduced using the transduction protocol 12/500 as described above. Then, β-lactamase protein in 5× transduction buffer was diluted 1/5 with mES transduction media. The complete mixture was then added to cells. After 12 hrs. of transduction, cells were washed 2 times with DMEM phenol-red free. β-lactamase activity was measured using the CCF2-AM kit following the manufacturer's instructions. In brief, 120 μl of CCF2-AM loading media was added to each well and cells were incubated for 1 hrs at room temperature. Cells were washed 2 times with DMEM phenol-red free media and incubated for extra 30-60 min. Fluorescence emission was read at 409 nm and 510 nm and analyzed following manufacturer's instructions. All tests were done in triplicate.

EXAMPLE 2

CRE Transduction and Quantification of CRE Incorporation

MEFs were transduced with CRE following the protocol 3/700 in a 96 well format. In brief, 12,000 Lox-RFP/STOP-Lox-eGFP MEF cells were seeded per well in gelatin coated plates using MEF media. Next day, CRE protein in 5× transduction buffer was diluted 1/5 with DMEM phenol-red free without antibiotics. The complete mixture was then added to cells. After 3 hrs. of transduction, media was replaced by fresh mES media and incubated for 24-48 hrs. Cells were then analyzed by measuring of green and red signal in a fluorescent microscope or in a flow cytometer.

mES cells were transduced with CRE following the protocol 12/500 in a 96 well format. In brief, 75,000 Lox-STOP-Lox-GFP mES cells per well were seeded gelatin coated plates using mES media. Next day, Cre protein in 5× transduction buffer was diluted 1/5 with mES transduction media. The complete mixture was then added to cells. After 12 hrs. the transduction media was replaced by mES media and cells were incubated for 24-48 hrs. Cells were then analyzed by measuring of green signal in a fluorescent microscope or in a flow cytometer.

Mouse Neural Stem Lox-RED/STOP-Lox-eGFP cells were transduced with CRE protein following the transduction protocol 12/500. Neurospheres were transferred to a 96 well plate with 80 μl of the neuronal stem cells media. Right after, 20 μl of CRE in 5× Transduction buffer was added to cell and mixed carefully. 12 hrs. later, transduction media was replaced by fresh neural stem cell media and cells were incubated for 24-48 hrs. Cells were then analyzed by measuring of green and red signal in a fluorescent microscope or in a flow cytometer.

Human ES Lox-RED/STOP-Lox-eGFP cells were transduced with CRE following the protocol 12/500 in a 96 well format Cell were passaged by mechanical dissociation into small clumps following mTeSR1 or TeSR-E8 manufacturer's instructions and seeded on a matrigel coated plate to reach a 50% confluency. Next day, CRE protein in 5× transduction buffer was diluted 1/5 with mTeSR1 or TeSR-E8. The complete mixture was then added to cells. After 12 hrs. of transduction, media was replaced by fresh mTeSR1 or TeSR-E8 media and cells were incubated for 24-48 hrs. Cells were then analyzed by measuring of green and red signal in a fluorescent microscope or in a flow cytometer.

EXAMPLE 3

TALEN Transduction

TALEN proteins were expressed and purified under native conditions as described above. The recombinant TALEN proteins were purified in 5× transduction buffer. Human ES cells were transduced with TALEN proteins using the transduction protocol 12/500. For HPRT gene disruption, a pair of TALEN proteins targeting the HPRT gene was used. 4 days after the transduction, 2.5 μM 6-TG was added to select for HPRT knockout cells. Two weeks later, surviving clones were picked and expanded for genomic DNA purification and HPRT gene sequencing.

Male human iPS cells were transduced with 2 μM TALEN protein for 12 hs. In brief, 20 μl HPRT talen proteins in 5× transduction buffer were mixed with 80 μl of human iPS cell media. Final mixture was added to cell for 12 hs. After that, media was replaced by 150 μl of human iPS cell culture media. After 5 days 3 μM 6-TG was added into culture media to select HPRT deficient cells. After 10 days, individual clones were picked and culture them separately. Genomic DNA was purified of each clone and HPRT gene sequence were performed. Blast alignment was executed to determine the rate of insertions and deletion in HPRT gene cause by TALEN proteins (see FIG. 15).

EXAMPLE 4

Transduction Enhancers

EGF, FGF and PDGF were used as protein transduction enhancers. The Growth factors were added in transduction buffer at their active final concentration (in the case of listed growth factors about 10 ng/ml each). Fusion peptides were used in transduction buffer at a concentration ranging from 1 to 10 μM.

EXAMPLE 5

BrdU and Caspase Measurements

Cell proliferation was determined using the Cell Proliferation Elisa kit, Brdu (Roche) following manufacturer's instructions (Roche). Quantification of caspase-3 and caspase-7 activities were measured using the Caspase-Glo 3/7 Assay kit (Promega) following the manufacturer's protocol (Promega).

EXAMPLE 6

Assays for the Optimization of the Transduction Procedure and the Transduction Buffer It is important to note that tonicity is defined by the concentration of all solutes that don't cross the cell membrane. In our examples, we use NaCl or RbCl typically at 500-700 mOsm/KG, but buffer tonicity as well as transduction time should be optimized for a specific application (transduction target and target cell type) as outlined below (I). Also, in our examples we use NDSB201 as the transduction compound, but the ability and efficiency of other compounds in inducing or facilitate transduction can be determined as outlined below, and should be optimized for the specific application (transduction target and target cell type) as outlined below (II). As stated above, in our examples we use NaCl or RbCl to induce transduction hypertonicity, but other salts or compounds can be used. We have outlined below (III) an assay to test if a molecule or compound can effectively induce the transduction hypertonicity. Salts, molecules or compounds that are found to induce transduction should be further optimized for time and buffer tonicity as outlined in (I). In our examples, the osmoprotectants used in our transduction buffer are Glycine and Glycerol, but the effectiveness of other compounds as osmoprotectants can be determined as outlined below, and should be optimized for the specific application and cell type as outlined below (IV). Optimization of above parameters will require iterative adjustments of the other components. For example, after determination and optimization of a novel transduction compound, the transduction hypertonicity and time may need re-adjustment.

(I) Assay to Optimize Transduction Tonicity and Transduction Time.

To optimize the transduction procedure for a specific application (transduction target and target cell type), consider as starting point the protocols 12/500 and 3/700 described before. Here, we describe how to optimize the transduction protocol with respect to efficiency of intracellular uptake, cell survival and, if applicable, cell proliferation. In our example, we use β-lactamase protein to optimize transduction, but other proteins, DNA, RNA, siRNA, (small) molecules or nanostructures can be used, as long as there is an essay available to determine the intracellular delivery of the transduction target.

To optimize transduction media tonicity and transduction time, set up a titration matrix in a 96-well format as shown in FIG. 11.

Prepare a beta-lactamase solution of at least 80 to 100 microM in 5× transduction buffer. This β-lactamase protein solution is used as a 100× concentrate to obtain a final β-lactamase concentration of 0.8 to 1 μM.

To optimize buffer tonicity and transduction time, target cells are plated in the appropriate phenol-red-free culture media without antibiotics in 3 different multi-well plates (Plate "A", to determine intracellular β-lactamase activity, plate "B" for cell proliferation measurement and plate "C" for apoptosis analysis).

Prepare a series of culture media with different tonicities ranging from 300 to 1000 mOsm/Kg, by adding 50 mM NDSB201, 15 mM Glycine and 30 mM Glycerol to phenol-red-free culture media without antibiotics and adjusting the tonicity using NaCl, RbCl or other transduction hypertonicity-inducing salt (for optimization of transduction hypertonicity inducing salts see (III) below). Incubate cells at different tonicities for 2-24 hrs (see schematic FIG. 11) and proceed to measure β-lactamase activity in plate A as described above and replace media with standard culture media in plates B and C. After 6-8 hrs., add BrdU in plate B in regular culture media and measure caspases 3/7 activities in plate C. Incubate plate B with BrdU for the additional time required for BrDU incorporation into the proliferating target cells (see manufacturers protocol) and proceeded to determine BrdU incorporation (Manufacturers instructions; Cell Proliferation ELISA, BrdU, Roche, Cat 11669915001). The optimal conditions will be those with highest β-lactamase protein incorporation and minimal effect on cell survival, cell proliferation (if applicable) and cell function.

(II) Assay to Optimize Type and Concentration of Transduction Compound

In our examples we used the transduction compound NDSB201, but different transduction compounds can be used depending on the application and transduction target. Here we describe how to test the performance of potential transduction compounds and optimize the final concentration of the transduction compound. In this example we use transduction protocol 3/700 to transfer β-lactamase protein into murine embryonic fibroblasts (MEFs), but depending on target cell type the transduction protocol should be adjusted as described in (I). Prepare a 100× β-lactamase stock as described in (I). To optimize transduction compound, this stock β-lactamase solution will need to be prepared in the to be tested transduction compound of interest or dialyzed against 5× transduction buffer with 250 mM of transduction compound of interest.

Prepare culture media at optimized tonicity determined in (I). Add to this media, the to be tested transduction compound in a concentration range of 5 to 150 mM. As described in (I) prepare multi-well plates with target cells to test intracellular transfer of transduction target, cell apoptosis and, if applicable, cell proliferation. Add transduction media with transduction target (In our example β-lactamase) and different concentrations of the tested transduction compound. Incubate cells at the time determined in (I) and measure β-lactamase transduction, apoptosis and BrdU incorporation as described in (I).

(III) Assay to Optimize the Type of Hypertonicity-Inducing Salt.

Several salts are capable of inducing transduction hypertonicity, but as demonstrated in our examples, not all hypertonicity-inducing molecules induce transduction. Here we describe how to determine if a specific salt is capable of inducing transduction and how to optimize the type of transduction salt for a specific application.

Prepare a 100× β-lactamase stock as described in (I). To optimize transduction salt, this stock β-lactamase solution will need to be prepared in the to be tested transduction salt of interest or dialyzed against 5× transduction buffer with 250 mM of transduction salt of interest.

Ideally, in the following steps, sodium-free media is used for the preparation of the transduction media, since sodium present in standard culture media can confound results. Prepare culture media using a control transduction salt (see examples) or the salt(s) to be tested at a tonicity ranging from 300-1000 mOsm/Kg and combine with transduction target (In this example β-lactamase). (Alternatively, an initial test can be performed using the salt to be tested in the transduction protocols 12/500 or 3/700 to determine transduction activity of a specific salt or molecule, with subsequent further optimization of this salt or molecule as described in (I)).

As described in (I) prepare multi-well plates with target cells to test intracellular transfer of transduction target, cell apoptosis and, if applicable, cell proliferation. Add transduction media with different concentrations of the tested transduction salt Incubate cells at the optimal transduction time determined in (I) and measure β-lactamase transduction, apoptosis and BrdU incorporation as described in (I).

(IV) Assay to Optimize the Type and Concentration of Osmoprotectant

In our examples we use a combination of Glycerol and Glycine as osmoprotectants, but different osmoprotectants can be used depending on the application and transduction target. Here we describe how to test the performance of potential osmoprotectants and optimize the final concentration of the osmoprotectants.

Prepare a 100× β-lactamase stock as described in (I). Prepare transduction culture media using a control osmoprotectant(s) (see examples) or the osmoprotectant(s) to be tested at a concentration ranging from 1-250 mM and combine with transduction target (In this example β-lactamase). As described in (I) prepare multi-well plates with target cells to test intracellular transfer of transduction target, cell apoptosis and, if applicable, cell proliferation. Add transduction media with different concentrations of the tested osmoprotectant(s). Incubate cells at the optimal transduction time determined in (I) and measure β-lactamase transduction, apoptosis and BrdU incorporation as described in (I).

EXAMPLE 7

Transduction Buffer Enhances DNA-Lipid Transfection on Primary Cells

One day before transduction, 75,000 mouse ES cells were plated per well in a 96-well plate. Next day, cells were transfected with 100 μl transfection media. In brief, transfection media contains 100 ng plasmid DNA, 0.8 μl LTX lipid, 0.1 μl plus reagent (LifeTechnologies) and 20 μl of 5× transduction buffer. Total volume included 100 μl mESC media+LIF. Control cells were similarly transfected; transduction buffer was replaced with mESC media+LIF.

Figure 12:
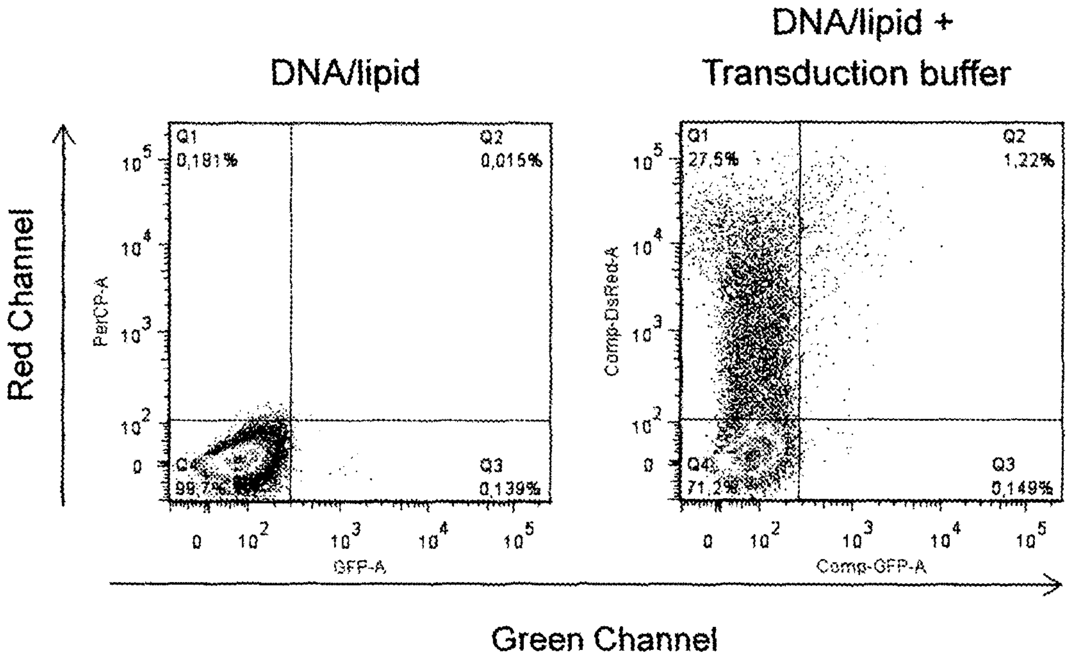

The results are shown in FIG. 12. Addition of transduction buffer to the plasmid DNA/Lipofectamine LTX transfection mix results in efficient transfection of reporter DNA into the murine ESCs.

EXAMPLE 8

Dual Intracellular Incorporation of DNA and Protein Using Transduction Buffer

One day before transduction, 75,000 mouse ES cells were plated per well of a 96-well plate. Next day, cells were incubated with 100 μl of transduction media. Cre transduction media was prepared by combining 2 μl CRE protein in 5× transduction buffer plus an additional 8 μl of mESC media+LIF. RFP/DNA-Lipid transfection media contained 100 ng plasmid DNA, 0.41 LTX lipid, 0.1 μl plus reagent (Life Technologies) and 20 μl of 5× transduction buffer. Total volume included 100 μl mESC media+LIF. CRE and DNA/LIPID transduction media contains 100 ng plasmid DNA, 0.8 μl LTX lipid, 0.1 μl plus reagent (Life Technologies) and 20 μl CRE protein in 5× transduction buffer. Total volume included 100 μl mESC media+LIF. Cells were incubated for 12 hrs and media replaced with mESC media. Cells were analysed 32 hrs after transduction by FACS analysis.

The results are shown in FIG. 13. Addition of transduction buffer results in efficient transfection of: Cre recombinase protein; plasmid RFP-DNA; and CRE protein together with RFP-DNA/Lipid complexes. into the murine ESCs.

EXAMPLE 9

Transduction Buffer Enhances Viral Incorporation in Human iPS Cells

Lentiviral transduction on human iPS cells with a cell density of 75% confluency in 96-well format Viral transduction consisted of 1 μl concentrated viral stock, 4 μg/ml polybrene, plus human iPSC culture media for a final volume of 100 μl.

Viral transduction under transduction buffer conditions were performed by combining 1 μl concentrated viral stock, 4 μg/ml polybrene, 20 μl of 5× transduction buffer, plus human iPSC culture media for a final volume of 100 μl. Cells were incubated for 12 hrs and media changed for regular human iPSC media. Cells were analysed 36 hrs after transduction. Next day, cells were transfected with 100 μl transfection media. In brief, transfection media consisted of 100 ng plasmid DNA, 0.8 μl LTX lipid, 0.1 μl plus reagent (LifeTechnologies) and 2 μl of 5× transduction buffer. Total volume included 100 μl mESC media+LIF. Control cells were similarly transfected; transduction buffer was replaced with mESC media+LIF.

The results are shown in FIG. 14. Addition of transduction buffer results in efficient transfection of lentiviral particles into the human iPS cells.

EXAMPLE 10

Transduction Buffer for Protein with Low Solubility

2/1000 Transduction Buffer—Final Composition.

500 mM NaCl, 250 mM NDSB-201, 300 mM glycine, 150 mM Glycerol in D-MEM N2/B27+LIF.

2/1000 Transduction Buffer Protocol.

In brief, mES cells were transduced by adding 80 μl of 2/1000 transduction buffer+20 μl CRE protein in 5× transduction buffer 500/12. Cells were incubated for 2 hrs. Following incubation, media was replaced with mESC media. Cells were analyzed by FACS 36 hrs after transduction.

EXAMPLE 11

Transduction of TALENs into Human iPS Cells

Male human iPS cells were transduced with 2 μM TALEN protein for 12 hs. In brief, 2 μl HPRT TALEN proteins in 5× transduction buffer were mixed with 8 μl of human iPS cell media. Final mixture was added to cell for 12 hs. After that, media was replaced by 150 μl of human iPS cell culture media. After 5 days 3 μM 6-TG was added into culture media to select HPRT deficient cells. After 10 days, individual clones were picked and culture them separately. Genomic DNA was purified of each clone and HPRT gene sequence were performed. Blast alignment was executed to determine the rate of insertions and deletion in HPRT gene cause by TALEN proteins.

The results are shown in FIG. 15. The results show that functional TALENs were transduced into the iPS cells because insertions and deletions were generated in the genetic material inside the cell at the TALEN target site.

EXAMPLE 12

Simultaneous Transduction of Proteins and Large Molecules

To assess if the transduction buffer would permit the simultaneous transduction of proteins and large molecules, we analyzed macropinocytosis mediated uptake of TMR-dextran (red) and fluorescently labeled BSA protein (cyan) by GFP-expressing murine embryonic fibroblasts (MEFs). In brief, MEFs expressing eGFP protein (green) were incubated with 5 μg/ml of high molecular weight TMR-Dextran (red) and 1 μg of BSA-Alexa-647 (far-red) in 1× transduction media (protocol 700/3) for 30 min. Subsequently, cells were washed twice in 1× transduction buffer. Finally, cells were maintained in 1× transduction buffer and immediately analyzed by confocal microscopy. Dextran and BSA uptake was inhibited by incubating cells with 100 μM Ethylisopropylamiloride (EIPA) 30 min before and during transduction procedure.

Results are shown in FIGS. 16A-16B. Simultaneous transduction of Dextran (polysaccharide) and BSA protein was observed in the presence of transduction buffer. Transduction was inhibited by macropinocytosis inhibitor EIPA.

EXAMPLE 13

Gene Editing by Transduction

The high efficiency of protein osmocytosis has appealing application in gene editing. In addition to the TALEN gene editing system described above, the recently discovered CRISPR-Cas9 system provides an additional gene editing system. CAS/CRISPR consists of the *Streptococcus pyrogenes* Cas9 nuclease protein, which is guided to specific genomic loci by a small guide RNA (sgRNA) [1, 2]. The appeal of the CAS/CRISPR system is its simplicity in design. In contrast to the TALEN and Zinc-finger systems, in which the nuclease protein itself needs to be designed and modified for each specific target site, the CAS/CRISPR system requires a single nuclease protein (Cas9) and varies the associated short guide RNA for target selection. Upon target binding, the Cas9 nuclease creates a double-strand break (DSB) at the target locus, which, when repaired by the cellular DSB-repair system frequently creates a frameshift deletion resulting in gene disruption. The Cas/CRISPR system is typically introduced into target cells using viral vectors, which hampers clinical application and, without further drug-selection of infected cells, is inefficient in some target cell types. Given the efficiency of our osmocytosis system in several difficult-to-infect cell lines, including human stem cells, we explored whether this system would allow protein-mediated gene editing as well.

To this end, we first tested whether osmocytosis would allow the efficient transduction of RNA into cells. To test this, we performed siRNA (small interfering RNA) transduction into KBM7 cells using the 700/3 protocol. We transduced siRNA targeting GAPDH (Invitrogen) and measured GAPDH knockdown by western blot. As shown in FIG. 18, transduction of siRNA resulted in efficient knockdown of GAPDH protein expression level. Above data demonstrates that our osmocytosis system allows the efficient transduction of small RNAs such as siRNA into target cells.

Figure 19C:
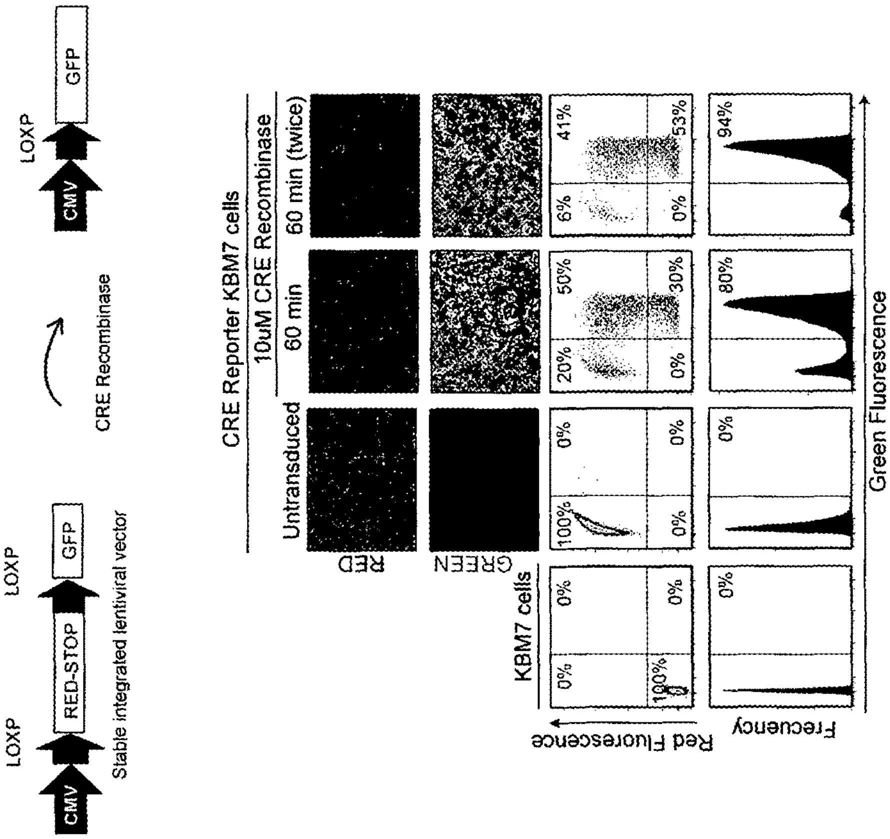
Figure 19A:
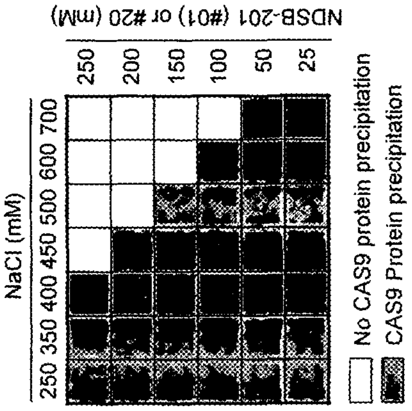
Figure 19B:
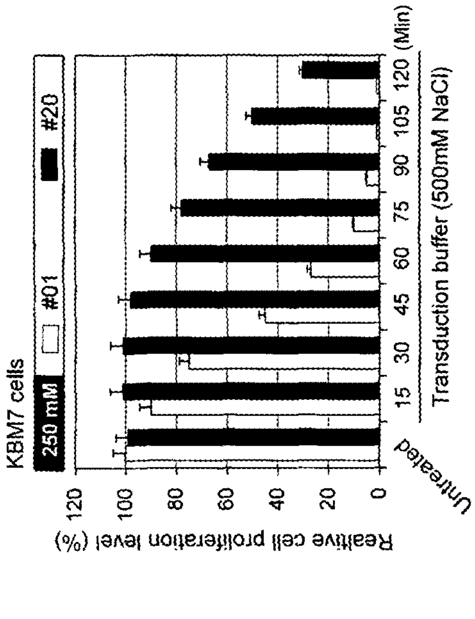

Next we optimized the transduction media to allow the transduction of recombinant Cas9. In our first attempt to transduce Cas9 protein using the 700/3 and 500/12 media, we noticed that Cas9 protein was insoluble in both transduction conditions. However, Cas9 protein remained soluble when higher concentrations of both NaCl and NDSB-201 (#01) or GABA (#20) were used (FIG. 19A). For this reason we developed a "Cas9-adapted transduction protocol" (the "fourth protocol") with a final osmolality of 1250 mOsmol/Kg and a concentration of 250 mM of NDSB-201 (transduction compound #01) or other transduction compounds selected from the FIGS. 7A-7D. We expected that higher osmolalities and NDSBs will induce faster protein transduction but also could possibly increase the cellular toxicity. To characterize this new transduction conditions we measured BrdU incorporation upon high osmolarity (1250 mOsm/Kg) transduction at different short time points, in KBM7 cells. We observed that the different transduction compounds displayed varying survival rates compare to NDBS-201 in KBM7, and compound #20 for example gave much better survival than NDSB-201 (FIG. 19B).

To further test the duration of the transduction with the modified transduction buffer, we performed a Cre recombinase protein transduction at 1250 mOsmol/Kg and 250 mM GABA at different time points and measured the percentage of cells with successful cre-mediated reporter activation as well as BrdU incorporation as a measure of cell proliferation and survival. Under these conditions, the optimal transduction time based on cell survival and Cre transduction was around 60 minutes. At those time points, one round of Cre protein transduction gave an 80% of GFP positive KBM7 cells. And two subsequent rounds of Cre protein transduction yielded 94% positive KBM7 (FIG. 19C). A second round of protein transduction didn't affect cell survival rate. Thus, these data shows the flexibility of the osmocytosis method and demonstrate that, based on the properties of the protein to be transduced, it is possible to adjust transduction conditions (type and concentration of the transduction compound and/or buffer osmolality) for optimal protein incorporation efficiency and cell survival.

Figures 19D, 19E, 19F:
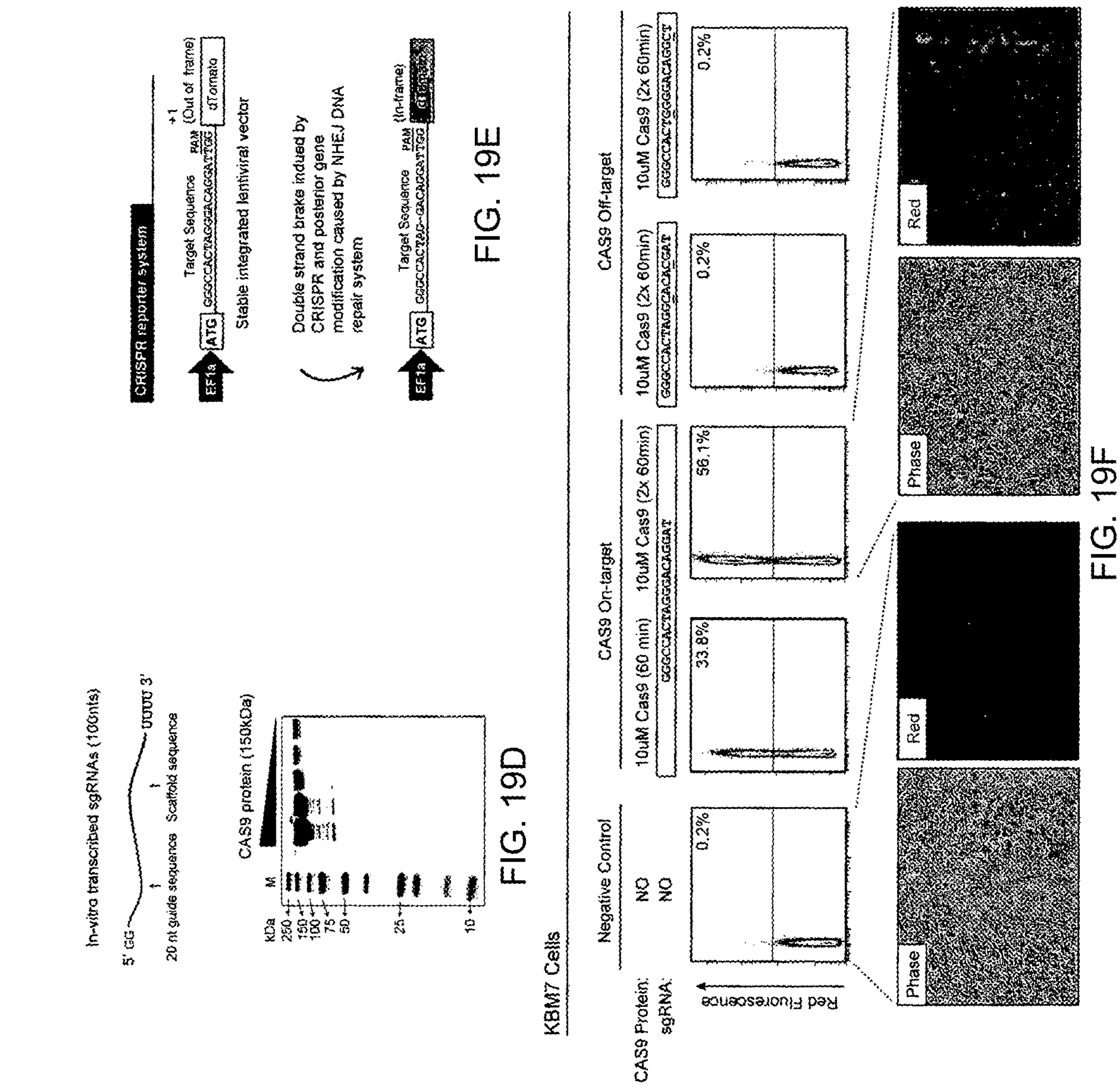

Using the Cas9-adapted transduction media, we aimed to simultaneously transduce Cas9 protein with the corresponding sgRNA into KMB7 cells. sgRNAs were produced by in-vitro transcription from DNA templates. The sgRNAs contain a 20 nt guide sequence, conferring its target specificity and an 80 nts scaffold sequence (FIG. 19D, top panel). Recombinant Cas9 protein was expressed in *E. coli* (FIG. 19D, bottom panel). To monitor the introduction of CAS9-sgRNA into cells, we developed reporter cells lines having a stable integrated lentiviral construct with 20 nts of AAVS1 target sequence coupled to an out-of-frame silent tdtomato gene (FIG. 19E). Successful Cas9-sgRNA mediated introduction of a frameshift deletion upstream of the tdTomato gene will restore the reading frame of the tdTomato reporter and allow analysis of targeting efficiency (FIG. 19F). KBM7 reporter cells were transduced with Cas9 protein together the corresponding on-target AAVS1 sgRNA. After the first round of Cas9-sgRNA transduction, 30% of the reporter KBM7 cells reestablished tdtomato protein expression (FIG. 19F, top panel). After a second round of Cas9-sgRNA transduction, 56% of the KBM7 cells expressed the tdtomato reporter. As specificity control, KMB7 reporter cells were transduced with Cas9 protein and off-target sgRNAs with 2 nucleotide substitutions compared to the AAVS1-target sequence (FIG. 19F, top panel). As shown in FIG. 19F, off-target sgRNAs did not activate the tdtomato reporter. Together, our data demonstrate that our osmocytosis buffer allows the efficient tandem transduction of protein and RNA, and allows highly efficient and specific gene editing using the Cas9/CRISPR system. Recently, several variations to the Cas9/CRISPR system have been reported, including enhanced specificity by introducing heterologous FokI nucleases [3, 4], alternative Cas analogs from different species [5] or alternative targeting systems based on other bacterial immune complexes such as the Cascade system [6] or bacterial argonaute proteins (reviewed in: [7]). We have shown that our osmocytosis system allows the efficient introduction of gene editing proteins or protein-nucleotide complexes into mammalian (stem) cells as exemplified by our successful transduction of recombinant TALEN proteins and recombinant Cas9 protein together with its small guide RNA. It is expected that our transduction system will allow efficient introduction of other gene editing proteins or protein-complexes (such as the ones mentioned above) as well.

Since we used a lentiviral reporter system for measuring CAS9/sgRNA transduction, it is likely that each cell contained multiple copies of the reporter, which may distort the perceived transduction efficiency. To obtain an accurate estimate of CRISPR-Cas9 osmocytosis mediated targeting efficiency, and to demonstrate that this system can be used to modulate endogenous genes as well, we tested the capacity of our gene-editing protein transduction system to modify an endogenous gene WDR85 (DPH7). WDR85 Knockout cells are resistant to Diphtheria toxin-induced cell death, thus providing a simple and reliable assay for measuring successful biallelic gene knockout. Diploid KBM7 cells were transduced twice with Cas9 protein and 6 different sgRNAs against WDR85 gene (FIG. 20A). 7 days after the second Cas9 protein/sgRNA transduction (to allow the gene knockout to become effective at the protein level), cells were treated with diphtheria toxin for 48 hs. Cell survival was observed only in cells transduced with Cas9 protein and WDR85 sgRNAs, while no viable cells were detected in diphtheria toxin treated wild type KBM7 cells or in cells transduced with Cas9 protein with an off-target sgRNAs (FIG. 20B). The different sgRNA displayed different efficiencies in knocking out WDR85. 4 out of 6 sgRNAs gave particularly high cell survival rates (FIG. 20B, bar graph). Since the KBM7 cells used in this experiment were diploid, this means that in surviving cells endogenous WDR85 was deleted on both alleles. DNA sequence analysis was performed in a pool of diphtheria toxin resistant cells transduced with the different WDR85 sgRNAs and CAS9 protein. We observed for every WDR85 sgRNAs a 100% of gene disruption (FIGS. 20C-20E) confirming that diphtheria toxin resistant cells were WDR85 gene Knockout.

Figure 20F:
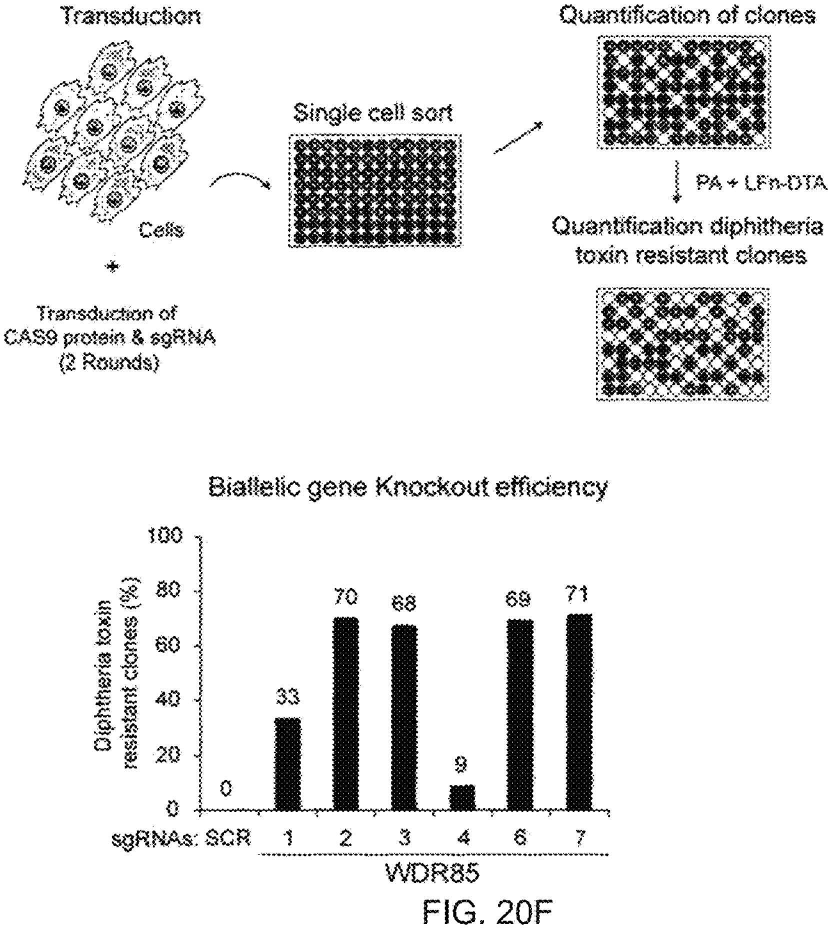
Figure 20G:
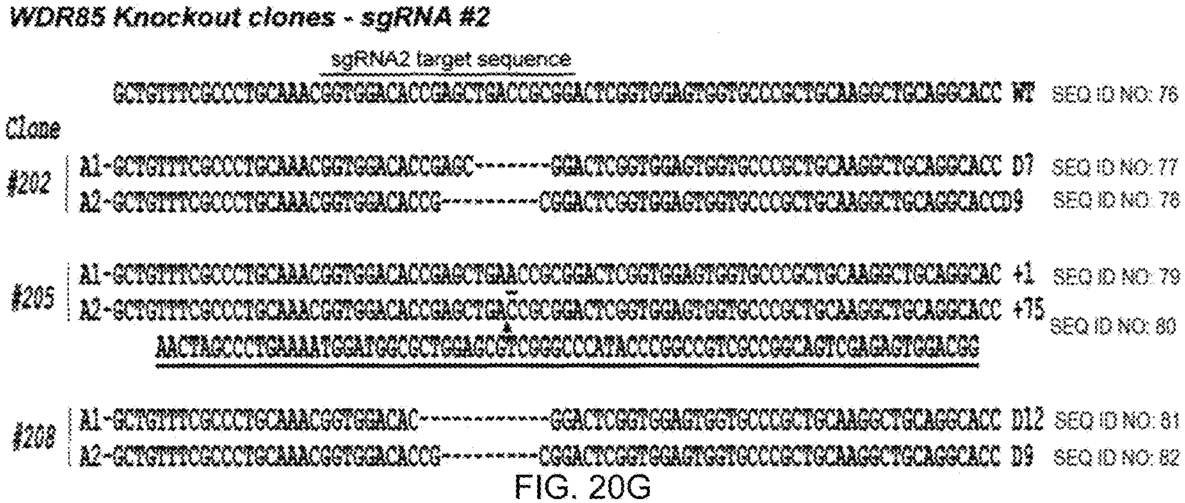

To accurately estimate the knockout frequency, we transduced KMB7 cells with CAS9 protein and the different WDR85 sgRNAs. 4 days later, we performed single cell sort in 384 well plates and after a week we identified the clones that survived the single-cell sorting procedure. These clones were then treated for 48 hs with diphtheria toxin. Surviving clones were counted allowing us to determine the percentage of diphtheria toxin resistant clones, in which both alleles of WDR85 were knocked out, thus estimating the efficiency to make WDR85 knockout cells. As before, the different sgRNA demonstrated different efficiencies in generating WDR85 knockouts, ranging from 10-70% of biallelic knockout (FIGS. 20F-20H). We sequenced the CAS/CRIPSR target site in 3 single cell-clones for the four sgRNAs that were highly efficient to confirm that ditheria toxin surviving clones indeed contained a biallelic WDR85 gene disruption. As shown in FIGS. 20F-20H, diphtheria-resistant clones indeed demonstrated biallelic WDR85 gene disruption. The efficiency of generating biallelic knockouts by osmocytosis of recombinant Cas9 protein and sgRNA is much higher than previously reported [2], demonstrating that this method allows the highly efficient, non-viral generation of targeted gene mutations in human cells.

In all of these methods 15 mM Glycine and 30 mM Glycerol were included in the transduction buffer as osmoprotectants.

We observed a significant cell survival effect using the interferon inhibitor protein "B18R" when we transduced RNA or DNA into cells (Nat Protoc. 2013 March; 8(3):568-82. doi: 10.1038/nprot.2013.019. Epub 2013 Feb. 21. Reprogramming human fibroblasts to pluripotency using modified mRNA. Mandal PK1, Rossi D J.). In brief, cells were incubated with 250 ng/ml of B18R protein 3 hs before transduction, during transduction and 48 hs after transduction. In recent years, two essentially different gene editing systems have been developed that differ in the way they find their specific genomic target sequence. One type, represented by the zinc-finger nucleases and TALENs uses customizable domains within the nuclease protein itself to recognize specific target DNA sequence in the genome. The other type is represented by the Cas9/CRISPR, Cascade, TtAgo and other Argonaute protein systems, which use a common protein (complex) that is the same regardless of the genomic target site, which is targeted to a specific target by an associated nucleotide sequence. Our data demonstrate that the transduction system described here is capable of delivering both types of gene editing systems into mammalian cells and by doing so allows rapid, non-viral and highly efficient gene editing.

EXAMPLE 14

Evidence for Macropinocytosis Mechanisms of Transduction and a Simple Assay for Evaluating the Efficacy of a Transduction Compound Candidate For transduction to occur, proteins that have been taken by macropinocytosis have to be released into the cytosol. We hypothesized that this happens by permeation of the macropinocytic vesicles. To test the efficacy of potential transduction compound candidates, we set up an assay to monitor macropinosome vesicle permeation. We used a Galectin3-GFP reporter system that has been described before to monitor vesicle leakage induced by drugs or pathogens [8, 9]. Galectin-3 is a small soluble cytosolic protein that can bind beta-galactoside sugar containing carbohydrates. These are normally present only on the exterior of the plasma membrane and the interior of intracellular endocytic vesicles. Upon intracellular permeation of the membrane of macropinocytic vesicles, cytoplasmic Galectin-3 can penetrate the vesicle and bind to the intravascular carbohydrates. Galectin-3 relocalization has therefore been utilized as a tool to identify rupture of vesicles in studies of bacteria and viruses which rely on vesicle rupture to enter the cytoplasm during infection [8, 9]. We set up a reporter system in which Galectin-3 protein is fused to GFP (GAL3-GFP). Cytosolic GAL3-GFP protein relocalises to the interior of permeabilized macropinosomes, whereby a multimer complex is formed with intense green fluorescent emission. MEFs cells expressing GAL3-GFP protein were transduced using the 700/3 conditions. As expected, we observed bright vesicle formation in cells under transduction media, demonstrating macropinosome leakage under protein transduction conditions (FIGS. 17A-17B). Gal3-GFP did not relocalize to vesicles when cells were pre-incubated with macropinocytosis inhibitor EIPA (which potently inhibits protein transduction) or when cells were left untreated (FIGS. 17A-17B). Furthermore, when the transduction compound (NDSB-201) was replaced by a compound with little to no transduction activity (compound 09 and 18) Gal3-GFP did not localize into the macropinocytic vesicles (FIGS. 17A-17B). These results indicate the transduction media is promoting protein uptake from extracellular space via macropinocytosis and inducing macropinosome vesicle leakage to release proteins into the cytosol. The Gal3-GFP assay is a simple and effective means to test candidate transduction compounds for efficacy in protein transduction.

REFERENCES FOR EXAMPLES 13 AND 14

1. Jinek, M., et al., *A programmable dual-RNA-guided DNA endonuclease in adaptive bacterial immunity*. Science, 2012. 337(6096): p. 816-21.
2. Mali, P., et al., *RNA-guided human genome engineering via Cas*9. Science, 2013. 339(6121): p. 823-6.
3. Tsai, S. Q., et al., *Dimeric CRISPR RNA-guided FokI nucleases for highly specific genome editing*. Nat Biotechnol, 2014. 32(6): p. 569-76.
4. Guilinger, J. P., D. B. Thompson, and D. R. Liu, *Fusion of catalytically inactive Cas*9 *to FokI nuclease improves the specificity of genome modification*. Nat Biotechnol, 2014. 32(6): p. 577-82.
5. Esvelt, K. M., et al., *Orthogonal Cas*9 *proteins for RNA-guided gene regulation and editing*. Nat Methods, 2013. 10(11): p. 1116-21.
6. Westra, E. R., et al., *Cascade-mediated binding and bending of negatively supercoiled DNA*. RNA Biol, 2012. 9(9): p. 1134-8.
7. Makarova, K. S., et al., *Prokaryotic homologs of Argonaute proteins are predicted to function as key components of a novel system of defense against mobile genetic elements*. Biol Direct, 2009. 4: p. 29.
8. Paz, I., et al., *Galectin*-3, *a marker for vacuole lysis by invasive pathogens*. Cell Microbiol, 2010. 12(4): p. 530-44.
9. Maejima, I., et al., *Autophagy sequesters damaged lysosomes to control lysosomal biogenesis and kidney injury*. EMBO J, 2013. 32(17): p. 2336-47.

The invention claimed is:

1. An in vitro method for transducing a molecule of interest into a cell, wherein the method comprises contacting said cell with the molecule of interest and a transduction buffer thereby transducing the molecule of interest into the cell, wherein the molecule of interest comprises a protein, wherein the transduction buffer comprises (i) a transduction compound, (ii) a salt selected from a sodium, lithium, potassium, caesium or rubidium salt, or an activator/enhancer of a sodium-hydrogen transporter;

wherein the transduction compound is selected from compounds 42, 31, 45, 43, 34, 41, 40, 39, 33, 44, 22, 20, 03, 30, 15, 38, 35, 11, 10, 28, 37, 01, 29, 02, 21, 36, 26, 16, 04, 19, 23, 24, 12, 14, 13, 05, 08 and 27 in Table 1;

and wherein the transduction buffer has an osmolality of at least 750 mOsm/kg and a pH of between about 6 and about 8.

2. The method of claim 1, wherein the transduction buffer comprises (a) an osmoprotectant and the osmoprotectant is glycine and/or glycerol, and/or (b) a biological pH buffer, a viscosity enhancer, an inhibitor of the interferon response pathway and/or a growth factor, (c) compound 01 in Table 1 as the transduction compound or compound 20 in Table 1 as the transduction compound, and/or (d) compounds 01 and 20 in Table 1 as transduction compounds; sodium chloride as the salt; and glycine and/or glycerol as the osmoprotectant.

3. The method of claim 1, wherein the salt is sodium chloride.

4. The method of claim 1, wherein the transduction buffer comprises a biological pH buffer, a viscosity enhancer, an inhibitor of the interferon response pathway and/or a growth factor, and the biological pH buffer is PBS, TES or HEPES.

5. The method of claim 1, wherein the transduction buffer comprises a biological pH buffer, a viscosity enhancer, an inhibitor of the interferon response pathway and/or a growth factor, and the viscosity enhancer is polyvinylpyrrolidone (PVP).

6. The method of claim 1, wherein the transduction buffer comprises a biological pH buffer, a viscosity enhancer, an inhibitor of the interferon response pathway and/or a growth factor, and the growth factor is selected from EGF, FGF, HGF, BDNF, PDGF, VEGF or IGF, or is any combination thereof.

7. The method of claim 1, wherein the transduction buffer further comprises (iii) an osmoprotectant.

8. The method of claim 7, wherein the osmoprotectant is at a concentration of between about 5 and about 500 mM.

9. The method of claim 1, wherein the molecule of interest is an enzyme.

10. The method of claim 1, wherein the cell is an animal cell, a plant cell, a yeast cell, an insect cell or a bacterial cell.

11. The method of claim 1, wherein the transduction compound is selected from compounds 45, 43, 34, 39, 20, 01, 44, 15, 30, 03, 35, 11 and 10 in Table 1.

12. The method of claim 1, wherein the transduction compound is selected from compounds 45, 43, 34, 39, 20 and 01 in Table 1.

13. A method for modifying a nucleic acid in a cell, wherein the method comprises contacting said cell with a protein capable of modifying a nucleic acid and a transduction buffer, wherein the transduction buffer comprises (i) a transduction compound selected from compounds 42, 31, 45, 43, 34, 41, 40, 39, 33, 44, 22, 20, 03, 30, 15, 38, 35, 11, 10, 28, 37, 01, 29, 02, 21, 36, 26, 16, 04, 19, 23, 24, 12, 14, 13, 05, 08 and 27 in Table 1, and (ii) a salt selected from a sodium, lithium, potassium, caesium or rubidium salt, or an activator/enhancer of a sodium-hydrogen transporter, wherein the transduction buffer has an osmolality of at least 750 mOsm/kg and a pH of between about 6 and about 8, thereby transducing the protein into said cell and creating a modified cell.

14. The method of claim 13, wherein the method further comprises isolating or using the modified cell.

15. The method of claim 13, wherein the protein capable of modifying a nucleic acid is targeted to a specific target sequence.

16. The method of claim 13, wherein the cell is further contacted with a guide molecule to direct the protein to a target genetic sequence.

17. The method of claim 13, wherein the nucleic acid comprises or consists of a genetic sequence.

18. The method of claim 13, wherein the transduction buffer further comprises (iii) an osmoprotectant.

19. The method of claim 15, wherein the protein is a zinc finger nuclease, a TALEN, Cas9, a Cas9 analog, a DNA-targeted FokI-nuclease-associated protein, a Cascade complex, a TtAgo protein, another Argonaute protein, or their derivatives.

20. The method of claim 13, wherein the transduction compound is selected from compounds 45, 43, 34, 39, 20, 01, 44, 15, 30, 03, 35, 11 and 10 in Table 1.

21. The method of claim 13, wherein the transduction compound is selected from compounds 45, 43, 34, 39, 20 and 01 in Table 1.

* * * * *